(12) United States Patent
Araldi et al.

(10) Patent No.: US 8,044,041 B2
(45) Date of Patent: Oct. 25, 2011

(54) PHTHALAZINE DERIVATIVES AS INHIBITORS OF PROTEIN KINASE

(75) Inventors: Gian-Luca Araldi, East Setauket, NY (US); Matthew Ronsheim, Port Jefferson, NY (US); Melanie Ronsheim, Port Jefferson, NY (US)

(73) Assignee: Forest Laboratories Holdings Limited (BM)

( * ) Notice: Subject to any disclaimer, the term of this patent is extended or adjusted under 35 U.S.C. 154(b) by 961 days.

(21) Appl. No.: 11/939,564

(22) Filed: Nov. 14, 2007

(65) Prior Publication Data
US 2008/0146547 A1    Jun. 19, 2008

Related U.S. Application Data

(60) Provisional application No. 60/865,947, filed on Nov. 15, 2006, provisional application No. 60/913,593, filed on Apr. 24, 2007.

(51) Int. Cl.
| | |
|---|---|
| C07D 237/30 | (2006.01) |
| C07D 237/32 | (2006.01) |
| C07D 237/34 | (2006.01) |
| C07D 413/12 | (2006.01) |
| C07D 243/08 | (2006.01) |
| C07D 498/04 | (2006.01) |
| A61K 31/502 | (2006.01) |
| A61K 31/5355 | (2006.01) |
| A61K 31/551 | (2006.01) |
| A61K 31/5365 | (2006.01) |

(52) U.S. Cl. ............ 514/218; 514/248; 514/234.5; 514/230.5; 540/492; 544/237; 544/116; 544/105

(58) Field of Classification Search ........... 544/237, 544/116, 105; 514/248, 234.5, 230.5, 218; 540/492
See application file for complete search history.

(56) References Cited

U.S. PATENT DOCUMENTS

| | | |
|---|---|---|
| 6,589,951 B1 | 7/2003 | Napoletano et al. |
| 6,686,347 B2 | 2/2004 | Bold et al. |
| 2006/0205743 A1 | 9/2006 | Kataoku et al. |
| 2007/0053910 A1 | 3/2007 | Frigerio et al. |
| 2009/0221599 A1* | 9/2009 | Boyd et al. ......... 514/252.05 |
| 2010/0204240 A1* | 8/2010 | Aicher et al. ........ 514/252.03 |

FOREIGN PATENT DOCUMENTS

| | | |
|---|---|---|
| WO | WO 00/05218 | 2/2000 |
| WO | WO 2004/099177 | 11/2004 |
| WO | WO 2005/039506 | 5/2005 |
| WO | WO 2005/117909 | 12/2005 |
| WO | WO 2006/071819 | 7/2006 |
| WO | WO 2006/094187 | 9/2006 |

OTHER PUBLICATIONS

Griesser, Chapter 8, The Importance of Solvates (pp. 211-230), Polymorphism: In the Pharmaceutical Industry, Hilfiker, 2006.*
Britain, <http://www.netlibrary.com/nlreader.dll?bookid=12783&filename=Page_126.html>, pp. 126-127, 2008.*
Hackh's Chemical Dictionary, 3$^{rd}$ Ed., 1944, p. 18, "acyl."*
Wikipedia, Acyl, last modified Mar. 11, 2010.*
IUPAC http://www.iupac.org/goldbook/A00123.pdf, downloaded Oct. 29, 2010.*
Hawley's Condensed Chem. Dict., 14th Ed., 2002.*
International Search Report for PCT/US2007/084602, mailed Apr. 3, 2008.
Written Opinion of the International Searching Authority for PCT/US2007/084602, mailed Apr. 3, 2008.
Choi et al., Protein Kinsase Cδ-mediated Proteasonal Degradation of MAP Kinase Phosphatase-1 Contributes to Glutamate-induced Neuronal Cell Death, Journal of Cell Science 199, 1329-1340, 2006.
Inagaki et al., Cardioprotection by ε-Protein Kinase C Activation From Ischemia, Continous Delivery and Antiarrythmic Effect of an ε-Protein Kinase C-Activating Peptide, Circulation, 2005; 111:44-50.
Koya et al., Protein Kinase C Activation and the Development of Diabetic Complications, Diabetes, vol. 47, 859-866, Jun. 1998.
Piatnitski et al., Arylphthalazines: Identification of a New Phthalazine Chemotype as Inhibitors of VEGFR Kinase, Bioorganice & Medicinal Chemistry Letters 15 (2005) 4696-4698.
Street et al., Synthesis and Biological Evaluation of 3-Heterocyclyl-7,8,9,10-tetrahydro-(7,10-ethano)-1,2,4-triazolo[3,4-a]phthalazines and Analogues as Subtype-Selective Inverse Agonists for the GABA$_A$α5 Benzodiazepine Binding Site, J. Med. Chem 2004, 47, 3642-2657.
Tortora et al., Protein Kinase A Type I: A Target for Cancer Therapy, Clinical Cancer Research, vol. 8, 303-304, Feb. 2002.
Watanabe et al., 4-(3-Chloro-4-methoxybenzyl)aminophthalazines: Synthesis and Inhibitory Activity Toward Phosphodiesterase 5, J. Med. Chem. 2000, 43, 2523-2529.

* cited by examiner

Primary Examiner — James O Wilson
Assistant Examiner — Cecilia M Jaisle
(74) Attorney, Agent, or Firm — Charles Ryan; Michael Ciradlo; Hemant Khama

(57) ABSTRACT

The present invention relates to novel phthalazine derivatives and, more particularly, to phthalazine derivatives of formula (III) that are useful as protein kinase inhibitors. The invention also relates to methods of preparing the compounds, compositions containing the compounds, and methods of treatment using the compounds.

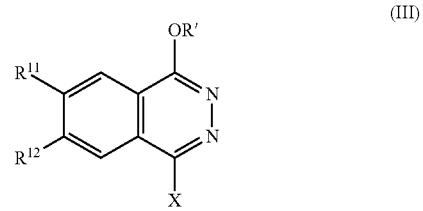

32 Claims, No Drawings

PHTHALAZINE DERIVATIVES AS INHIBITORS OF PROTEIN KINASE

This application claims the benefit of U.S. Provisional Application Ser. No. 60/865,947, filed Nov. 15, 2006 and U.S. Provisional Application Ser. No. 60/913,593, filed Apr. 24, 2007, the entire disclosures of each of which are hereby incorporated by reference.

FIELD OF THE INVENTION

The present invention relates to novel phthalazine derivatives and, more particularly, to phthalazine derivatives that are useful as protein kinase inhibitors. The invention also relates to methods of preparing the compounds, compositions containing the compounds, and methods of treatment using the compounds.

BACKGROUND OF THE INVENTION

Protein kinase is an enzyme that can modify the functioning of other proteins by changing enzyme activity, cellular location or protein association. Kinases are known to regulate cellular pathways, especially those involved in signal transduction (i.e., the transmission of signals within the cell).

Hundreds of protein kinases have been identified in the human genome. Protein kinase cell signalling has been implicated in numerous human diseases, including cancer, cardiovascular disease, diabetes, inflammation, arthritis, and Alzheimer's disease. See e.g., Tortora et al., *Clin. Cancer Research*, Vol. 8, 303-304, 2002; Inagaki et al., Circulation, 111: 44-50, 2005; Koya et al., *Diabetes*, Vol. 47, 1998; Choi et al., *J Cell Science,* 119 (7), 1329-1340. 2006.

Compounds that inhibit one or more protein kinases have been investigated for the treatment of various disorders. For example, the inhibition of protein kinase S6K1 has been implicated in diabetes, insulin sensitivity, insulin resistance, obesity, angiogenesis and cancer. See, e.g., Um, et al., *Nature,* 431, 485, 2004; International Publication No. WO 2005/019829. Consequently, there is continued interest in the development of compounds that act as protein kinase inhibitors.

SUMMARY OF THE INVENTION

The present invention relates to novel phthalazine derivatives and, more particularly, to phthalazine derivatives that are useful as protein kinase inhibitors. The invention also relates to methods of preparing the compounds, compositions containing the compounds, and methods of treatment using the compounds.

DETAILED DESCRIPTION OF THE INVENTION

In one aspect, the present invention relates to compounds of formula I:

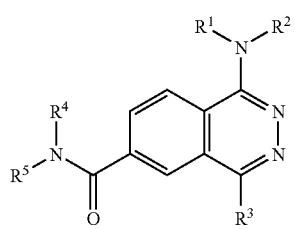

(I)

wherein $R^1$ and $R^2$ are each independently hydrogen, carboxyl, alkyl, alkenyl, alkynyl, aryl, alkylaryl, haloaryl, heteroaryl, alkylheteroaryl, heterocycle, alkylheterocycle, acyl, alkoxy, alkythio, arylthio, or alkoxycarbonyl, wherein, if present, the aryl, alkylaryl, haloaryl, heteroaryl, alkylheteroaryl, heterocycle, or alkylheterocycle may be substituted by one or more halogen, hydroxy, cyano, nitro, amino, carboxyl, alkyl, alkenyl, alkynyl, alkoxy, alkylamine or alkylthio and combinations thereof;

$R^3$ is hydrogen, halogen, hydroxy, cyano, amino, carboxyl, alkyl, alkenyl, alkynyl, aryl, alkylaryl, haloaryl, heteroaryl, alkylheteroaryl, heterocycle, alkylheterocycle, acyl, alkoxy, alkythio, arylthio, -alkylene-$NR^aR^b$, —$C(O)R^a$, —$C(O)NR^aR^b$, $C(O)OR^a$, —$C(S)NR^aR^b$, —$C(S)R^a$, —$C(O)SR^a$, $NO_2$, $NH_2$, —$NR^aC(O)R^b$, —$NR^aR^b$, —$NR^aOR^b$, —$NR^aC(S)R^b$, —$NR^aC(O)NR^bR^c$, —$NR^aC(S)NR^bR^c$, —$NR^a(CO-OR^b)$, —$NR^aS(O)_2NR^bR^c$, —$NR^aS(O)R^b$, —$NR^aS(O)_2R^b$, —$OR^a$, —$OC(O)R^a$, —$ONR^aR^b$, —$OC(O)NR^aR^b$, —$SR^a$, —$S(O)_2R^a$, or —$S(O)_2 NR^aR^b$, wherein $R^a$, $R^b$ and $R^c$ are each independently hydrogen, halogen, hydroxy, cyano, nitro, amino, carboxyl, alkyl, alkenyl, alkynyl, aryl, alkylaryl, haloaryl, heteroaryl, alkylheteroaryl, heterocycle, alkylheterocycle, acyl, alkoxy, alkythio, arylthio, or alkoxycarbonyl, wherein, if present, the aryl, alkylaryl, haloaryl, heteroaryl, alkylheteroaryl, heterocycle, or alkylheterocycle may be substituted by one or more halogen, hydroxy, cyano, nitro, amino, carboxyl, alkyl, alkenyl, alkynyl, alkoxy, alkylamine or alkylthio and combinations thereof; and $R^4$ and $R^5$ are each independently hydrogen, carboxyl, alkyl, alkenyl, alkynyl, aryl, alkylaryl, haloaryl, heteroaryl, alkylheteroaryl, heterocycle, alkylheterocycle, acyl, alkoxy, alkythio, arylthio, or alkoxycarbonyl, wherein, if present, the aryl, alkylaryl, haloaryl, heteroaryl, alkylheteroaryl, heterocycle, or alkylheterocycle may be substituted by one or more halogen, hydroxy, cyano, nitro, amino, carboxyl, alkyl, alkenyl, alkynyl, alkoxy, alkylamine, alkylthio, —$C(O)NR^d$-alkylheterocycle (in which $R^d$ is H or alkyl), O-alkylheterocycle, or combinations thereof, and pharmaceutically acceptable salts or solvates (e.g., hydrates) thereof, or solvates of pharmaceutically acceptable salts thereof, provided that when $R^3$ is heterocycle, said heterocycle is other than 4-hydroxy-1-piperidinyl.

In one embodiment, $R^3$ is other than piperidinyl.

In a further embodiment, the present invention relates to compounds of formula I wherein:

$R^1$ and $R^2$ are each independently hydrogen, alkyl, alkenyl or alkylaryl, wherein, if present, the alkylaryl may be substituted by one or more halogen, hydroxy, cyano, nitro, amino, carboxyl, alkyl, alkenyl, alkynyl, alkoxy, alkylamine or alkylthio and combinations thereof;

$R^3$ is hydrogen, halogen or cyano;

$R^4$ and $R^5$ are each independently hydrogen or aryl, wherein, if present, the aryl may be substituted by one or more halogen, hydroxy, cyano, nitro, amino, carboxyl, alkyl, alkenyl, alkynyl, alkoxy, alkylamine, alkylthio, —$C(O)NR^d$-alkylheterocycle (in which $R^d$ is H or alkyl), O-alkylheterocycle, or combinations thereof, In certain embodiments, the present invention provides compounds of formula I wherein:

$R^1$ and $R^2$ are each independently hydrogen, alkyl (e.g., methyl), alkenyl (e.g., —$CH_2$—CH═$CH_2$) or alkylaryl (e.g., benzyl);

$R^3$ is hydrogen, halogen (e.g., Cl, I) or cyano; and $R^4$ and $R^5$ are each independently hydrogen or aryl (e.g., phenyl), wherein, if present, the aryl may be substituted by one or more halogen, hydroxy, cyano, nitro, amino, carboxyl, alkyl, alkenyl, alkynyl, alkoxy, alkylamine or alkylthio and combinations thereof.

In certain embodiments, when $R^4$ and/or $R^5$ are aryl, the aryl (e.g., phenyl) may be substituted by one or more alkyl, alkoxy, and combinations thereof (e.g., trifluoromethylphenyl, methoxyphenyl, such as 3-trifluoromethylphenyl, 3-methoxyphenyl).

In additional embodiments, one of $R^4$ and $R^5$ is H and the other is phenyl, trifluoromethylphenyl or methoxyphenyl.

In one embodiment, the compounds of formula I do not include 4-(3-Chloro-4-methoxybenzyl)aminophthalazines.

In another embodiment, $R^1$ and $R^2$ are not both hydrogen.

According to another embodiment, the compound of formula I is not 4-[[(3-chloro-4-methoxyphenyl)methyl]amino]-1-(4-hydroxy-1-piperidinyl)-6-phthalazinecarboxamide or 4-[[(3-chloro-4-methoxyphenyl)methyl]amino]-1-(4-hydroxy-1-piperidinyl)-N,N-dimethyl-6-phthalazinecarboxamide, or a pharmaceutically acceptable salt thereof.

In a compound and/or method aspect, the present invention includes compounds of formula I chosen from:
1) 1-Allylamino-4-chloro-phthalazine-6-carboxylic acid (3-trifluoromethyl-phenyl)-amide,
3) 1-Methylamino-4-chloro-phthalazine-6-carboxylic acid (3-trifluoromethyl-phenyl)-amide,
5) 1-benzylamino-4-chloro-phthalazine-6-carboxylic acid (3-trifluoromethyl-phenyl)-amide,
7) 4-Cyano-1-methylamino-phthalazine-6-carboxylic acid (3-trifluoromethyl-phenyl)-amide,
9) 1-Benzylamino-4-iodo-phthalazine-6-carboxylic acid (3-trifluoromethyl-phenyl)-amide,
11) 1-Benzylamino-phthalazine-6-carboxylic acid (3-trifluoromethyl-phenyl)-amide,
12) 4-Cyano-1-benzylamino-phthalazine-6-carboxylic acid (3-trifluoromethyl-phenyl)-amide,
13) 1-Benzylamino-4-chloro-phthalazine-6-carboxylic acid phenylamide,
15) 1-Benzylamino-4-chloro-phthalazine-6-carboxylic acid (3-methoxy-phenyl)-amide, and 17) 1-Dimethylamino-4-chloro-phthalazine-6-carboxylic acid (3-trifluoromethyl-phenyl)-amide, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof,) can also be in the form of a polymorph, and wherein if the compound exhibits chirality it can be in the form of a mixture of enantiomers such as a racemate, or a mixture of diastereomers, or can be in the form of a single enantiomer or a single diastereomer.

In another aspect, the present invention relates to compounds of formula II:

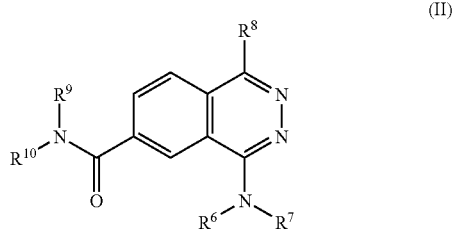

(II)

wherein $R^6$ and $R^7$ are each independently hydrogen, carboxyl, alkyl, alkenyl, alkynyl, aryl, alkylaryl, haloaryl, heteroaryl, alkylheteroaryl, heterocycle, alkylheterocycle, acyl, alkoxy, alkythio, arylthio, or alkoxycarbonyl, wherein, if present, the aryl, alkylaryl, haloaryl, heteroaryl, alkylheteroaryl, heterocycle, or alkylheterocycle may be substituted by one or more halogen, hydroxy, cyano, nitro, amino, carboxyl, alkyl, alkenyl, alkynyl, alkoxy, alkylamine or alkylthio and combinations thereof;

$R^8$ is hydrogen, halogen, hydroxy, cyano, amino, carboxyl, alkyl, alkenyl, alkynyl, aryl, alkylaryl, haloaryl, heteroaryl, alkylheteroaryl, heterocycle, alkylheterocycle, acyl, alkoxy, alkythio, arylthio, $-NR^aR^b$, $-C(O)R^a$, $-C(O)NR^aR^b$, $-C(O)OR^a$, $-C(S)NR^aR^b$, $-C(S)R^a$, $-C(O)SR^a$, $NO_2$, $NH_2$, $-NR^aC(O)R^b$, $-NR^aR^b$, $R^aOR^b$, $-NR^aC(S)R^b$, $-NR^aC(O)NR^bR^c$, $-NR^aC(S)NR^bR^c$, $-NR^a(COOR^b)$, $-NR^aS(O)_2NR^bR^c$, $-NR^aS(O)R^b$, $-NR^aS(O)_2R^b$, $-OR^a$, $OC(O)R^a$, $ONR^aR^b$, $-OC(O)NR^aR^b$, $-SR^a$, $-S(O)_2R^a$, or $-S(O)_2 NR^aR^b$, wherein $R^a$, $R^b$ and $R^c$ are each independently hydrogen, halogen, hydroxy, cyano, nitro, amino, carboxyl, alkyl, alkynyl, aryl, alkylaryl, haloaryl, heteroaryl, alkylheteroaryl, heterocycle, alkylheterocycle, acyl, alkoxy, alkythio, arylthio, or alkoxycarbonyl, wherein, if present, the aryl, alkylaryl, haloaryl, heteroaryl, alkylheteroaryl, heterocycle, or alkylheterocycle may be substituted by one or more halogen, hydroxy, cyano, nitro, amino, carboxyl, alkyl, alkenyl, alkynyl, alkoxy, alkylamine or alkylthio and combinations thereof; and $R^9$ and $R^{10}$ are each independently hydrogen, carboxyl, alkyl, alkenyl, alkynyl, aryl, alkylaryl, haloaryl, heteroaryl, alkylheteroaryl, heterocycle, alkylheterocycle, acyl, alkoxy, alkythio, arylthio, or alkoxycarbonyl, wherein, if present, the aryl, alkylaryl, haloaryl, heteroaryl, alkylheteroaryl, heterocycle, or alkylheterocycle may be substituted by one or more halogen, hydroxy, cyano, nitro, amino, carboxyl, alkyl, alkenyl, alkynyl, alkoxy, alkylamine, alkylthio, $-C(O)NR^d$-alkylheterocycle (in which $R^d$ is H or alkyl), O-alkylheterocycle, or combinations thereof, and pharmaceutically acceptable salts or solvates (e.g., hydrates) thereof, or solvates of pharmaceutically acceptable salts thereof, provided that when $R^8$ is heterocycle, said heterocycle is other than 4-hydroxy-1-piperidinyl.

In one embodiment, $R^8$ is other than piperidinyl.

In a further embodiment, the present invention relates to compounds of formula II wherein:

$R^6$ and $R^7$ are each independently hydrogen, alkyl, alkenyl or alkylaryl, wherein, if present, the alkylaryl may be substituted by one or more halogen, hydroxy, cyano, nitro, amino, carboxyl, alkyl, alkenyl, alkynyl, alkoxy, alkylamine or alkylthio and combinations thereof;

$R^8$ is hydrogen, halogen or cyano; and $R^9$ and $R^{10}$ each independently represents hydrogen or aryl, wherein, if present, the aryl may be substituted by one or more halogen, hydroxy, cyano, nitro, amino, carboxyl, alkyl, alkenyl, alkynyl, alkoxy, alkylamine, alkylthio, $-C(O)NR^d$—alkylheterocycle (in which $R^d$ is H or alkyl), O-alkylheterocycle, or combinations thereof, In certain embodiments, the present invention provides compounds of formula II wherein:

$R^6$ and $R^7$ are each independently hydrogen, alkyl (e.g., methyl), alkenyl (e.g., $-CH_2-CH=CH_2$) or alkylaryl (e.g., benzyl);

$R^8$ is hydrogen, halogen (e.g., Cl, I) or cyano; and $R^9$ and $R^{10}$ each independently represent hydrogen or aryl (e.g., phenyl), wherein, if present, the aryl may be substituted by a halogen, hydroxy, cyano, nitro, amino, carboxyl, alkyl, alkenyl, alkynyl, alkoxy, alkylamine or alkylthio.

In certain embodiments, when $R^9$ and/or $R^{10}$ are aryl, the aryl (e.g., phenyl) may be substituted by alkyl or alkoxy (e.g., trifluoromethylphenyl, methoxyphenyl, such as 3-trifluoromethylphenyl, 3-methoxyphenyl).

In additional embodiments, one of $R^9$ and $R^{10}$ is H and the other is phenyl, trifluoromethylphenyl or methoxyphenyl.

In one embodiment, the compounds of formula II do not include 4-(3-Chloro-4-methoxybenzyl)aminophthalazines.

In another embodiment, $R^6$ and $R^7$ are not both hydrogen. According to another embodiment, the compound of formula II is not 4-[[(3-chloro-4-methoxyphenyl)methyl]amino]-1-(4-hydroxy-1-piperidinyl)-6-phthalazinecarboxamide or 4-[[(3-chloro-4-methoxyphenyl)methyl]amino]-1-(4-hydroxy-1-piperidinyl)-N,N-dimethyl-6-phthalazinecarboxamide, or a pharmaceutically acceptable salt thereof.

In a compound and/or method aspect, the present invention includes compounds of formula II chosen from:
2) 4-Allylamino-1-chloro-phthalazine-6-carboxylic acid (3-trifluoromethyl-phenyl)-amide,
4) 4-Methylamino-1-chloro-phthalazine-6-carboxylic acid (3-trifluoromethyl-phenyl)-amide,
6) 4-benzylamino-1-chloro-phthalazine-6-carboxylic acid (3-trifluoromethyl-phenyl)-amide,
8) 1-Cyano-4-methylamino-phthalazine-6-carboxylic acid (3-trifluoromethyl-phenyl)-amide,
10) 4-Benzylamino-1-iodo-phthalazine-6-carboxylic acid (3-trifluoromethyl-phenyl)-amide,
14) 4-Benzylamino-1-chloro-phthalazine-6-carboxylic acid phenylamide,
16) 4-Benzylamino-1-chloro-phthalazine-6-carboxylic acid (3-methoxy-phenyl)-amide,
18) 4-Dimethylamino-1-chloro-phthalazine-6-carboxylic acid (3-trifluoromethyl-phenyl)-amide,
21) 1-Cyano-4-dimethylamino-phthalazine-6-carboxylic acid (3-trifluoromethyl-phenyl)-amide, and
22) 4-Cyano-1-dimethylamino-phthalazine-6-carboxylic acid (3-trifluoromethyl-phenyl)-amide,
wherein free base forms listed above can also be in the form of a pharmaceutically acceptable salt,
wherein a compound listed above (in either a free base form or in the form of a pharmaceutically acceptable salt) can also be in the form of a solvate (such as a hydrate),
wherein a compound listed above (in a free base form or solvate thereof, or in the form of a pharmaceutically acceptable salt or solvate thereof,) can also be in the form of a polymorph, and
wherein if the compound exhibits chirality it can be in the form of a mixture of enantiomers such as a racemate, or a mixture of diastereomers, or can be in the form of a single enantiomer or a single diastereomer.

According to a further aspect, the present invention relates to compounds of formula III:

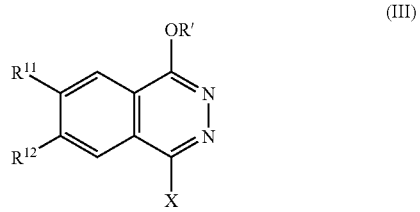

(III)

wherein
X is hydrogen, halogen, alkyl, aryl, heteroaryl, cyano or alkoxy;
R' is hydrogen, alkyl (e.g., methyl), —C(O)$R_x$, —SO$_2R_x$ or —P(O)(O$R_x$)$_2$, where $R_x$ is hydrogen or alkyl;
$R^{11}$ and $R^{12}$ are each independently hydrogen, halogen, hydroxy, cyano, amino, alkyl, alkenyl, alkynyl, aryl, alkylaryl, heteroaryl, alkylheteroaryl, heterocycle, alkylheterocycle, acyl, alkoxy, alkythio, arylthio, -alkylene-NR$^a$R$^b$, C(O)R$^a$, —C(O)NR$^a$R$^b$, -alkylene-C(O)NR$^a$R$^b$, —C(O)OR$^a$, —C(S)NR$^a$R$^b$, —C(S)R$^a$, C(O)SR$^a$, NO$_2$, NH$_2$, —NR$^a$C(O)R$^b$, —NR$^a$R$^b$, —NR$^a$OR$^b$, —NR$^a$C(S)R$^b$, —NR$^a$C(O)NR$^b$R$^c$, —NR$^a$C(S)NR$^b$R$^c$, —NR$^a$(COOR$^b$), —NR$^a$S(O)$_2$NR$^b$R$^c$, —NR$^a$S(O)R$^b$, —NR$^a$S(O)$_2$R$^b$, —OR$^a$, —OC(O)R$^a$, —ONR$^a$R$^b$, —OC(O)NR$^a$R$^b$, —SR$^a$, —S(O)$_2$R$^a$, or —S(O)$_2$ NR$^a$R$^b$, wherein R$^a$, R$^b$ and R$^c$ are each independently hydrogen, hydroxy, cyano, nitro, alkyl, alkenyl, alkynyl, cycloalkyl, aryl, alkylaryl, haloaryl, heteroaryl, alkylheteroaryl, heterocycle, alkylheterocycle, acyl, alkoxy, alkythio, arylthio, or alkoxycarbonyl, wherein, if present, an aryl, alkylaryl, heteroaryl, alkylheteroaryl, heterocycle, or alkylheterocycle may be substituted by one or more halogen, hydroxy, cyano, nitro, amino, carboxyl, alkyl, alkenyl, alkynyl, alkoxy, alkylamine, alkylthio, —C(O)NR$^d$-alkylheterocycle (in which R$^d$ is H or alkyl), O-alkylheterocycle, alkylheterocycle, aryl, heteroaryl, heterocycle, aryloxy, alkylamino, dialkylamino, aminoalkyl, —O-alkylene-O—, -alkylene-O—, —O-alkylene-O-alkylene-, -alkylene-O-alkyl, —NR$^e$C(O)R$^f$, —NR$^e$(alkylene-NR$^e$R$^f$), —NR$^e$(alkylheterocycle), —O-alkylene-NR$^e$R$^f$ (in which R$^e$ and R$^f$ are independently hydrogen or alkyl, e.g., methyl), or combinations thereof;
wherein at least one of $R^{11}$ or $R^{12}$ is -alkylene-C(O)NR$^a$R$^b$, -alkylene-NR$^a$R$^b$, —C(O)NR$^a$R$^b$, —NR$^a$C(O)R$^b$ or —NR$^a$R$^b$;
and pharmaceutically acceptable salts or solvates (e.g., hydrates) thereof, or solvates of pharmaceutically acceptable salts thereof.

provided that said compound is not:
N-(3,4-dihydro-4-oxo-6-phthalazinyl)-2-methyl-2-propenamide,
N-(1,2-dihydro-1-oxo-6-phthalazinyl)-2-methyl-2-propenamide, 7-(cyclohexylamino)-6-(phenylamino)-1(2H)-phthalazinone,
6,7-bis(phenylamino)-1(2H)-phthalazinone,
6-amino-7-chloro-1(2H)-phthalazinone,
or a pharmaceutically acceptable salt thereof.

In one embodiment, R' is hydrogen or alkyl (e.g., methyl).
In additional embodiments $R^{11}$ and/or $R^{12}$ are other than OR$^a$ where R$^a$ is alkyl (e.g., methyl). In additional embodiments, (i) when R' and X are hydrogen and one of $R^{11}$ and $R^{12}$ is NR$^a$C(O)R$^b$, then R$^b$ is not —C(=CH2)CH3, (ii) when R' and X are hydrogen and one of $R^{11}$ and $R^{12}$ is —NHC$_6$H$_5$, then the other of $R^{11}$ and $R^{12}$ is not —NHC$_6$H$_5$ or —NH(cyclohexyl), (iii) when R' and X are hydrogen and one of $R^{11}$ and $R^{12}$ is —NH$_2$, then the other of $R^{11}$ and $R^{12}$ is not halogen.

According to another embodiment, the present invention relates to compounds of formula III wherein:
X is hydrogen, halogen, alkyl (e.g., methyl), aryl, heteroaryl, cyano or alkoxy;
R' is hydrogen or alkyl (e.g., methyl);
$R^{11}$ and $R^{12}$ are each independently hydrogen, -alkylene-NR$^a$R$^b$, —C(O)NR$^a$R$^b$, -alkylene-C(O)NR$^a$R$^b$, —NR$^a$C(O)R$^b$ or —NR$^a$R$^b$;

wherein $R^a$, $R^b$ and $R^c$ are each independently hydrogen, alkyl, aryl, alkylaryl, alkylheteroaryl or alkylheterocycle, wherein, if present, an aryl, alkylaryl, alkylheteroaryl or alkylheterocycle may be substituted by one or more halogen, hydroxy, cyano, nitro, amino, carboxyl, alkyl, alkenyl, alkynyl, alkoxy, alkylamine, alkylthio, —C(O)NR$^d$-alkylheterocycle (in which R$^d$ is H or alkyl), O-alkylheterocycle, alkylheterocycle, aryl, heteroaryl, heterocycle, aryloxy, alkylamino, dialkylamino, aminoalkyl, —O-alkylene-O—, -alkylene-O—, —O-alkylene-O-alkylene-, -alkylene-O-alkyl, —NR$^e$C(O)R$^f$, —NR$^e$(alkylene-NR$^e$R$^f$), —NR$^e$(alkylheterocycle), —O-alkylene-NR$^e$R$^f$, (in which R$^e$ and R$^f$ are independently hydrogen or alkyl, e.g., methyl), or combinations thereof.

In one embodiment, one of $R^{11}$ and $R^{12}$ is hydrogen and the other of $R^{11}$ and $R^{12}$ is -alkylene-NR$^a$R$^b$, —C(O)NR$^a$R$^b$, -alkylene-C(O)NR$^a$R$^b$, —NR$^a$C(O)R$^b$ or —NR$^a$R$^b$.

One of ordinary skill in the art will readily appreciate that some compounds of formula III may exist in different tautomeric forms, e.g., as shown below:

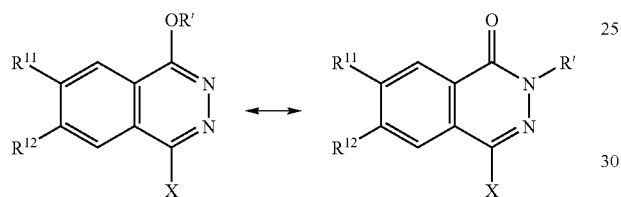

These two forms of formula III are used interchangeably herein, and both are encompassed within the present invention.

In certain embodiments, the present invention provides compounds of III wherein:

X represents hydrogen, halogen (e.g., Cl), alkyl (e.g., methyl), aryl (e.g., phenyl) or heteroaryl (e.g., pyridyl);

$R^{11}$ and $R^{12}$ each independently represent hydrogen, —C(O)NR$^a$R$^b$, —NR$^a$C(O)R$^b$, or —NR$^a$R$^b$, wherein each $R^a$ and $R^b$ independently represents hydrogen, aryl, heteroaryl or alkylaryl, wherein, if present, the aryl, heteroaryl or alkylaryl may be substituted by a halogen, hydroxy, cyano, nitro, amino, carboxyl, alkyl, alkenyl, alkynyl, alkoxy, alkylamine, alkylthio, —C(O)NR-alkylheterocycle (in which R$^d$ is H or alkyl), or O-alkylheterocycle. For example, the aryl or alkylaryl may be substituted by a halogen, alkoxy, —C(O)NR$^d$-alkylheterocycle (in which R$^d$ is H or alkyl), or O-alkylheterocycle.

In additional embodiments, the compounds of formula III are represented by subformulas IIIa-IIIj, in which R is -alkylene- (e.g., —CH$_2$—, —CH$_2$CH$_2$—):

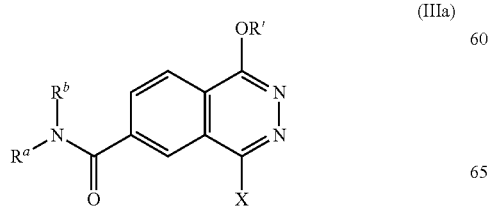
(IIIa)

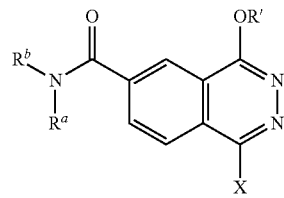
(IIIb)

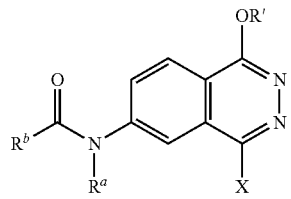
(IIIc)

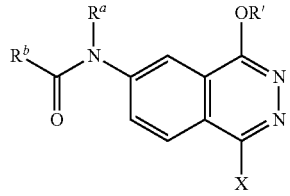
(IIId)

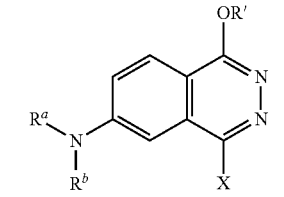
(IIIe)

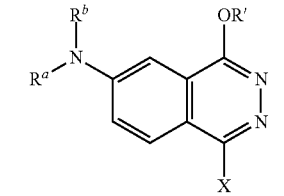
(IIIf)

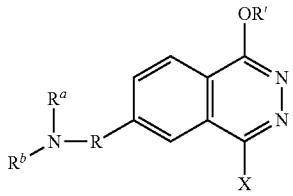
(IIIg)

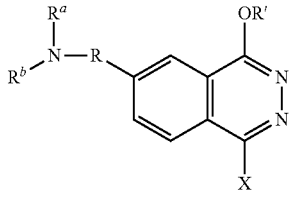
(IIIh)

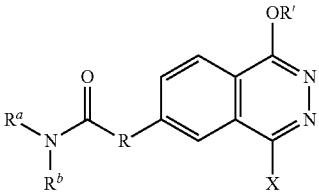
(IIIi)

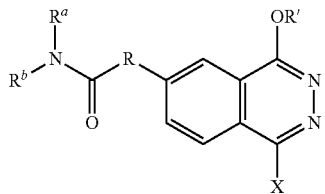

(IIIj)

In one embodiment, the compound of formula III is represented by formulas IIIa and IIIb. In another embodiment, the compound of formula III is represented by formulas IIIc and IIId. In another embodiment, the compound of formula III is represented by formulas IIIe and IIIf. In another embodiment, the compound of formula III is represented by formulas IIIg and IIIh. In another embodiment, the compound of formula III is represented by formulas IIIi and IIIj. In further embodiments, the compound of formula III is represented by formulas IIIa-IIIf. In other embodiments, the compound of formula III is represented by formulas IIIa, IIIb and IIIe.

In certain embodiments, the compound is represented by formula IIIa-IIIj in which X is hydrogen, halogen (e.g., Cl), alkyl (e.g., methyl), aryl (e.g., phenyl), alkoxy (e.g., methoxy), cyano or heteroaryl (e.g., pyridyl); R' is hydrogen or alkyl (e.g., methyl), R is alkylene (e.g., —CH$_2$— or —CH$_2$CH$_2$—) and R$^a$ and R$^b$ are each independently hydrogen, alkyl (e.g., methyl), aryl (e.g., phenyl), heteroaryl (e.g., pyridinyl), alkylaryl (e.g., benzyl, phenethyl), alkylheterocycle (e.g., morpholinylethyl, piperidinylethyl) or alkylheteroaryl (e.g., furanylmethyl). Where present, any aryl, heteroaryl or heterocycle group may be optionally substituted.

In certain embodiments, the compound is represented by formula IIIa or IIIb in which X is halogen (e.g., Cl), alkyl (e.g., methyl), aryl (e.g., phenyl) or heteroaryl (e.g., pyridyl) and R$^a$ and R$^b$ each independently represent hydrogen, aryl (e.g., phenyl), heteroaryl (e.g., pyridinyl) or alkylaryl (e.g., benzyl). Where present, any aryl, arylalkyl or heteroaryl group may be optionally substituted.

In additional embodiments, the compound is represented by formula IIIa or IIIb in which one of R$^a$ and R$^b$ is hydrogen or alkyl (e.g. methyl) and the other is phenyl, hydroxybiphenyl, trifluoromethylphenyl, bis(trifluoromethyl)phenyl, difluorophenyl, fluoro(trifluoromethyl)phenyl, fluoro(methyl)phenyl, trifluoromethylpyridyl, methyl(trifluoromethyl)phenyl, methoxybenzyl, trifluoromethylbenzyl, (trifluoromethyl)(morpholinyl)phenyl, (piperidinylmethyl)phenyl, furanylphenyl, methylphenyl, difluoromethoxyphenyl, trifluoromethoxyphenyl, chloro(dimethylaminoethoxyphenyl)phenyl (e.g., 4-chloro-3'-(2-dimethylaminoethoxy)biphenyl-3-yl), or (ethoxymethyl)(methyl)-(pyrrolidinylethylamino)phenyl (e.g., 5-ethoxymethyl-2-methyl-3-(2-pyrrolidin-1-yl)ethylamino)phenyl).

In certain embodiments, the compound is represented by formula IIIc or IIId in which X is halogen (e.g., Cl) and R$^a$ and R$^b$ are each independently hydrogen or aryl. Where present, any aryl group may be optionally substituted. For example, the aryl may be substituted by alkyl or alkoxy (e.g., trifluoromethylphenyl, methoxyphenyl).

In certain embodiments, the compound is represented by formula IIIe or IIIf in which X is halogen (e.g., Cl) or alkyl (e.g., methyl) and R$^a$ and R$^b$ are each independently hydrogen, alkyl (e.g., methyl), aryl (e.g., phenyl), alkylheteroaryl (e.g., pyridinylmethyl), heteroaryl (e.g., furanyl) or alkylaryl (e.g., benzyl, phenethyl). Where present, any aryl, alkylheteroaryl, alkylaryl or heteroaryl group may be optionally substituted.

For example, any aryl, alkylheteroaryl, alkylaryl or heteroaryl group present may be optionally substituted by alkyl (e.g., methyl, trifluoromethyl), halogen (e.g., F, Cl), alkoxy (e.g., methoxy, isopropoxy, difluoromethoxy, trifluoromethoxy), hydroxyl, amino, alkylamino, dialkylamino (e.g., —N(CH$_3$)$_2$), aminoalkyl (e.g., CH$_2$N(CH$_3$)$_2$), aryloxy (e.g., OC$_6$H$_5$), heteroaryloxy (e.g., pyrazinyloxy, methylpyrazinyloxy), —O-alkylheterocycle (e.g., O-morpholinylethyl), —O-aminoalkyl (e.g., —OCH$_2$CH$_2$N(CH$_3$)$_2$), NH-aminoalkyl (e.g., NHCH$_2$CH$_2$CH$_2$N(CH$_3$)$_2$, NHCH$_2$CH$_2$N(CH$_3$)$_2$), NHalkylheterocycle (e.g., NH-morpholinylethyl), —C(O)NH-alkylheterocycle (e.g., —C(O)NHpyrrolidinylethyl), —OCH$_2$CH$_2$O—, —OCH$_2$CH$_2$—, —OCH$_2$CH$_2$CH$_2$O—, —OCH$_2$OCH$_2$—, NHC(O)alkyl (e.g., —NHC(O)CH$_3$), optionally substituted aryl (e.g., phenyl), heteroaryl (e.g., pyrazolyl, pyridinyl, thiophenyl, pyrrolyl, imidazolyl, triazolyl), heterocycle (e.g., piperidinyl, methylpiperidinyl, aminopiperidinyl, morpholinyl, piperazinyl, methylpiperazinyl, diazepanyl, methyldiazepanyl, pyrrolidinyl, hexahydropyrrol[3,4-c]pyrrolyl, perhydrodiazepanyl), alkylheterocycle (e.g., piperidinylmethyl, morpholinylmethyl, morpholinylethyl, pyrrolidinylmethyl) and combinations thereof.

In additional embodiments, the compound is represented by formula IIIe or IIIf in which one of R$^a$ and R$^b$ is hydrogen or alkyl (e.g., methyl) and the other is benzyl, trifluoromethylbenzyl (e.g., 2-trifluoromethylbenzyl, 3-trifluoromethylbenzyl), dichlorobenzyl (e.g., 2,4-dichlorophenyl, 2,5-dichlorobenzyl, 3,5-dichlorobenzyl), chlorobenzyl (e.g., 2-chlorobenzyl, 3-chlorobenzyl, 4-chlorobenzyl), methoxybenzyl (e.g., 2-methoxybenzyl, 3-methoxybenzyl, 4-methoxybenzyl), fluorobenzyl (e.g., 3-fluorobenzyl), difluorobenzyl (e.g., 2,3-difluorobenzyl, 2,5-difluorobenzyl, 3,4-difluorophenyl, 3,5-difluorobenzyl), methylbenzyl (e.g., 3-methylbenzyl), trifluoromethylphenyl (e.g., 3-trifluoromethylphenyl), phenethyl, (morpholinylethoxy)benzyl (e.g., 3-(2-morpholin-4-yl-ethoxy)benzyl, 2-(2-morpholin-4-yl-ethoxy)benzyl), (pyrrolidinylethylamido)benzyl (e.g., —CH$_2$—C$_6$H$_4$—C(O)NH—CH$_2$CH$_2$-pyrrolidinyl), (piperidinylmethyl)benzyl (e.g., 2-piperidin-1-ylmethyl-benzyl, 3-piperidin-1-ylmethylbenzyl), piperidinylbenzyl, chlorofluorobenzyl (e.g., 2-chloro-6-fluorobenzyl), (pyrazolyl)benzyl (e.g., 2-pyrazol-1-ylbenzyl, 3-pyrazol-1-ylbenzyl), (pyridinyl)benzyl (e.g., 2-pyridin-3-ylbenzyl, (thiophenyl)benzyl (e.g., 2-thiophen-2-ylbenzyl, 3-thiophen-2-ylbenzyl, 3-thiophen-3-ylbenzyl), (furanyl)benzyl (e.g., 2-furan-2-ylbenzyl, 3-furan-2-ylbenzyl), (piperazinyl)benzyl (e.g., 2-piperazinylbenzyl), (methylpiperazinyl)benzyl (e.g., 2-(4-methylpiperazin-1-yl)benzyl, 3-(4-methylpiperazin-1-yl)benzyl, 2-(3-methylpiperazin-1-yl)benzyl), (morpholinylmethyl)benzyl (e.g., 2-morpholin-4-ylmethyl-benzyl, 3-morpholin-4-ylmethylbenzyl), (phenoxy)benzyl (e.g., 2-phenoxybenzyl), dihydrobenzodioxinylmethyl (e.g., 2,3-dihydro-benzo[1,4]dioxin-5-ylmethyl), dihydrobenzofuranylmethyl (e.g., 2,3-dihydro-benzofuran-5-ylmethyl), (fluoro)(trifluoromethyl)benzyl (e.g., 2-fluoro-5-trifluoromethylbenzyl), (methyl)(chloro)benzyl (e.g., 5-chloro-2-methylbenzyl), (chloro)(trifluoromethyl)benzyl (e.g., 2-chloro-5-trifluoromethylbenzyl), (fluoro)(trifluoromethyl)benzyl (e.g., 2-fluoro-3-trifluoromethylbenzyl), (chloro)(phenoxy)benzyl (e.g., 2-chloro-6-phenoxybenzyl), dimethylbenzyl (e.g., 2,3-dimethylbenzyl, 3,4-dimethylbenzyl, 2,5-dimethylbenzyl), (morpholinyl)benzyl (e.g., 3-morpholin-4-ylbenzyl), dihydrobenzodioxepinylmethyl (e.g., 3,4-dihydro-2H- benzo[b][1,4]dioxepin-6-ylmethyl), fluoro(benzodioxinylmethyl (e.g., 6-fluoro-4H-benzo[1,3]dioxin-8-ylmethyl), (methyl)(phenyl)furanylmethyl (e.g., 5-methyl-2-phenyl-furan-3-ylmethyl), trifluoromethoxybenzyl (e.g., 2-trifluoromethoxybenzyl, 3-trifluoromethoxybenzyl, 4-trifluoromethoxybenzyl), difluoromethoxybenzyl (e.g., 2-difluoromethoxybenzyl, 3-difluoromethoxybenzyl), dimethoxybenzyl (e.g., 3,5-dimethoxybenzyl, 2,3-dimethoxybenzyl, 2,5-dimethoxybenzyl), hydroxybenzyl (e.g., 3-hydroxybenzyl), ($CH_3C(O)NH$)benzyl, biphenylmethyl (e.g., biphenyl-3-ylmethyl), dimethylminobenzyl (e.g., 3-dimethylaminobenzyl), isopropoxybenzyl (e.g., 3-isopropoxybenzyl), (pyrrolyl)benzyl (e.g., 2-pyrrol-1-yl-benzyl, 3-pyrrol-1-yl-benzyl), pyridinylmethyl (e.g., pyridin-3-ylmethyl, pyridin-2-ylmethyl), (imidazolyl)benzyl (e.g., 2-imidazol-1-yl-benzyl), (triazolyl)benzyl (e.g., 2-[1,2,4]triazol-1-yl-benzyl), (methylpiperidinylmethyl)benzyl (e.g., 3-(4-methyl-piperidin-1-ylmethyl)benzyl), (dimethylaminopropylamino)benzyl (e.g., 3-(3-dimethylamino-propylamino)benzyl), (morpholinylethylamino)benzyl (e.g., 3-(2-morpholin-4-yl-ethylamino)benzyl), (methyldiazepanyl)benzyl (e.g., (3-(4-methyl-[1,4]diazepam-1-yl)benzyl), (dimethylaminomethyl)benzyl (e.g., 3-dimethylaminomethyl-benzyl), (dimethylaminoethylamino)benzyl (e.g., 3-(2-dimethylamino-ethylamino)benzyl), (pyrrolidinylmethyl)benzyl (e.g., 3-pyrrolidin-1-ylmethylbenzyl), (pyrrolidinyl)benzyl (e.g., 2-pyrrolidin-1-ylbenzyl, 3-pyrrolidin-1-ylbenzyl), (pyrrolidinyl)pyridinylmethyl (e.g., 6-pyrrolidin-1-yl-pyridin-2-ylmethyl), (morpholinyl)benzyl (e.g., 2-morpholin-4-ylbenzyl), pyrazinyloxybenzyl (e.g., 3-(6-methyl-pyrazin-2-yloxy)benzyl), dihydropyridooxazinylmethyl (e.g., 3-methyl-3,4-dihydro-2H-pyrido[3,2-b][1,4]oxazin-7-ylmethyl), hexahydropyrrolo[3,4-c]pyrrolyl-benzyl (e.g., 2-(hexahydro-pyrrolo[3,4-c]pyrrol-2-ylbenzyl), (perhydrodiazepinyl)benzyl (e.g., 2-perhydro-1,4-diazepin-1-yl-benzyl), (piperazinyl)(trifluoromethyl)benzyl (e.g., 2-piperazin-1-yl-5-trifluoromethylbenzyl), (piperazinyl(methoxy)benzyl (e.g., 5-methoxy-2-piperazin-1-ylbenzyl), aminopiperidinylbenzyl (e.g., 4-amino-piperidin-1-ylbenzyl) or (fluoro)piperazinylbenzyl (e.g., 5-fluoro-2-piperazin-1-ylbenzyl).

In certain embodiments, the compound is represented by formula IIIg or IIIh in which X is halogen (e.g., Cl), R is alkylene (e.g., —$CH_2$—) and $R^a$ and $R^b$ are each independently hydrogen or aryl, wherein the aryl may be substituted. For example, one of $R^a$ and $R^b$ is hydrogen and the other is (dimethylaminoethyl)methylamino)phenyl (e.g., 2-dimethylaminoethyl)methylamino)phenyl.

In certain embodiments, the compound is represented by formula IIIi or IIIj in which X is halogen (e.g., Cl), R is alkylene (e.g., —$CH_2CH_2$—) and $R^a$ and $R^b$ are each independently hydrogen or aryl, wherein the aryl may be substituted. For example, one of $R^a$ and $R^b$ is hydrogen and the other is (dimethylaminoethyl)methylamino)phenyl (e.g., 2-dimethylaminoethyl)methylamino)phenyl.

In a further compound and/or method aspect, the present invention includes compounds of formula III chosen from:
19) 1-Methoxy-4-chloro-phthalazine-6-carboxylic acid (3-trifluoromethyl-phenyl)-amide,
20) 4-Methoxy-1-chloro-phthalazine-6-carboxylic acid (3-trifluoromethyl-phenyl)-amide,
23) 4-Chloro-7-(3-trifluoromethyl-benzylamino)-phthalazin-1-ol
24) 4-chloro-6-(3-trifluoromethyl-benzylamino)-phthalazin-1-ol,
27) 1-Chloro-4-hydroxy-phthalazine-6-carboxylic acid (3-trifluoromethyl-phenyl)-amide,
28) 1-chloro-4-hydroxy-phthalazine-6-carboxylic acid (4-trifluoromethyl-phenyl) amide,
29) 4-chloro-1-hydroxy-phthalazine-6-carboxylic acid (4-trifluoromethyl-phenyl) amide,
30) 1-Chloro-4-hydroxy-phthalazine-6-carboxylic acid phenylamide,
31) 4-Chloro-1-hydroxy-phthalazine-6-carboxylic acid phenylamide,
32) 1-Chloro-4-hydroxy-phthalazine-6-carboxylic acid (2-methyl-3-trifluoromethyl-phenyl) amide,
33) 4-chloro-1-hydroxy-phthalazine-6-carboxylic acid (2-methyl-3-trifluoromethyl-phenyl) amide,
34) 1-chloro-4-hydroxy-phthalazine-6-carboxylic acid (2,5-difluoro-phenyl) amide,
35) 4-chloro-1-hydroxy-phthalazine-6-carboxylic acid (2,5-difluoro-phenyl) amide,
36) 1-chloro-4-hydroxy-phthalazine-6-carboxylic acid (2-fluoro-5-trifluoromethyl-phenyl) amide,
37) 4-chloro-1-hydroxy-phthalazine-6-carboxylic acid (2-fluoro-5-trifluoromethyl -phenyl) amide,
38) 1-chloro-4-hydroxy-phthalazine-6-carboxylic acid (2-fluoro-5-methyl-phenyl) amide,
39) 4-chloro-1-hydroxy-phthalazine-6-carboxylic acid (2-fluoro-5-methyl-phenyl) amide,
40) 4-Chloro-1-hydroxy-phthalazine-6-carboxylic acid (3-trifluoromethyl-phenyl)-amide,
41) 1-Iodo-4-hydroxy-phthalazine-6-carboxylic acid (3-trifluoromethyl-phenyl)-amide,
42) 4-Iodo-1-hydroxy-phthalazine-6-carboxylic acid (3-trifluoromethyl-phenyl)-amide,
43) 1-Hydroxy-phthalazine-6-carboxylic acid (3-trifluoromethyl-phenyl)-amide,
44) 1-hydroxy-4-phenyl-phthalazine-6-carboxylic acid (3-trifluoromethyl-phenyl)-amide,
45) 1-hydroxy-4-pyridin-2-yl-phthalazine-6-carboxylic acid (3-trifluoromethyl-phenyl)-amide,
46) 4-hydroxy-1-methoxy-phthalazine-6-carboxylic acid (4-trifluoromethyl-pyridin-2-yl)-amide,
47) 1-hydroxy-4-methoxy-phthalazine-6-carboxylic acid (4-trifluoromethyl-pyridin-2-yl)-amide,
48) 6-{[(2,4-Dichlorophenyl)methyl]amino}-4-chloro-2H-phthalazin-1-one,
49) 7-{[(2,4-dichlorophenyl)methyl]amino}-4-chloro-2H-phthalazin-1-one,
50) 6-{[(4-Chlorophenyl)methyl]amino}-4-chloro-2H-phthalazin-1-one,
51) 7-{[(4-Chlorophenyl)methyl]amino}-4-chloro-2H-phthalazin-1-one,
52) 6-{[(3-Methoxyphenyl)methyl]amino}-4-chloro-2H-phthalazin-1-one,
53) 7-{[(3-Methoxyphenyl)methyl]amino}-4-chloro-2H-phthalazin-1-one,
54) 6-{[(3,4-Difluorophenyl)methyl]amino}-4-chloro-2H-phthalazin-1-one,
55) 7-{[(3,4-Difluorophenyl)methyl]amino}-4-chloro-2H-phthalazin-1-one,
56) 6-{[(3-Methylphenyl)methyl]amino}-4-chloro-2H-phthalazin-1-one,
57) 7-{[(3-Methylphenyl)methyl]amino}-4-chloro-2H-phthalazin-1-one,
58) 6-{[(2-Methoxyphenyl)methyl]amino}-4-chloro-2H-phthalazin-1-one,
59) 7-{[(2-Methoxyphenyl)methyl]amino}-4-chloro-2H-phthalazin-1-one,
60) 6-(4-Methoxy-benzylamino)-2H-phthalazin-1-one, 61) 6-Benzylamino-4-chloro-2H-phthalazin-1-one
62) 7-Benzylamino-4-chloro-2H-phthalazin-1-one,
63) 4-Chloro-6-(3-trifluoromethyl-phenylamino)-2H-phthalazin-1-one,
64) 4-Chloro-7-(3-trifluoromethyl-phenylamino)-2H-phthalazin-1-one,
65) 4-Chloro-6-phenethylamino-2H-phthalazin-1-one,
66) 4-Chloro-7-phenethylamino-2H-phthalazin-1-one,
67) 4-[(4-Chloro-1-oxo-1,2-dihydro-phthalazin-6-ylamino)-methyl]-N-(2-pyrrolidin-1-yl-ethyl)-benzamide,
68) 4-[(1-Chloro-4-oxo-3,4-dihydro-phthalazin-6-ylamino)-methyl]-N-(2-pyrrolidin-1-yl-ethyl)-benzamide,
69) 3-[(4-Chloro-1-oxo-1,2-dihydro-phthalazin-6-ylamino)-methyl]-N-(2-pyrrolidin-1-yl-ethyl)-benzamide,
70) 3-[(1-Chloro-4-oxo-3,4-dihydro-phthalazin-6-ylamino)-methyl]-N-(2-pyrrolidin-1-yl-ethyl)-benzamide,
71) N-(4-Chloro-1-oxo-1,2-dihydro-phthalazin-6-yl)-3-trifluoromethyl-benzamide,
72) N-(1-Chloro-4-oxo-3,4-dihydro-phthalazin-6-yl)-3-trifluoromethyl-benzamide,
73) 4-Chloro-6-[3-(2-morpholin-4-yl-ethoxy)-benzylamino]-phthalazin-1-ol,
74) 4-Chloro-7-[3-(2-morpholin-4-yl-ethoxy)-benzylamino]-phthalazin-1-ol,
75) 4-Methyl-1-oxo-1,2-dihydro-phthalazine-6-carboxylic acid (3-trifluoromethyl-phenyl)-amide,
76) 4-Methyl-1-oxo-1,2-dihydro-phthalazine-6-carboxylic acid 3-trifluoromethyl-benzylamide,
77) 4-Methyl-1-oxo-1,2-dihydro-phthalazine-6-carboxylic acid 3-methoxy-benzylamide,
78) 4-Chloro-6-(3-piperidin-1-ylmethyl-benzylamino)-2H-phthalazin-1-one,
79) 4-Chloro-6-[2-(2-morpholin-4-yl-ethoxy)-benzylamino]-2H-phthalazin-1-one,
80) 6-(Benzyl-methyl-amino)-4-chloro-2H-phthalazin-1-one,
81) 4-Chloro-6-(2,5-dichloro-benzylamino)-2H-phthalazin-1-one,
82) 4-Chloro-6-(2-methyl-benzylamino)-2H-phthalazin-1-one,
83) 4-Chloro-6-(2-chloro-6-fluoro-benzylamino)-2H-phthalazin-1-one,
84) 4-Chloro-6-(2-pyrazol-1-yl-benzylamino)-2H-phthalazin-1-one,
85) 4-Chloro-6-(3-pyrazol-1-yl-benzylamino)-2H-phthalazin-1-one,
86) 4-Chloro-6-(2-pyridin-3-yl-benzylamino)-2H-phthalazin-1-one,
87) 4-Chloro-6-(2-piperidin-1-yl-benzylamino)-2H-phthalazin-1-one,
88) 4-Chloro-6-(2-thiophen-2-yl-benzylamino)-2H-phthalazin-1-one,
89) 4-Chloro-6-(3-thiophen-2-yl-benzylamino)-2H-phthalazin-1-one,
90) 4-Chloro-6-(2-furan-2-yl-benzylamino)-2H-phthalazin-1-one,
91) 4-Chloro-6-[3-(4-methyl-piperazin-1-yl)-benzylamino]-2H-phthalazin-1-one,
92) 4-Chloro-6-(2-morpholin-4-ylmethyl-benzylamino)-2H-phthalazin-1-one,
93) 4-Chloro-6-(3-thiophen-3-yl-benzylamino)-2H-phthalazin-1-one,
94) 4-Chloro-6-[2-(4-methyl-piperazin-1-yl)-benzylamino]-2H-phthalazin-1-one,
95) 4-Chloro-6-(2-phenoxy-benzylamino)-2H-phthalazin-1-one,
96) 4-Chloro-6-[(2,3-dihydro-benzo[1,4]dioxin-5-ylmethyl)-amino]-2H-phthalazin-1-one,
97) 4-Chloro-6-[(2,3-dihydro-benzo furan-5-ylmethyl)-amino]-2H-phthalazin-1-one,
98) 4-Chloro-6-(2-piperazin-1-yl-benzylamino)-2H-phthalazin-1-one,
99) 4-Chloro-6-(2-fluoro-5-trifluoromethyl-benzylamino)-2H-phthalazin-1-one,
100) 4-Chloro-6-(5-chloro-2-methyl-benzylamino)-2H-phthalazin-1-one,
101) 4-Chloro-6-(2-chloro-5-trifluoromethyl-benzylamino)-2H-phthalazin-1-one,
102) 4-Chloro-6-(2-chloro-3-trifluoromethyl-benzylamino)-2H-phthalazin-1-one,
103) 4-Chloro-6-(2-chloro-6-phenoxy-benzylamino)-2H-phthalazin-1-one,
104) 4-Chloro-6-(2,5-dimethyl-benzylamino)-2H-phthalazin-1-one,
105) 4-Chloro-6-(3-morpholin-4-yl-benzylamino)-2H-phthalazin-1-one,
106) 4-Chloro-6-(2,3-dimethyl-benzylamino)-2H-phthalazin-1-one,
107) 4-Chloro-6-[(3,4-dihydro-2H-benzo[b][1,4]dioxepin-6-ylmethyl)-amino]-2H-phthalazin-1-one,
108) 4-Chloro-6-(3-furan-2-yl-benzylamino)-2H-phthalazin-1-one,
109) 4-Chloro-6-[(6-fluoro-4H-benzo[1,3]dioxin-8-ylmethyl)-amino]-2H-phthalazin-1-one,
110) 4-Chloro-6-[(5-methyl-2-phenyl-furan-3-ylmethyl)-amino]-2H-phthalazin-1-one,
111) 1-Chloro-4-oxo-3,4-dihydro-phthalazine-6-carboxylic acid (3-difluoromethoxy-phenyl)-amide,
112) 4-Chloro-1-oxo-1,2-dihydro-phthalazine-6-carboxylic acid (3-difluoromethoxy-phenyl)-amide,
113) 4-Chloro-7-(3-fluoro-benzylamino)-2H-phthalazin-1-one
114) 4-Chloro-6-(3-fluoro-benzylamino)-2H-phthalazin-1-one,
115) 4-Chloro-7-(3-trifluoromethoxy-benzylamino)-2H-phthalazin-1-one
116) 4-Chloro-6-(3-trifluoromethoxy-benzylamino)-2H-phthalazin-1-one,
117) 4-Chloro-6-(3-chloro-benzylamino)-2H-phthalazin-1-one,
118) 4-Chloro-6-(2-trifluoromethyl-benzylamino)-2H-phthalazin-1-one,
119) 4-Chloro-6-(3,5-dimethoxy-benzylamino)-2H-phthalazin-1-one,
120) 4-Chloro-6-(3-hydroxy-benzylamino)-2H-phthalazin-1-one,
121) 4-Chloro-6-(3,5-difluoro-benzylamino)-2H-phthalazin-1-one,
122) 4-Chloro-6-(2,5-difluoro-benzylamino)-2H-phthalazin-1-one,
123) N-{3-[(4-Chloro-1-oxo-1,2-dihydro-phthalazin-6-ylamino)-methyl]-phenyl}-acetamide,
124) 4-Chloro-6-(3,5-dichloro-benzylamino)-2H-phthalazin-1-one,
125) 6-[(Biphenyl-3-ylmethyl)-amino]-4-chloro-2H-phthalazin-1-one,
127) 4-Chloro-6-(3-difluoromethoxy-benzylamino)-2H-phthalazin-1-one,
128) 4-Chloro-6-(2,3-difluoro-benzylamino)-2H-phthalazin-1-one,
129) 4-Chloro-6-(2-chloro-benzylamino)-2H-phthalazin-1-one, 130) 4-Chloro-6-(3,4-dimethyl-benzylamino)-2H-phthalazin-1-one,
131) 4-Chloro-6-(3-dimethylamino-benzylamino)-2H-phthalazin-1-one,
132) 4-Chloro-6-(3-isopropoxy-benzylamino)-2H-phthalazin-1-one,
133) 4-Chloro-6-(2-pyrrol-1-yl-benzylamino)-2H-phthalazin-1-one,
134) 6-(4-tert-Butoxy-benzylamino)-4-chloro-2H-phthalazin-1-one,
135) 4-Chloro-6-[(pyridin-3-ylmethyl)-amino]-2H-phthalazin-1-one,
136) 4-Chloro-6-(2,3-dimethoxy-benzylamino)-2H-phthalazin-1-one,
137) 4-Chloro-6-(2,5-dimethoxy-benzylamino)-2H-phthalazin-1-one,
138) 4-Chloro-6-[(pyridin-2-ylmethyl)-amino]-2H-phthalazin-1-one,
139) 4-Chloro-6-(2-trifluoromethoxy-benzylamino)-2H-phthalazin-1-one,
140) 4-Chloro-6-(2-difluoromethoxy-benzylamino)-2H-phthalazin-1-one,
141) 4-Chloro-6-(2-imidazol-1-yl-benzylamino)-2H-phthalazin-1-one,
143) 4-Chloro-6-(2-[1,2,4]triazol-1-yl-benzylamino)-2H-phthalazin-1-one,
144) 4-Chloro-6-(3-morpholin-4-ylmethyl-benzylamino)-2H-phthalazin-1-one,
145) 4-Chloro-6-(3-pyrrol-1-yl-benzylamino)-2H-phthalazin-1-one,
146) 4-Chloro-6-[3-(4-methyl-piperidin-1-ylmethyl)-benzylamino]-2H-phthalazin-1-one,
150) 4-Chloro-6-[3-(3-dimethylamino-propylamino)-benzylamino]-2H-phthalazin-1-one,
151) 4-Chloro-6-[3-(2-morpholin-4-yl-ethylamino)-benzylamino]-2H-phthalazin-1-one,
152) 4-Chloro-1-oxo-1,2-dihydro-phthalazine-6-carboxylic acid (3-piperidin-1-ylmethyl-phenyl)-amide,
153) 4-Chloro-6-[3-(4-methyl-[1,4]diazepan-1-yl)-benzylamino]-2H-phthalazin-1-one,
154) 1-Chloro-4-oxo-3,4-dihydro-phthalazine-6-carboxylic acid (2-morpholin-4-yl-5-trifluoromethyl-phenyl)-amide,
155) 4-Chloro-1-oxo-1,2-dihydro-phthalazine-6-carboxylic acid (2-morpholin-4-yl-5-trifluoromethyl-phenyl)-amide,
156) 1-chloro-4-oxo-3,4-dihydro-phthalazine-6-carboxylic acid (3-furan-2-yl-phenyl)-amide,
157) 4-chloro-1-oxo-1,2-dihydro-phthalazine-6-carboxylic acid (3-furan-2-yl-phenyl)-amide,
158) 4-Chloro-6-(3-dimethylaminomethyl-benzylamino)-2H-phthalazin-1-one,
159) 4-Chloro-6-[3-(2-dimethylamino-ethylamino)-benzylamino]-2H-phthalazin-1-one,
160) 1-Chloro-4-oxo-3,4-dihydro-phthalazine-6-carboxylic acid m-tolylamide,
161) 4-Chloro-1-oxo-1,2-dihydro-phthalazine-6-carboxylic acid m-tolylamide,
162) 1-Chloro-4-oxo-3,4-dihydro-phthalazine-6-carboxylic acid (3-trifluoromethoxy-phenyl)-amide,
163) 4-Chloro-1-oxo-1,2-dihydro-phthalazine-6-carboxylic acid (3-trifluoromethoxy-phenyl)-amide,
164) 1-Chloro-3-methyl-4-oxo-3,4-dihydro-phthalazine-6-carboxylic acid (3-trifluoromethyl-phenyl)-amide,
165) 4-Chloro-2-methyl-1-oxo-1,2-dihydro-phthalazine-6-carboxylic acid (3-trifluoromethyl-phenyl)-amide,
166) 1-chloro-4-oxo-3,4-dihydro-phthalazine-6-carboxylic acid [5-ethoxymethyl-2-methyl-3-(2-pyrrolidin-1-yl-ethylamino)-phenyl]-amide,
167) 4-chloro-1-oxo-1,2-dihydro-phthalazine-6-carboxylic acid [5-ethoxy methyl-2-methyl-3-(2-pyrrolidin-1-yl-ethylamino)-phenyl]-amide,
168) 1-Oxo-1,2-dihydro-phthalazine-6-carboxylic acid [5-ethoxymethyl-2-methyl-3-(2-pyrrolidin-1-yl-ethylamino)-phenyl]-amide,
169) 1-Chloro-4-oxo-3,4-dihydro-phthalazine-6-carboxylic acid 3-trifluoromethyl-benzylamide,
170) 4-Chloro-1-oxo-1,2-dihydro-phthalazine-6-carboxylic acid 3-trifluoromethyl-benzylamide,
171) N-(4-Chloro-1-oxo-1,2-dihydro-phthalazin-6-yl)-3-methoxy-benzamide,
174) 2-(4-Chloro-1-oxo-1,2-dihydro-phthalazin-6-yl)-N-{2-[(2-dimethylamino-ethyl)-methyl-amino]-phenyl}-acetamide,
175) 2-(1-Chloro-4-oxo-3,4-dihydro-phthalazin-6-yl)-N-{2-[(2-dimethylamino-ethyl)-methyl-amino]-phenyl}-acetamide,
176) 4-Chloro-6-(2-{2-[(2-dimethylamino-ethyl)-methyl-amino]-phenylamino}-ethyl)-2H-phthalazin-1-one,
177) 4-Chloro-7-(2-{2-[(2-dimethylamino-ethyl)-methyl-amino]-phenylamino}-ethyl)-2H-phthalazin-1-one,
178) 4-Chloro-1-hydroxy-phthalazine-6-carboxylic acid [4-chloro-3'-(2-dimethylamino-ethoxy)-biphenyl-3-yl]-amide,
179) 1-Chloro-4-hydroxy-phthalazine-6-carboxylic acid [4-chloro-3'-(2-dimethylamino-ethoxy)-biphenyl-3-yl]-amide,
180) 4-Chloro-1-hydroxy-phthalazine-6-carboxylic acid (3'-hydroxy-biphenyl-3-yl)-amide,
181) 1-Chloro-4-hydroxy-phthalazine-6-carboxylic acid (3'-hydroxy-biphenyl-3-yl)-amide,
182) 4-Chloro-6-(3-pyrrolidin-1-ylmethyl-benzylamino)-2H-phthalazin-1-one,
183) 4-Chloro-6-(3-pyrrolidin-1-yl-benzylamino)-2H-phthalazin-1-one,
184) 4-Chloro-6-[(6-pyrrolidin-1-yl-pyridin-2-ylmethyl)-amino]-2H-phthalazin-1-one,
185) 4-Chloro-6-(2-pyrrolidin-1-yl-benzylamino)-2H-phthalazin-1-one,
186) 4-Chloro-6-(2-morpholin-4-yl-benzylamino)-4a,8a-dihydro-2H-phthalazin-1-one,
187) 4-Chloro-6-{methyl-[3-(6-methyl-pyrazin-2-yloxy)-benzyl]-amino}-4a,8a-dihydro-2H-phthalazin-1-one,
188) 4-Chloro-6-[methyl-(4-methyl-3,4-dihydro-2H-pyrido[3,2-b][1,4]oxazin-7-ylmethyl)-amino]-4a,8a-dihydro-2H-phthalazin-1-one,
189) 4-Chloro-6-[2-((R)-3-methyl-piperazin-1-yl)-benzyl amino]-4a,8a-dihydro-2H-phthalazin-1-one,
190) 4-Chloro-6-[2-(hexahydro-pyrrolo[3,4-c]pyrrol-2-yl)-benzylamino]-2H-phthalazin-1-one,
191) 4-Chloro-6-(2-perhydro-1,4-diazepin-1-yl-benzylamino)-2H-phthalazin-1-one,
192) 4-Chloro-6-(2-piperazin-1-yl-5-trifluoromethyl-benzylamino)-2H-phthalazin-1-one,
193) 4-Chloro-6-(5-methoxy-2-piperazin-1-yl-benzylamino)-2H-phthalazin-1-one,
194) 6-[2-(4-Amino-piperidin-1-yl)-benzylamino]-4-chloro-2H-phthalazin-1-one, and
195) 4-Chloro-6-(5-fluoro-2-piperazin-1-yl-benzylamino)-2H-phthalazin-1-one, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof,) can also be in the form of a polymorph, and wherein if the compound exhibits chirality it can be in the form of a mixture of enantiomers such as a racemate, or a mixture of diastereomers, or can be in the form of a single enantiomer or a single diastereomer.

In a further compound and/or method aspect, the present invention includes compounds of formula III chosen from:
4-Chloro-1-hydroxy-phthalazine-6-carboxylic acid (3-trifluoromethyl-phenyl)-amide sodium salt,
4-Chloro-6-[(pyridin-3-ylmethyl)-amino]-2H-phthalazin-1-one hydroformate,
4-Chloro-6-[3-(3-dimethylamino-propylamino)-benzylamino]-2H-phthalazin-1-one hydroformate,
4-Chloro-6-[3-(2-morpholin-4-yl-ethylamino)-benzylamino]-2H-phthalazin-1-one hydroformate,
4-Chloro-1-oxo-1,2-dihydro-phthalazine-6-carboxylic acid (3-piperidin-1-ylmethyl-phenyl)-amide hydroformate,
4-Chloro-6-[3-(4-methyl-[1,4]diazepan-1-yl)-benzylamino]-2H-phthalazin-1-one hydroformate,
4-Chloro-6-(3-dimethylaminomethyl-benzylamino)-2H-phthalazin-1-one hydroformate,
4-Chloro-6-[3-(2-dimethylamino-ethylamino)-benzylamino]-2H-phthalazin-1-one hydroformate,
1-chloro-4-oxo-3,4-dihydro-phthalazine-6-carboxylic acid [5-ethoxymethyl-2-methyl-3-(2-pyrrolidin-1-yl-ethylamino)-phenyl]-amide hydroformate,
4-chloro-1-oxo-1,2-dihydro-phthalazine-6-carboxylic acid [5-ethoxy methyl-2-methyl-3-(2-pyrrolidin-1-yl-ethylamino)-phenyl]-amide hydroformate,
wherein if the compound exhibits chirality it can be in the form of a mixture of enantiomers such as a racemate, or a mixture of diastereomers, or can be in the form of a single enantiomer or a single diastereomer.

In another aspect, the present invention relates to compound of formula IV:

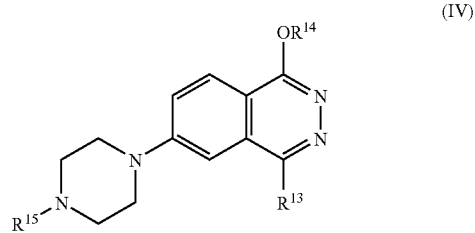

(IV)

wherein $R^{13}$ is hydrogen, halogen, alkyl (e.g., methyl), aryl, heteroaryl, cyano or alkoxy;

$R^{14}$ is hydrogen, alkyl (e.g., methyl), —C(O)$R_y$, —SO$_2R_y$, or —P(O)(O$R_y$)$_2$, where $R_y$ is hydrogen or alkyl; and $R^{15}$ is hydrogen, alkyl, aryl, heteroaryl, heterocycle, alkylaryl, alkylheteraryl, alkylheterocycle or aminoalkyl; wherein an aryl, heteroaryl, heterocycle, alkylaryl, alkylheteraryl, alkylheterocycle may be optionally substituted by halogen, alkyl, alkenyl, alkynyl, cyano, nitro, amino, alkylamino, dialkylamino, hydroxyl, carboxyl, aryl, heteroaryl, heterocycle, alkylaryl, alkylheteroaryl, alkylheterocycle, alkylalkoxy, or NR$^x$(alkylheterocycle) where R$^x$ is hydrogen or alkyl (e.g., methyl). For example, the aryl, heteroaryl, heterocycle, alkylaryl, alkylheteraryl, alkylheterocycle may be optionally substituted by alkyl (e.g., methyl), alkylalkoxy (e.g., ethoxymethyl) or NR$^x$(alkylheterocycle) (e.g., pyrrolidinylethylamino).

In one embodiment, $R^{14}$ is hydrogen or alkyl (e.g., methyl).

In one embodiment, $R^{13}$ is halogen, $R^{14}$ is hydrogen and $R^{15}$ is aryl, heteroaryl, alkylheterocycle, or alkylamino. For example, $R^{15}$ is phenyl, trifluoromethylphenyl (e.g., 3-trifluoromethylphenyl), (pyrrolidinylethylamino)phenyl (e.g., 3-(2-pyrrolidin-1-yl-ethylamino)phenyl), (ethoxymethyl)(methyl)(pyrrolidinylethylamino)phenyl (e.g., 5-ethoxymethyl-2-methyl-3-(2-pyrrolidin-1-yl-ethylamino)phenyl), pyrazinyl, morpholinylethyl (e.g., 2-morpholin-4-yl-ethyl) or dimethylaminopropyl (e.g., 3-dimethylaminopropyl).

One of ordinary skill in the art will readily appreciate that some compounds of formula IV may exist in different tautomeric forms, e.g., in a similar manner to the compounds of formula III, as described above. These two forms of formula IV are used interchangeably herein, and both are encompassed within the present invention.

In a compound and/or method aspect, the present invention includes compounds of formula IV chosen from:
126) 4-Chloro-6-(4-phenyl-piperazin-1-yl)-2H-phthalazin-1-one,
142) 4-Chloro-6-[4-(3-trifluoromethyl-phenyl)-piperazin-1-yl]-2H-phthalazin-1-one,
147) 4-Chloro-6-(2,3,5,6-tetrahydro-[1,2']bipyrazinyl-4-yl)-2H-phthalazin-1-one,
148) 4-Chloro-6-[4-(2-morpholin-4-yl-ethyl)-piperazin-1-yl]-2H-phthalazin-1-one,
149) 4-Chloro-6-[4-(3-dimethylamino-propyl)-piperazin-1-yl]-2H-phthalazin-1-one, and
172) 4-Chloro-6-{4-[3-(2-pyrrolidin-1-yl-ethylamino)-phenyl]-piperazin-1-yl}-2H-phthalazin-1-one,
173) 4-Chloro-6-{4-[5-ethoxymethyl-2-methyl-3-(2-pyrrolidin-1-yl-ethylamino)-phenyl]-piperazin-1-yl}-2H-phthalazin-1-one,
wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof,) can also be in the form of a polymorph, and wherein if the compound exhibits chirality it can be in the form of a mixture of enantiomers such as a racemate, or a mixture of diastereomers, or can be in the form of a single enantiomer or a single diastereomer.

In a further compound and/or method aspect, the present invention includes compounds of formula IV chosen from:
4-Chloro-6-[4-(2-morpholin-4-yl-ethyl)-piperazin-1-yl]-2H-phthalazin-1-one hydroformate,
4-Chloro-6-[4-(3-dimethylamino-propyl)-piperazin-1-yl]-2H-phthalazin-1-one hydroformate,
4-Chloro-6-{4-[3-(2-pyrrolidin-1-yl-ethylamino)-phenyl]-piperazin-1-yl}-2H-phthalazin-1-one hydroformate, and
4-Chloro-6-{4-[5-ethoxymethyl-2-methyl-3-(2-pyrrolidin-1-yl-ethylamino)-phenyl]-piperazin-1-yl}-2H-phthalazin-1-one hydroformate,
wherein if the compound exhibits chirality it can be in the form of a mixture of enantiomers such as a racemate, or a mixture of diastereomers, or can be in the form of a single enantiomer or a single diastereomer.

In a further compound and/or method aspect, the present invention includes compounds chosen from:
178) 4-Chloro-1-hydroxy-phthalazine-6-carboxylic acid [4-chloro-3'-(2-dimethylamino-ethoxy)-biphenyl-3-yl]-amide, 180) 4-Chloro-1-hydroxy-phthalazine-6-carboxylic acid (3'-hydroxy-biphenyl-3-yl)-amide,
98) 4-Chloro-6-(2-piperazin-1-yl-benzylamino)-2H-phthalazin-1-one,
95) 4-Chloro-6-(2-phenoxy-benzylamino)-2H-phthalazin-1-one,
89) 4-Chloro-6-(3-thiophen-2-yl-benzylamino)-2H-phthalazin-1-one,
92) 4-Chloro-6-(2-morpholin-4-ylmethyl-benzylamino)-2H-phthalazin-1-one,
93) 4-Chloro-6-(3-thiophen-3-yl-benzylamino)-2H-phthalazin-1-one,
88) 4-Chloro-6-(2-thiophen-2-yl-benzylamino)-2H-phthalazin-1-one,
87) 4-Chloro-6-(2-piperidin-1-yl-benzylamino)-2H-phthalazin-1-one,
86) 4-Chloro-6-(2-pyridin-3-yl-benzylamino)-2H-phthalazin-1-one,
84) 4-Chloro-6-(2-pyrazol-1-yl-benzylamino)-2H-phthalazin-1-one,
145) 4-Chloro-6-(3-pyrrol-1-yl-benzylamino)-2H-phthalazin-1-one,
112) 4-Chloro-1-oxo-1,2-dihydro-phthalazine-6-carboxylic acid (3-difluoromethoxy-phenyl)-amide,
23) 4-Chloro-7-(3-trifluoromethyl-benzylamino)-phthalazin-1-ol, and
26) 4-Chloro-1-hydroxy-phthalazine-6-carboxylic acid (3-trifluoromethyl-phenyl)-amide, wherein free base forms listed above can also be in the form of a pharmaceutically acceptable salt, wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof,) can also be in the form of a polymorph, and wherein if the compound exhibits chirality it can be in the form of a mixture of enantiomers such as a racemate, or a mixture of diastereomers, or can be in the form of a single enantiomer or a single diastereomer.

As used herein the term "halogen" means F, Cl, Br, and I.

The term "alkyl" means a substituted or unsubstituted saturated hydrocarbon radical which may be straight-chain or branched-chain and contains about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, carboxy, and cyano, and combinations thereof (e.g., $CF_3$, $CHF_2$).

The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, cyano, and combinations thereof.

The term "alkylcycloalkyl" means a cycloalkyl-alkyl-group, where cycloalkyl and alkyl are as described above.

The term "amino" means $-NH_2$.

The term "alkylamino" means $-NH(alkyl)$, wherein alkyl is as described above.

The term "dialkylamino" means $-N(alkyl)_2$, wherein alkyl is as described above.

The term "alkylsulfonyl" means an $-SO_2$-alkyl group, wherein alkyl is as described above.

The term "alkylsulfinyl" means an $-SO$-alkyl group, wherein alkyl is as described above.

The term "aryl" means a substituted or unsubstituted aromatic monocyclic or bicyclic ring system comprising about 5 to about 14 carbon atoms, preferably about 6 to about 10 carbon atoms. Suitable aryl groups include, but are not limited to, phenyl, naphthyl, tetrahydronaphthyl, indanyl and indenyl.

Substituted aryl groups include the above-described aryl groups which are substituted one or more times by, for example, alkyl, alkenyl, alkynyl, cycloalkyl, alkylcycloalkyl, aryl, alkylaryl, heteroaryl, alkylheteroaryl, heterocycle, alkylheterocycle, halogen, hydroxyl, cyano, alkoxy, arylaoxy, cycloalkyloxy, alkoxycarbonyl, carboxyl, amino, alkylamino, dialkylamino, —SH, thioalkyl, alkylsulfonyl, alkylsulfinyl, arylsulfonyl, arylsulfinyl, aminosulfonyl, aminosulfinyl, aroyl, acyl, and combinations thereof.

The term "arylsulfonyl" means an $-SO_2$-aryl group, wherein aryl is as described above.

The term "arylsulfinyl" means an $-SO$-aryl group, wherein aryl is as described above.

The term "carboxyl" means $-C(O)OH$.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "heteroaryl" means a substituted or unsubstituted aromatic monocyclic or multicyclic ring system comprising 5 to about 10 ring atoms, preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyrimidinyl, indolyl, quinolinyl, isoquinolinyl, naphthyridinyl and the like.

Substituted heteroaryl groups include the above-described heteroaryl groups which are substituted one or more times by, for example, alkyl, alkenyl, alkynyl, cycloalkyl, alkylcycloalkyl, aryl, alkylaryl, heteroaryl, alkylheteroaryl, heterocycle, alkylheterocycle, halogen, hydroxyl, cyano, alkoxy, arylaoxy, cycloalkyloxy, alkoxycarbonyl, carboxyl, amino, alkylamino, dialkylamino, —SH, thioalkyl, alkylsulfonyl, alkylsulfinyl, arylsulfonyl, arylsulfinyl, aminosulfonyl, aminosulfinyl, aroyl, acyl, and combinations thereof.

The term "heterocycle" means a substituted or unsubstituted non-aromatic mono- or multicyclic ring system comprising 3 to 10 atoms, preferably 5 or 6 atoms, wherein at least one of the ring atoms is an N, O or S atom. Suitable heterocyle groups include, but are not limited to tetrahydrofuranyl, tetrahydrothienyl, tetrahydropyranyl, dihydropyranyl, pyrrolidinyl, piperidinyl, piperazinyl, morpholinyl, isoxazolinyl, and the like Substituted heterocycle groups include the above-described heterocycle groups which are substituted one or more times by, for example, alkyl, alkenyl, alkynyl, cycloalkyl, alkylcycloalkyl, aryl, alkylaryl, heteroaryl, alkylheteroaryl, heterocycle, alkylheterocycle, halogen, hydroxyl, cyano, alkoxy, arylaoxy, cycloalkyloxy, alkoxycarbonyl, carboxyl, amino, alkylamino, dialkylamino, —SH, thioalkyl, alkylsulfonyl, alkylsulfinyl, arylsulfonyl, arylsulfinyl, aminosulfonyl, aminosulfinyl, aroyl, acyl, and combinations thereof.

The term "aroyl" means an aryl-C(O)—, in which the aryl group is as previously described. Suitable aroyl groups include, but are not limited to, benzoyl and 1-naphthoyl.

The term "acyl" means an HC(O)—, alkyl-C(O)—, or cycloalkyl-C(O)—, in which the alkyl and cycloalkyl groups are as previously described.

The term "alkoxy" means alkyl-O— groups and in which the alkyl portion is in accordance with the previous discussion. Suitable alkoxy groups include, but are not limited to, methoxy, difluoromethoxy, trifluoromethoxy, ethoxy, n-propoxy, iso-propoxy, n-butoxy, t-butoxy, pentoxy, hexoxy, heptoxy, octoxy, and the like. For example, the alkoxy can be methoxy, difluoromethoxy, trifluoromethoxy or ethoxy.

The term "alkylaryl" refers to an aryl-alkyl-radical in which the aryl and alkyl portions are in accordance with the previous descriptions. Suitable examples include, but are not limited to, benzyl, 1-phenethyl, 2-phenethyl, phenpropyl, phenbutyl, phenpentyl, and napthylmethyl The term "alkylheterocycle" refers to a heterocycle-alkyl-group wherein the heterocycle and alkyl portions are in accordance with the previous discussions.

The term "alkylheteroaryl" refers to a heteroaryl-alkyl-group wherein the heteroaryl and alkyl portions are in accordance with the previous discussions. Suitable examples include, but are not limited to, pyridylmethyl, thiazolylmethyl, thienylmethyl, pyrimidinylmethyl, pyrazinylmethyl, and isoquinolinylmethyl The term "aryloxy" means an aryl-O— group, in which the aryl group is as previously described.

The term "alkylaryloxy" means aryl-alkyl-O—, in which the aryl and alkyl groups are as previously described.

The term "alkylthio" means an alkyl-S— group, in which the alkyl group is as previously described.

The term "arylthio" means an aryl-S— group, in which the aryl group is as previously described.

The term "alkoxycarbonyl" means an alkyl-O—CO—group, in which the alkyl group is as previously described.

The term "aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —COR$^a$ where R$^a$ is alkyl, and R' is selected from hydrogen, alkyl, hydroxyalkyl, alkoxyalkyl, aryl, aralkyl, heteroaryl, heteroaralkyl, or haloalkyl, e.g, aminomethyl, methylaminoethyl, 2-ethylamino-2-methylethyl, 1,3-diaminopropyl, dimethylaminoethyl, dimethylaminomethyl, diethylaminoethyl, acetylaminopropyl, and the like.

The term "amidoalkyl" means a linear monovalent hydrocarbon radical of one to six carbon atoms or a branched monovalent hydrocarbon radical of three to six carbons substituted with at least one, preferably one or two, —(CO)NRR' where R is hydrogen, alkyl, or —COR$^a$ where R$^a$ is alkyl, and R' is selected from hydrogen, alkyl, hydroxyalkyl, alkoxyalkyl, aryl, aralkyl, heteroaryl, heteroaralkyl, or haloalkyl, e.g, $CH_2CONH_2$, $CH_2CONH$alkyl (e.g., $CH_2CONHCH_3$), $CH_2CONH(alkyl)_2$ (e.g., $CH_2CON(CH_3)_2$), and the like.

The term aminosulfinyl" means a —SONRR' radical where R is independently hydrogen, alkyl, hydroxyalkyl, alkoxyalkyl, or aminoalkyl and R' is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl as defined above, e.g., —SONH$_2$, methylaminosulfinyl, 2-dimethylaminosulfinyl, and the like.

The term "aminosulfonyl" means a —SO$_2$NRR' radical where R is independently hydrogen, alkyl, hydroxyalkyl, alkoxyalkyl, or aminoalkyl and R' is hydrogen, alkyl, cycloalkyl, cycloalkylalkyl, aryl, aralkyl, heteroaryl, heteroaralkyl, heterocyclyl, heterocyclylalkyl, hydroxyalkyl, alkoxyalkyl, or aminoalkyl as defined above, e.g., —SO$_2$NH$_2$, methylaminosulfonyl, 2-dimethylaminosulfonyl, and the like.

The term "aryloxycarbonyl" means an aryl-O—C(O)— group, in which the aryl group is as previously described.

In another aspect, the present invention relates to methods for preparing the compounds of formulas I-IV. The compounds of the present invention may be prepared by conventional methods, known to one or ordinary skill in the art. For example, some of the processes that can be used are given in the general reaction schemes outlined below. Modifications to these exemplary reaction schemes will be readily apparent to those skilled in the art upon reading the present disclosure and examples which follow. All starting materials are commercially available or can be conventionally prepared from known starting materials, unless otherwise indicated. 1,2,4-benzene tricarboxylic anhydride, 4-nitrophthalic anhydride and 4-bromophthalic anhydride are commercially available from Sigma Aldrich (St. Louis, Mo.).

For example, as outlined in Scheme 1,1,2,4-benzene tricarboxylic anhydride 1 may be reacted with hydrazine in a suitable solvent, e.g., ethanol, isopropyl alcohol, or n-methyl-2-pyrrolidinone, to produce dihydroxy-phthalazine 2. Compound 2 may then be reacted with SOCl$_2$ and POCl$_3$ to produce a trichloride intermediate that is reacted immediately with an amine X$_1$X$_2$NH (where X$^1$ and X$^2$ are, e.g., hydrogen, alkyl, aryl, etc.) to produce an amide compound 3. Compound 3 may then be reacted with NaI and HI in a suitable solvent, e.g., acetone, to produce a di-iodo compound 4. Compound 4 may then be further reacted with a suitable nucleophile in a suitable solvent to form a mixture of the two correspondent regioisomers 5 and 6. Replacement of any remaining iodine atoms may be achieved using standard nucleophilic substitution and/or transition metal reactions known to one of skill in the art, for example, Stille and Suzuki type reactions.

A chlorine atom in compound 3 may also be directly replaced with a suitable nucleophile (where, for example, Y is $HNR_1R_2$ or NaOR) by reacting compound 3 with the nucleophile in a suitable solvent to form a mixture of the two correspondent regioisomers 7 and 8.

It will be readily apparent to those skilled in the art upon reading the present disclosure that numerous amines and hydroxyl derivatives may be chosen and may be used to produce compounds that are within the scope of the present invention.

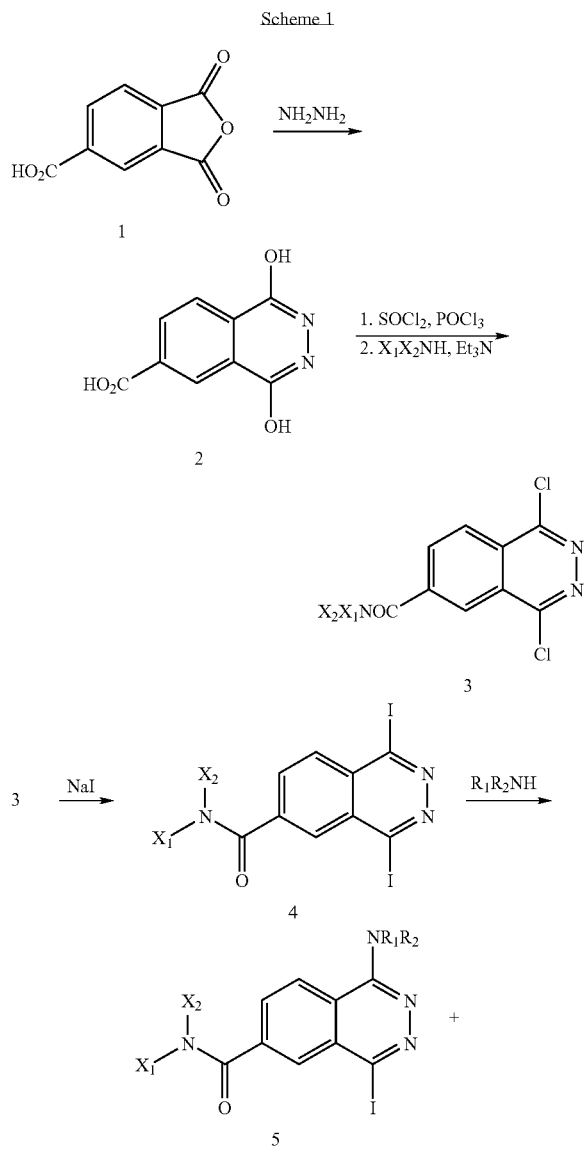

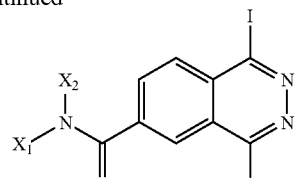

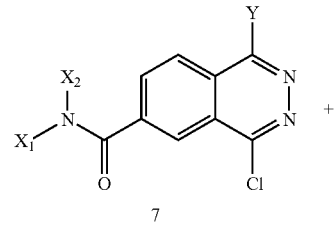

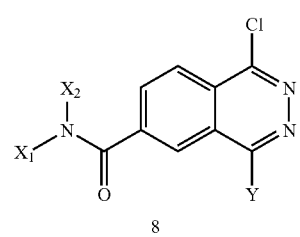

The synthesis of phthalazine derivatives of general formulas 13-20 may be achieved as outlined in Scheme II. In general, a mixture of 4-nitrophthalic anhydride 9 and hydrazine may be refluxed in a suitable solvent, e.g., isopropyl alcohol, to provide 6-amino-phthalazine-1,4-diol 10 in almost quantitative yield. Compound 10 may then be treated with phosphorus oxychloride and N,N-diisopropylethylamine to form 1,4-dichloro-phthalazin-6-ylamine 11. Reduction of compound 11 with a suitable reducing agent, e.g., iron, may be used to produce the amino derivative 12. Alkylation or acylation of the amino group of compound 12 using A-B-X (where, for example, A is alkyl, aryl, arylalkyl, arylheteroalkyl, B is absent, CO, $SO_2$, and X is a suitable leaving group, such as, Cl, Br, I, OTosyl, etc.) may be used to provide the dichloro derivative of general formula 13. Treatment of compound 13 with a nucleophile of general formula $R^1R^2NH$ affords two isomers of general formulas 17 and 18. Alternatively, compound 13 may be treated with NaI and HI in, e.g., acetone to obtain the di-iodo derivative 14. Compound 14 may then be reacted with an appropriate nucleophile (e.g., of general formula $R^1R^2NH$) to produce compounds 15 and 16. Compounds 15 and 16 may then be treated with CuCN to produce the corresponding cyano derivatives 19 and 20.

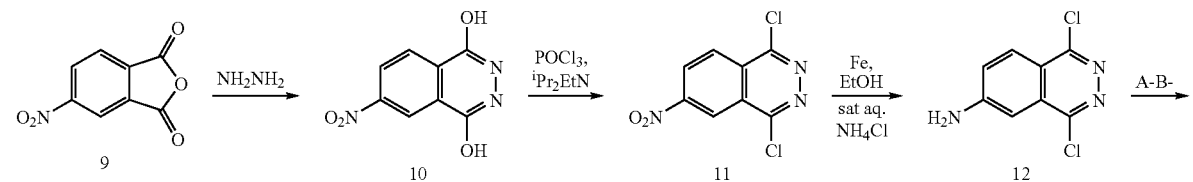

-continued

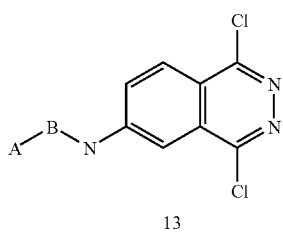 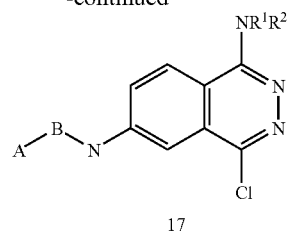 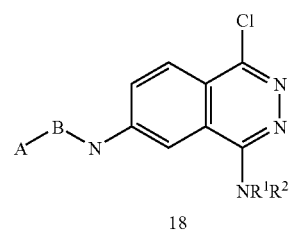

13        17        18

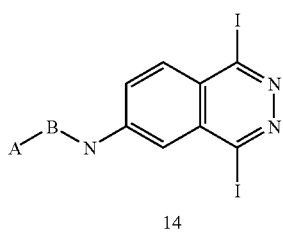 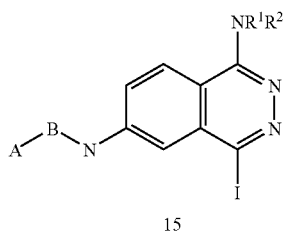 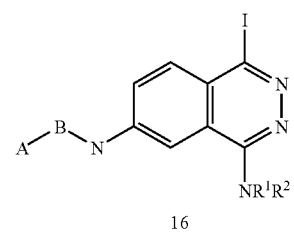

14        15        16

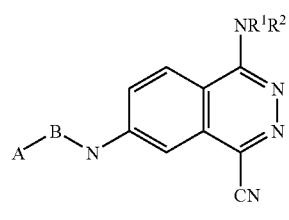 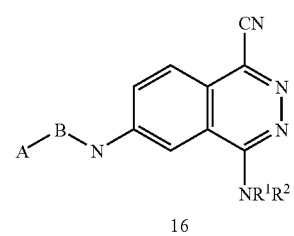

15        16

The synthesis of phthalazine derivatives of general formulas 25-26 may be achieved as outlined in Scheme III. In general, a mixture of 4-bromophthalic anhydride and hydrazine may be refluxed in a suitable solvent, e.g., isopropyl alcohol, to provide 6-bromo-phthalazine-1,4-diol 21 in almost quantitative yield. Compound 21 may then be treated with phosphorus oxychloride to form 1,4-dichloro-6-bromo phthalazine 22. Treatment of compound 22 with a suitable nucleophile (where, for example, Y is $NR_1R_2$ or NaOR) affords two isomers of general formulas 23 and 24. Displacement of the bromine atom with a suitable amino or alcohol derivative A-B-X (where, for example, A is alkyl, aryl, arylalkyl, arylheteroalkyl, B is absent, CO, and X is OH, $NH_2$), using a suitable Pd complex derivative in the presence of a base like sodium tert-butoxide in a suitable solvent, affords the desired 6-amino or 6-alkoxy phthalazine derivatives of general formula 25-26.

Scheme III

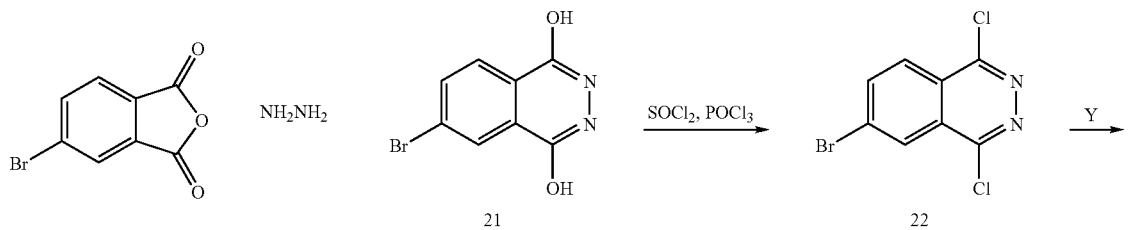

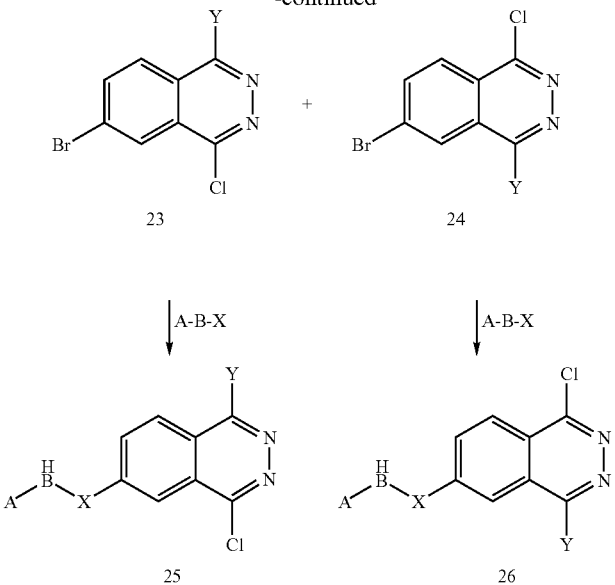

The selective synthesis of phthalazine derivatives of general formulas 30 may be undertaken as outlined in Scheme IV. Treatment of bromo di ester 27 with the desired anhydride in presence of zinc and cobalt bromide affords the desired intermediate 28. Saponification using a suitable base followed by treatment with hydrazine gives the desired phthalazine intermediate that may be refluxed in thionyl chloride to provide intermediate 29 in good yield. Reaction of this acid chloride 29 derivative with the desired amino group $R^aR^bNH$ in presence of a suitable base and solvent affords the desired product of general formula 30.

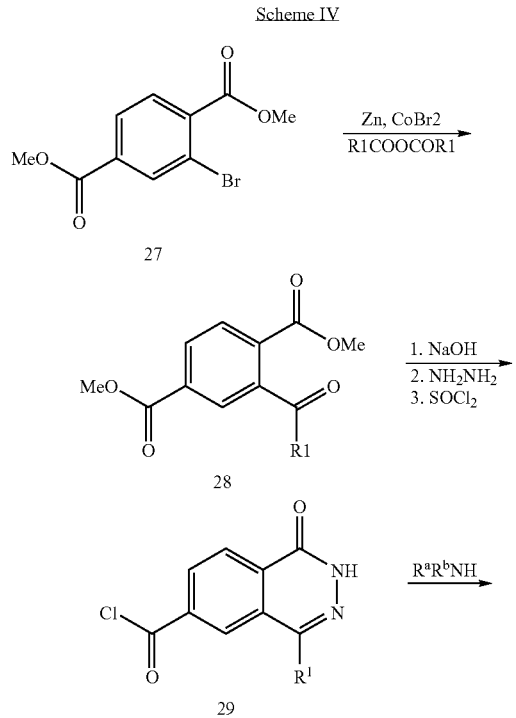

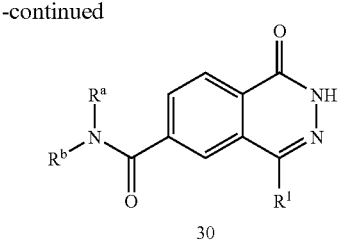

One of ordinary skill in the art will recognize that compounds of formulas I-IV can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of formulas I-IV can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in, for example, Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as base free forms, and pharmaceutically acceptable salts or prodrugs of all the compounds of the present invention for which salts or prodrugs can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, a maleate or a sodium salt.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of formulas I-IV can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of formulas I-IV can exist in different solvate forms. Solvates of the compounds of the invention may also form when solvent molecules are incorporated into the crystalline lattice structure of the compound molecule during the crystallization process.

The term "prodrug" means a compound that is a drug precursor which upon administration to a subject undergoes chemical conversion by metabolic or chemical processes to yield a compound of the present invention. Such prodrugs are considered to be within the scope of this invention.

The compounds of the invention can be administered alone or as an active ingredient of a formulation. Thus, the present invention also includes pharmaceutical compositions of compounds of formulas I-IV, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the compounds of the present invention may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

According to other embodiments, methods for treating a condition that responds to a protein kinase inhibitor are provided. In certain embodiments, the compounds of the present invention may be useful as serine/threonine protein kinase inhibitors. For example, the compounds of the present invention may be useful as S6 Kinase 1 (S6K1) and/or S6 Kinase 2 (S6K2) inhibitors. In other embodiments, the compounds of the present invention may be useful as Rho Kinase, PIM, and/or Polo-Like Kinase (PLK) inhibitors.

For example, some embodiments provide methods of treating a condition that responds to a kinase inhibitor comprising administering to a patient in need thereof an effective amount of a compound of the present invention.

In exemplary embodiments, the present invention provides methods of treatment of conditions related to cancer, the endocrine system, the cardiovascular system, inflammation, hematological disorders, metabolic disorders, immune disorders and neurological disorders. For example, the present invention provides methods of treatment of diseases and conditions such as, but not limited to, tumors, metastases, breast cancer, lung cancer, melanoma, colorectal cancer, bladder cancer, ovarian cancer, prostate cancer, renal cancer, squamous cell cancer, glioblastoma, pancreatic cancer, Kaposi's sarcoma, multiple myeloma, leukemia, diabetes, diabetic retinopathy, insulin resistance, Type II diabetes, non insulin dependent diabetes mellitus, obesity, transplant rejection, multiple sclerosis, IBS, Crohn's disease, ulcerative colitis, renal disease, cachexia, septic shock, lupus, psoriasis, dermatitis, eczema, COPD, asthma, arthritic, osteoarthritis, rheumatoid arthritis, AIDS, depression, Alzheimer's disease, Parkinson's disease, ocular disease, macular degeneration, glaucoma, apoptosis, ischaemic disease, stroke, neural injury, myocardial infarction, angina, acute or congestive heart failure, hypertension, nephropathy, electrolyte abnormality, and vasospasm.

In certain embodiments, the present invention provides methods of treating cancer and/or metabolic disorders. For example, in one embodiment, the present invention provides methods of treating cancer. In another embodiment, the present invention provides methods of treating obesity. In a further embodiment, the present invention provides methods of treating type II diabetes.

The term "treating" means to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition. The compounds of the present invention may be administered as a mono-therapy or administered as part of a combination therapy. For example, one or more of the compounds of the present invention may be co-administered or used in combination with one or more additional therapies known in the art.

An "effective amount" means the amount of a compound of formula I-IV that, when administered to a patient (e.g., a mammal) for treating a disease, is sufficient to effect such treatment for the disease, or an amount of a compound of formulas I-IV that is sufficient for inhibiting serine/threonine protein kinases (such as, e.g., S6K1 and/or S6K2) to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In some embodiments, the compounds of the present invention are administered as a mono-therapy. In other embodiments, the compounds of the present invention are administered as part of a combination therapy. For example, a compound of formulas I-IV may be used in combination with other drugs or therapies that are used in the treatment/prevention/suppression or amelioration of the diseases or conditions for which compounds of formulas I-IV are useful. In such combinations, each active ingredient can be administered either in accordance with their usual dosage range or a dose below their usual dosage range.

Such other drug(s) may be administered, by a route and in an amount commonly used therefor, contemporaneously or sequentially with a compound of formulas I-IV. When a compound of formulas I-IV is used contemporaneously with one or more other drugs, a pharmaceutical unit dosage form containing such other drugs in addition to the compound of formulas I-IV may be employed. Accordingly, the pharmaceutical compositions of the present invention include those that also contain one or more other active ingredients, in addition to a compound of formula I-IV.

The following examples are merely illustrative of the present invention and should not be construed as limiting the scope of the invention in any way as many variations and equivalents that are encompassed by the present invention will become apparent to those skilled in the art upon reading the present disclosure.

EXAMPLES

Examples 1 and 2

Synthesis of 1-Allylamino-4-chloro-phthalazine-6-carboxylic acid (3-trifluoromethyl-phenyl)-amide and 4-Allylamino-1-chloro-phthalazine-6-carboxylic acid (3-trifluoromethyl-phenyl)-amide

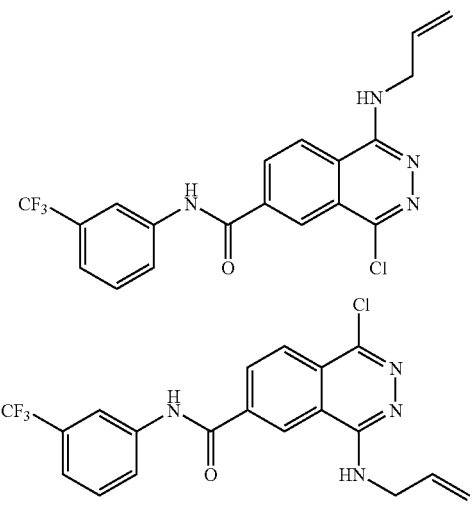

A mixture of 1,2,4 benzenetricarboxylic anhydride (5 g, 0.026 mol) and anhydrous hydrazine (1.67 g, 0.052 mol) in isopropyl alcohol (50 mL) was refluxed for 5 hours. The resulting mixture was neutralized with concentrated HCl and stirred at room temperature for an additional 1 hour. The mixture was filtered and the white residue washed with isopropyl alcohol to provide 1,4-dihydroxy-phthalazine-6-carboxylic acid (5.1 g, 95%) as a white solid.

A mixture of 1,4-dihydroxy-phthalazine-6-carboxylic acid (2 g, 9.7 mmol) in thionyl chloride (20 mL) was refluxed for 3 hours. Phosphorous oxychloride (20 mL) was added and the resulting solution stirred at reflux for an additional 15 hours. The solution was concentrated under vacuum and treated 3 times with toluene in order to remove the excess of chloride. The crude residue was dissolved in DMF (100 mL) and cooled to 0° C. A solution of 3-(trifluoromethyl)aniline (2.34 g, 14.6 mmol) and Et$_3$N (2.9 g, 29.1 mmol) in DMF (50 mL) was added dropwise. The solution was stirred at 0° C. for 1 hour. The solution was then diluted with ether (200 mL) and washed with water (2×), saturated solution of NH$_4$Cl (1×), brine (1×), dried and concentrated under reduced pressure. The crude mixture was purified by chromatography using EtOAc/hexane to provide 1,4-dichloro-phthalazine-6-carboxylic acid (3-trifluoromethyl-phenyl)-amide (1.0 g, 30%).

A mixture of 1,4-dichloro-phthalazine-6-carboxylic acid (3-trifluoromethyl-phenyl)-amide (900 mg, 2.33 mmol), allylamine (134 mg, 2.35 mmol), and Et$_3$N (263 mg, 2.6 mmol) in 5 mL of DMF was heated at 65-70° C. for 15 hours. After cooling to room temperature, the reaction mixture was poured into water (100 mL) and extracted with EtOAc (3×50 mL). Combined extracts were washed with water (2×50 mL), saturated solution of NaHCO$_3$ (1×50 mL), brine (1×50 mL), and concentrated under reduced pressure. The crude mixture containing the two isomers was purified by chromatography using EtOAc/hexane. The following two compounds were obtained:

1-Allylamino-4-chloro-phthalazine-6-carboxylic acid (3-trifluoromethyl-phenyl)-amide (270 mg, 28.5%), m/z (M+H)=408, $^1$H NMR (500 MHz, d6-DMSO, ppm): 10.93 (1H, s); 8.90 (1H, s); 8.48-7.50 (7H, m); 6.26 (1H, m); 5.32-5.14 (2H, dd); 4.24 (2H, m); and 4-Allylamino-1-chloro-phthalazine-6-carboxylic acid (3-trifluoromethyl-phenyl)-amide (520 mg, 54.8%), m/z (M+H)=408, $^1$H NMR (500 MHz, d6-DMSO): δ 10.95 (1H, s); 8.60-7.50 (8H, m); 6.26 (1H, m); 5.30-5.10 (2H, dd); 4.22 (2H, m).

Examples 3 and 4

Synthesis of 1-Methylamino-4-chloro-phthalazine-6-carboxylic acid (3-trifluoromethyl-phenyl)-amide and 4-Methylamino-1-chloro-phthalazine-6-carboxylic acid (3-trifluoromethyl-phenyl)-amide

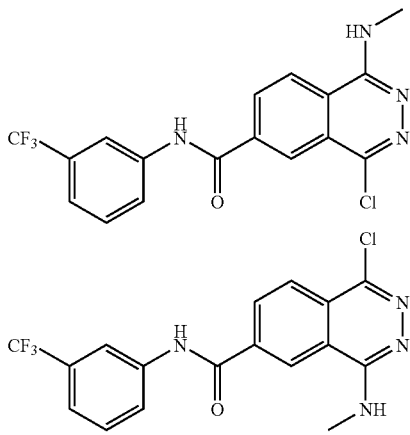

The experimental procedure for Examples 3 and 4 is analogous to the procedure for Examples 1 and 2. In preparing Examples 3 and 4, methyl amine rather than allylamine is reacted with 1,4-dichloro-phthalazine-6-carboxylic acid (3-trifluoromethyl-phenyl)-amide. Accordingly, the following two compounds were obtained: 1-Methylamino-4-chloro-phthalazine-6-carboxylic acid (3-trifluoromethyl-phenyl)-amide (12 mg, 6.1%), m/z (M+H)=381, $^1$H NMR (500 MHz, d6-DMSO): δ 9.85 (1H, s); 8.75 (1H, s); 8.45-7.25 (7H, m); 6.60 (1H, m); 3.16 (3H, d); and 4-Methylamino-1-chloro-phthalazine-6-carboxylic acid (3-trifluoromethyl-phenyl)-amide (80 mg, 40.5%), m/z (M+H)=381, $^1$H NMR (500 MHz, d6-DMSO): δ 10.5 (1H, s); 8.64 (1H, s); 8.36-7.28 (8H, m); 3.12 (3H, d).

Examples 5 and 6

Synthesis of 1-benzylamino-4-chloro-phthalazine-6-carboxylic acid (3-trifluoromethyl-phenyl)-amide and 4-benzylamino-1-chloro-phthalazine-6-carboxylic acid (3-trifluoromethyl-phenyl)-amide

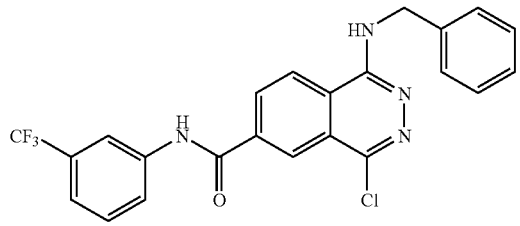

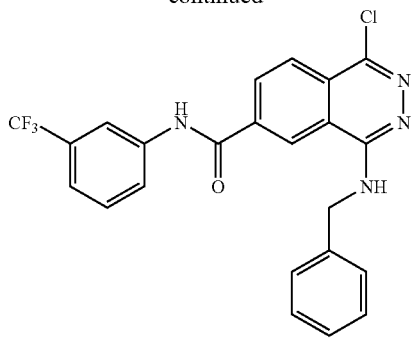

The experimental procedure for Examples 5 and 6 is analogous to the procedure for Examples 1 and 2. In preparing Examples 5 and 6, benzylamine rather than allylamine is reacted with 1,4-dichloro-phthalazine-6-carboxylic acid (3-trifluoromethyl-phenyl)-amide. Accordingly, the following two compounds were obtained: 1-Benzylamino-4-chloro-phthalazine-6-carboxylic acid (3-trifluoromethyl-phenyl)-amide (11 mg, 3.1%), m/z (M+H)=457, $^1$H NMR (500 MHz, d6-DMSO): δ 9.30 (1H, s); 8.78-6.86 (12H, m); 6.61 (1H, s); 4.55 (2H, d); and 4-Benzylamino-1-chloro-phthalazine-6-carboxylic acid (3-trifluoromethyl-phenyl)-amide (23 mg, 6.5%), m/z (M+H)=457, $^1$H NMR (500 MHz, d6-DMSO): δ 9.42 (1H, s); 8.34-7.20 (12H, m); 5.77 (1H, s); 4.72 (2H, d).

Examples 7 and 8

Synthesis of 4-Cyano-1-methylamino-phthalazine-6-carboxylic acid (3-trifluoromethyl-phenyl)-amide and 1-Cyano-4-methylamino-phthalazine-6-carboxylic acid (3-trifluoromethyl-phenyl)-amide

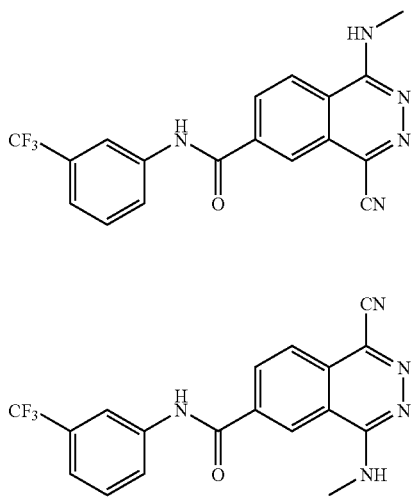

To a solution of 1,4-dichloro-phthalazine-6-carboxylic acid (3-trifluoromethyl-phenyl)-amide (3.3 g, 8.55 mmol) in acetone (100 mL) were added NaI (6.44 g, 42.96 mmol) and HI (few drops). The solution was refluxed for 1 hour then concentrated under vacuum and purified by chromatography (hexanes/EtOAc) to provide 1,4-di-iodo-phthalazine-6-carboxylic acid (3-trifluoromethyl-phenyl)-amide (4.01 g, 82.5%) as a colored solid.

To a solution of 1,4-di-iodo-phthalazine-6-carboxylic acid (3-trifluoromethyl-phenyl)-amide (200 mg, 0.35 mmol) in THF was added a solution of methyl amine in THF (2 mL, 2 M solution). The solution was stirred at room temperature for 40 hours then concentrated under vacuum. The crude mixture was diluted with pyridine (10 mL) and CuCN was added (94 mg, 1.05 mmol). The solution was refluxed for 30 minutes then concentrated under vacuum. Flash chromatography (EtOAc/hexane) was used to obtain the two desired compounds: 1-Cyano-4-methylamino-phthalazine-6-carboxylic acid (3-trifluoromethyl-phenyl)-amide (20 mg, white solid), $^1$H-NMR (DMSO-d6) δ: 3.18 (d, 3H), 7.52 (d, 1H), 7.66 (t, 1H), 8.08 (d, 1H), 8.26 (s, 1H), 8.4-8.55 (m, 3H), 8.72 (m, 1H), 11.06 (s, 1H); and 4-Cyano-1-methylamino-phthalazine-6-carboxylic acid (3-trifluoromethyl-phenyl)-amide (6 mg, colored solid) $^1$H-NMR (DMSO-d6) δ: 3.18 (d, 3H), 7.52 (d, 1H), 7.66 (t, 1H), 8.08 (d, 2H), 8.24 (s, 1H), 8.49 (dd, 1H), 8.81 (m, 1H), 8.94 (s, 1H) 10.95 (s, 1H).

Examples 9 and 10

Synthesis of 1-Benzylamino-4-iodo-phthalazine-6-carboxylic acid (3-trifluoromethyl-phenyl)-amide and 4-Benzylamino-1-iodo-phthalazine-6-carboxylic acid (3-trifluoromethyl-phenyl)-amide

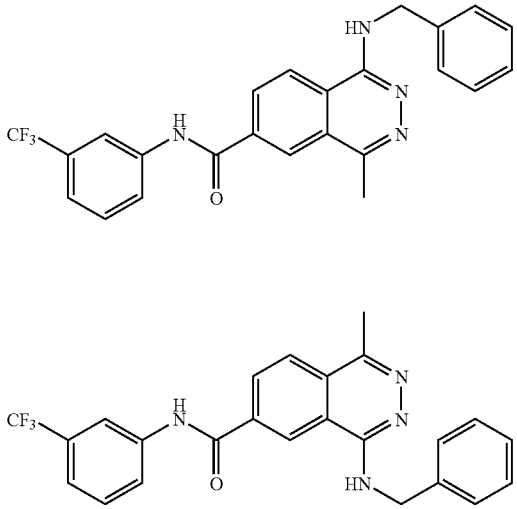

To a solution of 1,4-di-iodo-phthalazine-6-carboxylic acid (3-trifluoromethyl-phenyl)-amide (2.0 g, 3.52 mmol) in THF (15 mL) was added benzylamine (0.77 mL, 7.03 mmol). The solution was stirred at room temperature overnight then concentrated under vacuum. Chromatography (hexanes/EtOAc) was used to obtain: 1-Benzylamino-4-iodo-phthalazine-6-carboxylic acid (3-trifluoromethyl-phenyl)-amide $^1$H-NMR (DMSO-d6) δ: 4.75 (d, 2H), 7.24 (t, 1H), 7.33 (t, 2H), 7.41 (d, 2H), 7.52 (d, 1H), 7.65 (t, 1H), 8.09 (d, 1H), 8.27 (s, 1H), 8.36 (s, 1H), 8.42 (t, 1H), 8.48 (m, 2H), 11.0 (s, 1H). m/z (M+1) 549.03; and 4-Benzylamino-1-iodo-phthalazine-6-carboxylic acid (3-trifluoromethyl-phenyl)-amide $^1$H-NMR (DMSO-d6) δ: 4.79 (d, 2H), 7.23 (t, 1H), 7.32 (t, 2H), 7.42 (d, 2H), 7.50 (d, 1H), 7.65 (t, 1H), 7.97 (d, 1H), 8.07 (d, 1H), 8.24 (s, 1H), 8.41 (m, 1H), 8.49 (t, 1H), 8.90 (s, 1H), 10.91 (s, 1H).

Example 11

Synthesis of 1-Benzylamino-phthalazine-6-carboxylic acid (3-trifluoromethyl-phenyl)-amide

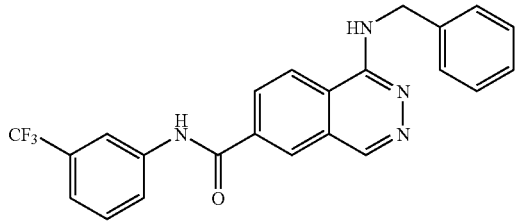

A mixture of 1-benzylamino-4-iodo-phthalazine-6-carboxylic acid (3-trifluoromethyl-phenyl)-amide (24 mg, 0.04 mmol), MeOH (5 mL) and 10% wet Pd/C (catalytic) was evacuated and flushed (3×) with hydrogen. The mixture was stirred under hydrogen for 5 hours. The mixture was filtered through celite, rinsed with MeOH and concentrated under vacuum. Chromatography (hexanes/EtOAc) was used to obtain 1-Benzylamino-phthalazine-6-carboxylic acid (3-trifluoromethyl-phenyl)-amide (9 mg, 50%) as a solid, $^1$H-NMR (CDCl$_3$) δ: 4.80 (bs, 2H), 7.35 (m, 7H), 8.10 (m, 3H), 8.30 (bs, 2H), 8.80 (bs, 1H). m/z (M+1) 423.23.

Example 12

Synthesis of 4-Cyano-1-benzylamino-phthalazine-6-carboxylic acid (3-trifluoromethyl-phenyl)-amide

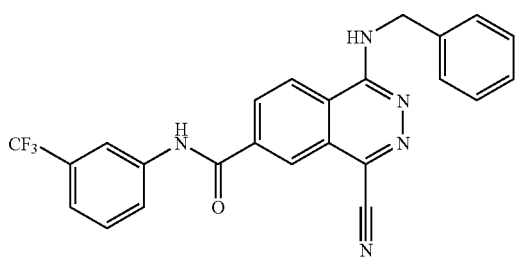

To a solution of 1-benzylamino-4-iodo-phthalazine-6-carboxylic acid (3-trifluoromethyl-phenyl)-amide (62 mg, 0.11 mmol) in pyridine was added CuCN (30 mg, 0.34 mmol). The solution was heated to 90° C. for 1 hour, then concentrated under vacuum. Flash chromatography (hexanes/EtOAc) was used to obtain 4-Cyano-1-benzylamino-phthalazine-6-carboxylic acid (3-trifluoromethyl-phenyl)-amide (25 mg, 50%) as a yellow solid. $^1$H-NMR (DMSO-d6) δ: 4.94 (d, 2H), 7.26 (m, 1H), 7.34 (t, 2H), 7.43 (d, 2H), 7.52 (d, 1H), 7.66 (t, 1H), 8.10 (d, 1H), 8.26 (s, 1H), 8.52 (m, 2H), 8.65 (s, 1H), 9.21 (t, 1H), 11.0 (s, 1H).

Examples 13 and 14

Synthesis of 1-Benzylamino-4-chloro-phthalazine-6-carboxylic acid phenylamide and 4-Benzylamino-1-chloro-phthalazine-6-carboxylic acid phenylamide

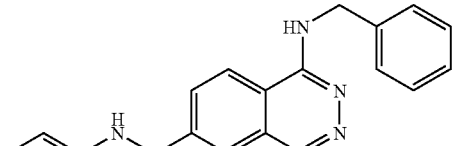

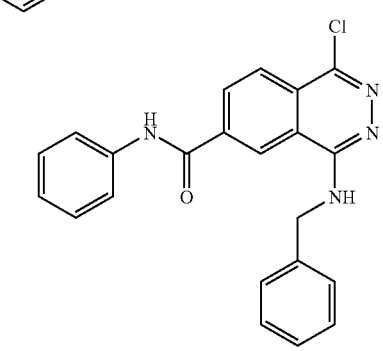

A mixture of 1,4-dihydroxy-phthalazine-6-carboxylic acid (2 g, 9.7 mmol) in thionyl chloride (20 mL) was refluxed for 3 hours. Phosphorous oxychloride (20 mL) was added and the resulting solution stirred at reflux for an additional 15 hours. The solution was concentrated under vacuum and treated 3 times with toluene in order to remove the excess of chloride.

The crude residue was dissolved in DMF (50 mL) and cooled to 0° C. A solution of aniline (1.3 mL, 14.6 mmol) and Et$_3$N (5.4 mL, 38.8 mmol) in DMF (20 mL) was added dropwise. The solution was stirred at 0° C. for 1 hour, then diluted with ether (200 mL) and washed with water (2×), saturated solution of NH$_4$Cl (1×), brine (1×), dried and concentrated under reduced pressure. The crude mixture was purified by chromatography using EtOAc/hexane to provide 1,4-dichloro-phthalazine-6-carboxylic acid phenylamide (0.34 g, 11%), $^1$H-NMR (DMSO-d6) δ: 7.18 (t, 1H), 7.38-7.46 (m, 2H), 7.81 (d, 2H), 8.50 (d, 1H), 8.71 (dd, 1H), 8.85 (d, 1H), 10.88 (s, 1H).

A mixture of 1,4-dichloro-phthalazine-6-carboxylic acid phenylamide (340 mg, 1.07 mmol), benzylamine (0.175 mL, 1.61 mmol), and Et$_3$N (0.30 mL, 2.14 mmol) in 5 mL of DMF was heated at 65-70° C. for 15 hours. After cooling to room temperature, reaction mixture was poured in water (500 mL) and extracted with EtOAc (2×25 mL). Combined extracts were washed with water (2×50 mL), saturated solution of NaHCO$_3$ (50 mL), brine (50 mL), and concentrated under reduced pressure. The crude mixture containing the two isomers was purified by chromatography using EtOAc/hexane. The following two compounds were obtained: 4-Benzylamino-1-chloro-phthalazine-6-carboxylic acid phenylamide (50 mg), $^1$H-NMR (DMSO-d6) δ: 4.68 (d, 2H), 6.25 (bs, 1H), 7.02-7.20 (m, 6H), 7.28-7.34 (m, 2H), 7.58 (d, 2H), 8.13 (d, 1H), 8.33 (d, 1H), 8.60 (s, 1H), 8.85 (s, 1H); and 1-Benzylamino-4-chloro-phthalazine-6-carboxylic acid phenylamide (25 mg), $^1$H-NMR (DMSO-d6) δ: 4.81 (s, 2H), 7.06-7.14 (m, 2H), 7.19-7.24 (m, 1H), 7.25-7.34 (m, 4H), 7.41 (d, 2H), 7.75 (d, 2H), 8.20 (d, 1H), 8.33 (dd, 1H), 8.61 (d, 1H), 9.98 (s, 1H).

Examples 15 and 16

Synthesis of 1-Benzylamino-4-chloro-phthalazine-6-carboxylic acid (3-methoxy-phenyl)-amide and 4-Benzylamino-1-chloro-phthalazine-6-carboxylic acid (3-methoxy-phenyl)-amide

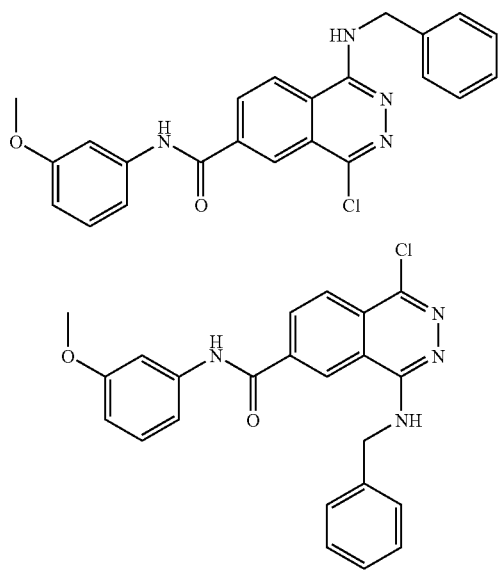

A mixture of 1,4-dihydroxy-phthalazine-6-carboxylic acid (2 g, 9.7 mmol) in thionyl chloride (20 mL) was refluxed for 3 hours. Phosphorous oxychloride (20 mL) was added and the resulting solution stirred at reflux for an additional 15 hours. The solution was concentrated under vacuum and treated 3 times with toluene in order to remove the excess of chloride.

The crude residue was dissolved in DMF (50 mL) and cooled to 0° C. A solution of m-anisidine (1.63 mL, 14.6 mmol) and $Et_3N$ (5.4 mL, 38.8 mmol) in DMF (20 mL) was added dropwise. The solution was stirred at 0° C. for 1 hour, then diluted with ether (200 mL) and washed with water (2×), saturated solution of $NH_4Cl$ (1×), brine (1×), dried and concentrated under reduced pressure. The crude mixture was purified by chromatography using EtOAc/hexane to provide 1,4-dichloro-phthalazine-6-carboxylic acid (3-methoxy-phenyl)-amide (0.62 g), $^1$H-NMR (DMSO-d6) δ: 3.79 (s, 3H), 6.76 (dd, 1H), 7.31 (t, 1H), 7.38-7.42 (m, 1H), 7.49 (t, 1H), 8.50 (d, 1H), 8.70 (dd, 1H), 8.84 (d, 1H), 10.85 (s, 1H).

A mixture of 1,4-dichloro-phthalazine-6-carboxylic acid (3-methoxy-phenyl)-amide (620 mg, 1.07 mmol), benzylamine (0.30 mL, 2.69 mmol), and $Et_3N$ (0.50 mL, 3.58 mmol) in 7 mL of DMF was heated at 65-70° C. for 15 hours. After cooling to room temperature, reaction mixture was poured in water (500 mL) and extracted with EtOAc (2×25 mL). Combined extracts were washed with water (2×50 mL), saturated solution of $NaHCO_3$ (50 mL), brine (50 mL), and concentrated under reduced pressure. The crude mixture containing the two isomers was purified by chromatography using EtOAc/hexane. The following two compounds were obtained: 4-benzylamino-1-chloro-phthalazine-6-carboxylic acid (3-methoxy-phenyl)-amide phenylamide (80 mg), $^1$H-NMR (CDCl$_3$) δ: 2.55 (bs, 2H), 3.76 (s, 3H), 4.79 (d, 2H), 6.63-6.68 (m, 1H), 7.03 (t, 1H), 7.14-7.24 (m, 4H), 7.33-7.38 (m, 3H), 8.11 (d, 1H), 8.83 (d, 1H), 9.58 (s, 1H); and 1-Benzylamino-4-chloro-phthalazine-6-carboxylic acid (3-methoxy-phenyl)-phenylamide (30 mg), $^1$H-NMR (DMSO-d$_6$) δ: 3.88 (s, 3H), 4.92 (s, 2H), 6.48 (bs, 1H), 6.77 (dt, 1H), 7.30-7.36 (m, 4H), 7.36-7.42 (m, 2H), 7.49-7.52 (m, 2H), 7.55 (s, 1H), 8.14 (d, 1H), 8.41 (dd, 1H), 8.68 (d, 1H), 9.44 (s, 1H).

Examples 17 and 18

Synthesis of 1-Dimethylamino-4-chloro-phthalazine-6-carboxylic acid (3-trifluoromethyl-phenyl)-amide and 4-Dimethylamino-1-chloro-phthalazine-6-carboxylic acid (3-trifluoromethyl-phenyl)-amide

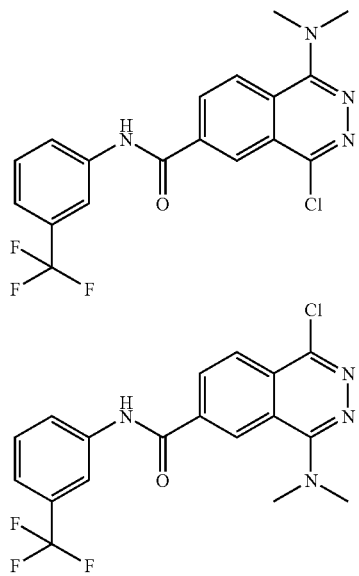

A mixture of 1,4-dichloro-phthalazine-6-carboxylic acid (3-trifluoromethyl-phenyl)-amide (0.30 g, 0.782 mmol), dimethylamine (0.78 mL, 1.56 mmol, 2 M solution in THF) and 8 mL of DMF was heated to 80-85° C. for 1 hour. The reaction was poured onto water, the solids filtered and washed with water. Chromatography (EtOAc/hexane) was used to obtain the following compounds: 1-Dimethylamino-4-chloro-phthalazine-6-carboxylic acid (3-trifluoromethyl-phenyl)-amide (22 mg, 7.1%, yellow solid), $^1$H-NMR (CDCl$_3$) δ: 3.17 (s, 6H), 7.40 (m, 1H), 7.44 (t, 1H), 8.04-8.14 (m, 3H), 8.34 (dd, 1H), 8.42 (s, 1H), 9.62 (s, 1H). m/z (M+1) 395.20; and 4-Dimethylamino-1-chloro-phthalazine-6-carboxylic acid (3-trifluoromethyl-phenyl)-amide (177 mg, 57.3%, white solid), $^1$H-NMR (CDCl$_3$) δ: 3.19 (s, 6H), 7.36 (m, 1H), 7.46 (t, 1H), 8.06-8.10 (m, 2H), 8.18 (d, 1H), 8.39 (dd, 1H), 8.66 (s, 1H), 10.13 (bs, 1H). m/z (M+1) 395.20.

Examples 19 and 20

Synthesis of 1-Methoxy-4-chloro-phthalazine-6-carboxylic acid (3-trifluoromethyl-phenyl)-amide and 4-Methoxy-1-chloro-phthalazine-6-carboxylic acid (3-trifluoromethyl-phenyl)-amide

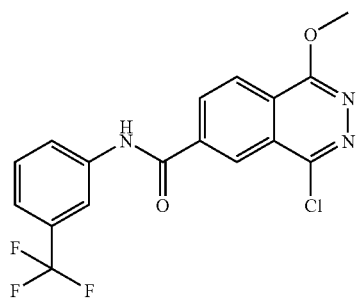

-continued

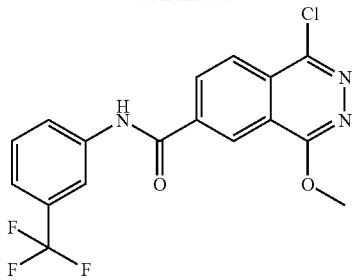

A mixture of 1,4-dichloro-phthalazine-6-carboxylic acid (3-trifluoromethyl-phenyl)-amide (0.327 g, 0.847 mmol), sodium methoxide (0.1 g, 1.85 mmol) and 8 mL of DMF was heated to 80-85° C. for 7 hours and then concentrated. Chromatography (EtOAc/hexane) was used to obtain the following compounds as a mixture (0.138 g, 42.7%, off white solid), $^1$H-NMR (CDCl$_3$) δ: 4.25 (s, 6H), 7.38 (m, 2H), 7.47 (m, 2H), 8.02-8.12 (m, 4H), 8.23 (d, 1H), 8.26 (1H), 8.47 (dd, 1H), 8.50 (dd, 1H), 8.73 (s, 1H), 8.79 (s, 1H), 9.92 (bs, 1H), 10.09 (bs, 1H). m/z (M+1) 382.11.

Example 21

Synthesis of 1-Cyano-4-dimethylamino-phthalazine-6-carboxylic acid (3-trifluoromethyl-phenyl)-amide

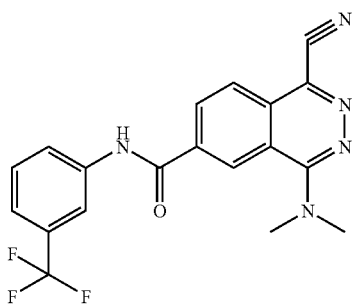

A mixture of 4-dimethylamino-1-iodo-phthalazine-6-carboxylic acid (3-trifluoromethyl-phenyl)-amide (85 mg, 0.175 mmol), pyridine (3 mL) and CuCN (46 mg, 0.514 mmol) was heated to 85° C. for 2 h and concentrated. Column chromatography (Hexanes/EtOAc) afforded the desired compound (38 mg, 56.7%) as a yellow solid. $^1$H-NMR (CDCl$_3$) δ: 3.44 (s, 6H), 7.30-7.34 (m, 1H), 7.42 (t, 1H), 8.00-8.04 (m, 2H), 8.07 (d, 1H), 8.66 (dd, 1H), 8.78 (s, 1H), 10.26 (bs, 1H). m/z (M+1) 386.20.

Example 22

Synthesis of 4-Cyano-1-dimethylamino-phthalazine-6-carboxylic acid (3-trifluoromethyl-phenyl)-amide

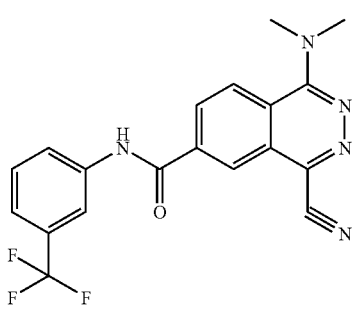

A mixture of 1-dimethylamino-4-iodo-phthalazine-6-carboxylic acid (3-trifluoromethyl-phenyl)-amide (40 mg, 0.082 mmol), pyridine (3 mL) and CuCN (22 mg, 0.247 mmol) was heated to 85° C. for 2 h and concentrated. Column chromatography (Hexanes/EtOAc) afforded the desired compound (14 mg, 44.2%) as a yellow solid. $^1$H-NMR (CDCl$_3$) δ: 3.45 (s, 6H), 7.40-7.44 (m, 1H), 7.49 (t, 1H), 8.01 (d, 1H), 8.12 (s, 1H), 8.23 (d, 1H), 8.31 (s, 1H), 8.38 (d, 1H), 9.13 (s, 1H). m/z (M+1) 386.20.

Example 23 and 24

Synthesis of 4-chloro-7-(3-trifluoromethyl-benzylamino)-phthalazin-1-ol and 4-chloro-6-(3-trifluoromethyl-benzylamino)-phthalazin-1-ol

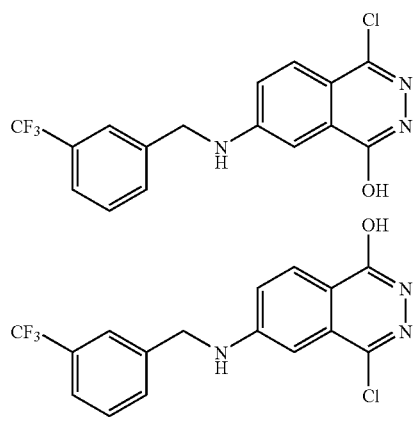

1,4-Dihydroxy-6-nitro-phthalazine

A mixture of 4-nitrophthalic anhydride (10.0 g, 51.78 mmol) and IPA (180 mL) was stirred by a mechanical stirrer. Anhydrous hydrazine (2.77 mL, 56.96 mmol) was added dropwise and the reaction heated to 85° C. for 5 h. The reaction was cooled then acidified to pH 3 with conc. HCl. The solids were filtered and washed with IPA to afford the desired compound (7.76 g, 72%) as a pale yellow solid.

1,4-Dichloro-6-nitro-phthalazine

A mixture of 1,4-dihydroxy-6-nitro-phthalazine (7.75 g, 37.41 mmol), POCl$_3$ (50 mL) and $^i$Pr$_2$EtN (8 mL) was heated to 85° C. for 3 h, then concentrated. The residue was dissolved in CH$_2$Cl$_2$, and poured onto ice water. The solution was filtered through celite. The organic layer of the filtrate was separated, washed with saturated aqueous NaHCO$_3$, 2NHCl, brine and dried (Na$_2$SO$_4$). Column chromatography (Hexanes/EtOAc) afforded the desired compound (1.26 g, 13.8%) as a brown coloured solid.

1,4-Dichloro-6-amino-phthalazine

A mixture of 1,4-dichloro-6-nitro-phthalazine (1.24 g, 5.09 mmol), EtOH (20 mL), saturated aqueous NH$_4$Cl (20 mL) and iron powder (1.42 g, 25.47 mmol) was heated to reflux for 4 h then concentrated. The residue was taken up in EtOAc washed with saturated aqueous NaHCO$_3$, brine, dried (Na$_2$SO$_4$) and concentrated. Column chromatography (Hexanes/EtOAc) afforded the desired product (0.33 g, 30%) as a pale yellow solid.

(1,4-Dichloro-phthalazin-6-yl)-(3-trifluoromethyl-benzyl)-amine

A mixture of 1,4-dichloro-6-amino-phthalazine (33 mg, 0.154 mmol), $K_2CO_3$ (79 mg, 0.57 mmol), DMF (5 mL) and 3-(trifluoromethyl)benzyl bromide (2.0 mL, 0.17 mmol) were heated to 85° C. for 18 h. The reaction was cooled, poured onto water and extracted with EtOAc. The combined organic layers were washed with $H_2O$, brine, dried ($Na_2SO_4$) and concentrated. Column chromatography (Hexanes/EtOAc) afforded the desired product (15 mg, 26.3%) as a yellow solid. m/z 372.08 (M+1).

4-chloro-7-(3-trifluoromethyl-benzylamino)-phthalazin-1-ol and 4-chloro-6-(3-trifluoromethyl-benzylamino)-phthalazin-1-ol A mixture of (1,4-Dichloro-phthalazin-6-yl)-(3-trifluoromethyl-benzyl)-amine (39 mg, 0.105 mmol), 2N NaOH (0.52 mL, 1.05 mmol) and dioxane (3 mL) was heated to 85° C. for 64 hours. The reaction was diluted with water, acidified with conc. HCl to ~pH 4 and extracted with EtOAc (×3). The combined organic phase was washed with brine, dried ($Na_2SO_4$) and concentrated. Chromatography (Hex/EtOAc) afforded 4-chloro-7-(3-trifluoromethyl-benzylamino)-phthalazin-1-ol (13 mg), $^1$H NMR (600 MHz, $CDCl_3$) δ: 4.36 (d, 2H), 6.25 (t, 1H), 7.00 (dd, 1H), 7.22 (d, 1H), 7.28-7.42 (m, 3H), 7.46 (s, 1H), 7.57 (d, 1H), 11.49 (s, 1H) ppm. m/z 354.08; and 4-chloro-6-(3-trifluoromethyl-benzylamino)-phthalazin-1-ol (8 mg), $^1$H NMR (500 MHz, $CDCl_3$) δ: 4.36 (d, 2H), 6.28 (t, 1H), 6.74 (d, 1H), 6.92 (dd, 1H), 7.32-7.46 (m, 3H), 7.51 (s, 1H), 7.95 (d, 1H), 11.60 (s, 1H) ppm. m/z 354.08.

Example 25

Synthesis of dimethyl-(6-phenylaminomethyl-phthalazin-1-yl)-amine

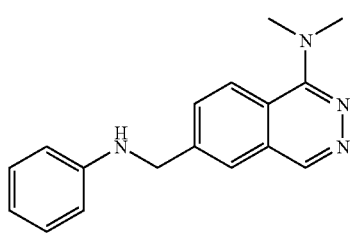

5-Bromo-3-hydroxy-2,3-dihydro-isoindol-1-one

A mixture of zinc powder (8.68 g, 132.7 mmol), copper (II) sulfate pentahydrate (0.11 g, 0.44 mmol) and aqueous sodium hydroxide (135 mL, 2M solution) were cooled to 0° C. Bromophthalimide (25 g, 110.6 mmol) was added in portions over 30 minutes, maintaining the temperature at 0° C. The reaction was stirred at 0° C. for 30 minutes, and at room temperature for 3 h. The reaction was filtered, neutralized to pH 7 with concentrated HCl, diluted with EtOH, and then extracted with EtOAc. The combined organic layers were washed with brine, dried ($Na_2SO_4$), filtered and concentrated in vacuo to afford the desired compound (15.75 g, 63%) as a colourless solid.

6-Bromo-2H-phthalazin-1-one

A mixture of 5-bromo-3-hydroxy-2,3-dihydro-isoindol-1-one (15.75 g, 69.06 mmol) and hydrazine hydrate (70 mL, 1439.2 mmol) was heated at 95° C. for 5 h. The precipitate was filtered, washed with water and the crude material triturated with hot EtOAc to afford the product (7.25 g, 46.6%) as a yellow solid.

6-Bromo-1-chloro-phthalazine

A mixture of 6-Bromo-2H-phthalazin-1-one (2.5 g), phosphorous oxychloride (11 mL) and diisopropyl ethyl amine (2 mL) was stirred at RT for 30 min then at 90° C. for 3 h. The reaction was then concentrated under reduced pressure, diluted with ethyl acetate and washed with a saturated solution of $NaHCO_3$, $NH_4Cl$, and brine to afford the desired compound (2.0 g). TLC Rf 0.8 (EA/hexane 2/3).

(6-Bromo-phthalazin-1-yl)-dimethyl-amine

A solution of 6-bromo-1-chloro-phthalazine (2 g) and dimethylamino (8 mL, 2M solution in THF) in DMF (30 mL) was stirred at 85° C. for 3 h. The reaction was then diluted with ethyl acetate (100 mL) and washed with water (2×100 mL), and brine (100 mL). Column chromatography (Hexanes/EtOAc) afforded the desired product (1.0 g) as a brown solid. TLC Rf 0.3 (EA). $^1$H-NMR ($CDCl_3$) δ: 3.21 (s, 6H), 7.86 (dd, 1H), 7.95 (d, 1H), 7.99 (d, 1H), 8.99 (s, 1H).

Dimethyl-(6-vinyl-phthalazin-1-yl)-amine

A mixture of (6-bromo-phthalazin-1-yl)-dimethyl-amine (0.32 g, 1.27 mmol) and toluene (8 mL) was purged with $N_2$. $Pd(PPh_3)_4$ (0.4 g, 0.346 mmol) and tributyl vinyl stannane (1.11 mL, 3.80 mmol) were added and the reaction heated to 85° C. for 4 h. The reaction was cooled, filtered through celite and rinsed with $CH_2Cl_2$. The organic layers were washed with water, brine, dried ($Na_2SO_4$) and concentrated. Column chromatography (Hexanes/EtOAc) afforded the desired product (0.15 g, 59.3%) as a white solid.

1-Dimethylamino-phthalazine-6-carbaldehyde

A mixture of dimethyl-(6-vinyl-phthalazin-1-yl)-amine (0.15 g, 0.753 mmol), water (0.1 mL), THF (2.6 mL) and $OsO_4$ (catalytic) were stirred at room temperature.
Sodium periodate (0.497 g, 2.32 mmol) was added to the reaction in 3 portions and the reaction stirred at room temperature for 14 h. The reaction mixture was diluted with EtOAc, washed with water, aq. $Na_2S_2O_3$, brine, dried ($Na_2SO_4$) and concentrated. Chromatography (40% Hexanes/EtOAc to 100% EtOAc to 10% MeOH/EtOAc) afforded the product (50 mg, 33.3%) was a coloured solid.

Dimethyl-(6-phenylaminomethyl-phthalazin-1-yl)-amine

A mixture of 1-dimethylamino-phthalazine-6-carbaldehyde (25 mg, 0.13 mmol), aniline (14 μL, 0.15 mmol), THF (1 mL) and $MgSO_4$ (43 mg, 0.357 mmol) were stirred at room temperature. To this mixture was added acetic acid (8 μL) followed by sodium cyanoborohydride (13 mg, 0.207 mmol) and the reaction stirred for 15 h. The reaction was diluted with $CH_2Cl_2$, washed with aq. $NaHCO_3$, dried ($Na_2SO_4$) and concentrated. Purification by prep. HPLC yielded the desired compound. m/z 279.22 (M+1).

Examples 26 and 27

Synthesis of 4-Chloro-1-hydroxy-phthalazine-6-carboxylic acid (3-trifluoromethyl-phenyl)-amide and 1-Chloro-4-hydroxy-phthalazine-6-carboxylic acid (3-trifluoromethyl-phenyl)-amide

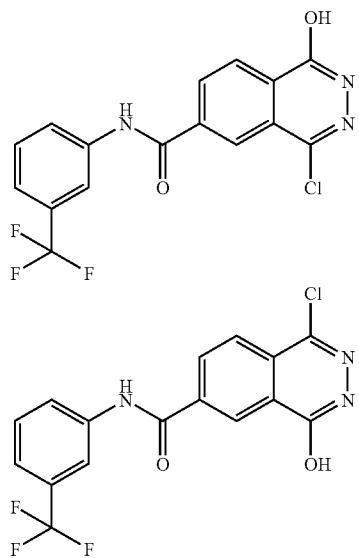

A mixture of 1,4-dichloro-phthalazine-6-carboxylic acid (3-trifluoromethyl-phenyl)-amide (0.304 mg, 0.787 mmol), 2N NaOH (4 mL, 8.00 mmol) and dioxane (6 mL) was stirred at 45° C. for 6 h. The reaction mixture was diluted with water, acidified with conc. HCl to ~pH 4 and extracted with EtOAc (×3). The combined organic phase was washed with brine, dried ($Na_2SO_4$) and concentrated to afforded 4-chloro-1-hydroxy-phthalazine-6-carboxylic acid (3-trifluoromethyl-phenyl)-amide (0.112 g) as a white solid, $^1$H NMR (600 MHz, $CDCl_3$) δ: 7.33 (d, 1H), 7.43 (t, 1H), 8.03 (s, 1H), 8.06 (d, 1H), 8.36 (dd, 1H), 8.42 (d, 1H), 8.56 (s, 1H), 10.28 (s, 1H), 11.9 (s, 1H) ppm, $^1$H NMR (500 MHz, $d_6$-DMSO) δ: 7.52 (d, 1H), 7.65 (t, 1H), 8.08 (d, 1H), 8.26 (s, 1H), 8.43 (d, 1H), 8.47 (dd, 1H), 8.52 (s, 1H), 11.02 (s, 1H), 13.02 (s, 1H) ppm. m/z 368.13; and 1-chloro-4-hydroxy-phthalazine-6-carboxylic acid (3-trifluoromethyl-phenyl)-amide (0.083 g) as a white solid, $^1$H NMR (500 MHz, $CDCl_3$) δ: 7.21 (d, 1H), 7.32 (t, 1H), 7.92 (d, 1H), 7.97 (d, 1H), 8.00 (s, 1H), 8.38 (d, 1H), 8.93 (s, 1H), 10.42 (s, 1H), 12.20 (s, 1H) ppm. m/z 368.13.

Examples 28 and 29

Synthesis of 1-chloro-4-hydroxy-phthalazine-6-carboxylic acid (4-trifluoromethyl-phenyl) amide and 4-chloro-1-hydroxy-phthalazine-6-carboxylic acid (4-trifluoromethyl-phenyl) amide

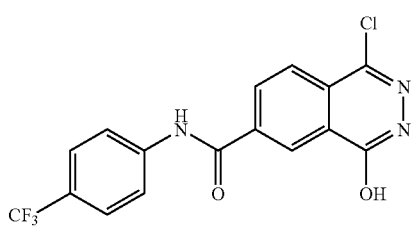

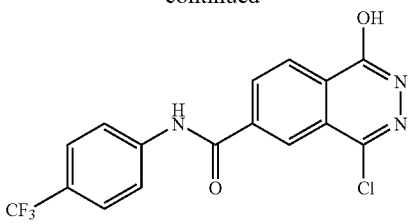

A mixture of 1,4-dihydroxy-phthalazine-6-carboxylic acid (0.6 g, 2.91 mmol) in thionyl chloride (6 mL) was refluxed for 3 hours. Phosphorous oxychloride (6 mL) was added and the reaction refluxed for an additional 15 hours. The solution was concentrated under vacuum and treated 3 times with toluene in order to remove the excess thionyl chloride. The crude residue was dissolved in DMF (5 mL) and added dropwise to a 0° C. solution of 4-(trifluoromethyl)aniline (0.54 mL, 4.34 mmol), DMF (5 mL) and $NEt_3$ (1.21 mL, 8.68 mmol). The reaction was stirred at 0° C. for 1 h, diluted with water and extracted with $CH_2Cl_2$. The combined organic layers were washed with water (×3), sat. aq. $NH_4Cl$, brine and dried ($Na_2SO_4$). Column chromatography (Hex/EtOAc) afforded 1,4-dichloro-phthalazine-6-carboxylic acid (4-trifluoromethyl) amide (0.22 g). m/z 386.06.

A mixture of 1,4-dichloro-phthalazine-6-carboxylic acid (4-trifluoromethyl) amide (0.22 g, 0.57 mmol), 2N NaOH (2.8 mL, 5.70 mmol) and dioxane (10 mL) was heated to 50° C. for 16 hours. The reaction was diluted with water, acidified with conc. HCl to ~pH 4 and extracted with EtOAc (×3). The combined organic phase was washed with brine, dried ($Na_2SO_4$) and concentrated. Chromatography (Hex/EtOAc) afforded 1-chloro-4-hydroxy-phthalazine-6-carboxylic acid (4-trifluoromethyl-phenyl) amide (7.6 mg) as a white solid, $^1$H NMR (500 MHz, $CDCl_3$) δ: 7.28 (d, 2H), 7.70 (d, 2H), 7.78 (d, 1H), 8.21 (dd, 1H), 8.75 (s, 1H), 10.40 (s, 1H), 12.35 (s, 1H) ppm. m/z 368.19; and 4-chloro-1-hydroxy-phthalazine-6-carboxylic acid (4-trifluoromethyl-phenyl) amide (46.86 mg) as a white solid, $^1$H NMR (600 MHz, $CDCl_3$) δ: 7.42 (d, 2H), 7.80 (d, 2H), 8.22 (dd, 1H), 8.29 (d, 1H), 8.41 (s, 1H), 10.37 (s, 1H), 12.37 (s, 1H) ppm. m/z 368.06.

Examples 30 and 31

Synthesis of 1-Chloro-4-hydroxy-phthalazine-6-carboxylic acid phenylamide and 4-Chloro-1-hydroxy-phthalazine-6-carboxylic acid phenylamide

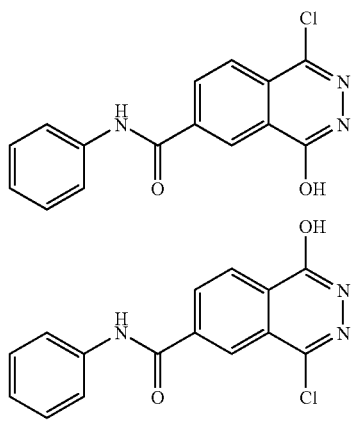

The experimental procedure for Examples 30 and 31 is analogous to the procedure for Examples 28 and 29. In preparing Examples 30 and 31, aniline rather than 4-(trifluoromethyl)aniline was used to form the desired amide. Accordingly, the following two compounds were obtained, which were separated by HPLC: 1-chloro-4-hydroxy-phthalazine- 6-carboxylic acid phenylamide (2.13 mg), m/z 300.22; and 4-chloro-1-hydroxy-phthalazine-6-carboxylic acid phenylamide (3.36 mg) ¹H NMR (500 MHz, CDCl₃) δ: 7.06 (t, 1H), 7.25 (d, 2H), 7.59 (d, 2H), 8.24 (dd, 1H), 8.35 (d, 1H), 8.46 (s, 1H) ppm. m/z 300.28.

Examples 32 and 33

Synthesis of 1-chloro-4-hydroxy-phthalazine-6-carboxylic acid (2-methyl-3-trifluoromethyl-phenyl) amide and 4-chloro-1-hydroxy-phthalazine-6-carboxylic acid (2-methyl-3-trifluoromethyl-phenyl) amide

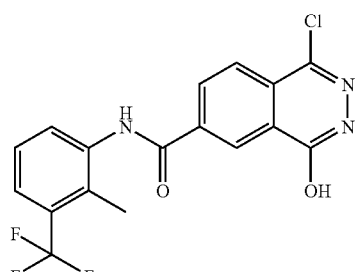

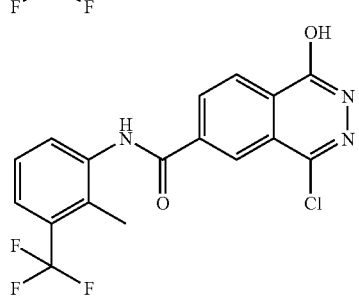

The experimental procedure for Examples 32 and 33 is analogous to the procedure for Examples 28 and 29. In preparing Examples 32 and 33, 2-methyl-3-(trifluoromethyl) aniline rather than 4-(trifluoromethyl)aniline was used to form the desired amide. Accordingly, the following two compounds were obtained: 1-chloro-4-hydroxy-phthalazine-6-carboxylic acid (2-methyl-3-trifluoromethyl-phenyl) amide (17 mg), ¹H NMR (400 MHz, CDCl₃) δ: 2.30 (s, 3H), 7.21 (t, 1H), 7.44 (d, 1H), 7.53 (d, 1H), 7.97 (d, 1H), 8.41 (dd, 1H), 8.94 (s, 1H), 9.84 (s, 1H), 12.15 (s, 1H) ppm. m/z 382.04; and 4-chloro-1-hydroxy-phthalazine-6-carboxylic acid (2-methyl-3-trifluoromethyl-phenyl) amide (50 mg), m/z 382.04.

Examples 34 and 35

Synthesis of 1-chloro-4-hydroxy-phthalazine-6-carboxylic acid (2,5-difluoro-phenyl) amide and 4-chloro-1-hydroxy-phthalazine-6-carboxylic acid (2,5-difluoro-phenyl) amide

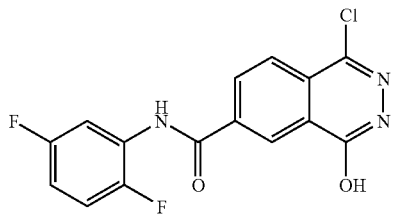

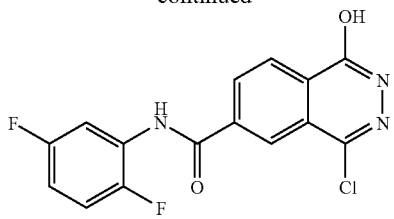

The experimental procedure for Examples 34 and 35 is analogous to the procedure for Examples 28 and 29. In preparing Examples 34 and 35, 2,5-difluoroaniline rather than 4-(trifluoromethyl) aniline was used to form the desired amide. Accordingly, the following two compounds were obtained: 1-chloro-4-hydroxy-phthalazine-6-carboxylic acid (2,5-difluoro-phenyl) amide (9 mg), ¹H NMR (500 MHz, CDCl₃) δ: 6.70-6.76 (m, 1H), 6.94-7.01 (m, 1H), 7.76-7.82 (m, 1H), 7.96 (d, 1H), 8.35 (dd, 1H), 8.83 (s, 1H), 9.75 (s, 1H), 12.34 (s, 1H) ppm. m/z 336.08; and 4-chloro-1-hydroxy-phthalazine-6-carboxylic acid (2,5-difluoro-phenyl-phenyl) amide (9 mg), ¹H NMR (500 MHz, CDCl₃) δ: 6.70-6.76 (m, 1H), 6.94-67.02 (m, 1H), 7.75-7.82 (m, 1H), 8.23 (dd, 1H), 8.35 (d, 1H), 8.43 (s, 1H), 9.60 (s, 1H), 12.36 (s, 1H) ppm. m/z 336.15.

Examples 36 and 37

Synthesis of 1-chloro-4-hydroxy-phthalazine-6-carboxylic acid (2-fluoro-5-trifluoromethyl-phenyl) amide and 4-chloro-1-hydroxy-phthalazine-6-carboxylic acid (2-fluoro-5-trifluoromethyl-phenyl) amide

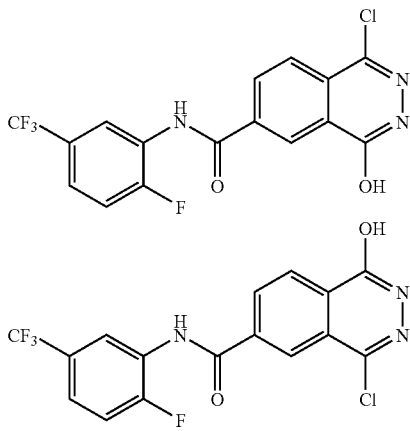

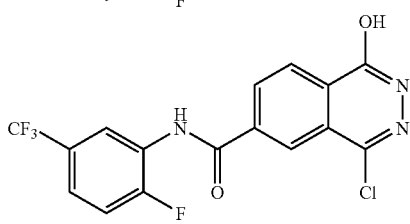

The experimental procedure for Examples 36 and 37 is analogous to the procedure for Examples 28 and 29. In preparing Examples 36 and 37, 2-fluoro-5-(trifluoromethyl) aniline rather than 4-(trifluoromethyl) aniline was used to form the desired amide. Accordingly, the following two compounds were obtained: 1-chloro-4-hydroxy-phthalazine-6-carboxylic acid (2-fluoro-5-trifluoromethyl-phenyl) amide (18 mg), ¹H NMR (500 MHz, CDCl₃) δ: 7.18 (t, 1H), 7.32-7.37 (m, 1H), 8.00 (d, 1H), 8.28 (d, 1H), 8.41 (dd, 1H), 8.90 (s, 1H), 9.81 (s, 1H), 12.27 (s, 1H) ppm. m/z 386.06; and 4-chloro-1-hydroxy-phthalazine-6-carboxylic acid (2-fluoro-5-trifluoromethyl-phenyl) amide (11 mg) ¹H NMR (500 MHz, CDCl₃) δ: 7.24 (t, 1H), 7.39-7.44 (m, 1H), 8.32

(dd, 1H), 8.41 (d, 1H), 8.46 (d, 1H), 8.54 (s, 1H), 9.60 (s, 1H), 12.10 (s, 1H) ppm. m/z 386.06.

Examples 38 and 39

Synthesis of 1-chloro-4-hydroxy-phthalazine-6-carboxylic acid (2-fluoro-5-methyl-phenyl) amide and 4-chloro-1-hydroxy-phthalazine-6-carboxylic acid (2-fluoro-5-methyl-phenyl) amide

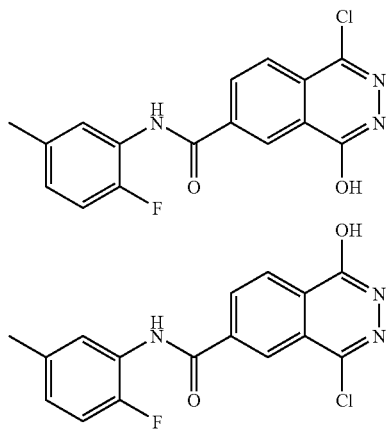

The experimental procedure for Examples 38 and 39 is analogous to the procedure for Examples 28 and 29. In preparing Examples 38 and 39, 2-fluoro-5-methylaniline rather than 4-(trifluoromethyl) aniline was used to form the desired amide. Accordingly, the following two compounds were obtained: 1-chloro-4-hydroxy-phthalazine-6-carboxylic acid (2-fluoro-5-methyl-phenyl) amide (8 mg), $^1$H NMR (500 MHz, CDCl$_3$) δ: 2.22 (s, 3H), 6.80-6.85 (m, 1H), 6.88-6.92 (m, 1H), 7.73 (d, 1H), 7.96 (d, 1H), 8.37 (dd, 1H), 8.83 (d, 1H), 9.28 (s, 1H), 12.30 (s, 1H) ppm. m/z 332.05; and 4-chloro-1-hydroxy-phthalazine-6-carboxylic acid (2-fluoro-5-methyl-phenyl) amide (15 mg) $^1$H NMR (500 MHz, CDCl$_3$) δ: 2.41 (s, 3H), 6.95-7.00 (m, 1H), 7.05-7.10 (m, 1H), 8.11 (s, 1H), 8.26-8.33 (m, 2H), 8.53 (s, 1H), 8.60 (d, 1H), 9.92 (s, 1H) ppm. m/z 332.05.

Example 40

Synthesis of 4-Chloro-1-hydroxy-phthalazine-6-carboxylic acid (3-trifluoromethyl-phenyl)-amide sodium salt

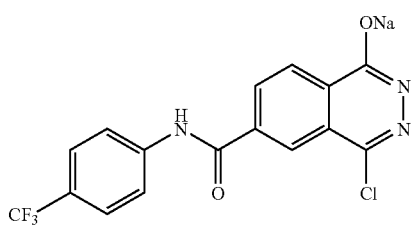

A mixture of 4-chloro-1-hydroxy-phthalazine-6-carboxylic acid (3-trifluoromethyl-phenyl)-amide (38 mg, 0.103 mmol) and THF was stirred at room temperature. 60% NaH (4 mg, 0.172 mmol) was added and the reaction stirred for 30 minutes (solids appeared). The reaction was concentrated to afford 4-chloro-1-hydroxy-phthalazine-6-carboxylic acid (3-trifluoromethyl-phenyl)-amide sodium salt (39 mg), $^1$H NMR (500 MHz, d$_6$-DMSO) δ: 7.45 (d, 1H), 7.60 (t, 1H), 8.06 (d, 1H), 8.26 (s, 1H), 8.29 (d, 1H), 8.35 (dd, 1H), 8.42 (s, 1H), 11.75 (bs, 1H) ppm.

Example 41 and 42

Synthesis of 1-Iodo-4-hydroxy-phthalazine-6-carboxylic acid (3-trifluoromethyl-phenyl)-amide and 4-Iodo-1-hydroxy-phthalazine-6-carboxylic acid (3-trifluoromethyl-phenyl)-amide

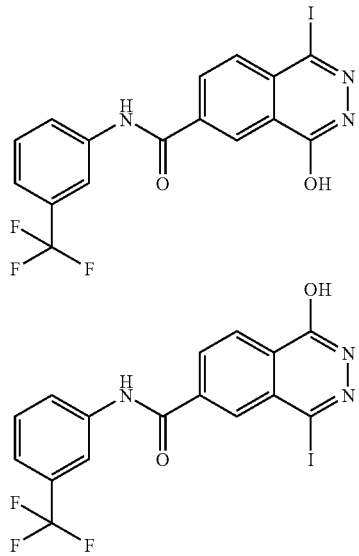

A mixture of 1,4-di-iodo-phthalazine-6-carboxylic acid (3-trifluoromethyl-phenyl)-amide (0.15 g, 0.264 mmol), 2N NaOH (1.32 mL, 2.64 mmol) and dioxane (3 mL) was stirred at 50° C. for 16 h. The reaction mixture was diluted with water, acidified with conc. HCl to ~pH 4 and extracted with EtOAc (×3). The combined organic phase was washed with brine, dried (Na$_2$SO$_4$) and concentrated to afford 1-iodo-4-hydroxy-phthalazine-6-carboxylic acid (3-trifluoromethyl-phenyl)-amide (27 mg), $^1$H NMR (600 MHz, CDCl$_3$) δ: 7.20 (d, 1H), 7.31 (t, 1H), 7.72 (d, 1H), 7.96 (d, 1H), 8.00 (s, 1H), 8.33 (dd, 1H), 8.86 (s, 1H), 10.40 (s, 1H), 12.39 (s, 1H) ppm. m/z 460.07; and 4-iodo-1-hydroxy-phthalazine-6-carboxylic acid (3-trifluoromethyl-phenyl)-amide (27 mg), $^1$H NMR (500 MHz, CDCl$_3$) δ: 7.27 (d, 1H), 7.38 (t, 1H), 8.00 (m, 2H), 8.24 (m, 2H), 8.30 (d, 1H), 10.32 (s, 1H), 12.34 (s, 1H) ppm. m/z 460.07.

Example 43

Synthesis of 1-Hydroxy-phthalazine-6-carboxylic acid (3-trifluoromethyl-phenyl)-amide

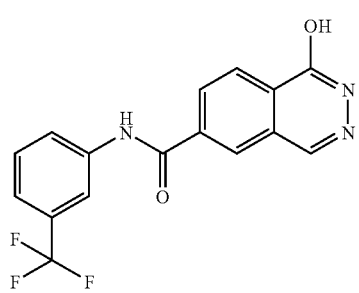

A mixture of 4-chloro-1-hydroxy-phthalazine-6-carboxylic acid (3-trifluoromethyl-phenyl)-amide (64 mg, 0.174 mmol) (example 25), MeOH (3 mL) and 10% wet Pd/C (catalytic) was evacuated and flushed (3×) with hydrogen. The mixture was stirred under hydrogen for 16 h. The mixture was filtered through celite, rinsed with MeOH and concentrated under vacuum. Chromatography (Hex/EtOAc) was used to obtain 1-hydroxy-phthalazine-6-carboxylic acid (3-trifluoromethyl-phenyl)-amide (20 mg) as a white solid. $^1$H NMR (400 MHz, CDCl$_3$) δ: 7.35 (d, 1H), 7.45 (t, 1H), 8.03 (s, 1H), 8.08 (d, 1H), 8.19 (s, 1H), 8.30-8.37 (m, 2H), 8.44 (d, 1H), 10.05 (s, 1H), 11.26 (s, 1H) ppm. m/z 334.10.

Example 44

Synthesis of 1-hydroxy-4-phenyl-phthalazine-6-carboxylic acid (3-trifluoromethyl-phenyl)-amide

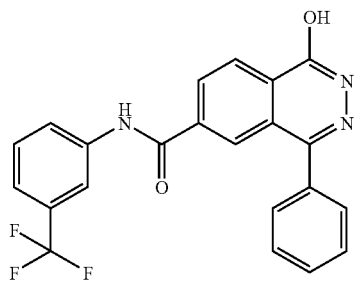

1-iodo-4-methoxy-phthalazine-6-carboxylic acid (3-trifluoromethyl-phenyl)-amide and 4-iodo-1-methoxy-phthalazine-6-carboxylic acid (3-trifluoromethyl-phenyl)-amide A mixture of 1,4-di-iodo-phthalazine-6-carboxylic acid (3-trifluoromethyl-phenyl)-amide (0.59 g, 1.037 mmol), sodium methoxide (0.11 g, 2.036 mmol) in DMF (8 mL) was stirred at room temperature for 18 hours. The reaction was poured onto water, neutralized with 2N HCl. The product was extracted with EtOAc (×3), the combined organic extracts washed with water (×3), brine and dried (Na$_2$SO$_4$). Chromatography (Hex/EtOAc) afforded 1-iodo-4-methoxy-phthalazine-6-carboxylic acid (3-trifluoromethyl-phenyl)-amide (134 mg), m/z 473.91; and 4-iodo-1-methoxy-phthalazine-6-carboxylic acid (3-trifluoromethyl-phenyl)-amide (132 mg), m/z 473.91.

1-methoxy-4-phenyl-phthalazine-6-carboxylic acid (3-trifluoromethyl-phenyl)-amide A mixture of 4-iodo-1-methoxy-phthalazine-6-carboxylic acid (3-trifluoromethyl-phenyl)-amide (0.123 g, 0.26 mmol), K$_2$CO$_3$ (0.072 g, 0.52 mmol), water (0.5 mL), toluene (3 mL), methanol (3 mL), phenylboronic acid (0.035 g, 0.286 mmol), Pd(PPh$_3$)$_4$ (0.09 g, 0.078 mmol) was heated to 65° C. for 1 hour. The reaction was cooled, filtered through celite, rinsed with methanol and concentrated. The residue was taken up in EtOAc, washed with sat. aq. NaHCO$_3$ and dried (Na$_2$SO$_4$). Chromatography (Hex/EtOAc) afforded 1-methoxy-4-phenyl-phthalazine-6-carboxylic acid (3-trifluoromethyl-phenyl)-amide (89 mg), m/z 424.05.

1-hydroxy-4-phenyl-phthalazine-6-carboxylic acid (3-trifluoromethyl-phenyl)-amide A mixture of 1-methoxy-4-phenyl-phthalazine-6-carboxylic acid (3-trifluoromethyl-phenyl)-amide (80 mg, 0.189 mmol), dioxane (2 mL) and 48% HBr (4 mL) was stirred at 40° C. for 48 hours. Concentration followed by chromatography (Hex/EtOAc) afforded 1-hydroxy-4-phenyl-phthalazine-6-carboxylic acid (3-trifluoromethyl-phenyl)-amide (12 mg) as a white solid, 1H (500 MHz, CDCl$_3$, 55° C.) δ: 7.47 (d, 1H), 7.52 (t, 1H), 7.56-7.65 (m, 5H), 7.84 (d, 1H), 7.90-7.96 (m, 2H), 8.21 (d, 1H), 8.29 (s, 1H), 8.65 (d, 1H), 10.40 (s, 1H) ppm. m/z 410.00.

Example 45

Synthesis of 1-hydroxy-4-pyridin-2-yl-phthalazine-6-carboxylic acid (3-trifluoromethyl-phenyl)-amide

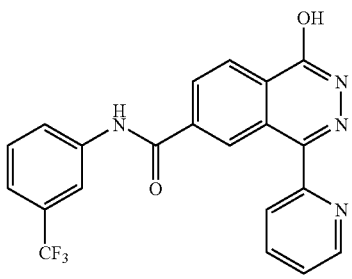

1-methoxy-4-pyridin-2-yl-phthalazine-6-carboxylic acid (3-trifluoromethyl-phenyl)-amide A mixture of 4-iodo-1-methoxy-phthalazine-6-carboxylic acid (3-trifluoromethyl-phenyl)-amide (0.128 g, 0.27 mmol), K$_2$CO$_3$ (0.075 g, 0.54 mmol), water (0.5 mL), toluene (3 mL), methanol (3 mL), 3-pyridineboronic acid (0.04 g, 0.325 mmol), Pd(PPh$_3$)$_4$ (0.094 g, 0.081 mmol) was heated to 65° C. for 2 hour. The reaction was cooled, filtered through celite, rinsed with methanol and concentrated. The residue was taken up in EtOAc, washed with sat. aq. NaHCO$_3$ and dried (Na$_2$SO$_4$). Column chromatography (Hex/EtOAc) afforded 1-methoxy-4-pyridin-2-yl-phthalazine-6-carboxylic acid (3-trifluoromethyl-phenyl)-amide (57 mg), m/z 425.01

1-hydroxy-4-pyridin-2-yl-phthalazine-6-carboxylic acid (3-trifluoromethyl-phenyl)-amide A mixture of 1-methoxy-4-pyridin-2-yl-phthalazine-6-carboxylic acid (3-trifluoromethyl-phenyl)-amide (57 mg, 0.134 mmol), dioxane (3 mL) and 48% HBr (4 mL) was stirred at 40° C. for 1.5 hours. Concentration followed by chromatography (Hex/EtOAc) afforded 1-hydroxy-4-pyridin-2-yl-phthalazine-6-carboxylic acid (3-trifluoromethyl-phenyl)-amide (56 mg) as a white solid, $^1$H NMR (400 MHz, 4:1 CDCl$_3$:d6-DMSO) δ: 7.27 (d, 1H), 7.36-7.44 (m, 2H), 7.90-7.95 (m, 2H), 8.05 (s, 1H), 8.21 (s, 1H), 8.33 (dd, 1H), 8.47 (d, 1H), 8.65 (dd, 1H), 8.81 (d, 1H), 10.50 (s, 1H), 12.80 (s, 1H) ppm. m/z 410.96.

Example 46 and 47

Synthesis of 4-hydroxy-1-methoxy-phthalazine-6-carboxylic acid (4-trifluoromethyl-pyridin-2-yl)-amide and 1-hydroxy-4-methoxy-phthalazine-6-carboxylic acid (4-trifluoromethyl-pyridin-2-yl)-amide

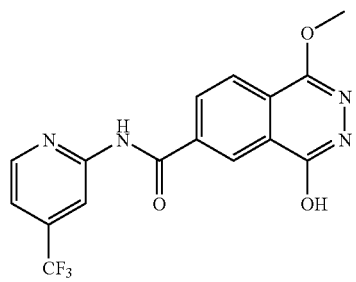

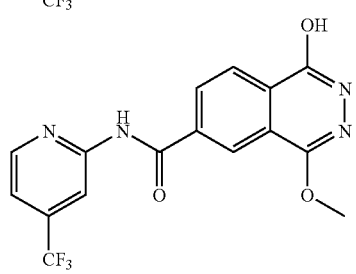

1,4-dichloro-phthalazine-6-carboxylic acid (4-trifluoromethyl-pyridin-2-yl)-amide A mixture of 1,4-dihydroxy-phthalazine-6-carboxylic acid (1.429 g, 6.931 mmol) in thionyl chloride (13 mL) was refluxed for 3 hours. Phosphorous oxychloride (13 mL) was added and the reaction refluxed for an additional 15 hours. The solution was concentrated under vacuum and treated 3 times with toluene in order to remove the excess thionyl chloride. The crude residue was dissolved in DMF (7 mL) and added dropwise to a 0° C. solution of 2-amino-4-(trifluoromethyl)pyridine (1.35 g, 7.00 mmol), DMF (4 mL) and NEt$_3$ (2.9 mL, 21.0 mmol). The reaction was stirred at 0° C. for 1 h, diluted with water and extracted with CH$_2$Cl$_2$. The combined organic layers were washed with water, sat. aq. NH$_4$Cl, brine and dried (Na$_2$SO$_4$). Column chromatography (Hex/EtOAc) afforded 1,4-dichloro-phthalazine-6-carboxylic acid (4-trifluoromethyl-pyridin-2-yl) amide (0.487 g, 18.1%). m/z 386.95.

1,4-dimethoxy-phthalazine-6-carboxylic acid (4-trifluoromethyl-pyridin-2-yl)-amide A mixture of 1,4-dichloro-phthalazine-6-carboxylic acid (4-trifluoromethyl-pyridin-2-yl) amide (0.487 g, 1.258 mmol), NaOMe (0.333 g, 6.164 mmol) and DMF (5 mL) was stirred at room temperature for 16 hours. The reaction was poured onto water, neutralized with 2N HCl and extracted into EtOAc (×3). The combined organic layer was washed with water, brine and dried (Na$_2$SO$_4$). Chromatography (Hex/EtOAc) afforded 1,4-dimethoxy-phthalazine-6-carboxylic acid (4-trifluoromethyl-pyridin-2-yl)-amide (0.24 g), m/z (M+1) 379.11.

4-hydroxy-1-methoxy-phthalazine-6-carboxylic acid (4-trifluoromethyl-pyridin-2-yl)-amide and 1-hydroxy-4-methoxy-phthalazine-6-carboxylic acid (4-trifluoromethyl-pyridin-2-yl)-amide A mixture of 1,4-dimethoxy-phthalazine-6-carboxylic acid (4-trifluoromethyl-pyridin-2-yl)-amide (0.24 g, 0.634 mmol), dioxane (3 mL) and 48% HBr (0.1 mL) was stirred at room temperature for 18 hours. The reaction was poured onto water, neutralized with 2N NaOH and extracted with EtOAc. The combined organic layers were washed with water, brine and dried (Na$_2$SO$_4$). Chromatography (Hex/EtOAc) afforded 4-hydroxy-1-methoxy-phthalazine-6-carboxylic acid (4-trifluoromethyl-pyridin-2-yl)-amide (5 mg), m/z (M+1) 379.11; and 1-hydroxy-4-methoxy-phthalazine-6-carboxylic acid (4-trifluoromethyl-pyridin-2-yl)-amide (16 mg), $^1$H NMR (600 MHz, CDCl$_3$) δ: 3.94 (s, 3H), 7.26 (d, 1H), 8.29 (dd, 1H), 8.41 (d, 1H), 8.46 (d, 1H), 8.50 (s, 1H), 8.62 (s, 1H), 9.75 (s, 1H), 10.53 (s, 1H) ppm. m/z 364.95.

Example 48 and 49

Synthesis of 6-{[(2,4-Dichlorophenyl)methyl]amino}-4-chloro-2H-phthalazin-1-one and 7-{[(2,4-dichlorophenyl)methyl]amino}-4-chloro-2H-phthalazin-1-one

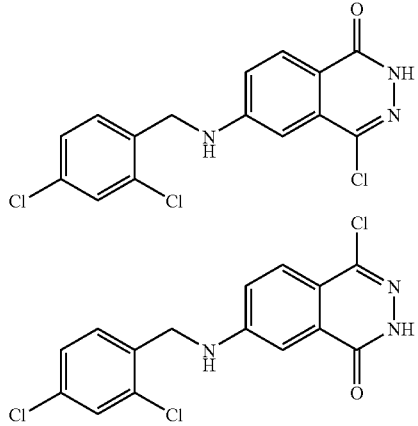

6-Bromo-2,3-dihydro-phthalazine-1,4-dione

A mixture of 5-Bromo-isobenzofuran-1,3-dione (6.0 g, 26.4 mmol) and hydrazine hydrate (1.51 mL, 32.4 mmol) in isopropanol (120 mL) was heated at reflux for 4 h. The mixture was allowed to cool and the precipitate was filtered and washed with water (50 mL). The filter cake was dried to afford the title compound (4.6 g, 72.3%) as a white solid. m/z (M+1)=241.05

Bromo-4-chloro-2H-phthalazin-1-one and 7-Bromo-4-chloro-2H-phthalazin-1-one

A mixture of 6-Bromo-2,3-dihydro-phthalazine-1,4-dione (4.6 g, 19.1 mmol) in SOCl$_2$ (50 mL) and POCl$_3$ (50 mL) was heated at reflux for 4 h. The mixture was allowed to cool and concentrated. The residue was taken up in EtOAc (100 mL) and neutralize with sodium bicarbonate. The layers were separated and the organic layer was dried over anhydrous sodium sulfate and concentrated. The residue was dissolved in dioxane (200 mL) and 2N NaOH (96 mL, 191 mmol). The mixture was heated at 40° C. for 2.5 h then allowed to cool and concentrated. The residue was triturated with EtOAc (300 mL) and water (200 mL) and the solids were filtered. The organic phase was dried over anhydrous sodium sulfate and concentrated to yield the title compounds (2.3 g, 46%); m/z (M+1)=259.32.

6-{[(2,4-Dichlorophenyl)methyl]amino}-4-chloro-2H-phthalazin-1-one and 7-{([(2,4-dichlorophenyl)methyl]amino}-4-chloro-2H-phthalazin-1-one A mixture 6-Bromo-4-chloro-2H-phthalazin-1-one and 7-Bromo-4-chloro-2H-phthalazin-1-one (50 mg, 0.58 mmol), (2,4-dichlorophenyl)methylamine (0.100 mL, 0.75 mmol), Pd$_2$(dba)$_3$ (53 mg, 0.058 mmol), rac-BINAP (108 mg, 0.17 mmol) and NaOt-Bu (164 mg, 1.74 mmol) in DMA (12 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compounds. 6-{[(2,4-Dichlorophenyl)methyl]amino}-4-chloro-2H-phthalazin-1-one: 33 mg (18.0%): m/z (M+H)=354. $^1$H-NMR (DMSO-d$_6$) δ: 12.4 (s, 1H), 7.96 (d, 1H), 7.68 (m, 2H), 7.42 (d, 2H), 7.15 (dd, 1H), 6.81 (s, 1H), 4.51 (d, 2H). 7-{[(2,4-Dichlorophenyl)methyl]amino}-4-chloro-2H-phthalazin-1-one: 16 mg (8.7%): m/z (M+H)=354. $^1$H-NMR (DMSO-d$_6$) δ: 12.45 (s, 1H), 7.72 (d, 1H), 7.66 (m, 2H), 7.41 (dd, 1H), 7.36 (m, 1H). 7.27 (dd, 1H), 7.13 (s, 1H), 4.49 (d, 2H).

Example 50 and 51

Synthesis of 6-{[(4-Chlorophenyl)methyl]amino}-4-chloro-2H-phthalazin-1-one and 7-{[(4-Chlorophenyl)methyl]amino}-4-chloro-2H-phthalazin-1-one

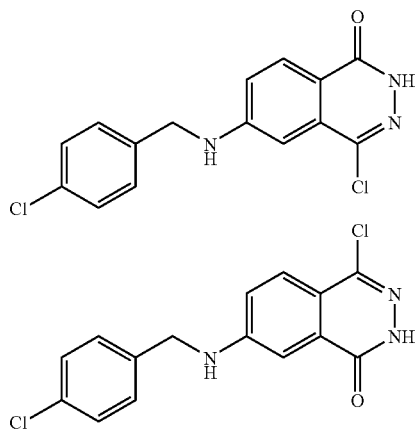

A mixture 6-bromo-4-chloro-2H-phthalazin-1-one and 7-Bromo-4-chloro-2H-phthalazin-1-one (150 mg, 0.58 mmol), (4-chlorophenyl)methylamine (0.092 mL, 0.75 mmol), Pd$_2$(dba)$_3$ (53 mg, 0.058 mmol), rac-BINAP (108 mg, 0.17 mmol) and NaOt-Bu (164 mg, 1.74 mmol) in DMA (12 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compounds. 6-{[(4-Chlorophenyl)methyl]amino}-4-chloro-2H-phthalazin-1-one: 38 mg (20.5%): m/z (M+H)=320. $^1$H-NMR (DMSO-d$_6$) δ: 12.36 (s, 1H), 7.94 (d, 1H), 7.68 (m, 1H), 7.41 (m, 4H), 7.15 (dd, 1H), 6.81 (s, 1H), 4.44 (d, 2H); and 7-{[(4-Chlorophenyl)methyl]amino}-4-chloro-2H-phthalazin-1-one: 21 mg (11.3%): m/z (M+H)=320. $^1$H-NMR (DMSO-d$_6$) δ: 12.4 (s, 1H), 7.68 (m, 2H), 7.39 (m, 4H), 7.26 (dd, 1H), 7.25 (s, 1H), 4.45 (d, 2H).

Example 52 and 53

Synthesis of 6-{[(3-Methoxyphenyl)methyl]amino}-4-chloro-2H-phthalazin-1-one and 7-{[(3-Methoxyphenyl)methyl]amino}-4-chloro-2H-phthalazin-1-one

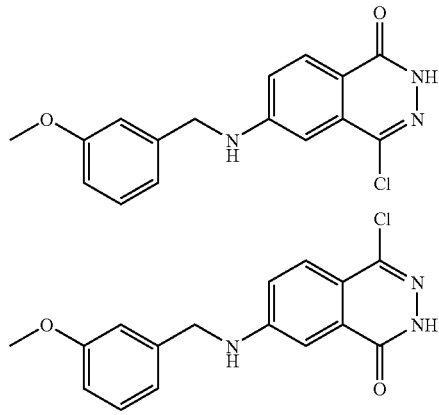

A mixture 6-bromo-4-chloro-2H-phthalazin-1-one and 7-Bromo-4-chloro-2H-phthalazin-1-one (150 mg, 0.58 mmol), (3-methoxyphenyl)methylamine (0.097 mL, 0.75 mmol), Pd$_2$(dba)$_3$ (53 mg, 0.058 mmol), rac-BINAP (108 mg, 0.17 mmol) and NaOt-Bu (164 mg, 1.74 mmol) in DMA (12 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compounds. 6-{[(3-Methoxyphenyl)methyl]amino}-4-chloro-2H-phthalazin-1-one: 46 mg (25.1%): m/z (M+H)=316. $^1$H-NMR (DMSO-d$_6$) δ: 12.34 (s, 1H), 7.93 (d, 1H), 7.65 (m, 1H), 7.26 (m, 1H), 7.16 (dd, 1H), 6.96 (m, 2H), 6.83 (m, 2H), 4.40 (d, 2H), 3.73 (s, 3H); and 7-{[(3-Methoxyphenyl)methyl]amino}-4-chloro-2H-phthalazin-1-one: 21 mg (11.5%): m/z (M+H)=316. $^1$H-NMR (DMSO-d$_6$) δ: 12.40 (s, 1H), 7.69 (d, 1H), 7.64 (m, 1H), 7.26 (m, 2H), 7.18 (s, 1H), 6.94 (m, 2H), 6.82 (dd, 1H), 4.42 (d, 2H), 3.72 (s, 3H).

Example 54 and 55

Synthesis of 6-{[(3,4-Difluorophenyl)methyl]amino}-4-chloro-2H-phthalazin-1-one and 7-{[(3,4-Difluorophenyl)methyl]amino}-4-chloro-2H-phthalazin-1-one

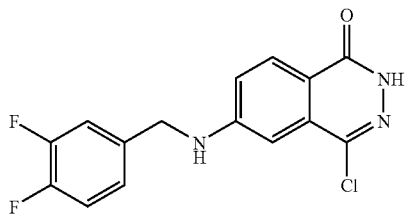

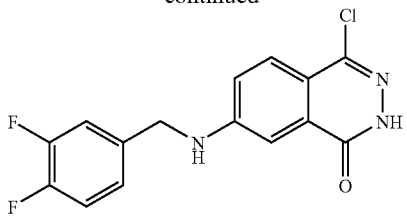

A mixture 6-bromo-4-chloro-2H-phthalazin-1-one and 7-Bromo-4-chloro-2H-phthalazin-1-one (150 mg, 0.58 mmol), (2,4-dichlorophenyl)methylamine (0.100 mL, 0.75 mmol), Pd$_2$(dba)$_3$ (53 mg, 0.058 mmol), rac-BINAP (108 mg, 0.17 mmol) and NaOt-Bu (164 mg, 1.74 mmol) in DMA (12 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compounds. 6-{[(3,4-Difluorophenyl)methyl]amino}-4-chloro-2H-phthalazin-1-one: 37 mg (19.8%): m/z (M+H)=322. $^1$H-NMR (DMSO-d$_6$) δ: 12.38 (s, 1H), 7.95 (d, 1H), 7.66 (m, 1H), 7.42 (m, 2H), 7.24 (m, 1H), 7.16 (dd, 1H) 6.82 (s, 1H), 4.44 (d, 2H); and 7-{[(3,4-Difluorophenyl)methyl]amino}-4-chloro-2H-phthalazin-1-one: 27 mg (14.5%): m/z (M+H)=322. $^1$H-NMR (DMSO-d$_6$) δ: 12.41 (s, 1H), 7.70 (d, 1H), 7.65 (m, 1H), 7.41 (m, 2H), 7.27 (dd, 1H), 7.21 (m, 1H), 7.16 (s, 1H), 4.45 (d, 2H).

Example 56 and 57

Synthesis of 6-{[(3-Methylphenyl)methyl]amino}-4-chloro-2H-phthalazin-1-one and 7-{[(3-Methylphenyl)methyl]amino}-4-chloro-2H-phthalazin-1-one

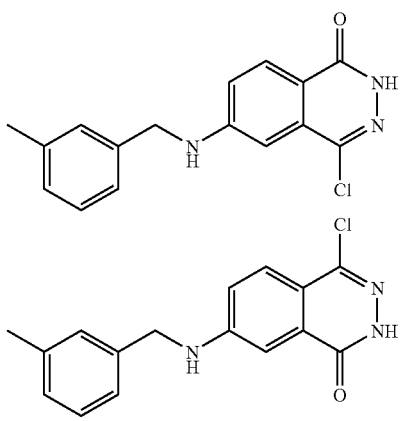

A mixture 6-bromo-4-chloro-2H-phthalazin-1-one and 7-Bromo-4-chloro-2H-phthalazin-1-one (150 mg, 0.58 mmol), (3-methylphenyl)methylamine (0.094 mL, 0.75 mmol), Pd$_2$(dba)$_3$ (53 mg, 0.058 mmol), rac-BINAP (108 mg, 0.17 mmol) and NaOt-Bu (164 mg, 1.74 mmol) in DMA (12 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compounds. 6-{[(3-Methylphenyl)methyl]amino}-4-chloro-2H-phthalazin-1-one: 23 mg (13.2%): m/z (M+H)=300. $^1$H-NMR (DMSO-d$_6$) δ: 12.34 (s, 1H), 7.92 (d, 1H), 7.64 (m, 1H), 7.20 (m, 5H), 6.84 (s, 1H), 4.40 (d, 2H), 2.90 (s, 3H); and 7-{[(3-Methylphenyl)methyl]amino}-4-chloro-2H-phthalazin-1-one: 35 mg (20.1%): m/z (M+H)=300. $^1$H-NMR (DMSO-d$_6$) δ: 12.40 (s, 1H), 7.68 (d, 1H), 7.62 (m, 1H), 7.26 (dd, 1H), 7.20 (m, 4H), 7.06 (m, 1H), 4.40 (d, 2H), 2.28 (s, 3H).

Example 58 and 59

Synthesis of 6-{[(2-Methoxyphenyl)methyl]amino}-4-chloro-2H-phthalazin-1-one and 7-{[(2-Methoxyphenyl)methyl]amino}-4-chloro-2H-phthalazin-1-one

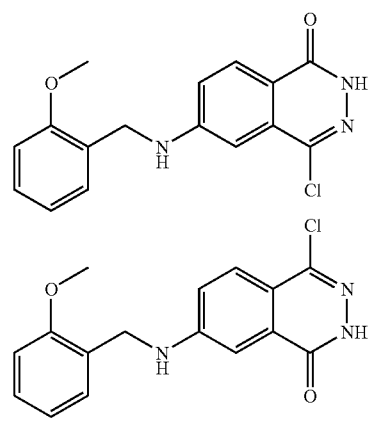

A mixture 6-bromo-4-chloro-2H-phthalazin-1-one and 7-Bromo-4-chloro-2H-phthalazin-1-one (150 mg, 0.58 mmol), (2-methoxyphenyl)methylamine (0.097 mL, 0.75 mmol), Pd$_2$(dba)$_3$ (53 mg, 0.058 mmol), rac-BINAP (108 mg, 0.17 mmol) and NaOt-Bu (164 mg, 1.74 mmol) in DMA (12 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compounds. 6-{[(2-Methoxyphenyl)methyl]amino}-4-chloro-2H-phthalazin-1-one: 26 mg (14.2%): m/z (M+H)=316. $^1$H-NMR (DMSO-d$_6$) δ: 12.24 (s, 1H), 7.92 (dd, 1H), 7.52 (m, 1H), 7.26 (m, 2H), 7.14 (dd, 1H), 7.04 (d, 1H), 6.91 (m, 1H), 6.83 (s, 1H), 4.37 (d, 2H), 3.86 (s, 3H); and 7-{[(2-Methoxyphenyl)methyl]amino}-4-chloro-2H-phthalazin-1-one: 35 mg (19.1%): m/z (M+H)=316. $^1$H-NMR (DMSO-d$_6$) δ: 12.40 (s, 1H), 7.68 (d, 1H), 7.50 (m, 1H), 7.26 (m, 2H), 7.20 (dd, 1H), 7.14 (s, 1H), 7.04 (d, 1H), 6.89 (m, 1H), 4.39 (d, 2H), 3.86 (s, 3H).

Example 60

Synthesis of 6-(4-Methoxy-benzylamino)-2H-phthalazin-1-one

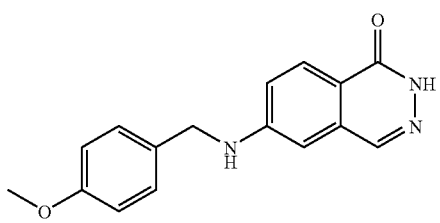

A mixture of 6-bromo-2H-phthalazin-1-one (50 mg, 0.22 mmol), 4-methoxybenzylamine (0.030 mL, 0.24 mmol), Pd$_2$(dba)$_3$ (20 mg, 0.022 mmol), rac-BINAP (41 mg, 0.066 mmol) and NaOt-Bu (52 mg, 0.55 mmol) in toluene (10 mL) was heated at reflux for 3 h. The mixture was allowed to cool, diluted with EtOAc (25 mL) and washed with NaHCO$_3$ (25 mL). The organic layer was dried over anhydrous sodium sulfate and concentrated. Chromatography on silica (EtOAc/hexanes) yielded the title compound (22 mg, 35%). $^1$H-NMR (DMSO-d$_6$) δ: 12.1 (s, 1H), 8.05 (s, 1H), 7.88 (d, 1H), 7.30 (m, 3H), 7.10 (dd, 1H), 6.90 (d, 2H), 6.75 (s, 1H), 4.20 (d, 2H), 3.85 (s, 3H); m/z (M+1)=282.22.

Example 61 and 62

Synthesis of 6-Benzylamino-4-chloro-2H-phthalazin-1-one and 7-Benzylamino-4-chloro-2H-phthalazin-1-one

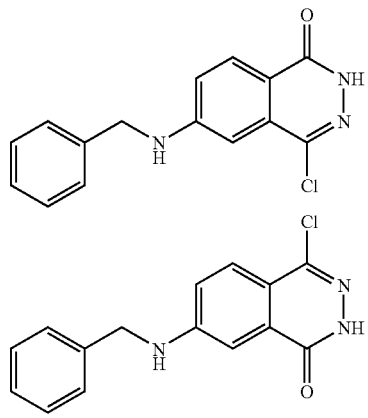

A mixture 6-bromo-4-chloro-2H-phthalazin-1-one and 7-bromo-4-chloro-2H-phthalazin-1-one (100 mg, 0.39 mmol), benzylamine (0.055 mL, 0.50 mmol), Pd$_2$(dba)$_3$ (36 mg, 0.039 mmol), rac-BINAP (73 mg, 0.12 mmol) and NaOt-Bu (110 mg, 1.17 mmol) in toluene (10 mL) was heated at reflux for 3 h. The mixture was allowed to cool, diluted with EtOAc (25 mL) and washed with NaHCO$_3$ (25 mL). The organic layer was dried over anhydrous sodium sulfate and concentrated. Chromatography on silica (EtOAc/hexanes) yielded the title compounds. 6-Benzylamino-4-chloro-2H-phthalazin-1-one. $^1$H-NMR (DMSO-d$_6$) δ: 12.32 (s, 1H), 7.90 (d, 1H), 7.65 (t, 1H), 7.35 (m, 4H), 7.24 (m, 1H), 7.14 (dd, 1H), 6.81 (s, 1H), 4.41 (d, 2H); 7-Benzylamino-4-chloro-2H-phthalazin-1-one. $^1$H-NMR (DMSO-d$_6$) δ: 12.38 (s, 1H), 7.65 (m, 2H), 7.32 (m, 4H), 7.23 (m, 2H), 7.25 (m, 1H), 3.91 (d, 2H).

Example 63 and 64

Synthesis of 4-Chloro-6-(3-trifluoromethyl-phenylamino)-2H-phthalazin-1-one and 4-Chloro-7-(3-trifluoromethyl-phenylamino)-2H-phthalazin-1-one

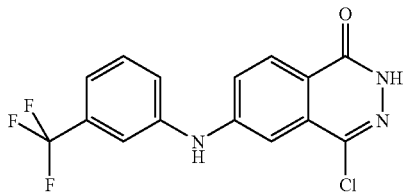

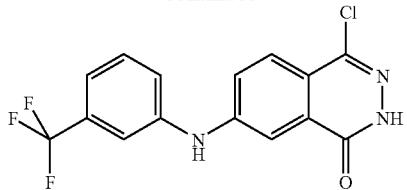

A mixture 6-bromo-4-chloro-2H-phthalazin-1-one and 7-bromo-4-chloro-2H-phthalazin-1-one (200 mg, 0.77 mmol), 3-trifluoromethylaniline (0.14 mL, 1.16 mmol), Pd$_2$(dba)$_3$ (71 mg, 0.077 mmol), rac-BINAP (144 mg, 0.23 mmol) and NaOt-Bu (217 mg, 2.31 mmol) in DMF (10 mL) was heated at 80° C. for 2 h. The mixture was allowed to cool, diluted with EtOAc (25 mL) and washed with NaHCO$_3$ (25 mL). The organic layer was dried over anhydrous sodium sulfate and concentrated. Chromatography on silica (EtOAc/hexanes) yielded the title compounds. 4-Chloro-6-(3-trifluoromethyl-phenylamino)-2H-phthalazin-1-one: $^1$H-NMR (DMSO-d$_6$) δ: 12.56 (s, 1H), 9.49 (s, 1H), 8.10 (d, 1H), 7.54 (m, 4H), 7.42 (d, 1H), 7.36 (m, 1H); m/z (M+1)=340.10; and 4-Chloro-7-(3-trifluoromethyl-phenylamino)-2H-phthalazin-1-one: $^1$H-NMR (DMSO-d$_6$) δ: 12.61 (s, 1H), 9.47 (s, 1H), 7.86 (d, 1H), 7.75 (d, 1H), 7.60 (m, 3H), 7.47 (s, 1H), 7.36 (d, 1H); m/z (M+1) 340.10.

Example 65 and 66

Synthesis of 4-Chloro-6-phenethylamino-2H-phthalazin-1-one and 4-Chloro-7-phenethylamino-2H-phthalazin-1-one

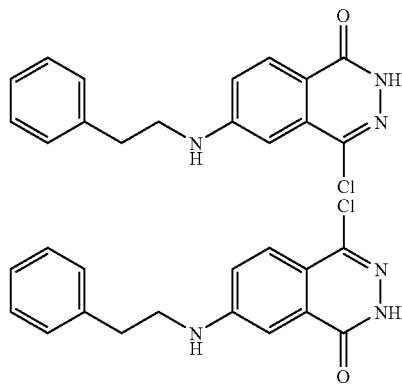

A mixture 6-bromo-4-chloro-2H-phthalazin-1-one and 7-bromo-4-chloro-2H-phthalazin-1-one (200 mg, 0.77 mmol), phenethylamine (0.14 mL, 1.16 mmol), Pd$_2$(dba)$_3$ (71 mg, 0.077 mmol), rac-BINAP (144 mg, 0.23 mmol) and NaOt-Bu (217 mg, 2.31 mmol) in DMF (10 mL) was heated at 80° C. for 2 h. The mixture was allowed to cool, diluted with EtOAc (25 mL) and washed with NaHCO$_3$ (25 mL). The organic layer was dried over anhydrous sodium sulfate and concentrated. Chromatography on silica (EtOAc/hexanes) yielded the title compounds. 4-Chloro-6-phenethylamino-2H-phthalazin-1-one: $^1$H-NMR (DMSO-d$_6$) δ: 12.33 (s, 1H), 7.91 (d, 1H), 7.25 (s, 4H), 7.15 (m, 3H), 6.78 (s, 1H), 3.40 (q, 2H), 2.88 (t, 2H); m/z (M+1)=300.15; and 4-Chloro-7-phenethylamino-2H-phthalazin-1-one: $^1$H-NMR (DMSO-d$_6$) δ: 12.40 (s, 1H), 7.67 (d, 1H), 7.20 (m, 8H), 3.41 (q, 2H), 2.87 (t, 2H); m/z (M+1)=300.15.

Example 67 and 68

Synthesis of 4-[(4-Chloro-1-oxo-1,2-dihydro-phthalazin-6-ylamino)-methyl]-N-(2-pyrrolidin-1-yl-ethyl)-benzamide and 4-[(1-Chloro-4-oxo-3,4-dihydro-phthalazin-6-ylamino)-methyl]-N-(2-pyrrolidin-1-yl-ethyl)-benzamide

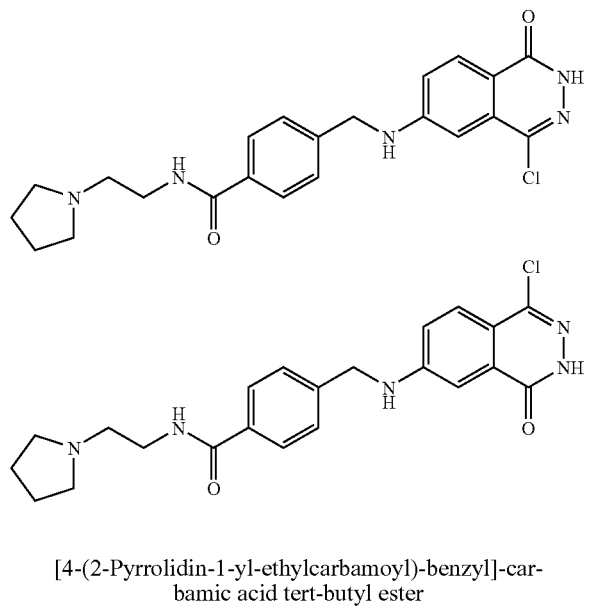

[4-(2-Pyrrolidin-1-yl-ethylcarbamoyl)-benzyl]-carbamic acid tert-butyl ester

A mixture of 4-(tert-Butoxycarbonylamino-methyl)-benzoic acid (500 mg, 1.99 mmol), 2-Pyrrolidin-1-yl-ethylamine (0.28 mL, 2.19 mmol), EDC (459 mg, 2.39 mmol), HOBt (323 mg, 2.39 mmol) and triethylamine (0.40 mL, 2.99 mmol) in DMF (10 mL) was stirred at ambient temperature for 15 h. The mixture was diluted with EtOAc (25 mL) and washed with water (25 mL) and NaHCO$_3$ (25 mL). The aqueous mixture was extracted with EtOAc (2×25 mL). The combined organic layers were dried over anhydrous sodium sulfate and concentrated to yield the title compound (421 mg, 61%). m/z (M+1) 348.23.

[3-(2-Pyrrolidin-1-yl-ethylcarbamoyl)-benzyl]-carbamic acid tert-butyl ester

A mixture of 3-(tert-Butoxycarbonylamino-methyl)-benzoic acid (500 mg, 1.99 mmol), 2-Pyrrolidin-1-yl-ethylamine (0.28 mL, 2.19 mmol), EDC (459 mg, 2.39 mmol), HOBt (323 mg, 2.39 mmol) and triethylamine (0.40 mL, 2.99 mmol) in DMF (10 mL) was stirred at ambient temperature for 15 h. The mixture was diluted with EtOAc (25 mL) and washed with water (25 mL) and NaHCO$_3$ (25 mL). The aqueous mixture was extracted with EtOAc (2×25 mL). The combined organic layers were dried over anhydrous sodium sulfate and concentrated to yield the title compound (403 mg, 58%). m/z (M+1) 348.21.

4-Aminomethyl-N-(2-pyrrolidin-1-yl-ethyl)-benzamide dihydrochloride

To a solution of [4-(2-Pyrrolidin-1-yl-ethylcarbamoyl)-benzyl]-carbamic acid tert-butyl ester (400 mg, 1.15 mmol) in MeOH (30 mL) was added 6M HCl in IPA (25 mL). The mixture was stirred at ambient temperature for 5 h. After this time a precipitate had formed and was filtered and dried to yield the title compound. m/z (M+1) 248.34.

4-[(4-Chloro-1-oxo-1,2-dihydro-phthalazin-6-ylamino)-methyl]-N-(2-pyrrolidin-1-yl-ethyl)-benzamide and 4-[(1-Chloro-4-oxo-3,4-dihydro-phthalazin-6-ylamino)-methyl]-N-(2-pyrrolidin-1-yl-ethyl)-benzamide A mixture 6-Bromo-4-chloro-2H-phthalazin-1-one and 7-Bromo-4-chloro-2H-phthalazin-1-one (200 mg, 0.77 mmol), 4-Aminomethyl-N-(2-pyrrolidin-1-yl-ethyl)-benzamide dihydrochloride (319 mg, 1.00 mmol), Pd$_2$(dba)$_3$ (71 mg, 0.077 mmol), rac-BINAP (144 mg, 0.23 mmol) and NaOt-Bu (217 mg, 2.31 mmol) in DMF (10 mL) was heated at 80° C. for 2 h. The mixture was allowed to cool, diluted with EtOAc (25 mL) and washed with NaHCO$_3$ (25 mL). The organic layer was dried over anhydrous sodium sulfate and concentrated. Chromatography on silica (MeOH/EtOAc) yielded the title compounds as a mixture of two regioisomers. $^1$H-NMR (DMSO-d$_6$) δ: 12.40 (bs, 2H), 3.38 (m, 2H), 7.92 (d, 1H), 7.80 (m, 4H), 7.68 (m, 3H), 7.41 (m, 4H), 7.25 (dd, 1H), 7.15 (m, 2H), 6.80 (s, 1H), 4.50 (t, 4H), 3.35 (q, 4H), 2.55 (t, 4H), 2.45 (m, 8H), 1.65 (m, 8H); m/z (M+1) 426.03.

Example 69 and 70

Synthesis of 3-[(4-Chloro-1-oxo-1,2-dihydro-phthalazin-6-ylamino)-methyl]-N-(2-pyrrolidin-1-yl-ethyl)-benzamide and 3-[(1-Chloro-4-oxo-3,4-dihydro-phthalazin-6-ylamino)-methyl]-N-(2-pyrrolidin-1-yl-ethyl)-benzamide

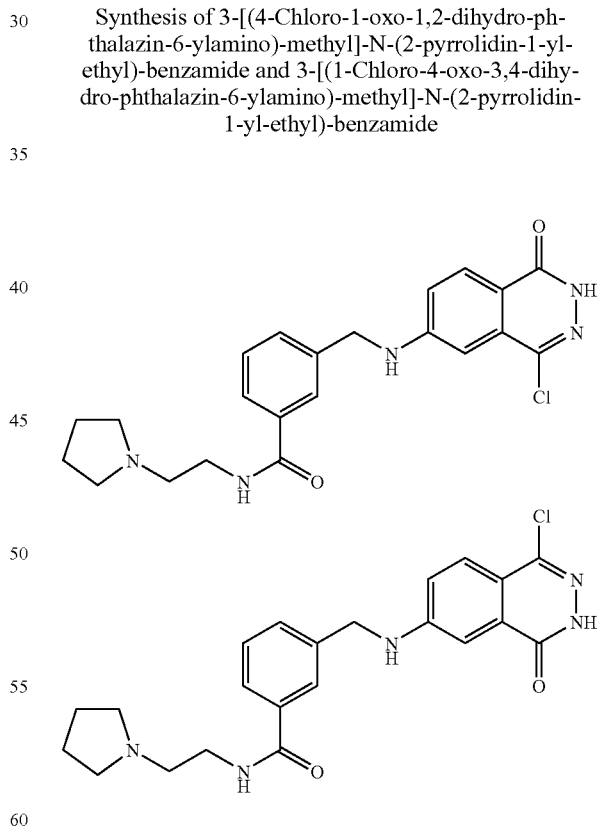

3-Aminomethyl-N-(2-pyrrolidin-1-yl-ethyl)-benzamide dihydrochloride

To a solution of [4-(2-Pyrrolidin-1-yl-ethylcarbamoyl)-benzyl]-carbamic acid tert-butyl ester (400 mg, 1.15 mmol) in MeOH (30 mL) was added 6M HCl in IPA (25 mL). The mixture was stirred at ambient temperature for 5 h. After this time the mixture was concentrated and dried to yield the title compound. m/z (M+1) 248.34.

3-[(4-Chloro-1-oxo-1,2-dihydro-phthalazin-6-ylamino)-methyl]-N-(2-pyrrolidin-1-yl-ethyl)-benzamide and 3-[(1-Chloro-4-oxo-3,4-dihydro-phthalazin-6-ylamino)-methyl]-N-(2-pyrrolidin-1-yl-ethyl)-benzamide A mixture 6-Bromo-4-chloro-2H-phthalazin-1-one and 7-Bromo-4-chloro-2H-phthalazin-1-one (200 mg, 0.77 mmol), 3-Aminomethyl-N-(2-pyrrolidin-1-yl-ethyl)-benzamide dihydrochloride (319 mg, 1.00 mmol), $Pd_2(dba)_3$ (71 mg, 0.077 mmol), rac-BINAP (144 mg, 0.23 mmol) and NaOt-Bu (217 mg, 2.31 mmol) in DMF (10 mL) was heated at 80° C. for 2 h. The mixture was allowed to cool, diluted with EtOAc (25 mL) and washed with $NaHCO_3$ (25 mL). The organic layer was dried over anhydrous sodium sulfate and concentrated. Chromatography on silica (MeOH/EtOAc) yielded the title compound as a mixture of two regioisomers. $^1$H-NMR (DMSO-$d_6$) δ: 12.40 (bs, 2H), 8.41 (t, 2H), 7.91 (d, 1H), 7.85 (m, 2H), 7.70 (m, 4H), 7.50 (m, 3H), 7.42 (m, 1H), 7.37 (m, 1H), 7.26 (m, 1H), 7.15 (m, 2H), 6.85 (s, 1H), 4.50 (t, 4H), 3.35 (m, 4H), 2.55 (t, 4H), 2.45 (m, 8H), 1.65 (m, 8H); m/z (M+1)=426.10.

Example 71 and 72

Synthesis of N-(4-Chloro-1-oxo-1,2-dihydro-phthalazin-6-yl)-3-trifluoromethyl-benzamide and N-(1-Chloro-4-oxo-3,4-dihydro-phthalazin-6-yl)-3-trifluoromethyl-benzamide

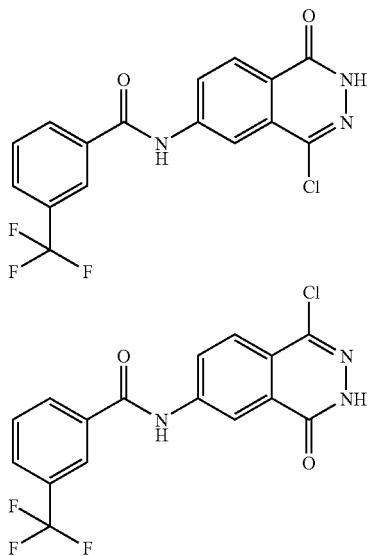

A mixture 6-Bromo-4-chloro-2H-phthalazin-1-one and 7-Bromo-4-chloro-2H-phthalazin-1-one (150 mg, 0.58 mmol), 3-Trifluoromethyl-benzamide (120 mg, 0.64 mmol), $Pd_2(dba)_3$ (53 mg, 0.054 mmol), xantphos (101 mg, 0.174 mmol) and cesium carbonate (472 mg, 1.45 mmol) in dioxane (10 mL) was heated at reflux for 3 h. The mixture was allowed to cool, diluted with EtOAc (25 mL) and washed with $NaHCO_3$ (25 mL). The organic layer was dried over anhydrous sodium sulfate and concentrated. Chromatography on silica (EtOAc/Hexanes) yielded the title compounds. N-(4-Chloro-1-oxo-1,2-dihydro-phthalazin-6-yl)-3-trifluoromethyl-benzamide: $^1$H-NMR (DMSO-$d_6$) δ: 12.80 (s, 1H), 11.05 (s, 1H), 8.59 (s, 1H), 8.34 (m, 4H), 8.02 (d, 1H), 7.82 (t, 1H); m/z (M+1)=368.06; and N-(1-Chloro-4-oxo-3,4-dihydro-phthalazin-6-yl)-3-trifluoromethyl-benzamide: $^1$H-NMR (DMSO-$d_6$) δ: 12.80 (s, 1H), 11.05 (s, 1H), 8.80 (d, 1H), 8.42 (dd, 1H), 8.36 (s, 1H), 8.32 (d, 1H), 8.03 (d, 1H), 8.01 (d, 1H), 7.82 (t, 1H); m/z (M+1)=367.99.

Example 73 and 74

Synthesis of 4-Chloro-6-[3-(2-morpholin-4-yl-ethoxy)-benzylamino]-phthalazin-1-ol and 4-Chloro-7-[3-(2-morpholin-4-yl-ethoxy)-benzylamino]-phthalazin-1-ol

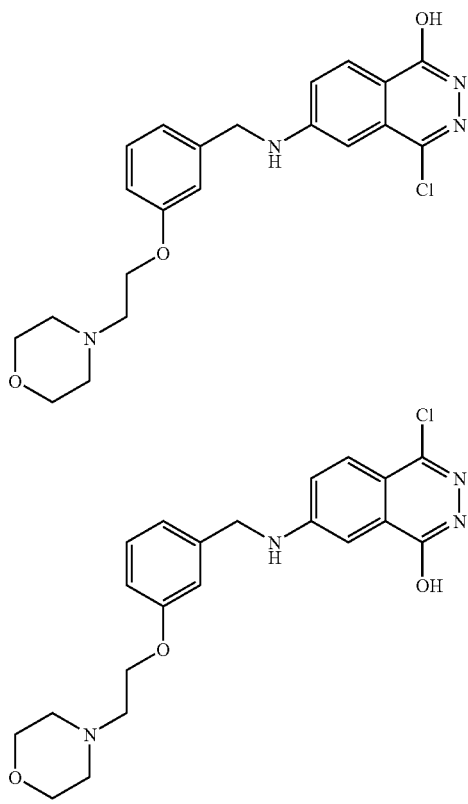

A mixture 6-Bromo-4-chloro-2H-phthalazin-1-one and 7-Bromo-4-chloro-2H-phthalazin-1-one (200 mg, 0.77 mmol), 3-(2-Morpholin-4-yl-ethoxy)-benzylamine (0.25 mL, 1.00 mmol), $Pd_2(dba)_3$ (71 mg, 0.077 mmol), rac-BINAP (144 mg, 0.23 mmol) and NaOt-Bu (217 mg, 2.31 mmol) in DMF (10 mL) was heated at 80° C. for 2 h. The mixture was allowed to cool, diluted with EtOAc (25 mL) and washed with $NaHCO_3$ (25 mL). The organic layer was dried over anhydrous sodium sulfate and concentrated. Chromatography on silica (EtOAc/MeOH) yielded the title compounds. $^1$H-NMR (DMSO-$d_6$) δ: 12.41 (s, 1H), 12.35 (s, 1H), 7.91 (d, 1H), 7.70 (d, 1H), 7.65 (m, 2H), 7.25 (m, 4H), 7.16 (m, 2H), 6.94 (m, 4H), 6.82 (m, 4H), 4.40 (t, 4H), 4.15 (m, 4H), 3.57 (m, 8H), 2.63 (m, 4H), 2.42 (m, 8H); m/z (M+1)=414.98.

Example 75

Synthesis of 4-Methyl-1-oxo-1,2-dihydro-phthalazine-6-carboxylic acid (3-trifluoromethyl-phenyl)-amide

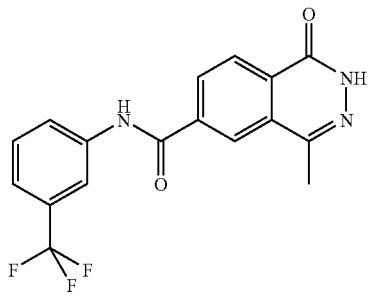

2-Acetyl-terephthalic acid dimethyl ester

A mixture of zinc powder (1.5 eq, 10.98 mmol, 718 mg), cobalt (11) bromide (0.1 eq, 0.732 mmol, 160 mg), allyl bromide (0.1 eq, 0.732 mmol, 62 μl), and trifluoroacetic acid (1 drop to activate the zinc) are stirred under argon in 7 ml of acetonitrile for 10 minutes at room temperature. 2-Bromo dimethyl ester (2 g, 7.32 mmol) and acetic anhydride (1.1 eq, 8.1 mmol, 0.766 ml) are then added simultaneously, and the reaction is carried out for 5 hours, until complete conversion of the starting aryl bromide. The reaction is quenched with aqueous sodium bicarbonate and water and extracted with ether. The combined organic layer was separated, dried with anhydrous sodium sulfate, filtered and evaporated under vacuum to give crude product, which was purified via column chromatography (5-10% EtOAc-Hex) to give 95 mg (55%) of the ketone. m/z [M+1]$^+$=237.

4-Methyl-1-oxo-1,2-dihydro-phthalazine-6-carboxylic acid

A solution of 2-Acetyl-terephthalic acid dimethyl ester (0.68 g, 2.88 mmol) in THF (6 ml), methanol (1.5 ml), and 1.5 ml of 2N (NaOH) was stirred overnight. Solvent was evaporated to dryness 3× (methanol). Isopropyl alcohol (5 ml) was then added to the crude salt followed by the addition of hydrazine hydrate (5 ml). The mixture was heated to reflux for 3 hours before evaporated to dryness (3×) via methanol to give the crude compound. m/z [M+1]$^+$=205.

The crude mixture was converted to the corresponding acid chloride by refluxing in thionyl chloride (neat) for 2 hours before evaporated under vacuum to give the crude acid-chloride, which was divided into 4 equal batches then used directly for the next step.

4-Methyl-1-oxo-1,2-dihydro-phthalazine-6-carboxylic acid (3-trifluoromethyl-phenyl)-amide A solution of the acid chloride (~100 mg, 2.25 mmol), prepared from above, in DMF (2.5 ml) was added the trifluoromethyl-aniline (2.5 eq, 5.62 mmol) and triethylamine (2.5 eq, 5.62 mmol). The reaction mixture was stirred at room temperature for 5 hrs before quenched with aqueous sodium bicarbonate and water and extracted with EtOAc. The combined organic layer was separated, dried with anhydrous sodium sulfate, filtered and evaporated under vacuum to give crude product, which was purified via column chromatography (60-80% EtOAc-Hex) to give 41 mg of the product. $^1$H NMR (DMSO) δ 12.61 (1H), 10.52 (1H), 8.48 (1H), 8.40 (1H), 8.35 (1H), 8.26 (1H), 8.09 (1H), 7.65 (1), 7.52 (1H), 2.62 (3H); m/z [M+1]$^+$=348.

Example 76

Synthesis of 4-Methyl-1-oxo-1,2-dihydro-phthalazine-6-carboxylic acid 3-trifluoromethyl-benzylamide

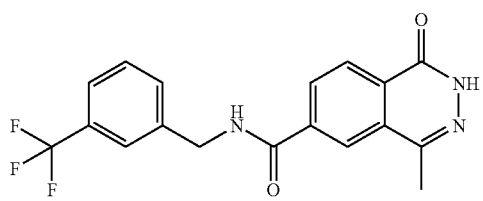

An equal batch of the acid chloride (see Example 74) was used for coupling with the trifluoromethyl-benzylamine. A similar procedure and work up to the previous reaction afforded the title compound. $^1$H NMR (DMSO) δ: 12.52 (1H), 9.58 (1H), 8.48 (1H), 8.38 (1H), 8.34 (1H), 8.28 (1H), 8.16 (1H), 7.78 (1), 7.66 (1H), 4.68 (2), 2.58 (3H); m/z [M+1]$^+$=362.

Example 77

Synthesis of 4-Methyl-1-oxo-1,2-dihydro-phthalazine-6-carboxylic acid 3-methoxy-benzylamide

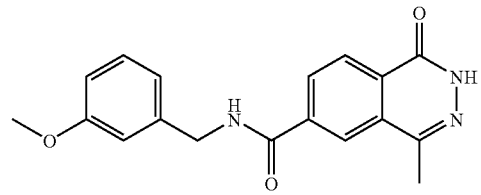

An equal batch of the acid chloride (see Example 74) was used for coupling with the methyl-oxy-benzylamine. A similar procedure and worked up to the previous reaction afforded the title compound. $^1$H NMR (DMSO) δ: 12.51 (1H), 9.48 (1H), 8.38 (1H), 8.33 (1H), 8.29 (1H), 7.28 (1H), 7.23 (1H), 6.94 (1), 6.82 (1H), 4.54 (2H), 3.75 (3H), 2.55 (3H); m/z [M+1]$^+$=324.

Example 78

4-Chloro-6-(3-piperidin-1-ylmethyl-benzylamino)-2H-phthalazin-1-one

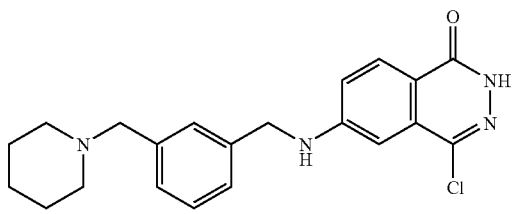

6-Bromo-4-chloro-2H-phthalazin-1-one

A mixture of 6-bromo-2,3-dihydro-phthalazine-1,4-dione (42.8 g, 178 mmol) in POCl$_3$ (300 mL) was heated at reflux for 3 h. The mixture was allowed to cool and concentrated. The residue was taken up in EtOAc (400 mL) and water (200 mL), and neutralized with sodium bicarbonate. The layers were separated, aqueous layer was extracted with EtOAc (3×200 mL), and combined organic layers were dried over anhydrous sodium sulfate and concentrated. The residue was dissolved in dioxane (300 mL) and 2N NaOH (250 mL). The mixture was heated at 50° C. for 30 min, poured into water (3 L), and stirred for 15 min. Solid was filtered and dried in vacuum at room temperature to give title compound as a greenish solid (12.0 g, 24.3%). M/z (M+1)=259.32.

4-Chloro-6-(3-piperidin-1-ylmethyl-benzylamino)-2H-phthalazin-1-one

A mixture 6-bromo-4-chloro-2H-phthalazin-1-one (70 mg, 0.27 mmol), 3-piperidin-1-ylmethyl-benzylamine (72 mg, 0.35 mmol), Pd$_2$(dba)$_3$ (25 mg, 0.027 mmol), rac-BINAP (51 mg, 0.081 mmol) and NaOt-Bu (76 mg, 0.81 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(3-piperidin-1-ylmethyl-benzylamino)-2H-phthalazin-1-one: 16 mg (15.5%): m/z (M+H)=383. $^1$H-NMR (DMSO-d$_6$) δ: 12.30 (s, 1H), 7.95 (d, 1H), 7.63 (m, 1H), 7.25 (m, 3H), 7.15 (m, 2H), 6.75 (s, 1H), 4.41 (d, 2H), 3.37 (s, 2H), 2.24 (m, 4H), 1.38 (m, 4H), 1.32 (m, 2H).

Example 79

4-Chloro-6-[2-(2-morpholin-4-yl-ethoxy)-benzylamino]-2H-phthalazin-1-one

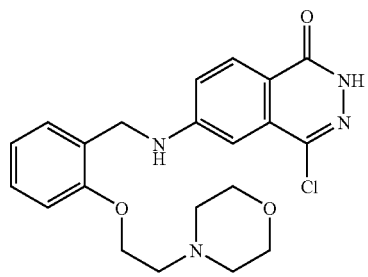

A mixture 6-bromo-4-chloro-2H-phthalazin-1-one (70 mg, 0.27 mmol), 2-(2-morpholin-4-yl-ethoxy)-benzylamine (83 mg, 0.35 mmol), Pd$_2$(dba)$_3$ (25 mg, 0.027 mmol), rac-BINAP (51 mg, 0.081 mmol) and NaOt-Bu (76 mg, 0.81 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-[2-(2-morpholin-4-yl-ethoxy)-benzylamino]-2H-phthalazin-1-one: 28 mg (25.0%): m/z (M+H)=415. $^1$H-NMR (DMSO-d$_6$) δ: 12.33 (s, 1H), 7.91 (d, 1H), 7.45 (m, 1H), 7.24 (m, 2H), 7.13 (m, 1H), 7.04 (m, 1H), 6.90 (m, 1H), 6.79 (s, 1H), 4.36 (d, 2H), 4.15 (t, 2H), 3.51 (t, 4H), 2.72 (t, 2H), 2.45 (m, 4H).

Example 80

6-(Benzyl-methyl-amino)-4-chloro-2H-phthalazin-1-one

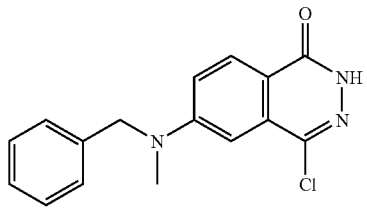

A mixture 6-bromo-4-chloro-2H-phthalazin-1-one (70 mg, 0.27 mmol), benzyl-methyl-amine (43 mg, 0.35 mmol), Pd$_2$(dba)$_3$ (25 mg, 0.027 mmol), rac-BINAP (51 mg, 0.081 mmol) and NaOt-Bu (76 mg, 0.81 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 6-(Benzyl-methyl-amino)-4-chloro-2H-phthalazin-1-one: 10 mg (12.4%): m/z (M+H)=300.

$^1$H-NMR (DMSO-d$_6$) δ: 12.25 (s, 1H), 7.95 (d, 1H), 7.35 (m, 3H), 7.23 (m, 3H), 6.87 (d, 1H), 4.79 (s, 2H), 3.28 (s, 3H).

Example 81

4-Chloro-6-(2,5-dichloro-benzylamino)-2H-phthalazin-1-one

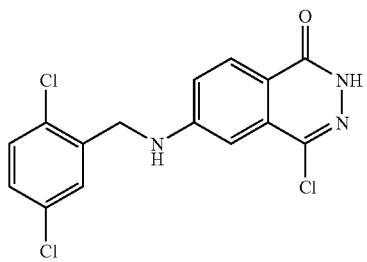

A mixture 6-bromo-4-chloro-2H-phthalazin-1-one (150 mg, 0.58 mmol), 2,5-dichloro-benzylamine (0.085 mL, 0.64 mmol), Pd$_2$(dba)$_3$ (53 mg, 0.058 mmol), rac-BINAP (108 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2,5-dichloro-benzylamino)-2H-phthalazin-1-one: 6 mg (2.9%): m/z (M+H)=354. $^1$H-NMR (DMSO-d$_6$) δ: 12.39 (s, 1H), 7.96

(d, 1H), 7.66 (m, 1H), 7.53 (d, 1H), 7.47 (m, 1H), 7.40 (dd, 1H), 7.16 (dd, 1H), 6.82 (s, 1H), 4.50 (d, 2H).

Example 82

4-Chloro-6-(2-methyl-benzylamino)-2H-phthalazin-1-one

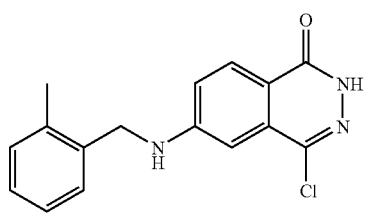

A mixture 6-bromo-4-chloro-2H-phthalazin-1-one (150 mg, 0.58 mmol), 2-methyl-benzylamine (0.080 mL, 0.64 mmol), Pd$_2$(dba)$_3$ (53 mg, 0.058 mmol), rac-BINAP (108 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-methyl-benzylamino)-2H-phthalazin-1-one: 36 mg (20.7%): m/z (M+H)=300. $^1$H-NMR (DMSO-d$_6$) δ: 12.34 (s, 1H), 7.93 (d, 1H), 7.50 (m, 1H), 7.26 (m, 1H), 7.16 (m, 4H) 6.84 (s, 1H), 4.37 (d, 2H), 2.48 (s, 3H).

Example 83

4-Chloro-6-(2-chloro-6-fluoro-benzylamino)-2H-phthalazin-1-one

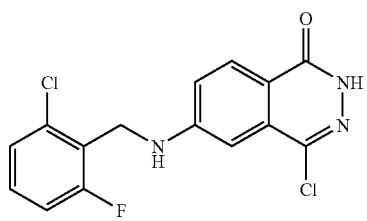

A mixture 6-bromo-4-chloro-2H-phthalazin-1-one (150 mg, 0.58 mmol), 2-chloro-6-fluoro-benzylamine (102 mg, 0.64 mmol), Pd$_2$(dba)$_3$ (53 mg, 0.058 mmol), rac-BINAP (108 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-chloro-6-fluoro-benzylamino)-2H-phthalazin-1-one: 31 mg (15.8%): m/z (M+H)=338. $^1$H-NMR (DMSO-d$_6$) δ: 12.38 (s, 1H), 7.94 (d, 1H), 7.42 (m, 3H), 7.30 (m, 1H), 7.21 (dd, 1H) 6.93 (s, 1H), 4.49 (d, 2H).

Example 84

4-Chloro-6-(2-pyrazol-1-yl-benzylamino)-2H-phthalazin-1-one

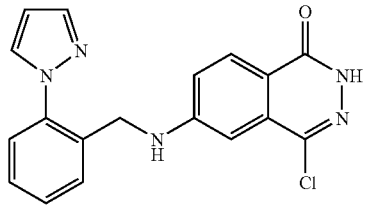

A mixture 6-bromo-4-chloro-2H-phthalazin-1-one (150 mg, 0.58 mmol), 2-pyrazol-1-yl-benzylamine (111 mg, 0.64 mmol), Pd$_2$(dba)$_3$ (53 mg, 0.058 mmol), rac-BINAP (108 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-pyrazol-1-yl-benzylamino)-2H-phthalazin-1-one: 46 mg (22.5%): m/z (M+H)=352. $^1$H-NMR (DMSO-d$_6$) δ: 12.34 (s, 1H), 8.13 (d, 1H), 7.90 (d, 1H), 7.78 (d, 1H), 7.59 (m, 1H), 7.50 (m, 1H), 7.43 (m, 3H), 7.05 (d, 1H), 6.68 (s, 1H), 6.54 (t, 1H), 4.38 (d, 2H).

Example 85

4-Chloro-6-(3-pyrazol-1-yl-benzylamino)-2H-phthalazin-1-one

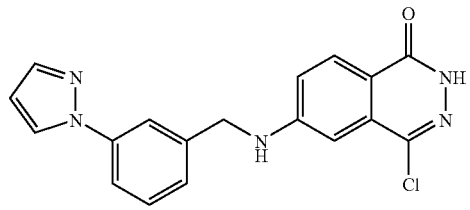

A mixture 6-bromo-4-chloro-2H-phthalazin-1-one (150 mg, 0.58 mmol), 3-pyrazol-1-yl-benzylamine (111 mg, 0.64 mmol), Pd$_2$(dba)$_3$ (53 mg, 0.058 mmol), rac-BINAP (108 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(3-pyrazol-1-yl-benzylamino)-2H-phthalazin-1-one: 60 mg (30.4%): m/z (M+H)=352. $^1$H-NMR (DMSO-d$_6$) δ: 12.34 (s, 1H), 8.46 (d, 1H), 7.93 (m, 2H), 7.72 (m, 3H), 7.45 (m, 1H), 7.32 (d, 1H), 7.19 (dd, 1H) 6.86 (s, 1H), 6.52 (t, 1H), 4.50 (d, 2H).

Example 86

4-Chloro-6-(2-pyridin-3-yl-benzylamino)-2H-phthalazin-1-one

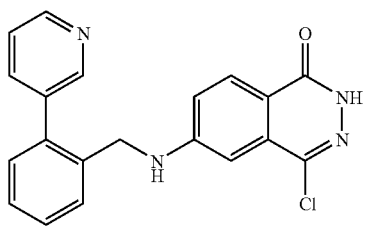

A mixture 6-bromo-4-chloro-2H-phthalazin-1-one (150 mg, 0.58 mmol), 2-pyridin-3-yl-benzylamine dihydrochloride (165 mg, 0.64 mmol), Pd$_2$(dba)$_3$ (53 mg, 0.058 mmol), rac-BINAP (108 mg, 0.17 mmol) and NaOt-Bu (251 mg, 2.61 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-pyridin-3-yl-benzylamino)-2H-phthalazin-1-one: 51 mg (24.2%): m/z (M+H)=363. $^1$H-NMR (DMSO-d$_6$) δ: 12.32 (s, 1H), 8.65 (d, 1H), 8.58 (dd, 1H), 7.88 (m, 2H), 7.61 (m, 1H), 7.46 (m, 4H), 7.34 (m, 1H), 7.06 (dd, 1H), 6.55 (s, 1H), 4.30 (d, 2H).

Example 87

4-Chloro-6-(2-piperidin-1-yl-benzylamino)-2H-phthalazin-1-one

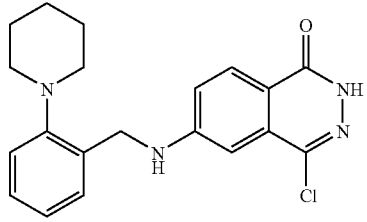

A mixture 6-bromo-4-chloro-2H-phthalazin-1-one (150 mg, 0.58 mmol), 2-piperidin-1-yl-benzylamine (122 mg, 0.64 mmol), Pd$_2$(dba)$_3$ (53 mg, 0.058 mmol), rac-BINAP (108 mg, 0.17 mmol) and NaOt-Bu (251 mg, 2.61 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-piperidin-1-yl-benzylamino)-2H-phthalazin-1-one: 62 mg (29.0%): m/z (M+H)=369. $^1$H-NMR (DMSO-d$_6$) δ: 12.35 (s, 1H), 7.90 (d, 1H), 7.77 (m, 1H), 7.32 (dd, 1H), 7.15 (m, 3H), 6.96 (m, 1H) 6.62 (s, 1H), 4.41 (d, 2H), 1.71 (m, 4H), 1.55 (m, 2H).

Example 88

4-Chloro-6-(2-thiophen-2-yl-benzylamino)-2H-phthalazin-1-one

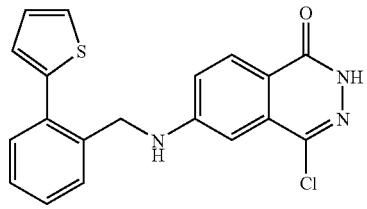

A mixture 6-bromo-4-chloro-2H-phthalazin-1-one (150 mg, 0.58 mmol), 2-thiophen-2-yl-benzylamine hydrochloride (145 mg, 0.64 mmol), Pd$_2$(dba)$_3$ (53 mg, 0.058 mmol), rac-BINAP (108 mg, 0.17 mmol) and NaOt-Bu (200 mg, 2.1 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-thiophen-2-yl-benzylamino)-2H-phthalazin-1-one: 65 mg (30.5%): m/z (M+H)=368. $^1$H-NMR (DMSO-d$_6$) δ: 12.34 (s, 1H), 7.91 (d, 1H), 7.64 (m, 2H), 7.47 (m, 2H), 7.37 (m, 2H), 7.25 (dd, 1H), 7.16 (m, 1H), 7.11 (m, 1H), 6.64 (s, 1H), 4.43 (d, 2H).

Example 89

4-Chloro-6-(3-thiophen-2-yl-benzylamino)-2H-phthalazin-1-one

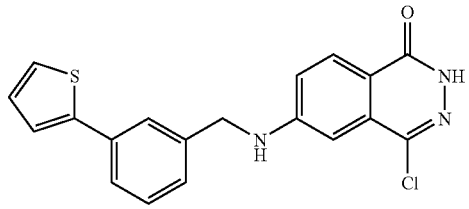

A mixture 6-bromo-4-chloro-2H-phthalazin-1-one (150 mg, 0.58 mmol), 3-thiophen-2-yl-benzylamine (121 mg, 0.64 mmol), Pd$_2$(dba)$_3$ (53 mg, 0.058 mmol), rac-BINAP (108 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(3-thiophen-2-yl-benzylamino)-2H-phthalazin-1-one: 69 mg (32.3%): m/z (M+H)=368. $^1$H-NMR (DMSO-d$_6$) δ: 12.34 (s, 1H), 7.93 (d, 1H), 7.70 (m, 2H), 7.54 (m, 2H), 7.48 (dd, 1H), 7.39 (m, 1H), 7.32 (m, 1H), 7.18 (dd, 1H), 7.13 (m, 1H), 6.86 (s, 1H), 4.47 (d, 2H).

Example 90

4-Chloro-6-(2-furan-2-yl-benzylamino)-2H-phthalazin-1-one

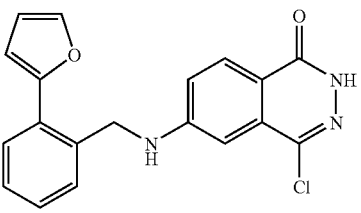

A mixture 6-bromo-4-chloro-2H-phthalazin-1-one (150 mg, 0.58 mmol), 2-furan-2-yl-benzylamine (111 mg, 0.64 mmol), Pd$_2$(dba)$_3$ (53 mg, 0.058 mmol), rac-BINAP (108 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/ hexanes) yielded the title compound. 4-Chloro-6-(2-furan-2-yl-benzylamino)-2H-phthalazin-1-one: 54 mg (26.5%): m/z (M+H)=351. $^1$H-NMR (DMSO-$d_6$) δ: 12.34 (s, 1H), 7.93 (d, 1H), 7.82 (m, 1H), 7.70 (dd, 1H), 7.64 (m, 1H), 7.44 (m, 1H), 7.35 (m, 2H), 7.12 (dd, 1H), 6.76 (m, 2H), 6.63 (m, 1H), 4.56 (d, 2H).

Example 91

4-Chloro-6-[3-(4-methyl-piperazin-1-yl)-benzylamino]-2H-phthalazin-1-one

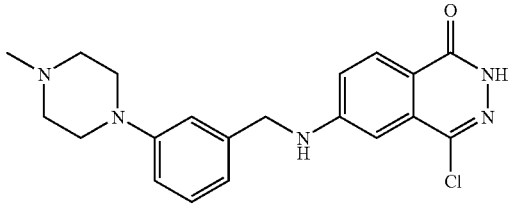

A mixture 6-bromo-4-chloro-2H-phthalazin-1-one (150 mg, 0.58 mmol), 3-(4-methyl-piperazin-1-yl)-benzylamine (111 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-[3-(4-methyl-piperazin-1-yl)-benzylamino]-2H-phthalazin-1-one: 50 mg (22.5%): m/z (M+H)=384. $^1$H-NMR (DMSO-$d_6$) δ: 12.33 (s, 1H), 7.91 (d, 1H), 7.59 (m, 1H), 7.16 (m, 2H), 6.98 (s, 1H), 6.80 (m, 3H), 4.34 (d, 2H), 3.11 (m, 4H), 2.42 (m, 4H), 2.20 (s, 3H).

Example 92

4-Chloro-6-(2-morpholin-4-ylmethyl-benzylamino)-2H-phthalazin-1-one

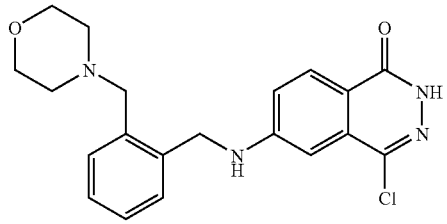

A mixture 6-bromo-4-chloro-2H-phthalazin-1-one (150 mg, 0.58 mmol), 2-morpholin-4-ylmethyl-benzylamine (132 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-morpholin-4-ylmethyl-benzylamino)-2H-phthalazin-1-one: 52 mg (23.3%): m/z (M+H)=385. $^1$H-NMR (DMSO-$d_6$) δ: 12.27 (s, 1H), 7.85 (d, 1H), 7.51 (m, 1H), 7.22 (m, 2H), 7.16 (m, 2H), 7.11 (dd, 1H), 6.73 (s, 1H), 4.55 (d, 2H), 3.50 (m, 6H), 2.23 (m, 4H).

Example 93

4-Chloro-6-(3-thiophen-3-yl-benzylamino)-2H-phthalazin-1-one

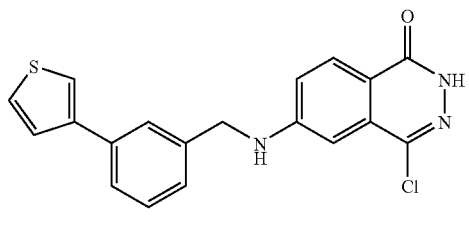

A mixture 6-bromo-4-chloro-2H-phthalazin-1-one (150 mg, 0.58 mmol), 3-thiophen-3-yl-benzylamine (122 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(3-thiophen-3-yl-benzylamino)-2H-phthalazin-1-one: 38 mg (17.8%): m/z (M+H)=368. $^1$H-NMR (DMSO-$d_6$) δ: 12.34 (s, 1H), 7.93 (d, 1H), 7.84 (m, 1H), 7.75 (m, 1H), 7.64 (m, 3H), 7.52 (dd, 1H), 7.39 (m, 1H), 7.31 (m, 1H), 7.19 (dd, 1H), 6.87 (s, 1H), 4.47 (d, 2H).

Example 94

4-Chloro-6-[2-(4-methyl-piperazin-1-yl)-benzylamino]-2H-phthalazin-1-one

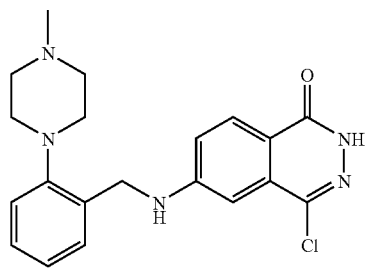

A mixture 6-bromo-4-chloro-2H-phthalazin-1-one (150 mg, 0.58 mmol), 2-(4-methyl-piperazin-1-yl)-benzylamine (132 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-[2-(4-methyl-piperazin-1-yl)-benzylamino]-2H-phthalazin-1-one: 46 mg (20.7%): m/z (M+H)=384. $^1$H-NMR (DMSO-$d_6$) δ: 12.31 (s, 1H), 7.89 (d, 1H), 7.77 (m, 1H), 7.33 (dd, 1H), 7.20 (m, 1H), 7.13 (m, 2H), 7.00 (m, 1H), 6.63 (s, 1H), 4.42 (d, 2H), 2.98 (m, 4H), 2.52 (m, 4H), 2.23 (s, 3H).

Example 95

4-Chloro-6-(2-phenoxy-benzylamino)-2H-phthalazin-1-one

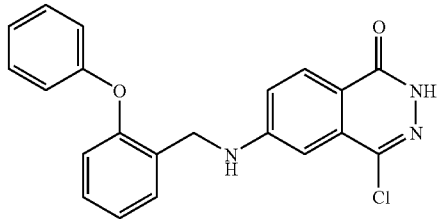

A mixture 6-bromo-4-chloro-2H-phthalazin-1-one (150 mg, 0.58 mmol), 2-phenoxy-benzylamine hydrochloride (151 mg, 0.64 mmol), Pd$_2$(dba)$_3$ (53 mg, 0.058 mmol), rac-BINAP (132 mg, 0.17 mmol) and NaOt-Bu (200 mg, 2.1 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-phenoxy-benzylamino)-2H-phthalazin-1-one: 81 mg (37.0%): m/z (M+H)=378. $^1$H-NMR (DMSO-d$_6$) δ: 12.77 (s, 1H), 8.34 (d, 1H), 8.03 (m, 1H), 7.82 (m, 3H), 7.71 (m, 1H), 7.56 (m, 3H), 7.42 (m, 2H), 7.33 (dd, 1H), 7.20 (s, 1H), 4.84 (d, 2H).

Example 96

4-Chloro-6-[(2,3-dihydro-benzo[1,4]dioxin-5-ylmethyl)-amino]-2H-phthalazin-1-one

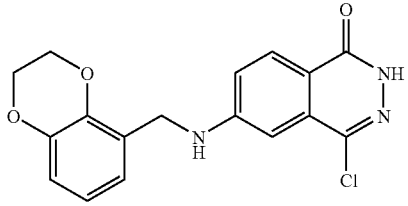

A mixture 6-bromo-4-chloro-2H-phthalazin-1-one (150 mg, 0.58 mmol), (2,3-dihydro-benzo[1,4]dioxin-5-yl)-methylamine hydrochloride (129 mg, 0.64 mmol), Pd$_2$(dba)$_3$ (53 mg, 0.058 mmol), rac-BINAP (132 mg, 0.17 mmol) and NaOt-Bu (200 mg, 2.1 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-[(2,3-dihydro-benzo[1,4]dioxin-5-ylmethyl)-amino]-2H-phthalazin-1-one: 41 mg (20.6%): m/z (M+H)=344. $^1$H-NMR (DMSO-d$_6$) δ: 12.33 (s, 1H), 7.92 (d, 1H), 7.53 (m, 1H), 7.13 (dd, 1H), 6.82 (m, 4H), 4.33 (m, 4H), 4.26 (m, 2H).

Example 97

4-Chloro-6-[(2,3-dihydro-benzofuran-5-ylmethyl)-amino]-2H-phthalazin-1-one

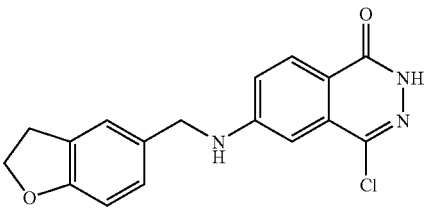

A mixture 6-bromo-4-chloro-2H-phthalazin-1-one (150 mg, 0.58 mmol), (2,3-dihydro-benzofuran-5-yl)-methylamine hydrochloride (119 mg, 0.64 mmol), Pd$_2$(dba)$_3$ (53 mg, 0.058 mmol), rac-BINAP (132 mg, 0.17 mmol) and NaOt-Bu (200 mg, 2.1 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-[(2,3-dihydro-benzofuran-5-ylmethyl)-amino]-2H-phthalazin-1-one: 25 mg (13.2%): m/z (M+H)=328. $^1$H-NMR (DMSO-d$_6$) δ: 12.28 (s, 1H), 7.86 (d, 1H), 7.51 (m, 1H), 7.19 (s, 1H), 7.10 (dd, 1H), 7.05 (d, 1H), 6.78 (s, 1H), 6.67 (d, 1H), 4.44 (t, 2H), 4.26 (d, 2H), 3.09 (t, 2H).

Example 98

4-Chloro-6-(2-piperazin-1-yl-benzylamino)-2H-phthalazin-1-one

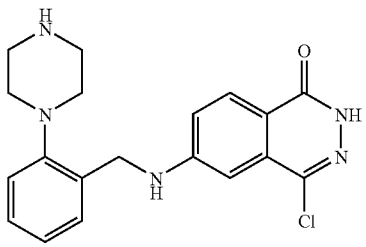

A mixture 6-bromo-4-chloro-2H-phthalazin-1-one (150 mg, 0.58 mmol), 4-(2-aminomethyl-phenyl)-piperazine-1-carboxylic acid tert-butyl ester (187 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded 4-{2-[(4-chloro-1-oxo-1,2-dihydro-phthalazin-6-ylamino)-methyl]-phenyl}-piperazine-1-carboxylic acid tert-butyl ester. Deprotection with TFA in DCM yielded the title compound. 4-Chloro-6-(2-piperazin-1-ylbenzylamino)-2H-phthalazin-1-one: 46 mg (16.9%): m/z (M+H)=370.00. ¹H-NMR (DMSO-d₆) δ: 12.31 (s, 1H), 7.89 (d, 1H), 7.77 (m, 1H), 7.33 (d, 1H), 7.21 (m, 1H), 7.14 (dd, 1H), 7.10 (m, 1H), 7.00 (m, 1H), 6.64 (s, 1H), 4.43 (d, 2H), 2.90 (m, 5H), 2.82 (m, 4H).

Example 99

4-Chloro-6-(2-fluoro-5-trifluoromethyl-benzylamino)-2H-phthalazin-1-one

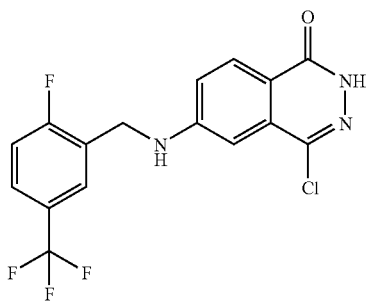

A mixture 6-bromo-4-chloro-2H-phthalazin-1-one (150 mg, 0.58 mmol), 2-fluoro-5-trifluoromethyl-benzylamine (124 mg, 0.64 mmol), Pd₂(dba)₃ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-fluoro-5-trifluoromethyl-benzylamino)-2H-phthalazin-1-one: 27 mg (12.5%): m/z (M+H)=372. ¹H-NMR (DMSO-d₆) δ: 12.38 (s, 1H), 7.95 (d, 1H), 7.85 (m, 1H), 7.75 (m, 1H), 7.65 (m, 1H), 7.49 (m, 1H), 7.19 (dd, 1H), 6.87 (s, 1H), 4.56 (d, 2H).

Example 100

4-Chloro-6-(5-chloro-2-methyl-benzylamino)-2H-phthalazin-1-one

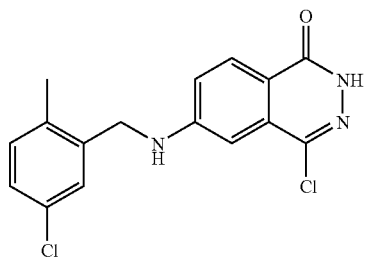

A mixture 6-bromo-4-chloro-2H-phthalazin-1-one (150 mg, 0.58 mmol), 5-chloro-2-methyl-benzylamine (100 mg, 0.64 mmol), Pd₂(dba)₃ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(5-chloro-2-methyl-benzylamino)-2H-phthalazin-1-one: 20 mg (10.3%): m/z (M+H)=334. ¹H-NMR (DMSO-d₆) δ: 12.63 (s, 1H), 8.21 (d, 1H), 7.78 (m, 1H), 7.56 (m, 1H), 7.50 (m, 2H), 7.42 (dd, 1H), 7.10 (s, 1H), 4.66 (d, 2H), 2.60 (s, 3H).

Example 101

4-Chloro-6-(2-chloro-5-trifluoromethyl-benzylamino)-2H-phthalazin-1-one

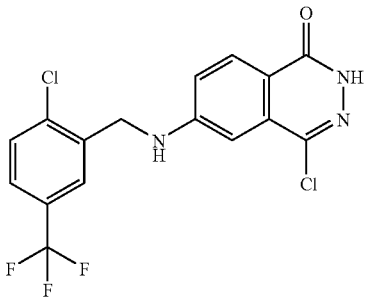

A mixture 6-bromo-4-chloro-2H-phthalazin-1-one (150 mg, 0.58 mmol), 2-chloro-5-trifluoromethyl-benzylamine (135 mg, 0.64 mmol), Pd₂(dba)₃ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-chloro-5-trifluoromethyl-benzylamino)-2H-phthalazin-1-one: 18 mg (8.0%): m/z (M+H)=388. ¹H-NMR (DMSO-d₆) δ: 12.39 (s, 1H), 7.96 (d, 1H), 7.80 (m, 1H), 7.75 (m, 1H), 7.70 (m, 2H), 7.18 (dd, 1H), 6.84 (s, 1H), 4.59 (d, 2H).

Example 102

4-Chloro-6-(2-chloro-3-trifluoromethyl-benzylamino)-2H-phthalazin-1-one

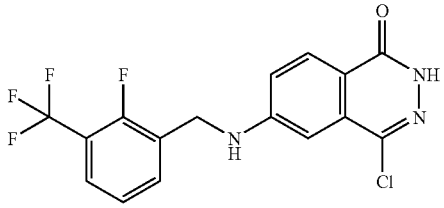

A mixture 6-bromo-4-chloro-2H-phthalazin-1-one (150 mg, 0.58 mmol), 2-chloro-3-trifluoromethyl-benzylamine (124 mg, 0.64 mmol), Pd₂(dba)₃ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-chloro-3-trifluoromethyl-benzylamino)-2H-phthalazin-1-one: 38 mg (17.6%): m/z (M+H)=372. ¹H-NMR (DMSO-d₆) δ: 12.38 (s, 1H), 7.95 (d, 1H), 7.71 (m, 3H), 7.39 (m, 1H), 7.19 (dd, 1H), 6.85 (s, 1H), 4.57 (d, 2H).

Example 103

4-Chloro-6-(2-chloro-6-phenoxy-benzylamino)-2H-phthalazin-1-one

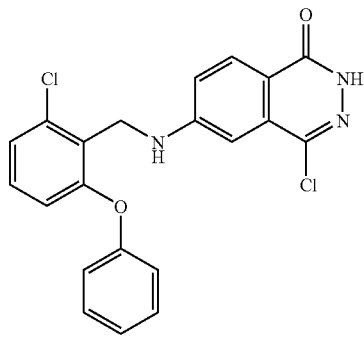

A mixture 6-bromo-4-chloro-2H-phthalazin-1-one (150 mg, 0.58 mmol), 2-chloro-6-phenoxy-benzylamine (150 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2-chloro-6-phenoxy-benzylamino)-2H-phthalazin-1-one: 39 mg (16.3%): m/z (M+H)=412. $^1$H-NMR (DMSO-d$_6$) δ: 12.34 (s, 1H), 7.90 (d, 1H), 7.35 (m, 5H), 7.21 (dd, 1H), 7.15 (m, 1H), 7.02 (m, 2H), 6.95 (d, 1H), 6.84 (dd, 1H), 4.50 (d, 2H).

Example 104

4-Chloro-6-(2,5-dimethyl-benzylamino)-2H-phthalazin-1-one

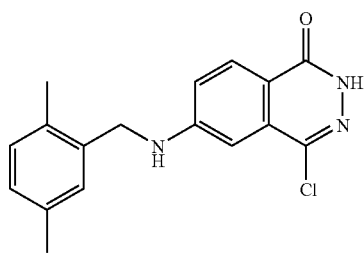

A mixture 6-bromo-4-chloro-2H-phthalazin-1-one (150 mg, 0.58 mmol), 2,5-dimethyl-benzylamine (87 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2,5-dimethyl-benzylamino)-2H-phthalazin-1-one: 31 mg (17.0%): m/z (M+H)=314. $^1$H-NMR (DMSO-d$_6$) δ: 12.34 (s, 1H), 7.92 (d, 1H), 7.45 (m, 1H), 7.16 (dd, 1H), 7.10 (m, 2H), 6.99 (m, 1H), 6.85 (s, 1H), 4.32 (d, 2H), 2.29 (s, 3H), 2.22 (s, 3H).

Example 105

4-Chloro-6-(3-morpholin-4-yl-benzylamino)-2H-phthalazin-1-one

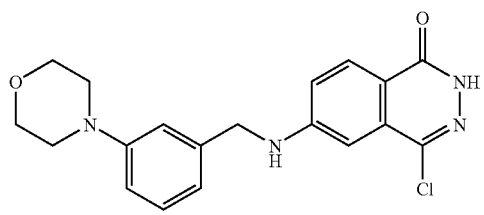

A mixture 6-bromo-4-chloro-2H-phthalazin-1-one (150 mg, 0.58 mmol), 3-morpholin-4-yl-benzylamine (123 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(3-morpholin-4-yl-benzylamino)-2H-phthalazin-1-one: 52 mg (24.2%): m/z (M+H)=371. $^1$H-NMR (DMSO-d$_6$) δ: 12.33 (s, 1H), 7.91 (d, 1H), 7.60 (m, 1H), 7.16 (m, 2H), 6.98 (m, 1H), 6.82 (m, 3H), 4.35 (d, 2H), 3.72 (m, 4H), 3.08 (m, 4H).

Example 106

4-Chloro-6-(2,3-dimethyl-benzylamino)-2H-phthalazin-1-one

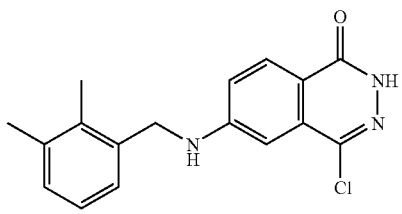

A mixture 6-bromo-4-chloro-2H-phthalazin-1-one (150 mg, 0.58 mmol), 2,3-dimethyl-benzylamine (87 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(2,3-dimethyl-benzylamino)-2H-phthalazin-1-one: 43 mg (23.6%): m/z (M+H)=314. $^1$H-NMR (DMSO-d$_6$) δ: 12.34 (s, 1H), 7.92 (d, 1H), 7.44 (m, 1H), 7.10 (m, 4H), 6.85 (s, 1H), 4.36 (d, 2H), 2.62 (s, 3H), 2.22 (s, 3H).

Example 107

4-Chloro-6-[(3,4-dihydro-2H-benzo[b][1,4]dioxepin-6-ylmethyl)-amino]-2H-phthalazin-1-one

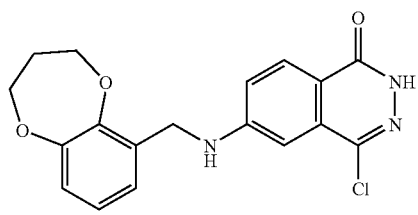

A mixture 6-bromo-4-chloro-2H-phthalazin-1-one (150 mg, 0.58 mmol), (3,4-dihydro-2H-benzo[b][1,4]dioxepin-6-yl)-methylamine hydrochloride (140 mg, 0.64 mmol), Pd$_2$(dba)$_3$ (53 mg, 0.058 mmol), rac-BINAP (132 mg, 0.17 mmol) and NaOt-Bu (200 mg, 2.1 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. (4-Chloro-6-[(3,4-dihydro-2H-benzo[b][1,4]dioxepin-6-ylmethyl)-amino]-2H-phthalazin-1-one: 52 mg (25.1%): m/z (M+H)=358. $^1$H-NMR (DMSO-d$_6$) δ: 12.33 (s, 1H), 7.92 (d, 1H), 7.51 (m, 1H), 7.15 (dd, 1H), 6.97 (m, 1H), 6.89 (m, 2H), 6.83 (s, 1H), 4.38 (d, 2H), 4.17 (t, 2H), 4.11 (t, 2H), 2.12 (m, 2H).

Example 108

4-Chloro-6-(3-furan-2-yl-benzylamino)-2H-phthalazin-1-one

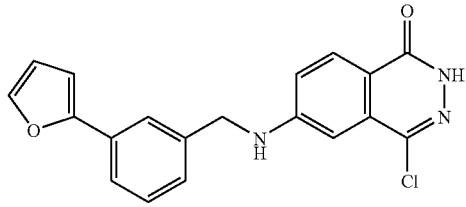

A mixture 6-bromo-4-chloro-2H-phthalazin-1-one (150 mg, 0.58 mmol), 3-furan-2-yl-benzylamine (112 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-(3-furan-2-yl-benzylamino)-2H-phthalazin-1-one: 59 mg (26.0%): m/z (M+H)=352. $^1$H-NMR (DMSO-d$_6$) δ: 12.34 (s, 1H), 7.93 (d, 1H), 7.72 (m, 3H), 7.59 (d, 1H), 7.40 (m, 1H), 7.30 (m, 1H), 7.18 (dd, 1H), 6.92 (d, 1H), 6.86 (s, 1H), 6.58 (m, 1H), 4.47 (d, 2H).

Example 109

4-Chloro-6-[(6-fluoro-4H-benzo[1,3]dioxin-8-ylmethyl)-amino]-2H-phthalazin-1-one

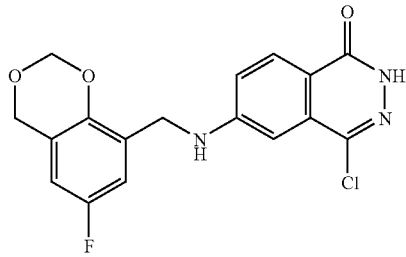

A mixture 6-bromo-4-chloro-2H-phthalazin-1-one (150 mg, 0.58 mmol), (6-fluoro-4H-benzo[1,3]dioxin-8-yl)-methylamine hydrochloride (141 mg, 0.64 mmol), Pd-$_2$(dba)$_3$ (53 mg, 0.058 mmol), rac-BINAP (132 mg, 0.17 mmol) and NaOt-Bu (200 mg, 2.1 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-[(6-fluoro-4H-benzo[1,3]dioxin-8-ylmethyl)-amino]-2H-phthalazin-1-one: 14 mg (6.7%): m/z (M+H)=362. $^1$H-NMR (DMSO-d$_6$) δ: 12.35 (s, 1H), 7.93 (d, 1H), 7.55 (m, 1H), 7.14 (dd, 1H), 6.97 (dd, 1H), 6.88 (dd, 1H), 6.84 (s, 1H), 5.34 (s, 2H), 4.89 (s, 2H), 4.35 (dd, 2H).

Example 110

4-Chloro-6-[(5-methyl-2-phenyl-furan-3-ylmethyl)-amino]-2H-phthalazin-1-one

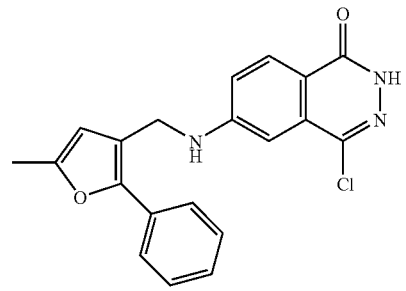

A mixture 6-bromo-4-chloro-2H-phthalazin-1-one (150 mg, 0.58 mmol), (5-methyl-2-phenyl-furan-3-yl)-methylamine (120 mg, 0.64 mmol), Pd$_2$(dba)$_3$ (53 mg, 0.058 mmol), rac-BINAP (132 mg, 0.17 mmol) and NaOt-Bu (140 mg, 1.45 mmol) in DMA (6 mL) was heated at 80° C. for 1 h. The mixture was allowed to cool, diluted with EtOAc (25 mL) and washed with water (25 mL). The organic layer was dried over anhydrous sodium sulfate and concentrated. Chromatography on silica (EtOAc/hexanes) yielded the title compound. 4-Chloro-6-[(5-methyl-2-phenyl-furan-3-ylmethyl)-amino]-2H-phthalazin-1-one: 30 mg (14.1%): m/z (M+H)=366. $^1$H-NMR (DMSO-d$_6$) δ: 12.34 (s, 1H), 7.91 (d, 1H), 7.58 (m, 2H), 7.52 (m, 1H), 7.45 (m, 2H), 7.32 (m, 1H), 7.14 (dd, 1H), 6.74 (s, 1H), 6.22 (s, 1H), 4.38 (d, 2H), 2.30 (s, 3H).

Examples 111 and 112

Synthesis of 1-Chloro-4-oxo-3,4-dihydro-phthalazine-6-carboxylic acid (3-difluoromethoxy-phenyl)-amide and 4-Chloro-1-oxo-1,2-dihydro-phthalazine-6-carboxylic acid (3-difluoromethoxy-phenyl)-amide

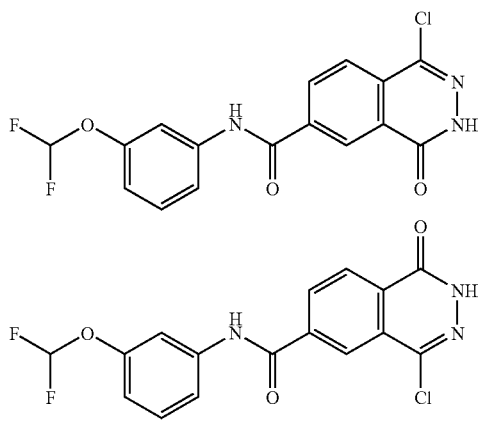

1,4-Dichloro-phthalazine-6-carboxylic acid (3-difluoromethoxy-phenyl)-amide

A mixture of 1,4-dihydroxy-phthalazine-6-carboxylic acid (0.6 g, 2.91 mmol) in thionyl chloride (6 mL) was refluxed for 3 hours. Phosphorous oxychloride (6 mL) was added and the reaction refluxed for an additional 15 hours. The solution was concentrated under vacuum and treated 3 times with toluene in order to remove the excess thionyl chloride. The crude residue was dissolved in DMF (5 mL) and added drop wise to a 0° C. solution of 3-difluoromethoxy-benzylamine (509 mg, 3.2 mmol), DMF (4 mL) and NEt$_3$ (1.22 mL, 8.73 mmol). The reaction was stirred at 0° C. for 1 h, diluted with water and extracted with CH$_2$Cl$_2$. The combined organic layers were washed with water (×3), sat. aq. NH$_4$Cl, brine and dried (Na$_2$SO$_4$). Column chromatography (Hex/EtOAc) afforded 1,4-dichloro-phthalazine-6-carboxylic acid (3-difluoromethoxy-phenyl)-amide (0.26 g). m/z (M+H)=384.

1-Chloro-4-oxo-3,4-dihydro-phthalazine-6-carboxylic acid (3-difluoromethoxy-phenyl)-amide and 4-Chloro-1-oxo-1,2-dihydro-phthalazine-6-carboxylic acid (3-difluoromethoxy-phenyl)-amide A mixture of 1,4-dichloro-phthalazine-6-carboxylic acid (3-difluoromethoxy-phenyl)-amide (0.26 g, 0.68 mmol), 2N NaOH (3.4 mL, 6.8 mmol) and dioxane (4 mL) was heated to 50° C. for 2 hours. The reaction was diluted with water, acidified with conc. HCl to ~pH 4 and extracted with EtOAc (×3). The combined organic phase was washed with brine, dried (Na$_2$SO$_4$) and concentrated. Chromatography (Hex/EtOAc) afforded 1-chloro-4-oxo-3,4-dihydro-phthalazine-6-carboxylic acid (3-difluoromethoxy-phenyl)-amide (60 mg), $^1$H-NMR (DMSO-d$_6$) δ: 13.02 (s, 1H), 10.88 (s, 1H), 8.88 (d, 1H), 8.52 (dd, 1H), 8.14 (d, 1H), 7.75 (m, 1H), 7.69 (m, 1H), 7.43 (m, 1H), 7.23 (t, 1H), 6.96 (dd, 1H). m/z (M+H)=366; and 4-chloro-1-oxo-1,2-dihydro-phthalazine-6-carboxylic acid (3-difluoromethoxy-phenyl)-amide (39 mg), $^1$H-NMR (DMSO-d$_6$) δ: 12.85 (s, 1H), 10.87 (s, 1H), 8.47 (m, 1H), 8.42 (m, 2H), 7.73 (m, 1H), 7.65 (m, 1H), 7.44 (m, 1H), 7.23 (t, 1H), 6.96 (dd, 1H). m/z (M+H)=366.

Example 113 and 114

Synthesis of 4-Chloro-7-(3-fluoro-benzylamino)-2H-phthalazin-1-one and 4-Chloro-6-(3-fluoro-benzylamino)-2H-phthalazin-1-one A mixture 6-bromo-4-chloro-2H-phthalazin-1-one and 7-bromo-4-chloro-2H-phthalazin-1-one (150 mg, 0.58 mmol), 3-fluorobenzylamine (0.08 mL, 0.70 mmol), Pd$_2$(dba)$_3$ (43 mg, 0.047 mmol), rac-BINAP (118 mg, 0.190 mmol) and NaO$^t$-Bu (139 mg, 1.45 mmol) in DMA (8 mL) was heated at 80° C. for 40 min. The mixture was allowed to cool, diluted with EtOAc (25 mL) and washed with water (25 mL). The organic layer was dried over anhydrous sodium sulfate and concentrated. Chromatography on silica (EtOAc/hexanes) afforded 4-chloro-7-(3-fluoro-benzylamino)-2H-phthalazin-1-one (32 mg) as a white solid, $^1$H (600 MHz, CDCl$_3$) δ: 4.44 (s, 2H), 6.92 (m, 1H), 7.00 (d, 1H), 7.05 (dd, 1H), 7.08 (d, 1H), 7.26 (m, 1H), 7.37 (d, 1H), 7.71 (d, 1H), 10.40 (s, 1H) ppm. m/z (M+1) 303.97; 4-chloro-6-(3-fluoro-benzylamino)-2H-phthalazin-1-one (23 mg) as an off white solid, $^1$H (600 MHz, CDCl$_3$) δ: 4.35 (s, 2H), 6.78 (d, 1H), 6.86 (m, 1H), 6.94 (dd, 1H), 6.97 (bd, 1H), 7.05 (d, 1H), 7.21 (m, 1H), 8.00 (d, 1H), 11.00 (s, 1H) ppm. m/z (M+1) 303.97.

Example 115 and 116

Synthesis of 4-Chloro-7-(3-trifluoromethoxy-benzylamino)-2H-phthalazin-1-one and 4-Chloro-6-(3-trifluoromethoxy-benzylamino)-2H-phthalazin-1-one A mixture 6-bromo-4-chloro-2H-phthalazin-1-one and 7-bromo-4-chloro-2H-phthalazin-1-one (150 mg, 0.58 mmol), 3-(trifluoromethoxy)benzylamine (0.08 mL, 0.636 mmol), Pd$_2$(dba)$_3$ (61 mg, 0.0667 mmol), rac-BINAP (120 mg, 0.193 mmol) and NaO$^t$-Bu (155 mg, 1.613 mmol) in DMA (8 mL) was heated at 80° C. for 1 h. The mixture was allowed to cool. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-7-(3-trifluoromethoxy-benzylamino)-2H-phthalazin-1-one (28 mg) as an off white solid, $^1$H (600 MHz, CDCl$_3$) δ: 4.50 (s, 2H), 7.06 (dd, 1H), 7.14 (d, 1H), 7.18 (s, 1H), 7.28 (d, 1H), 7.38 (t, 1H), 7.44 (d, 1H), 7.78 (d, 1H), 9.48 (s, 1H), m/z (M+1) 369.93; 4-chloro-6-(3-trifluoromethoxy-benzylamino)-2H-phthalazin-1-one (22 mg) as an off white solid, $^1$H (600 MHz, CDCl$_3$) δ: 4.41 (s, 2H), 6.83 (d, 1H), 6.98 (dd, 1H), 7.08 (bd, 1H), 7.16 (bs, 1H), 7.25 (s, 1H), 7.32 (t, 1H), 8.06 (d, 1H), 10.15 (s, 1H) ppm. m/z (M+1) 369.93.

Example 117

Synthesis of 4-Chloro-6-(3-chloro-benzylamino)-2H-phthalazin-1-one

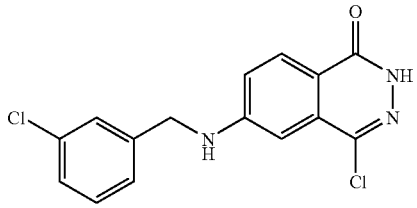

A mixture 6-bromo-4-chloro-2H-phthalazin-1-one (100 mg, 0.385 mmol), 3-chlorobenzylamine (0.052 mL, 0.424 mmol), Pd$_2$(dba)$_3$ (35 mg, 0.0385 mmol), rac-BINAP (75 mg, 0.120 mmol) and NaO$^t$-Bu (111 mg, 1.155 mmol) in DMA (6 mL) was heated at 80° C. for 1 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(3-chloro-benzylamino)-2H-phthalazin-1-one (15 mg) as a white solid, $^1$H (400 MHz, CDCl$_3$) δ: 4.23 (s, 2H), 6.69 (d, 1H), 6.88 (dd, 1H), 7.05 (m, 3H), 7.19 (s, 1H), 7.88 (d, 1H), 11.45 (s, 1H) ppm. m/z (M+1) 320.00.

Example 118

Synthesis of 4-Chloro-6-(2-trifluoromethyl-benzylamino)-2H-phthalazin-1-one

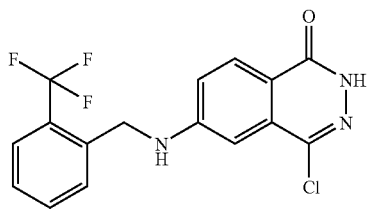

A mixture 6-bromo-4-chloro-2H-phthalazin-1-one (100 mg, 0.385 mmol), 2-(trifluoromethyl)benzylamine (0.31 mL, 0.424 mmol), Pd$_2$(dba)$_3$ (35 mg, 0.0385 mmol), rac-BINAP (81 mg, 0.120 mmol) and NaO$^t$-Bu (92 mg, 0.963 mmol) in DMA (6 mL) was heated at 80° C. for 1 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2-trifluoromethyl-benzylamino)-2H-phthalazin-1-one (7 mg) as a white solid, $^1$H (400 MHz, CDCl$_3$) δ: 4.63 (s, 2H), 6.84 (d, 1H), 6.97 (m, 1H), 7.35 (m, 1H), 7.43 (d, 1H), 7.47 (t, 2H), 8.09 (d, 1H), 10.15 (s, 1H) ppm. m/z (M+1) 353.97.

Example 119

Synthesis of 4-Chloro-6-(3,5-dimethoxy-benzylamino)-2H-phthalazin-1-one

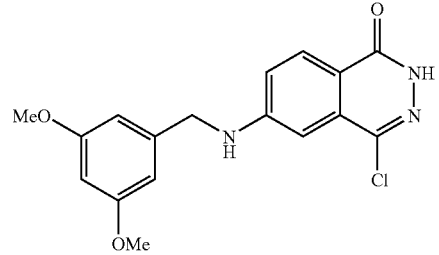

A mixture 6-bromo-4-chloro-2H-phthalazin-1-one (105 mg, 0.405 mmol), 3,5-dimethoxybenzylamine (0.64 mL, 0.424 mmol), Pd$_2$(dba)$_3$ (25 mg, 0.027 mmol), rac-BINAP (78 mg, 0.125 mmol) and NaO$^t$-Bu (92 mg, 0.963 mmol) in DMA (6 mL) was heated at 80° C. for 45 minutes. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(3,5-dimethoxy-benzylamino)-2H-phthalazin-1-one (3 mg) as a brown solid, $^1$H (400 MHz, CDCl$_3$) δ: 3.65 (d, 6H), 4.28 (s, 2H), 6.25 (m, 1H), 6.42 (m, 2H), 6.81 (m, 1H), 6.95 (m, 2H), 8.00 (m, 1H), ppm. m/z (M+1) 345.92.

Example 120

Synthesis of 4-Chloro-6-(3-hydroxy-benzylamino)-2H-phthalazin-1-one

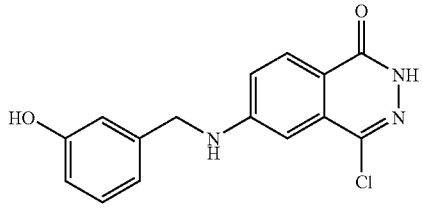

A mixture 6-bromo-4-chloro-2H-phthalazin-1-one (100 mg, 0.385 mmol), 3-(aminomethyl)phenol (59 mg, 0.479 mmol), Pd$_2$(dba)$_3$ (40 mg, 0.044 mmol), rac-BINAP (79 mg, 0.127 mmol) and NaO$^t$-Bu (92 mg, 0.963 mmol) in DMA (6 mL) was heated at 80° C. for 1.5 h. The mixture was allowed to cool, diluted with EtOAc and washed with water. The organic layer was washed with sat.aq. NaHCO$_3$, brine and dried (Na₂SO₄). Chromatography on silica (EtOAc/hexanes) afforded 4-chloro-6-(3-hydroxy-benzylamino)-2H-phthalazin-1-one (8 mg) as a brown solid, ¹H (400 MHz, CDCl₃) δ: 4.48 (s, 2H), 6.77 (dd, 1H), 6.83 (m, 2H), 6.92 (d, 1H), 7.02 (m, 1H), 7.17 (t, 1H), 8.15 (d, 1H), 10.34 (s, 1H) ppm. m/z (M+1) 301.99.

Example 121

Synthesis of 4-Chloro-6-(3,5-difluoro-benzylamino)-2H-phthalazin-1-one

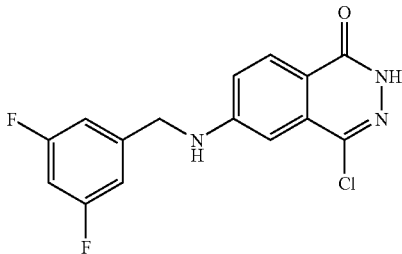

A mixture 6-bromo-4-chloro-2H-phthalazin-1-one (50 mg, 0.193 mmol), 3,5-difluorobenzylamine (0.026 mL, 0.212 mmol), Pd₂(dba)₃ (6 mg, 0.0066 mmol), rac-BINAP (18 mg, 0.029 mmol) and NaO$^t$-Bu (46 mg, 0.482 mmol) in DMA (3 mL) was heated at 80° C. for 1.5 h. The mixture was allowed to cool, diluted with EtOAc and washed with water. The organic layer was washed with sat.aq. NaHCO₃, brine and dried (Na₂SO₄). Chromatography on silica (EtOAc/hexanes) afforded 4-chloro-6-(3,5-difluoro -benzylamino)-2H-phthalazin-1-one (3 mg) as a brown solid, ¹H (400 MHz, CDCl₃) δ: 4.41 (s, 2H), 6.67 (m, 1H), 6.83 (m, 3H), 6.96 (dd, 1H), 8.10 (d, 1H), 9.58 (s, 1H) ppm; m/z (M+1) 321.98.

Example 122

Synthesis of 4-Chloro-6-(2,5-difluoro-benzylamino)-2H-phthalazin-1-one

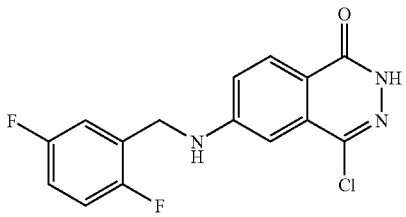

A mixture 6-bromo-4-chloro-2H-phthalazin-1-one (48 mg, 0.185 mmol), 2,5-difluorobenzylamine (0.026 mL, 0.222 mmol), Pd₂(dba)₃ (6 mg, 0.0066 mmol), rac-BINAP (21 mg, 0.021 mmol) and NaO$^t$Bu (45 mg, 0.468 mmol) in DMA (3 mL) was heated in a microwave at 90° C. for 5 minutes. The mixture was allowed to cool, diluted with EtOAc and washed with water. The organic layer was washed with sat.aq. NaHCO₃, brine and dried (Na₂SO₄). Column chromatography (Hex/EtOAc) afforded 4-chloro-6-(2,5-difluoro-benzylamino)-2H-phthalazin-1-one (3 mg) as an off white solid, ¹H (400 MHz, CDCl₃) δ: 4.46 (s, 2H), 6.90 (m, 2H), 7.00 (m, 3H), 8.10 (d, 1H), 10.09 (s, 1H) ppm; m/z (M+1) 321.98.

Example 123

Synthesis of N-{3-[(4-Chloro-1-oxo-1,2-dihydrophthalazin-6-ylamino)-methyl]-phenyl}-acetamide

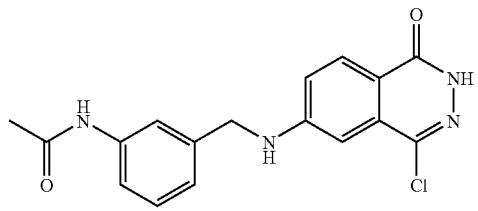

A mixture 6-bromo-4-chloro-2H-phthalazin-1-one (100 mg, 0.385 mmol), N-[3-(aminomethyl)phenyl]acetamide hydrochloride (90 mg, 0.448 mmol), Pd₂(dba)₃ (40 mg, 0.044 mmol), rac-BINAP (81 mg, 0.130 mmol) and NaO$^t$Bu (101 mg, 1.05 mmol) in DMA (6 mL) was heated at 80° C. for 3 h. The mixture was allowed to cool, diluted with EtOAc and washed with water. The organic layer was washed with sat.aq. NaHCO₃, brine and dried (Na₂SO₄). Chromatography on silica (EtOAc/hexanes) afforded N-{3-[(4-chloro-1-oxo-1,2-dihydro-phthalazin-6-ylamino)-methyl]-phenyl}-acetamide (3 mg) as a light brown solid, ¹H (400 MHz, CDCl₃) δ: 2.09 (s, 3H), 4.38 (s, 2H), 6.85 (d, 1H), 7.00 (m, 2H), 7.21 (t, 1H), 7.38 (m, 1H), 7.53 (m, 1H), 7.61 (s, 1H), 8.05 (d, 1H), 8.75 (bs, 1H), 10.90 (bs, 1H) ppm; m/z (M+1) 342.98.

Example 124

Synthesis of 4-Chloro-6-(3,5-dichloro-benzylamino)-2H-phthalazin-1-one

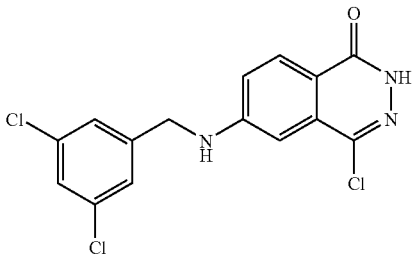

A mixture 6-bromo-4-chloro-2H-phthalazin-1-one (97 mg, 0.374 mmol), 3,5-dichlorobenzylamine (0.057 mL, 0.424 mmol), Pd₂(dba)₃ (29 mg, 0.032 mmol), rac-BINAP (70 mg, 0.112 mmol) and NaO$^t$Bu (104 mg, 1.08 mmol) in DMA (5 mL) was heated at 80° C. for 1.5 h. The mixture was allowed to cool, diluted with EtOAc and washed with water. The organic layer was washed with sat.aq. NaHCO₃, brine and dried (Na₂SO₄). Chromatography on silica (EtOAc/hexanes) afforded 4-chloro-6-(3,5-dichloro-benzylamino)-2H-phthalazin-1-one (3 mg) as a white solid, ¹H (400 MHz, CDCl$_3$) δ: 4.40 (s, 2H), 6.84 (m, 1H), 6.99 (m, 1H), 7.22 (m, 3H), 8.14 (m, 1H), 10.80 (s, 1H) ppm; m/z (M+1) 353.83.

Example 125

Synthesis of 6-[(Biphenyl-3-ylmethyl)-amino]-4-chloro-2H-phthalazin-1-one

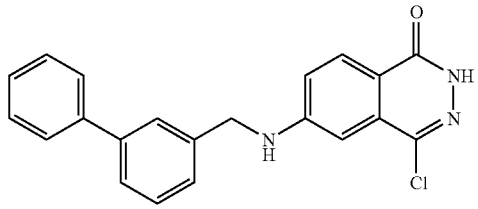

A mixture 6-bromo-4-chloro-2H-phthalazin-1-one (95 mg, 0.366 mmol), 3-phenylbenzylamine (95 mg, 0.518 mmol), Pd$_2$(dba)$_3$ (40 mg, 0.044 mmol), rac-BINAP (76 mg, 0.122 mmol) and NaO$^t$Bu (101 mg, 1.05 mmol) in DMA (5 mL) was heated at 80° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 6-[(biphenyl-3-ylmethyl)-amino]-4-chloro-2H-phthalazin-1-one (3 mg) as an off white solid, $^1$H (400 MHz, CDCl$_3$) δ: 4.49 (s, 2H), 7.00 (m, 2H), 7.50 (m, 9H), 8.05 (d, 1H), 10.87 (s, 1H) ppm; m/z (M+1) 361.95.

Example 126

Synthesis of 4-Chloro-6-(4-phenyl-piperazin-1-yl)-2H-phthalazin-1-one

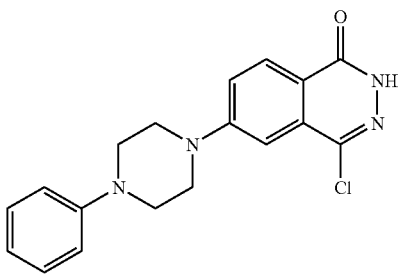

A mixture 6-bromo-4-chloro-2H-phthalazin-1-one (100 mg, 0.385 mmol), 1-phenylpiperazine (0.064 mL, 0.424 mmol), Pd$_2$(dba)$_3$ (15 mg, 0.016 mmol), rac-BINAP (36 mg, 0.058 mmol) and NaO$^t$Bu (46 mg, 0.479 mmol) in DMA (3 mL) was heated in a microwave at 90° C. for 10 minutes. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(4-phenyl-piperazin-1-yl)-2H-phthalazin-1-one (20 mg) as an orange solid, $^1$H (400 MHz, d$_6$-DMSO) δ: 3.32 (m, 4H), 3.61 (m, 4H), 6.81 (t, 1H), 7.00 (d, 2H), 7.15 (d, 1H), 7.24 (t, 2H), 7.62 (dd, 1H), 8.07 (d, 1H), 12.57 (s, 1H) ppm; m/z (M+1) 341.01.

Example 127

Synthesis of 4-Chloro-6-(3-difluoromethoxy-benzylamino)-2H-phthalazin-1-one

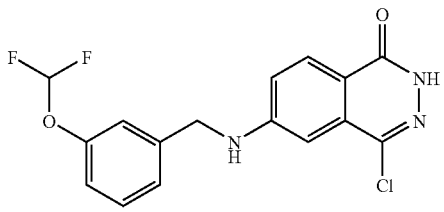

A mixture 6-bromo-4-chloro-2H-phthalazin-1-one (150 mg, 0.578 mmol), 3-(difluoromethoxy)benzylamine (0.074 mL, 0.645 mmol), Pd$_2$(dba)$_3$ (48 mg, 0.052 mmol), rac-BINAP (108 mg, 0.173 mmol) and NaO$^t$Bu (139 mg, 1.445 mmol) in DMA (6 mL) was heated at 80° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(3-difluoromethoxy-benzylamino)-2H-phthalazin-1-one (17 mg) as an off white solid, $^1$H (400 MHz, CDCl$_3$) δ: 4.32 (s, 2H), 6.36 (t, 1H), 6.77 (d, 1H), 6.90 (t, 2H), 6.99 (s, 1H), 7.08 (d, 1H), 7.21 (t, 1H), 8.00 (d, 1H), 10.15 (s, 1H) ppm; m/z (M+1) 351.92.

Example 128

Synthesis of 4-Chloro-6-(2,3-difluoro-benzylamino)-2H-phthalazin-1-one

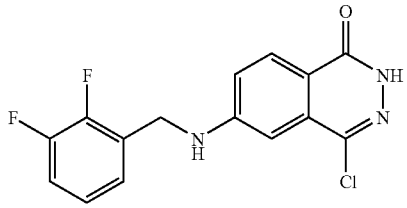

A mixture 6-bromo-4-chloro-2H-phthalazin-1-one (156 mg, 0.601 mmol), 2,3-difluorobenzylamine (0.074 mL, 0.646 mmol), Pd$_2$(dba)$_3$ (53 mg, 0.058 mmol), rac-BINAP (104 mg, 0.167 mmol) and NaO$^t$Bu (134 mg, 1.39 mmol) in DMA (6 mL) was heated at 80° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2,3-difluoro-benzylamino)-2H-phthalazin-1-one (27 mg) as an off white solid, $^1$H (400 MHz, CDCl$_3$) δ: 4.45 (s, 2H), 6.84 (d, 1H), 6.96 (m, 2H), 7.03 (m, 2H), 8.01 (d, 1H), 11.00 (s, 1H) ppm; m/z (M+1) 321.91.

Example 129

Synthesis of 4-Chloro-6-(2-chloro-benzylamino)-2H-phthalazin-1-one

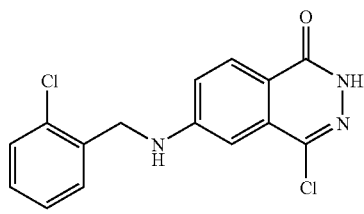

A mixture 6-bromo-4-chloro-2H-phthalazin-1-one (150 mg, 0.578 mmol), 2-chlorobenzylamine (0.078 mL, 0.644 mmol), Pd$_2$(dba)$_3$ (47 mg, 0.051 mmol), rac-BINAP (112 mg, 0.180 mmol) and NaO$^t$Bu (139 mg, 1.445 mmol) in DMA (6 mL) was heated at 80° C. for 2 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2-chloro-benzylamino)-2H-phthalazin-1-one (21 mg) as a beige solid, $^1$H (400 MHz, CDCl$_3$) δ: 4.45 (s, 2H), 6.82 (d, 1H), 6.95 (dd, 1H), 7.14 (m, 2H), 7.30 (m, 2H), 8.00 (d, 1H), 11.20 (s, 1H) ppm; m/z (M+1) 319.93.

Example 130

Synthesis of 4-Chloro-6-(3,4-dimethyl-benzylamino)-2H-phthalazin-1-one

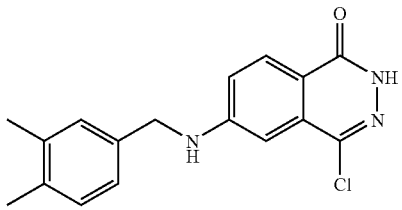

A mixture 6-bromo-4-chloro-2H-phthalazin-1-one (150 mg, 0.578 mmol), 3,4-dimethylbenzylamine (0.09 mL, 0.636 mmol), Pd$_2$(dba)$_3$ (58 mg, 0.063 mmol), rac-BINAP (104 mg, 0.167 mmol) and NaO$^t$Bu (155 mg, 1.613 mmol) in DMA (6 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(3,4-dimethyl-benzylamino)-2H-phthalazin-1-one (21 mg) as a white solid, 1H (400 MHz, d$_6$-DMSO) δ: 2.15 (d, 6H), 4.25 (d, 2H), 6.79 (s, 1H), 7.05 (s, 2H), 7.10 (m, 2H), 7.57 (t, 1H), 7.87 (d, 1H), 12.30 (s, 1H) ppm; m/z (M+1) 313.99.

Example 131

Synthesis of 4-Chloro-6-(3-dimethylamino-benzylamino)-2H-phthalazin-1-one

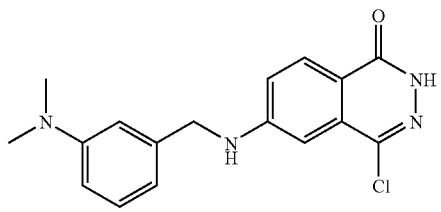

A mixture 6-bromo-4-chloro-2H-phthalazin-1-one (150 mg, 0.578 mmol), N-[3-(aminomethyl)phenyl]-N,N-dimethylamine (102 mg, 0.679 mmol), Pd$_2$(dba)$_3$ (53 mg, 0.0578 mmol), rac-BINAP (112 mg, 0.180 mmol) and NaO$^t$Bu (139 mg, 1.445 mmol) in DMA (6 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(3-dimethylamino-benzylamino)-2H-phthalazin-1-one (28 mg) as a beige solid, $^1$H (400 MHz, d$_6$-DMSO) δ: 2.87 (s, 6H), 4.33 (d, 2H), 6.61 (dd, 1H), 6.66 (d, 1H), 6.76 (m, 1H), 6.85 (m, 1H), 7.14 (m, 2H), 7.61 (t, 1H), 7.91 (d, 1H), 12.32 (s, 1H) ppm. m/z (M+1) 329.00.

Example 132

Synthesis of 4-Chloro-6-(3-isopropoxy-benzylamino)-2H-phthalazin-1-one

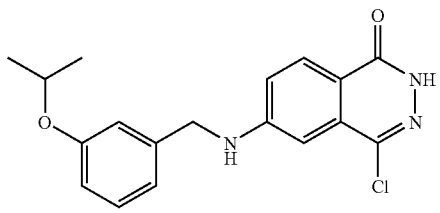

A mixture 6-bromo-4-chloro-2H-phthalazin-1-one (156 mg, 0.601 mmol), 1-(3-isopropoxyphenyl)methanamine (116 mg, 0.702 mmol), Pd$_2$(dba)$_3$ (53 mg, 0.0578 mmol), rac-BINAP (113 mg, 0.181 mmol) and NaO$^t$Bu (139 mg, 1.445 mmol) in DMA (6 mL) was heated at 85° C. for 2 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(3-isopropoxy-benzylamino)-2H-phthalazin-1-one (45 mg) as an off white solid, $^1$H (400 MHz, d$_6$-DMSO) δ: 1.22 (d, 6H), 4.40 (d, 2H), 4.57 (quintet, 1H), 6.80 (m, 2H), 6.91 (m, 2H), 7.16 (dd, 1H), 7.22 (t, 1H), 7.64 (t, 1H), 7.92 (d, 1H), 12.34 (s, 1H) ppm; m/z (M+1) 344.01.

Example 133

Synthesis of 4-Chloro-6-(2-pyrrol-1-yl-benzylamino)-2H-phthalazin-1-one

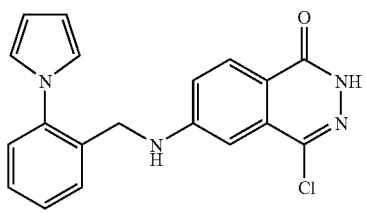

A mixture 6-bromo-4-chloro-2H-phthalazin-1-one (150 mg, 0.578 mmol), 2-(1-pyrrolyl)benzylamine (122 mg, 0.708 mmol), Pd$_2$(dba)$_3$ (56 mg, 0.061 mmol), rac-BINAP (108 mg, 0.173 mmol) and NaO$^t$Bu (139 mg, 1.445 mmol) in DMA (5 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2-pyrrol-1-yl-benzylamino)-2H-phthalazin-1-one (33 mg) as an off white solid, $^1$H (400 MHz, d$_6$-DMSO) δ: 4.22 (d, 2H), 6.26 (t, 2H), 6.60 (bs, 1H), 7.04 (t, 2H), 7.08 (d, 1H), 7.35 (m, 1H), 7.40 (m, 2H), 7.49 (m, 1H), 7.62 (t, 1H), 7.91 (d, 1H) ppm; m/z (M+1) 350.97.

Example 134

Synthesis of 6-(4-tert-Butoxy-benzylamino)-4-chloro-2H-phthalazin-1-one

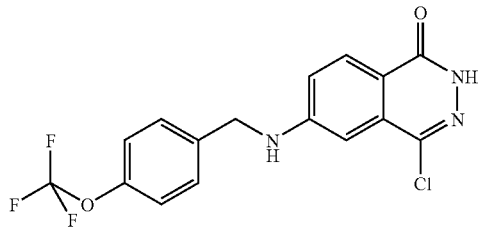

A mixture 6-bromo-4-chloro-2H-phthalazin-1-one (150 mg, 0.578 mmol), 4-(trifluoromethoxy)benzylamine (0.098 mL, 0.642 mmol), Pd$_2$(dba)$_3$ (50 mg, 0.055 mmol), rac-BINAP (112 mg, 0.180 mmol) and NaO$^t$Bu (151 mg, 1.571 mmol) in DMA (5 mL) was heated at 85° C. for 2 h. The mixture was allowed to cool, diluted with EtOAc and washed with water. The organic layer was washed with sat. aq. NaHCO$_3$, brine and dried (Na$_2$SO$_4$). Chromatography on silica (EtOAc/hexanes) afforded 6-(4-tert-butoxy-benzylamino)-4-chloro-2H-phthalazin-1-one (37 mg) as a beige solid, 1H (400 MHz, d$_6$-DMSO) δ: 4.47 (d, 2H), 6.81 (s, 1H), 7.16 (dd, 1H), 7.35 (d, 2H), 7.50 (d, 2H), 7.69 (t, 1H), 7.93 (d, 1H), 12.35 (s, 1H) ppm; m/z (M+1) 369.93.

Example 135

Synthesis of 4-Chloro-6-[(pyridin-3-ylmethyl)-amino]-2H-phthalazin-1-one hydroformate

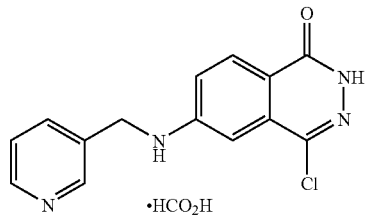

A mixture 6-bromo-4-chloro-2H-phthalazin-1-one (150 mg, 0.578 mmol), 3-(aminomethyl)pyridine (0.064 mL, 0.636 mmol), Pd$_2$(dba)$_3$ (53 mg, 0.058 mmol), rac-BINAP (115 mg, 0.185 mmol) and NaO$^t$Bu (169 mg, 1.759 mmol) in DMA (5 mL) was heated at 85° C. for 2 h. The mixture was allowed to cool, then filtered. Preparatory HPLC afforded 4-chloro-6-[(pyridin-3-ylmethyl)-amino]-2H-phthalazin-1-one hydroformate (31 mg) as a yellow solid, 1H (400 MHz, d$_6$-DMSO) δ: 4.41 (d, 2H), 6.78 (d, 1H), 7.12 (dd, 1H), 7.31 (dd, 1H), 7.60 (t, 1H), 7.10 (m, 1H), 7.88 (d, 1H), 8.09 (s, 1H), 8.41 (dd, 1H), 8.56 (d, 1H), 12.31 (s, 1H) ppm; m/z (M+1) 286.99.

Example 136

Synthesis of 4-Chloro-6-(2,3-dimethoxy-benzylamino)-2H-phthalazin-1-one

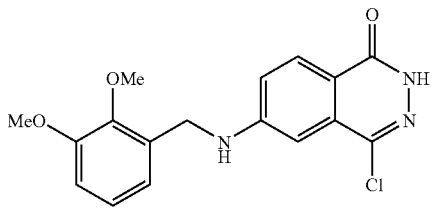

A mixture 6-bromo-4-chloro-2H-phthalazin-1-one (150 mg, 0.578 mmol), 2,3-dimethoxybenzylamine (0.094 mL, 0.636 mmol), Pd$_2$(dba)$_3$ (53 mg, 0.058 mmol), rac-BINAP (112 mg, 0.180 mmol) and NaO$^t$Bu (139 mg, 1.445 mmol) in DMA (5 mL) was heated at 85° C. for 2 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2,3-dimethoxy-benzylamino)-2H-phthalazin-1-one (37 mg) as an off white solid, $^1$H (400 MHz, d$_6$-DMSO) δ: 3.79 (s, 3H), 3.80 (s, 3H), 4.40 (d, 2H), 6.83 (s, 1H), 6.88 (dd, 1H), 7.00 (m, 2H), 7.14 (dd, 1H), 7.53 (t, 1H), 7.91 (d, 1H), 12.33 (bs, 1H) ppm; m/z (M+1) 345.92.

Example 137

Synthesis of 4-Chloro-6-(2,5-dimethoxy-benzylamino)-2H-phthalazin-1-one

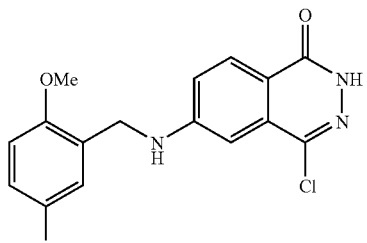

A mixture 6-bromo-4-chloro-2H-phthalazin-1-one (155 mg, 0.597 mmol), 2,5-dimethoxybenzylamine (0.096 mL, 0.636 mmol), Pd$_2$(dba)$_3$ (61 mg, 0.067 mmol), rac-BINAP (111 mg, 0.178 mmol) and NaO$^t$Bu (139 mg, 1.445 mmol) in DMA (5 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2,5-dimethoxy-benzylamino)-2H-phthalazin-1-one (37 mg) as an off white solid, $^1$H (400 MHz, d$_6$-DMSO) δ: 3.45 (s, 3H), 3.61 (s, 3H), 4.17 (d, 2H), 6.63 (m, 3H), 6.76 (d, 1H), 6.94 (dd, 1H), 7.33 (t, 1H), 7.72 (d, 1H), 12.14 (s, 1H) ppm; m/z (M+1) 345.92.

Example 138

Synthesis of 4-Chloro-6-[(pyridin-2-ylmethyl)-amino]-2H-phthalazin-1-one

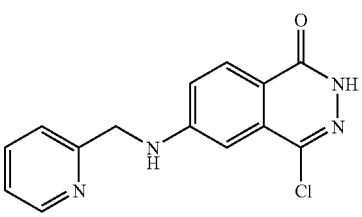

A mixture 6-bromo-4-chloro-2H-phthalazin-1-one (153 mg, 0.590 mmol), 2-(aminomethyl)pyridine (0.066 mL, 0.646 mmol), Pd$_2$(dba)$_3$ (49 mg, 0.0535 mmol), rac-BINAP (113 mg, 0.181 mmol) and NaO$^t$Bu (160 mg, 1.665 mmol) in DMA (5 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-[(pyridin-2-ylmethyl)-amino]-2H-phthalazin-1-one (3 mg) as a yellow brown solid, 1H (400 MHz, d$_6$-DMSO) δ: 4.53 (d, 2H), 6.84 (s, 1H), 7.18 (dd, 1H), 7.28 (m, 1H), 7.38 (d, 1H), 7.75 2H), 7.92 (d, 1H), 8.55 (d, 1H), 12.35 (s, 1H) ppm; m/z (M+1) 286.99.

Example 139

Synthesis of 4-Chloro-6-(2-trifluoromethoxy-benzylamino)-2H-phthalazin-1-one

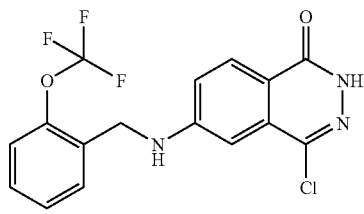

A mixture 6-bromo-4-chloro-2H-phthalazin-1-one (150 mg, 0.578 mmol), 2-(trifluoromethoxy)benzylamine (122 mg, 0.636 mmol), Pd$_2$(dba)$_3$ (49 mg, 0.0535 mmol), rac-BINAP (104 mg, 0.167 mmol) and NaO$^t$Bu (142 mg, 1.478 mmol) in DMA (5 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2-trifluoromethoxy-benzylamino)-2H-phthalazin-1-one (41 mg) as a beige solid, $^1$H (400 MHz, d$_6$-DMSO) δ: 4.50 (s, 2H), 6.78 (s, 1H), 7.16 (dd, 1H), 7.40 (m, 3H), 7.47 (d, 1H), 7.68 (t, 1H) m 7.95 (d, 1H), 12.37 (s, 1H) ppm; m/z (M+1) 369.86.

Example 140

Synthesis of 4-Chloro-6-(2-difluoromethoxy-benzylamino)-2H-phthalazin-1-one

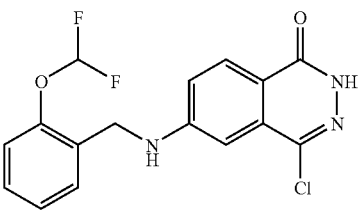

A mixture 6-bromo-4-chloro-2H-phthalazin-1-one (150 mg, 0.578 mmol), 2-(difluoromethoxy)benzylamine (110 mg, 0.636 mmol), Pd$_2$(dba)$_3$ (47 mg, 0.051 mmol), rac-BINAP (108 mg, 0.173 mmol) and NaO$^t$Bu (139 mg, 1.445 mmol) in DMA (5 mL) was heated at 85° C. for 2 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2-difluoromethoxy-benzylamino)-2H-phthalazin-1-one (14 mg) as a yellow solid, $^1$H (400 MHz, d$_6$-DMSO) δ: 4.43 (d, 2H), 6.81 (s, 1H), 7.14 (dd, 1H), 7.22 (m, 2H), 7.27 (t, 1H), 7.37 (m, 2H), 7.60 (t, 1H), 7.93 (d, 1H), 12.35 (s, 1H) ppm; m/z (M+1) 351.92.

Example 141

Synthesis of 4-Chloro-6-(2-imidazol-1-yl-benzylamino)-2H-phthalazin-1-one

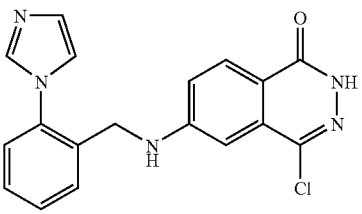

A mixture 6-bromo-4-chloro-2H-phthalazin-1-one (148 mg, 0.570 mmol), 2-imidazol-1-yl-benzylamine (110 mg, 0.635 mmol), Pd$_2$(dba)$_3$ (53 mg, 0.0578 mmol), rac-BINAP (117 mg, 0.188 mmol) and NaO$^t$Bu (227 mg, 2.362 mmol) in DMA (5 mL) was heated at 85° C. for 45 minutes. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2-imidazol-1-yl-benzylamino)-2H-phthalazin-1-one (17 mg) as a yellow solid, $^1$H (400 MHz, d$_6$-DMSO) δ: 4.24 (d, 2H), 6.64 (s, 1H), 7.06 (dd, 1H), 7.11 (s, 1H), 7.41 (m, 1H), 7.46 (m, 2H), 7.52 (m, 2H), 7.59 (t, 1H), 7.92 (m, 2H), 12.36 (1H) ppm; m/z (M+1) 351.99.

Example 142

Synthesis of 4-Chloro-6-[4-(3-trifluoromethyl-phenyl)-piperazin-1-yl]-2H-phthalazin-1-one

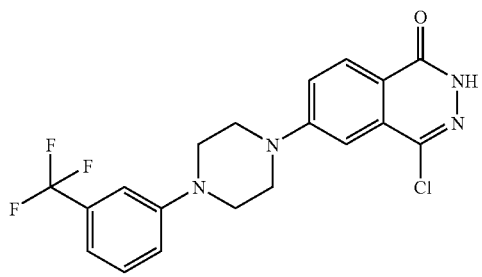

A mixture 6-bromo-4-chloro-2H-phthalazin-1-one (50 mg, 0.578 mmol), 1-(α,α,α-trifluoro-m-tolyl)piperazine (0.12 mL, 0.639 mmol), Pd$_2$(dba)$_3$ (53 mg, 0.0578 mmol), rac-BINAP (123 mg, 0.198 mmol) and NaO$^t$Bu (176 mg, 1.831 mmol) in DMA (5 mL) was heated at 85° C. for 1 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-[4-(3-trifluoromethyl-phenyl)-piperazin-1-yl]-2H-phthalazin-1-one (15 mg) as a beige solid, $^1$H (400 MHz, d$_6$-DMSO) δ: 3.21 (m, 4H), 3.40 (m, 4H), 6.86 (d, 1H), 6.91 (d, 1H), 6.98 (s, 1H), 7.05 (m, 1H), 7.22 (t, 1H), 7.38 (dd, 1H), 7.85 (d, 1H), 12.28 (s, 1H) ppm; m/z (M+1) 408.82.

Example 143

Synthesis of 4-Chloro-6-(2-[1,2,4]triazol-1-yl-benzylamino)-2H-phthalazin-1-one

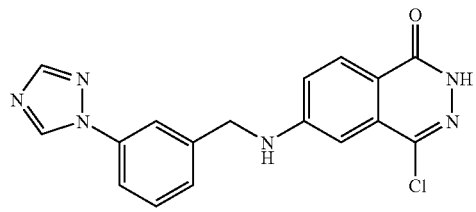

A mixture 6-bromo-4-chloro-2H-phthalazin-1-one (150 mg, 0.578 mmol), [3-(1H-1,2,4-triazol-1-yl)phenyl]methylamine (110 mg, 0.636 mmol), Pd$_2$(dba)$_3$ (53 mg, 0.0578 mmol), rac-BINAP (108 mg, 0.173 mmol) and NaO$^t$Bu (246 mg, 2.560 mmol) in DMA (5 mL) was heated at 85° C. for 45 minutes. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(2-[1,2,4]triazol-1-yl-benzylamino)-2H-phthalazin-1-one (24 mg) as a yellow solid, $^1$H (400 MHz, d$_6$-DMSO) δ: 4.54 (d, 2H), 6.86 (s, 1H), 7.18 (dd, 1H), 7.43 (d, 1H), 7.54 (t, 1H), 7.76 (m, 2H), 7.91 (s, 1H), 7.94 (d, 1H), 8.22 (s, 1H), 9.28 (s, 1H), 12.35 (s, 1H) ppm; m/z (M+1) 352.88.

Example 144

Synthesis of 4-Chloro-6-(3-morpholin-4-ylmethyl-benzylamino)-2H-phthalazin-1-one

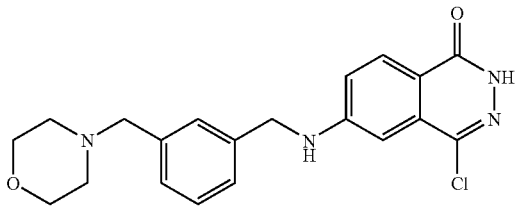

A mixture 6-bromo-4-chloro-2H-phthalazin-1-one (150 mg, 0.578 mmol), [3-(morpholinomethyl)phenyl]methylamine (131 mg, 0.636 mmol), Pd$_2$(dba)$_3$ (53 mg, 0.0578 mmol), rac-BINAP (108 mg, 0.173 mmol) and NaO$^t$Bu (139 mg, 1.445 mmol) in DMA (5 mL) was heated at 85° C. for 1 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(3-morpholin-4-ylmethyl-benzylamino)-2H-phthalazin-1-one (42 mg) as an off white solid, $^1$H (400 MHz, d$_6$-DMSO) δ: 2.11 (m, 4H), 3.23 (s, 2H), 3.30 (t, 4H), 4.25 (d, 2H), 6.60 (s, 1H), 6.98 (m, 2H), 7.10 (m, 3H), 7.50 (t, 1H), 7.74 (d, 1H), 12.16 (s, 1H) ppm; m/z (M+1) 384.94.

Example 145

Synthesis of 4-Chloro-6-(3-pyrrol-1-yl-benzylamino)-2H-phthalazin-1-one

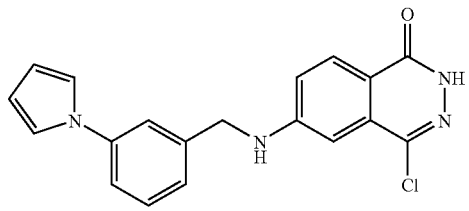

A mixture 6-bromo-4-chloro-2H-phthalazin-1-one (160 mg, 0.617 mmol), 3-(1H-pyrol-1-yl)benzylamine (100 mg, 0.581 mmol), Pd$_2$(dba)$_3$ (58 mg, 0.063 mmol), rac-BINAP (116 mg, 0.186 mmol) and NaO$^t$Bu (160 mg, 1.665 mmol) in DMA (5 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography on silica (EtOAc/hexanes) afforded 4-chloro-6-(3-pyrrol-1-yl-benzylamino)-2H-phthalazin-1-one (47 mg) as an off white solid, $^1$H (400 MHz, d$_6$-DMSO) δ: 4.49 (d, 2H), 6.26 (t, 2H), 6.87 (s, 1H), 7.19 (dd, 1H), 7.25 (d, 1H), 7.33 (t, 2H), 7.42 (t, 1H), 7.47 (m, 1H), 7.61 (s, 1H), 7.67 (t, 1H), 7.94 (d, 1H), 12.35 (s, 1H) ppm; m/z (M+1) 350.90.

3.62 (m, 4H), 3.78 (m, 4H), 7.12 (d, 1H), 7.60 (dd, 1H), 7.87 (d, 1H), 8.07 (d, 1H), 8.11 (m, 1H), 8.37 (s, 1H), 12.51 (s, 1H) ppm. m/z (M+1) 342.98.

Example 146

Synthesis of 4-Chloro-6-[3-(4-methyl-piperidin-1-ylmethyl)-benzylamino]-2H-phthalazin-1-one

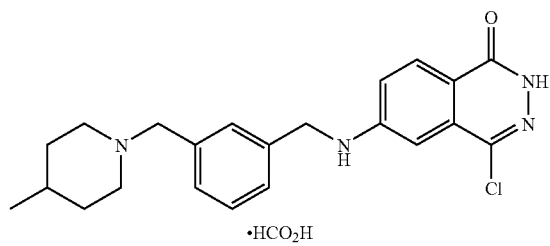

•HCO₂H

A mixture 6-bromo-4-chloro-2H-phthalazin-1-one (148 mg, 0.570 mmol), {3-[4-methylpiperidino)methyl]phenyl}methanamine (139 mg, 0.636 mmol), Pd₂(dba)₃ (60 mg, 0.0655 mmol), rac-BINAP (113 mg, 0.181 mmol) and NaO'Bu (152 mg, 1.580 mmol) in DMA (5 mL) was heated at 85° C. for 45 minutes. The mixture was allowed to cool, diluted with EtOAc and washed with water. The organic layer was washed with sat.aq. NaHCO₃, brine and dried (Na₂SO₄). Preparatory HPLC afforded 4-chloro-6-[3-(4-methyl-piperidin-1-ylmethyl)-benzylamino]-2H-phthalazin-1-one hydroformate (47 mg) as an off white solid, ¹H (400 MHz, d₆-DMSO) δ: 0.82 (d, 3H), 1.00 (m, 2H), 1.23 (bs, 1H), 1.44 (d, 2H), 1.81 (t, 2H), 2.67 (m, 2H), 3.39 (s, 2H), 4.43 (d, 2H), 6.78 (s, 1H), 7.14 (m, 2H), 7.26 (m, 3H), 7.68 (t, 1H), 7.90 (d, 1H), 8.16 (s, 1H), 12.33 (s, 1H) ppm; m/z (M+1) 397.01.

Example 147

Synthesis 4-Chloro-6-(2,3,5,6-tetrahydro-[1,2']bipyrazinyl-4-yl)-2H-phthalazin-1-one

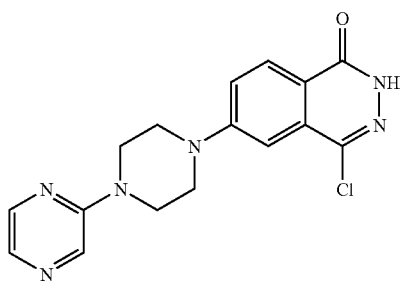

A mixture 6-bromo-4-chloro-2H-phthalazin-1-one (145 mg, 0.559 mmol), 1-(2-pyrazinyl)piperazine (104 mg, 0.633 mmol), Pd₂(dba)₃ (43 mg, 0.047 mmol), rac-BINAP (116 mg, 0.186 mmol) and NaO'Bu (167 mg, 1.738 mmol) in DMA (5 mL) was heated at 85° C. for 1.5 h. The mixture was allowed to cool, diluted with EtOAc and washed with water. The organic layer was washed with sat.aq. NaHCO₃, brine and dried (Na₂SO₄). Preparatory HPLC afforded 4-chloro-6-(2,3,5,6-tetrahydro-[1,2']bipyrazinyl-4-yl)-2H-phthalazin-1-one (32 mg) as a yellow solid, ¹H (400 MHz, d₆-DMSO) δ:

Example 148

Synthesis of 4-Chloro-6-[4-(2-morpholin-4-yl-ethyl)-piperazin-1-yl]-2H-phthalazin-1-one hydroformate

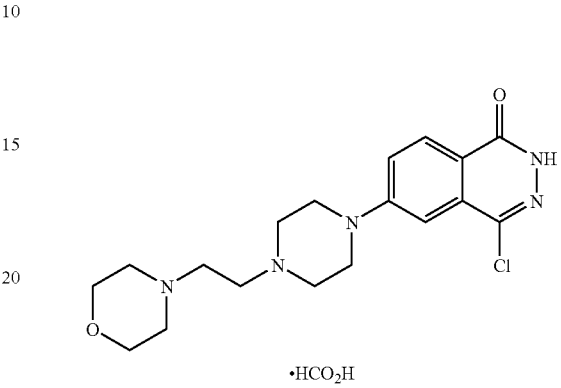

•HCO₂H

A mixture 6-bromo-4-chloro-2H-phthalazin-1-one (150 mg, 0.578 mmol), 1-[2-(morpholin-4-yl)ethyl]piperazine (127 mg, 0.636 mmol), Pd₂(dba)₃ (53 mg, 0.0578 mmol), rac-BINAP (108 mg, 0.173 mmol) and NaO'Bu (139 mg, 1.445 mmol) in DMA (5 mL) was heated at 85° C. for 2 h. The mixture was allowed to cool, diluted with EtOAc and washed with water. The organic layer was washed with sat.aq. NaHCO₃, brine and dried (Na₂SO₄). Preparatory HPLC afforded 4-chloro-6-[4-(2-morpholin-4-yl-ethyl)-piperazin-1-yl]-2H-phthalazin-1-one hydroformate (43 mg) as an orange solid, ¹H (400 MHz, d₆-DMSO) δ: 2.39 (m, 4H), 2.45 (m, 4H), 2.56 (m, 4H), 3.41 (m, 4H), 3.55 (t, 4H), 7.08 (d, 1H), 7.54 (dd, 1H), 8.03 (d, 1H), 8.15 (s, 1H), 12.49 (s, 1H) ppm; m/z (M+1) 378.05.

Example 149

Synthesis of 4-Chloro-6-[4-(3-dimethylamino-propyl)-piperazin-1-yl]-2H-phthalazin-1-one hydroformate

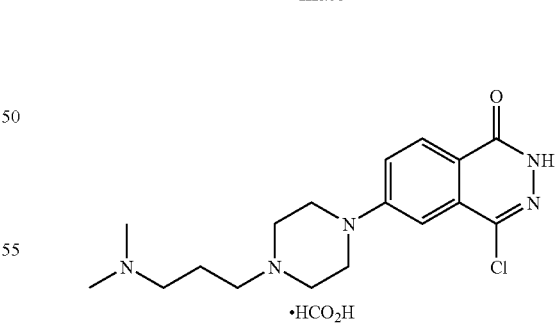

•HCO₂H

A mixture 6-bromo-4-chloro-2H-phthalazin-1-one (150 mg, 0.578 mmol), 1-[3-(dimethylamino)propyl]piperazine (112 mg, 0.654 mmol), Pd₂(dba)₃ (53 mg, 0.0578 mmol), rac-BINAP (108 mg, 0.173 mmol) and NaO'Bu (139 mg, 1.445 mmol) in DMA (5 mL) was heated at 85° C. for 1 h. The mixture was allowed to cool, diluted with EtOAc and washed with water. The organic layer was washed with sat.aq. NaHCO₃, brine and dried (Na₂SO₄). Preparatory HPLC afforded 4-chloro-6-[4-(3-dimethylamino-propyl)-piperazin-1-yl]-2H-phthalazin-1-one hydroformate (38 mg) as a pale brown solid, 1H (400 MHz, $d_6$-DMSO) δ: 1.66 (m, 2H), 2.30 (s, 6H), 2.34 (t, 2H), 2.53 (m, 6H), 3.43 (m, 4H), 7.09 (d, 1H), 7.55 (dd, 1H), 8.03 (d, 1H), 8.15 (s, 1H), 12.50 (s, 1H) ppm; m/z (M+1) 350.08.

Example 150

Synthesis of 4-Chloro-6-[3-(3-dimethylamino-propylamino)-benzylamino]-2H-phthalazin-1-one hydroformate

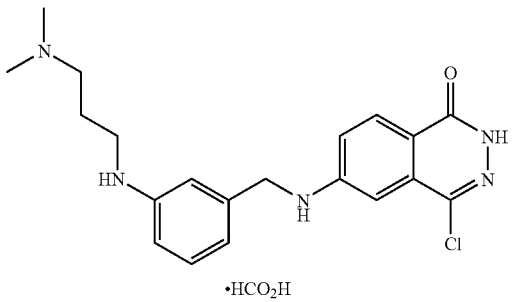

(3-Iodo-benzyl)-carbamic acid tert-butyl ester

A mixture of 3-iodobenzylamine hydrochloride (3 g, 11.131 mmol), $CH_2Cl_2$ (60 mL) and triethylamine (3.1 mL, 22.263 mmol) was stirred at room temperature. Boc-anhydride (2.60 g, 11.913 mmol) was added and the reaction stirred at room temperature for 1 h. The reaction was poured onto water, extracted with $CH_2Cl_2$ and dried ($Na_2SO_4$). Preparatory HPLC afforded (3-iodo-benzyl)-carbamic acid tert-butyl ester (3.494 g) as a white solid. m/z (M+1) 333.84.

[3-(3-dimethylamino-propylamino)-benzyl]-carbamic acid tert-butyl ester

A mixture of (3-iodo-benzyl)-carbamic acid tert-butyl ester (150 mg, 0.450 mmol), 3-(dimethylamino)-1-propylamine (0.084 mL, 0.675 mmol), $K_2CO_3$ (129 mg, 0.933 mmol), CuI (11 mg, 0.058 mmol), L-proline (13 mg, 0.113 mmol) and DMSO (3 mL) was heated at 80° C. for 1.5 h. The reaction was cooled, poured onto water and the aqueous layer extracted with EtOAc (×3). The organic layers were combined and washed with water, brine and dried ($Na_2SO_4$). Chromatography (MeOH/EtOAc) afforded [3-(3-dimethyl amino-propylamino)-benzyl]-carbamic acid tert-butyl ester (65 mg) as a yellow solid. m/z (M+1) 308.13.

N-(3-Aminomethyl-phenyl)-N',N'-dimethyl-propane-1,3-diamine hydrochloride

A mixture of [3-(3-dimethyl amino-propylamino)-benzyl]-carbamic acid tert-butyl ester (65 mg, 0.211 mmol), methanol (2 mL) and 4.89N isopropanolic hydrochloric acid (1.3 mL, 6.357 mmol) was stirred at room temperature overnight. The reaction was concentrated and dried to yield N-(3-aminomethyl-phenyl)-N',N'-dimethyl-propane-1,3-diamine hydrochloride (65 mg) as a yellow solid. m/z (M+1) 208.02.

4-Chloro-6-[3-(3-dimethylamino-propylamino)-benzylamino]-2H-phthalazin-1-one

A mixture of N-(3-aminomethyl-phenyl)-N',N'-dimethyl-propane-1,3-diamine hydrochloride (65 mg, 0.267 mmol), 6-bromo-4-chloro-2H-phthalazin-1-one (66 mg, 0.254), $Pd_2(dba)_3$ (31 mg, 0.0339 mmol), rac-BINAP (57 mg, 0.0915 mmol), NaOtBu (88 mg, 0.916 mmol) and DMA (5 mL) was heated to 85° C. until the reaction was completed by HPLC. The reaction was filtered through celite and purified by preparatory HPLC to yield 4-chloro-6-[3-(3-dimethylamino-propylamino)-benzylamino]-2H-phthalazin-1-one hydroformate (17 mg) as an orange solid. $^1$H (400 MHz, $d_6$-DMSO) δ: 1.62 (quintet, 2H), 2.11 (s, 6H), 2.26 (t, 2H), 2.98 (t, 2H), 4.29 (d, 2H), 6.42 (d, 1H), 6.53 (m, 2H), 6.81 (s, 1H), 7.10 (t, 1H), 7.12 (dd, 1H), 7.60 (t, 1H), 7.91 (d, 1H), 8.20 (s, 2H), 12.32 (s, 1H) ppm; m/z (M+1) 385.96.

Example 151

Synthesis of 4-Chloro-6-[3-(2-morpholin-4-yl-ethylamino)-benzylamino]-2H-phthalazin-1-one hydroformate

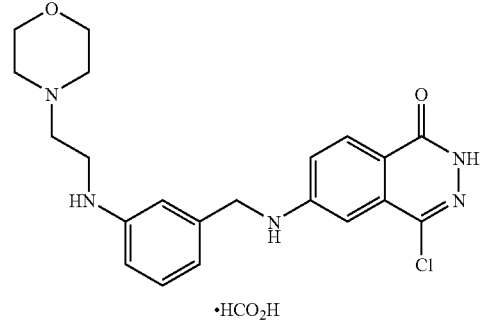

[3-(2-Morpholin-4-yl-ethylamino)-benzyl]-carbamic acid isopropyl ester

A mixture of (3-iodo-benzyl)-carbamic acid tert-butyl ester (272 mg, 0.816 mmol), 4-(2-aminoethyl)morpholine (0.16 mL, 1.225 mmol), $K_2CO_3$ (232 mg, 1.679 mmol), CuI (19 mg, 0.10 mmol), L-proline (19 mg, 0.163 mmol) and DMSO (5 mL) was heated at 85° C. for 1 h. The reaction was cooled, poured onto water and the aqueous layer extracted with EtOAc (×3). The organic layers were combined and washed with water, brine and dried ($Na_2SO_4$). Chromatography (MeOH/EtOAc) afforded [3-(2-morpholin-4-yl-ethylamino)-benzyl]-carbamic acid isopropyl ester (200 mg) as an orange viscous oil. m/z (M+1) 336.16.

(3-Aminomethyl-phenyl)-(2-morpholin-4-yl-ethyl)-amine hydrochloride

A mixture of [3-(2-morpholin-4-yl-ethylamino)-benzyl]-carbamic acid isopropyl ester (200 mg, 0.596 mmol), methanol (4 mL) and 4.89N isopropanolic hydrochloric acid (2.4 mL) was stirred at room temperature overnight. The reaction was concentrated and dried to yield (3-aminomethyl-phenyl)-(2-morpholin-4-yl-ethyl)-amine hydrochloride (212 mg) as an orange solid. m/z (M+1) 236.04.

4-Chloro-6-[3-(2-morpholin-4-yl-ethylamino)-benzylamino]-2H-phthalazin-1-one hydroformate A mixture of (3-aminomethyl-phenyl)-(2-morpholin-4-yl-ethyl)-amine hydrochloride (212 mg, 0.781 mmol), 6-bromo-4-chloro-2H-phthalazin-1-one (184 mg, 0.710), Pd$_2$(dba)$_3$ (65 mg, 0.071 mmol), rac-BINAP (142 mg, 0.228 mmol), NaOtBu (266 mg, 2.768 mmol) and DMA (5 mL) was heated to 85° C. until the reaction was completed by HPLC. The reaction was filtered through celite and purified by preparatory HPLC to yield 4-chloro-6-[3-(2-morpholin-4-yl-ethylamino)-benzylamino]-2H-phthalazin-1-one hydroformate (62 mg) as a light brown solid. $^1$H (400 MHz, d$_6$-DMSO) δ: 2.29 (m, 4H), 2.36 (t, 2H), 3.02 (m, 2H), 3.48 (m, 4H), 4.24 (d, 2H), 5.38 (bs, 1H), 6.40 (dd, 1H), 6.47 (d, 1H), 6.51 (s, 1H), 6.77 (s, 1H), 6.97 (t, 1H), 7.07 (dd, 1H), 7.54 (t, 1H), 7.85 (d, 1H), 8.10 (s, 1H), 12.26 (s, 1H) ppm; m/z (M+1) 413.93.

Example 152

Synthesis of 4-Chloro-1-oxo-1,2-dihydro-phthalazine-6-carboxylic acid (3-piperidin-1-ylmethyl-phenyl)-amide hydroformate

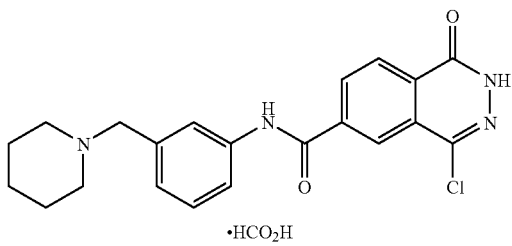

·HCO$_2$H 1,4-Dichloro-phthalazine-6-carboxylic acid (3-piperidin-1-ylmethyl-phenyl)-amide hydroformate A mixture of 1,4-dihydroxy-phthalazine-6-carboxylic acid (0.28 g, 1.358 mmol) in thionyl chloride (4 mL) was refluxed for 3 hours. Phosphorous oxychloride (4 mL) was added and the reaction refluxed for an additional 15 hours. The solution was concentrated under vacuum and treated 3 times with toluene in order to remove the excess thionyl chloride. The crude residue was dissolved in DMF (5 mL) and added dropwise to a 0° C. solution of 3-(piperidin-1-yl-methyl)aniline (0.485 g, 2.55 mmol), DMF (3 mL) and NEt$_3$ (0.71 mL, 5.09 mmol). The reaction was stirred at 0° C. for 1 h, diluted with water and extracted with CH$_2$Cl$_2$. The combined organic layers were washed with water (×3), sat. aq. NH$_4$Cl, brine and dried (Na$_2$SO$_4$). Column chromatography (Hex/EtOAc) afforded 1,4-dichloro-phthalazine-6-carboxylic acid (3-piperidin-1-ylmethyl-phenyl)-amide (257 mg). m/z (M+1) 414.96.

A mixture of 1,4-dichloro-phthalazine-6-carboxylic acid (3-piperidin-1-ylmethyl-phenyl)-amide (257 mg, 0.619 mmol), 2N NaOH (3.1 mL, 6.19 mmol) and dioxane (5 mL) was heated to 50° C. for 1 h. The reaction was diluted with water, acidified with conc. HCl to ~pH 6. The reaction mixture was concentrated to low volume and filtered through celite. Preparatory HPLC afforded the desired regioisomer 4-chloro-1-oxo-1,2-dihydro-phthalazine-6-carboxylic acid (3-piperidin-1-ylmethyl-phenyl)-amide hydroformate (16 mg) as a pale yellow solid, $^1$H NMR (400 MHz, d$_6$-DMSO) δ: 1.54 (m, 2H), 1.44 (m, 4H), 2.28 (m, 4H), 3.37 (s, 2H), 7.00 (m, 1H), 7.25 (m, 1H), 7.67 (m, 2H), 8.06 (d, 1H), 8.10 (s, 1H), 8.47 (dd, 1H), 8.82 (d, 1H), 10.63 (1H), 12.95 (s, 1H) ppm; m/z (M+1) 396.95.

Example 153

Synthesis of 4-Chloro-6-[3-(4-methyl-[1,4]diazepan-1-yl)-benzylamino]-2H-phthalazin-1-one hydroformate

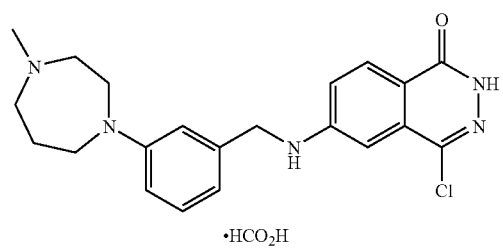

·HCO$_2$H

A mixture 6-bromo-4-chloro-2H-phthalazin-1-one (100 mg, 0.385 mmol), 3-(4-methyl-[1,4]diazepan-1-yl)-benzylamine (112 mg, 0.654 mmol), Pd$_2$(dba)$_3$ (53 mg, 0.0578 mmol), rac-BINAP (108 mg, 0.173 mmol) and NaO$^t$Bu (139 mg, 1.445 mmol) in DMA (5 mL) was heated at 85° C. for 1 h. The mixture was allowed to cool, diluted with EtOAc and washed with water. The organic layer was washed with sat.aq. NaHCO$_3$, brine and dried (Na$_2$SO$_4$). Preparatory HPLC afforded 4-chloro-6-[3-(4-methyl-[1,4]diazepan-1-yl)-benzylamino]-2H-phthalazin-1-one hydroformate (29 mg) as a pale brown solid. $^1$H (400 MHz, d$_6$-DMSO) δ: 1.83 (m, 2H), 2.21 (s, 3H). 2.39 (m, 2H), 2.54 (m, 2H), 3.38 (m, 2H), 3.46 (m, 2H), 4.32 (d, 2H), 6.56 (m, 2H), 6.71 (s, 1H), 6.83 (s, 1H), 7.09 (t, 1H), 7.16 (dd, 1H), 7.61 (m, 1H), 7.90 (d, 1H), 8.19 (s, 1H), 12.33 (s, 1H) ppm; m/z (M+1) 398.04.

Example 154 and 155

Synthesis of 1-Chloro-4-oxo-3,4-dihydro-phthalazine-6-carboxylic acid (2-morpholin-4-yl-5-trifluoromethyl-phenyl)-amide and 4-Chloro-1-oxo-1,2-dihydro-phthalazine-6-carboxylic acid (2-morpholin-4-yl-5-trifluoromethyl-phenyl)-amide

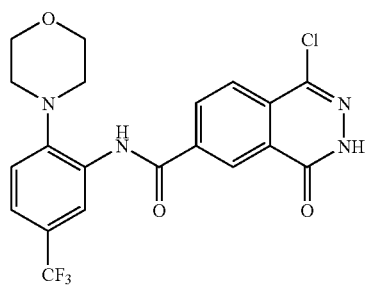

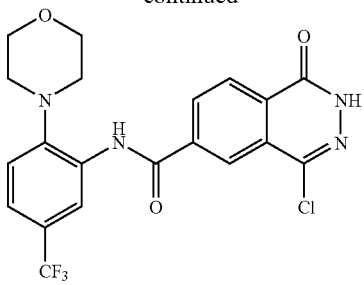

1,4-Dichloro-phthalazine-6-carboxylic acid (2-morpholin-4-yl-5-trifluoromethyl-phenyl)-amide A mixture of 1,4-dihydroxy-phthalazine-6-carboxylic acid (617 g, 2.99 mmol) in thionyl chloride (6 mL) was refluxed for 3 hours. Phosphorous oxychloride (6 mL) was added and the reaction refluxed for an additional 15 hours. The solution was concentrated under vacuum and treated 3 times with toluene in order to remove the excess thionyl chloride. The crude residue was dissolved in DMF (5 mL) and added dropwise to a 0° C. solution of 2-morpholino-5-(trifluoromethyl) aniline (780 mg, 3.168 mmol), DMF (4 mL) and NEt$_3$ (1.25 mL, 8.97 mmol). The reaction was stirred at 0° C. for 1 h, diluted with water and extracted with CH$_2$Cl$_2$. The combined organic layers were washed with water (×3), sat.aq. NH$_4$Cl, brine and dried (Na$_2$SO$_4$). Column chromatography (Hex/EtOAc) afforded 1,4-dichloro-phthalazine-6-carboxylic acid (2-morpholin-4-yl-5-trifluoromethyl-phenyl)-amide (322 mg). m/z (M+1) 470.91.

1-chloro-4-oxo-3,4-dihydro-phthalazine-6-carboxylic acid (2-morpholin-4-yl-5-trifluoromethyl-phenyl)-amide and 4-chloro-1-oxo-1,2-dihydro-phthalazine-6-carboxylic acid (2-morpholin-4-yl-5-trifluoromethyl-phenyl)-amide A mixture of 1,4-dichloro-phthalazine-6-carboxylic acid (2-morpholin-4-yl-5-trifluoromethyl-phenyl)-amide (322 mg, 0.683 mmol), 2N NaOH (3.4 mL, 6.83 mmol) and dioxane (5 mL) was heated to 50° C. for 1 h. The reaction was diluted with water, acidified with conc. HCl to ~pH 6. The reaction mixture was concentrated to low volume and filtered through celite. Chromatography (Hex/EtOAc) afforded 1-chloro-4-oxo-3,4-dihydro-phthalazine-6-carboxylic acid (2-morpholin-4-yl-5-trifluoromethyl-phenyl)-amide (49 mg) as a yellow solid, $^1$H NMR (400 MHz, d$_6$-DMSO) δ: 2.99 (m, 4H), 3.80 (m, 4H), 7.41 (d, 1H), 7.56 (dd, 1H), 8.18 (d, 1H), 8.28 (s, 1H), 8.51 (dd, 1H), 8.80 (d, 1H), 10.23 (s, 1H), 13.05 (s, 1H) ppm; m/z (M+1) 452.96; and 4-chloro-1-oxo-1,2-dihydro-phthalazine-6-carboxylic acid (2-morpholin-4-yl-5-trifluoromethyl-phenyl)-amide (40 mg) as a pale yellow solid. $^1$H NMR (400 MHz, d$_6$-DMSO) δ: 2.99 (m, 4H), 3.80 (m, 4H), 7.41 (d, 1H), 7.58 (dd, 1H), 8.29 (s, 1H), 8.43 (s, 2H), 8.46 (s, 1H), 10.23 (s, 1H), 13.02 (s, 1H) ppm; m/z (M+1) 452.96.

Example 156 and 157

Synthesis of 1-chloro-4-oxo-3,4-dihydro-phthalazine-6-carboxylic acid (3-furan-2-yl-phenyl)-amide and 4-chloro-1-oxo-1,2-dihydro-phthalazine-6-carboxylic acid (3-furan-2-yl-phenyl)-amide

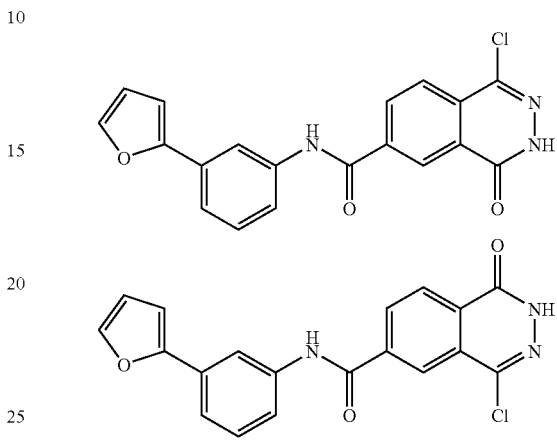

1,4-Dichloro-phthalazine-6-carboxylic acid (3-furan-2-yl-phenyl)-amide

A mixture of 1,4-dihydroxy-phthalazine-6-carboxylic acid (617 g, 2.99 mmol) in thionyl chloride (6 mL) was refluxed for 3 hours. Phosphorous oxychloride (6 mL) was added and the reaction refluxed for an additional 15 hours. The solution was concentrated under vacuum and treated 3 times with toluene in order to remove the excess thionyl chloride. The crude residue was dissolved in DMF (5 mL) and added dropwise to a 0° C. solution of 3-(2-furyl)aniline (490 mg, 3.078 mmol), DMF (4 mL) and NEt$_3$ (1.25 mL, 8.97 mmol). The reaction was stirred at 0° C. for 1 h, diluted with water and extracted with CH$_2$Cl$_2$. The combined organic layers were washed with water (×3), sat.aq. NH$_4$Cl, brine and dried (Na$_2$SO$_4$). Column chromatography (Hex/EtOAc) afforded 1,4-dichloro-phthalazine-6-carboxylic acid (3-furan-2-yl-phenyl)-amide (400 mg). m/z (M+1) 383.92.

1-Chloro-4-oxo-3,4-dihydro-phthalazine-6-carboxylic acid (3-furan-2-yl-phenyl)-amide and 4-Chloro-1-oxo-1,2-dihydro-phthalazine-6-carboxylic acid (3-furan-2-yl-phenyl)-amide A mixture of 1,4-dichloro-phthalazine-6-carboxylic acid (3-furan-2-yl-phenyl)-amide (400 mg, 1.041 mmol), 2N NaOH (5.2 mL, 10.41 mmol) and dioxane (5 mL) was heated to 50° C. for 5 h. The reaction was diluted with water, acidified with conc. HCl to pH 6. The reaction mixture was concentrated to low volume and filtered through celite. Chromatography (Hex/EtOAc) afforded 1-chloro-4-oxo-3,4-dihydro-phthalazine-6-carboxylic acid (3-furan-2-yl-phenyl)-amide (43 mg) as a pale yellow solid, $^1$H NMR (400 MHz, d$_6$-DMSO) δ: 6.76 (m, 1H), 7.08 (d, 1H), 7.58 (t, 1H), 7.64 (m, 1H), 7.90 (m, 2H), 8.30 (d, 1H), 8.34 (s, 1H), 8.70 (dd, 1H), 9.05 (s, 1H), 10.98 (s, 1H), 13.19 (s, 1H) ppm; m/z (M+1) 365.90; and 4-chloro-1-oxo-1,2-dihydro-phthalazine-6-carboxylic acid (3-furan-2-yl-phenyl)-amide (40 mg) as a pale yellow solid. $^1$H NMR (400 MHz, $d_6$-DMSO) δ: 6.62 (m, 1H), 6.92 (d, 1H), 7.44 (t, 1H), 7.50 (m, 1H), 7.74 (m, 1H), 7.78 (s, 1H), 8.17 (m, 1H), 8.45 (m, 2H), 8.52 (s, 1H), 10.80 (s, 1H), 13.01 (s, 1H) ppm; m/z (M+1) 365.97.

Example 158

Synthesis of 4-Chloro-6-(3-dimethylaminomethyl-benzylamino)-2H-phthalazin-1-one hydroformate

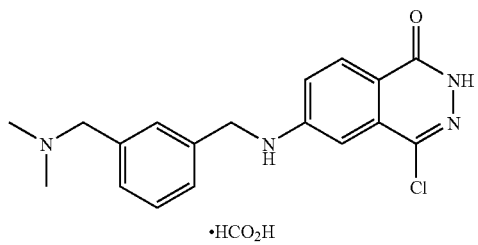

A mixture 6-bromo-4-chloro-2H-phthalazin-1-one (156 mg, 0.601 mmol), 3-dimethylaminomethylbenzylamine (110 mg, 0.67 mmol), $Pd_2(dba)_3$ (49 mg, 0.0535 mmol), rac-BINAP (108 mg, 0.173 mmol) and NaO$^t$Bu (143 mg, 1.488 mmol) in DMA (5 mL) was heated at 85° C. for 1 h. The mixture was allowed to cool, diluted with EtOAc and washed with water. The organic layer was washed with sat.aq. $NaHCO_3$, brine and dried ($Na_2SO_4$). Preparatory HPLC afforded 4-chloro-6-(3-dimethylaminomethyl-benzylamino)-2H-phthalazin-1-one hydroformate (50 mg) as a pale brown solid. $^1$H (400 MHz, $d_6$-DMSO) δ: 2.21 (s, 6H), 3.46 (s, 2H), 4.51 (d, 2H), 6.90 (s, 1H), 7.25 (m, 2H), 7.36 (m, 2H), 7.40 (s, 1H), 7.77 (t, 1H), 8.02 (s, 1H), 8.27 (s, 1H), 12.42 (s, 1H), ppm; m/z (M+1) 343.05.

Example 159

Synthesis of 4-Chloro-6-[3-(2-dimethylamino-ethylamino)-benzylamino]-2H-phthalazin-1-one hydroformate

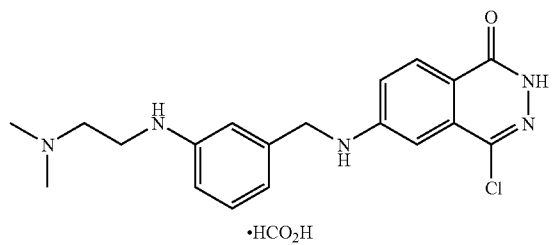

A mixture 6-bromo-4-chloro-2H-phthalazin-1-one (204 mg, 0.785 mmol), N-(3-Aminomethyl-phenyl)-N',N'-dimethyl-ethane-1,2-diamine hydrochloride (198 mg, 0.86 mmol), $Pd_2(dba)_3$ (72 mg, 0.0785 mmol), rac-BINAP (162 mg, 0.260 mmol) and NaO$^t$Bu (266 mg, 2.77 mmol) in DMA (6 mL) was heated at 85° C. for 3 h. The mixture was allowed to cool, diluted with EtOAc and washed with water. The organic layer was washed with sat.aq. $NaHCO_3$, brine and dried ($Na_2SO_4$). Preparatory HPLC afforded 4-chloro-6-[3-(2-dimethylamino-ethylamino)-benzylamino]-2H-phthalazin-1-one hydroformate (81 mg) as a yellow solid. $^1$H (400 MHz, $d_6$-DMSO) δ: 1.95 (s, 6H), 2.40 (m, 1H), 2.46 (m, 1H), 2.87 (m, 2H), 4.10 (d, 2H), 5.20 (bs, 1H), 6.26 (dd, 1H), 6.34 (d, 1H), 6.37 (s, 1H), 6.62 (s, 1H), 6.82 (t, 1H), 6.93 (dd, 1H), 7.40 (t, 1H), 7.70 (d, 1H), 7.95 (s, 1H), 12.12 (s, 1H) ppm; m/z (M+1) 372.04.

Example 160 and 161

Synthesis of 1-Chloro-4-oxo-3,4-dihydro-phthalazine-6-carboxylic acid m-tolylamide and 4-Chloro-1-oxo-1,2-dihydro-phthalazine-6-carboxylic acid m-tolylamide

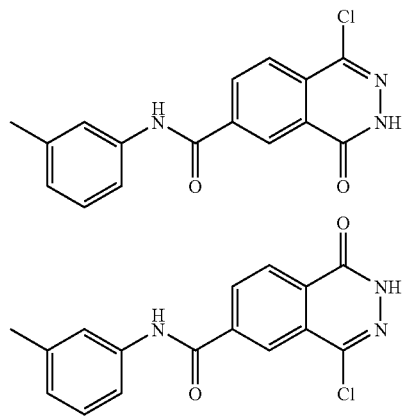

1,4-Dichloro-phthalazine-6-carboxylic acid m-tolylamide

A mixture of 1,4-dihydroxy-phthalazine-6-carboxylic acid (0.70 g, 3.395 mmol) in thionyl chloride (7 mL) was refluxed for 3 hours. Phosphorous oxychloride (7 mL) was added and the reaction refluxed for an additional 15 hours. The solution was concentrated under vacuum and treated 3 times with toluene in order to remove the excess thionyl chloride. The crude residue was dissolved in DMF (8 mL) and added dropwise to a 0° C. solution of m-toluidine (0.44 mL, 4.074 mmol), DMF (3 mL) and $NEt_3$ (1.42 mL, 10.186 mmol). The reaction was stirred at 0° C. for 2 h, diluted with water and extracted with $CH_2Cl_2$. The combined organic layers were washed with water (×3), sat.aq. $NH_4Cl$, brine and dried ($Na_2SO_4$). Column chromatography (Hex/EtOAc) afforded 1,4-dichloro-phthalazine-6-carboxylic acid m-tolylamide (100 mg). m/z (M+1) 332.04.

1-Chloro-4-oxo-3,4-dihydro-phthalazine-6-carboxylic acid m-tolylamide and 4-Chloro-1-oxo-1,2-dihydro-phthalazine-6-carboxylic acid m-tolylamide A mixture of 1,4-dichloro-phthalazine-6-carboxylic acid m-tolylamide (350 mg, 0.87 mmol), 2N NaOH (4.4 mL, 8.70 mmol) and dioxane (4 mL) was heated to 50° C. for 3 h. The reaction was diluted with water, acidified with conc. HCl to ~pH 6. The reaction mixture was concentrated to low volume and filtered through celite. Chromatography (Hex/EtOAc) afforded 1-chloro-4-oxo-3,4-dihydro-phthalazine-6-carboxylic acid m-tolylamide (8 mg) as a pale yellow solid, $^1$H NMR (400 MHz, $d_6$-DMSO) δ: 2.32 (s, 3H), 7.96 (d, 1H), 7.26 (t, 1H), 7.60 (d, 1H), 7.65 (s, 1H), 8.14 (d, 1H), 8.52 (dd, 1H), 8.87 (s, 1H), 10.67 (s, 1H), 13.00 (bs, 1H) ppm; m/z (M−1) 312.13; and 4-chloro-1-oxo-1,2-dihydro-phthalazine-6-carboxylic acid m-tolylamide (23 mg) as a pale yellow solid. $^1$H NMR (400 MHz, d$_6$-DMSO) δ: 2.11 (s, 3H), 6.76 (m, 1H), 7.05 (m, 1H), 7.40 (m, 2H), 8.25 (m, 3H), 10.42 (s, 1H), 12.80 (s, 1H) ppm; m/z (M−1) 312.13.

Example 162 and 163

Synthesis of 1-Chloro-4-oxo-3,4-dihydro-phthalazine-6-carboxylic acid (3-trifluoromethoxy-phenyl)-amide and 4-Chloro-1-oxo-1,2-dihydro-phthalazine-6-carboxylic acid (3-trifluoromethoxy-phenyl)-amide

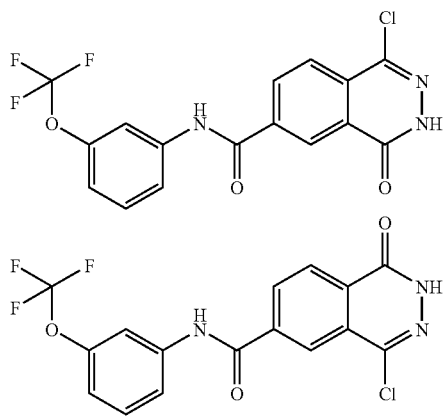

1,4-Dichloro-phthalazine-6-carboxylic acid (3-trifluoromethoxy-phenyl)-amide

A mixture of 1,4-dihydroxy-phthalazine-6-carboxylic acid (0.70 g, 3.395 mmol) in thionyl chloride (7 mL) was refluxed for 3 hours. Phosphorous oxychloride (7 mL) was added and the reaction refluxed for an additional 15 hours. The solution was concentrated under vacuum and treated 3 times with toluene in order to remove the excess thionyl chloride. The crude residue was dissolved in DMF (8 mL) and added dropwise to a 0° C. solution of 3-(trifluoromethoxy)aniline (0.54 mL, 4.074 mmol), DMF (3 mL) and NEt$_3$ (1.42 mL, 10.186 mmol). The reaction was stirred at 0° C. for 2 h, diluted with water and extracted with CH$_2$Cl$_2$. The combined organic layers were washed with water (×3), sat.aq. NH$_4$Cl, brine and dried (Na$_2$SO$_4$). Column chromatography (Hex/EtOAc) afforded 1,4-dichloro-phthalazine-6-carboxylic acid (3-trifluoromethoxy-phenyl)-amide (350 mg). m/z (M+1) 401.90.

1-Chloro-4-oxo-3,4-dihydro-phthalazine-6-carboxylic acid (3-trifluoromethoxy-phenyl)-amide and 4-Chloro-1-oxo-1,2-dihydro-phthalazine-6-carboxylic acid (3-trifluoro methoxy-phenyl)-amide A mixture of 1,4-dichloro-phthalazine-6-carboxylic acid (3-trifluoromethoxy-phenyl)-amide (350 mg, 0.87 mmol), 2N NaOH (4.4 mL, 8.70 mmol) and dioxane (4 mL) was heated to 50° C. for 3 h. The reaction was diluted with water, acidified with conc. HCl to ~pH 6. The reaction mixture was concentrated to low volume and filtered through celite. Chromatography (Hex/EtOAc) afforded 1-chloro-4-oxo-3,4-dihydro-phthalazine-6-carboxylic acid (3-trifluoromethoxy-phenyl)-amide (14 mg) as a white solid, $^1$H NMR (400 MHz, d$_6$-DMSO) δ: 7.14 (m, 1H), 7.52 (t, 1H), 7.82 (d, 1H), 7.95 (s, 1H), 8.14 (d, 1H), 8.53 (dd, 1H), 8.89 (s, 1H), 10.88 (s, 1H), 13.04 (s, 1H) ppm; m/z (M+1) 384.05; and 4-chloro-1-oxo-1,2-dihydro-phthalazine-6-carboxylic acid (3-trifluoromethoxy-phenyl)-amide (20 mg) as a white solid. $^1$H NMR (400 MHz, d$_6$-DMSO) δ: 7.06 (d, 1H), 7.44 (t, 1H), 7.70 (d, 1H), 7.85 (s, 1H), 8.34 (m, 2H), 8.39 (s, 1H), 10.87 (s, 1H), 12.92 (s, 1H) ppm; m/z (M+1) 384.05.

Example 164 and 165

Synthesis of 1-Chloro-3-methyl-4-oxo-3,4-dihydro-phthalazine-6-carboxylic acid (3-trifluoromethyl-phenyl)-amide and 4-Chloro-2-methyl-1-oxo-1,2-dihydro-phthalazine-6-carboxylic acid (3-trifluoromethyl-phenyl)-amide

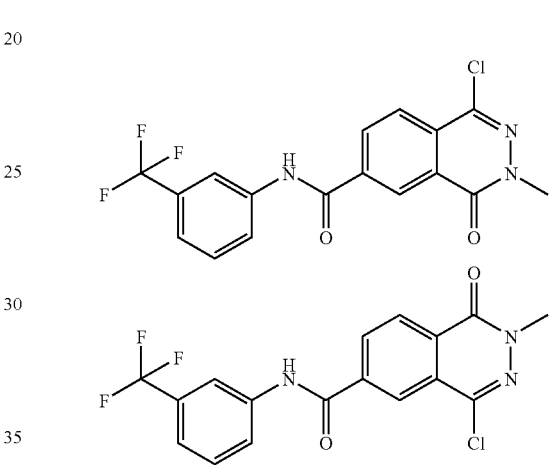

1,4-Dioxo-1,2,3,4-tetrahydro-phthalazine-6-carboxylic acid

A mixture of 1,2,4-benzenetricarboxylic acid (7.0 g, 36.43 mmol) and isopropyl alcohol (140 mL) was heated to reflux. Methylhydrazine (5 mL) was added to the reaction and heating continued for 2.5 h. The reaction was cooled, followed by acidification to pH3 with 2N HCl. The solids were filtered and rinsed with isopropyl alcohol to afforded 1,4-dioxo-1,2,3,4-tetrahydro-phthalazine-6-carboxylic acid (4.53 g). m/z (M+1) 221.15.

1-Chloro-3-methyl-4-oxo-3,4-dihydro-phthalazine-6-carboxylic acid (3-trifluoromethyl-phenyl)-amide and 4-Chloro-2-methyl-1-oxo-1,2-dihydro-phthalazine-6-carboxylic acid (3-trifluoromethyl-phenyl)-amide A mixture of 1,4-dioxo-1,2,3,4-tetrahydro-phthalazine-6-carboxylic acid (2.5 g, 9.14 mmol), in thionyl chloride (25 mL) was refluxed for 3 hours. Phosphorous oxychloride (25 mL) was added and the reaction refluxed for an additional 15 hours. The solution was concentrated under vacuum and treated 3 times with toluene in order to remove the excess thionyl chloride. The crude residue was dissolved in DMF (15 mL) and added dropwise to a 0° C. solution of 3-(trifluoromethyl)aniline (1.71 mL, 13.71 mmol), DMF (15 mL) and NEt$_3$ (3.82 mL, 27.42 mmol). The reaction was then heated to 85° C. for 1 h. The reaction was cooled to room temperature, diluted with water and extracted with EtOAc. The combined organic layers were washed with water (×3), sat.aq. NH₄Cl, brine and dried (Na₂SO₄). Column chromatography (Hex/EtOAc) afforded 1-chloro-3-methyl-4-oxo-3,4-dihydro-phthalazine-6-carboxylic acid (3-trifluoromethyl-phenyl)-amide (17 mg) as a white solid, ¹H NMR (400 MHz, d₆-DMSO) δ: 3.73 (s, 3H), 7.51 (d, 1H), 7.64 (t, 1H), 8.10 (d, 1H), 8.17 (d, 1H), 8.27 (s, 1H), 8.54 (dd, 1H), 8.93 (d, 1H), 11.03 (s, 1H) ppm; m/z (M+1) 382.09; and 4-chloro-2-methyl-1-oxo-1,2-dihydro-phthalazine-6-carboxylic acid (3-trifluoromethyl-phenyl)-amide (156 mg) as a white solid. ¹H NMR (400 MHz, d₆-DMSO) δ: 3.72 (s, 3H), 7.52 (d, 1H), 7.65 (t, 1H), 8.08 (d, 1H), 8.25 (s, 1H), 8.46 (s, 2H), 8.53 (m, 1H), 11.02 (s, 1H) ppm; m/z (M+1) 382.09.

Example 166 and 167

Synthesis of 1-chloro-4-oxo-3,4-dihydro-phthalazine-6-carboxylic acid [5-ethoxymethyl-2-methyl-3-(2-pyrrolidin-1-yl-ethylamino)-phenyl]-amide hydroformate and 4-chloro-1-oxo-1,2-dihydro-phthalazine-6-carboxylic acid [5-ethoxy methyl-2-methyl-3-(2-pyrrolidin-1-yl-ethylamino)-phenyl]-amide hydroformate

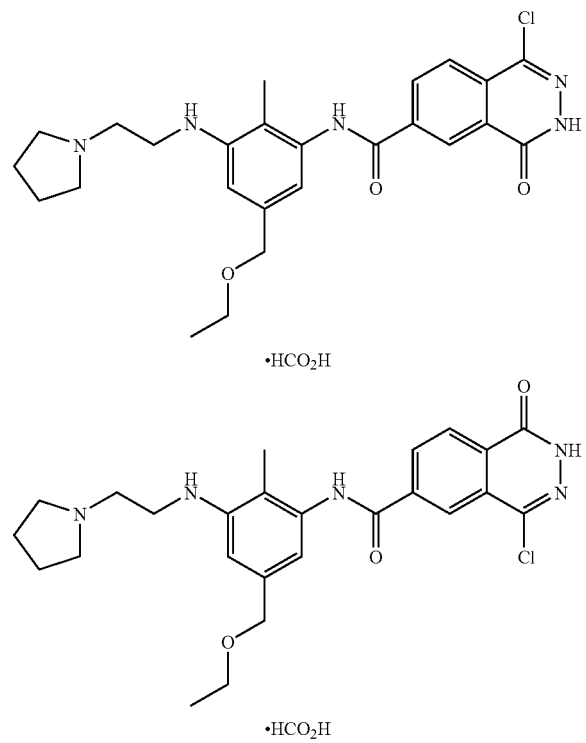

(3,5-Dibromo-4-methyl-phenyl)-methanol

A mixture of methyl 3,5-dibromo-4-methylbenzoate (15 g, 48.706 mmol), NaBH₄ (5.53 g, 146.18 mmol) and absolute ethanol (175 mL) was heated to reflux for 4 h. The mixture was cooled, followed by acidification with 2N HCl. The solids were filtered through celite and rinsed with EtOAc. The filtrate was poured onto water and extracted. The organic layer was washed with brine and dried (Na₂SO₄). Chromatography (Hexanes/EtOAc) afforded (3,5-dibromo-4-methyl-phenyl)-methanol (9.94 g) as a white solid. ¹H NMR (400 MHz, d₆-DMSO) δ: 2.48 (s, 3H), 4.45 (d, 2H), 5.38 (t, 1H), 7.57 (s, 2H) ppm.

1,3-Dibromo-5-ethoxymethyl-2-methyl-benzene

A mixture of (3,5-dibromo-4-methyl-phenyl)-methanol (4 g, 14.288 mmol), 60% NaH (690 mg, 28.75 mmol) and THF (72 mL) was heated to 70° C. in a sealed tube for 15 minutes. The reaction was cooled, bromoethane (3.2 mL, 42.86 mmol) was added and the reaction continued heating at 70° C. for 6 h. The reaction was cooled, poured onto water, extracted with EtOAc (×3). The organics were washed with water, brine and dried (Na₂SO₄). Chromatography (Hexanes/EtOAc) afforded 1,3-dibromo-5-ethoxymethyl-2-methyl-benzene (2.187 g) as a colourless oil. ¹H NMR (400 MHz, d₆-DMSO) δ: 1.15 (t, 3H), 2.48 (s, 3H), 3.46 (q, 2H), 4.41 (s, 2H), 7.57 (s, 2H) ppm.

Benzyl-(3-bromo-5-ethoxymethyl-2-methyl-phenyl)-amine

A mixture of 1,3-dibromo-5-ethoxymethyl-2-methyl-benzene (1.322 g, 4.29 mmol), benzylamine (0.49 mL, 4.507 mmol), Pd₂(dba)3 (409 mg, 0.447 mmol), rac-BINAP (811 mg, 1.302 mmol), NaOtBu (618 mg, 6.435 mmol) and toluene (30 mL) was heated at 80° C. for 1 h 45 minutes. The reaction was cooled, poured onto water and extracted with EtOAc (×3). The organics were washed with water, brine and dried (Na₂SO₄). Chromatography (Hexanes/EtOAc) afforded benzyl-(3-bromo-5-ethoxymethyl-2-methyl-phenyl)-amine (1.268 g) as a yellow liquid. ¹H NMR (400 MHz, d₆-DMSO) δ: 1.24 (t, 3H), 2.32 (s, 3H), 3.50 (q, 2H), 4.04 (bs, 1H), 4.41 (s, 4H), 6.61 (s, 1H), 7.00 (s, 1H), 7.35 (m, 5H) ppm.

N-Benzyl-5-ethoxymethyl-2-methyl-N'-(2-pyrrolidin-1-yl-ethyl)-benzene-1,3-diamine A mixture of benzyl-(3-bromo-5-ethoxymethyl-2-methyl-phenyl)-amine (1.253 g, 3.749 mmol), xantphos (134 mg, 0.232 mmol), 1-(2-aminoethyl)pyrrolidine (0.71 mL, 5.639 mmol), Pd₂(dba)₃ (10 mg, 0.120 mmol), NaOᵗBu (658 mg, 6.847 mmol) and anhydrous dioxane (40 mL) was heated to 95° C. for 14 h. The reaction was cooled, filtered through celite, rinsed with EtOAc and concentrated. Chromatography (EtOAc/MeOH) afforded N-benzyl-5-ethoxymethyl-2-methyl-N'-(2-pyrrolidin-1-yl-ethyl)-benzene-1,3-diamine (810 g) as an orange liquid. m/z (M+1) 368.36.

5-Ethoxymethyl-2-methyl-N-(2-pyrrolidin-1-yl-ethyl)-benzene-1,3-diamine hydrochloride A mixture of N-benzyl-5-ethoxymethyl-2-methyl-N'-(2-pyrrolidin-1-yl-ethyl)-benzene-1,3-diamine (810 mg, 2.204 mmol), 10% wet Pd/C (catalytic), 2 drops of conc. HCl and MeOH (12 mL) was evacuated and flushed (×3) with hydrogen. The reaction was stirred under a hydrogen balloon for 4 h. The reaction was filtered through celite, rinsed with MeOH and concentrated to yield 5-ethoxymethyl-2-methyl-N-(2-pyrrolidin-1-yl-ethyl)-benzene-1,3-diamine hydrochloride as a dark oil. m/z (M+1) 278.34 (Free Base).

Synthesis of 1-Chloro-4-oxo-3,4-dihydro-phthalazine-6-carboxylic acid and 4-Chloro-1-oxo-1,2-dihydro-phthalazine-6-carboxylic acid A mixture of 1,4-dihydroxy-phthalazine-6-carboxylic acid (2 g, 9.701 mmol) and thionyl chloride (25 mL) was heated to reflux for 3 h. To the reaction was added POCl₃ (25 mL) and the reaction heated at reflux for 15 h. The reaction was cooled, concentrated and stripped three times with toluene. The solids dissolved in dioxane and cooled in an ice/water bath. A solution of 2N NaOH (48.5 mL, 97.01 mmol) was carefully added to the reaction. Once addition was complete the reaction was heated to 50° C. for 1 h. The reaction mixture was cooled and concentrated to low volume. Water was added to the mixture and acidified to pH3. The solids were filtered and dried in vacuum to yield a mixture of 1-chloro-4-oxo-3,4-dihydro-phthalazine-6-carboxylic acid and 4-chloro-1-oxo-1,2-dihydro-phthalazine-6-carboxylic acid (1.465 g) as an orange solid. $^1$H NMR (400 MHz, $d_6$-DMSO) δ: 8.08 (s, d, 1H), 8.40 (m, 4H), 8.73 (s, 1H), 12.97 (s, 1H), 13.01 (s, 1H) ppm; m/z (M+1) 225.15 and 225.07.

1-Chloro-4-oxo-3,4-dihydro-phthalazine-6-carboxylic acid [5-ethoxymethyl-2-methyl-3-(2-pyrrolidin-1-yl-ethylamino)-phenyl]-amide formic acid salt and 4-Chloro-1-oxo-1,2-dihydro-phthalazine-6-carboxylic acid [5-ethoxymethyl-2-methyl-3-(2-pyrrolidin-1-yl-ethylamino)-phenyl]-amide formic acid salt A mixture of 5-ethoxymethyl-2-methyl-N-(2-pyrrolidin-1-yl-ethyl)-benzene-1,3-diamine hydrochloride (430 mg, 1.55 mmol), 1-chloro-4-oxo-3,4-dihydro-phthalazine-6-carboxylic acid and 4-chloro-1-oxo-1,2-dihydro-phthalazine-6-carboxylic acid (331 mg, 1.476 mmol), N-(3-dimethylaminopropyl)-N'-ethylcarbodiimide hydrochloride (863 mg, 4.50 mmol), NEt$_3$ (0.82 mL, 5.904), 1-hydroxybenzotriazole hydrate (259 mg, 1.919 mmol) and anhydrous DMF was stirred at room temperature for 2.5 h. The reaction mixture was filtered through celite, rinsed with CH$_2$Cl$_2$ and concentrated. Preparatory HPLC afforded 1-chloro-4-oxo-3,4-dihydro-phthalazine-6-carboxylic acid [5-ethoxymethyl-2-methyl-3-(2-pyrrolidin-1-yl-ethylamino)-phenyl]-amide formic acid salt (72 mg) as an orange solid.

$^1$H NMR (400 MHz, $d_6$-DMSO) δ: 1.15 (t, 3H), 1.72 (m, 4H), 1.93 (s, 3H), 2.58 (m, 4H), 2.74 (t, 2H), 3.22 (m, 2H), 3.46 (q, 2H), 4.38 (s, 2H), 4.93 (bs, 1H), 6.49 (s, 1H), 6.56 (s, 1H), 8.18 (s, 1H), 8.39 (d, 1H), 8.46 (d, 1H), 8.52 (s, 1H), 10.40 (s, 1H), 13.00 (s, 1H) ppm; m/z (M+1) 484.33; and 4-chloro-1-oxo-1,2-dihydro-phthalazine-6-carboxylic acid [5-ethoxymethyl-2-methyl-3-(2-pyrrolidin-1-yl-ethylamino)-phenyl]-amide formic acid salt (78 mg) as an orange solid. $^1$H NMR (400 MHz, $d_6$-DMSO) δ: 1.14 (t, 3H), 1.73 (m, 4H), 1.93 (s, 3H), 2.61 (m, 4H), 2.77 (t, 2H), 3.24 (m, 2H), 3.47 (m, 2H), 4.37 (s, 2H), 4.95 (bs, 1H), 6.50 (s, 1H), 6.57 (s, 1H), 8.12 (d, 1H), 8.18 (s, 1H), 8.52 (d, 1H), 8.88 (s, 1H), 10.40 (s, 1H), 13.02 (s, 1H) ppm; m/z (M+1) 484.33.

Example 168

Synthesis of 1-Oxo-1,2-dihydro-phthalazine-6-carboxylic acid [5-ethoxymethyl-2-methyl-3-(2-pyrrolidin-1-yl-ethylamino)-phenyl]-amide

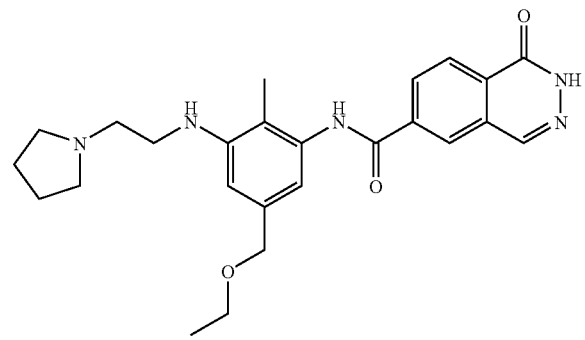

A mixture of 4-chloro-1-oxo-1,2-dihydro-phthalazine-6-carboxylic acid [5-ethoxymethyl-2-methyl-3-(2-pyrrolidin-1-yl-ethylamino)-phenyl]-amide formic acid salt (55 mg, 0.104 mmol), 10% wet Pd/C (catalytic), 1 drop of conc. HCl and MeOH (4 mL) was evacuated and flushed (×3) with hydrogen. The reaction was stirred under a hydrogen balloon for 2.5 h. The reaction was filtered through celite, rinsed with MeOH and concentrated to yield 1-oxo-1,2-dihydro-phthalazine-6-carboxylic acid [5-ethoxymethyl-2-methyl-3-(2-pyrrolidin-1-yl-ethylamino)-phenyl]-amide (43 mg) as a tan solid. $^1$H NMR (400 MHz, $d_6$-DMSO) δ: 1.16 (t, 3H), 1.93 (m, 4H), 2.00 (s, 3H), 2.53 (m, 4H), 3.47 (m, 6H), 4.39 (s, 2H), 5.23 (bs, 1H), 6.53 (s, 1H), 6.62 (s, 1H), 8.34 (s, 2H), 8.48 (s, 1H), 8.50 (s, 1H), 10.25 (s, 1H), 12.80 (s, 1H) ppm; m/z (M+1) 450.38.

Example 169 and 170

Synthesis of 1-Chloro-4-oxo-3,4-dihydro-phthalazine-6-carboxylic acid 3-trifluoromethyl-benzylamide and 4-Chloro-1-oxo-1,2-dihydro-phthalazine-6-carboxylic acid 3-trifluoromethyl-benzylamide

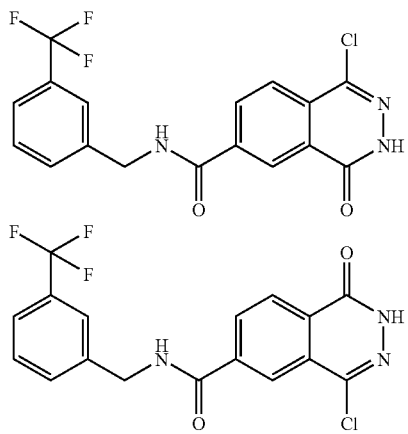

A mixture of 1-chloro-4-oxo-3,4-dihydro-phthalazine-6-carboxylic acid and 4-chloro-1-oxo-1,2-dihydro-phthalazine-6-carboxylic acid (311 mg, 1.385 mmol), catalytic DMF and thionyl chloride (7 mL) was refluxed for 3 hours. The solution was cooled, concentrated under vacuum and treated 3 times with toluene in order to remove the excess thionyl chloride. The crude residue was dissolved in DMF (3 mL) and added dropwise to a 0° C. solution of 3-(trifluoromethyl)benzylamine (0.22 mL, 1.524 mmol), DMF (5 mL) and 60% NaH (199 mg, 8.31 mmol). The reaction was stirred at room temperature overnight, diluted with water and extracted with EtOAc (×3). The combined organic layers were washed with water, brine and dried (Na$_2$SO$_4$). Column chromatography (Hex/EtOAc) afforded 1-chloro-4-oxo-3,4-dihydro-phthalazine-6-carboxylic acid 3-trifluoromethyl-benzylamide (30 mg) as a white solid. $^1$H NMR (400 MHz, $d_6$-DMSO) δ: 4.62 (d, 2H), 7.65 (m, 4H), 8.10 (d, 1H), 8.47 (dd, 1H), 8.80 (d, 1H), 9.65 (t, 1H), 12.99 (s, 1H) ppm; m/z (M+1) 382.17; and 4-chloro-1-oxo-1,2-dihydro-phthalazine-6-carboxylic acid 3-trifluoromethyl-benzylamide (33 mg) as a white solid.

¹H NMR (400 MHz, d₆-DMSO) δ: 4.63 (d, 2H), 7.65 (m, 4H), 8.38 (m, 2H), 8.46 (s, 1H), 9.63 (t, 1H), 12.98 (s, 1H) ppm; m/z (M+1) 382.24.

Example 171

Synthesis of N-(4-Chloro-1-oxo-1,2-dihydro-phthalazin-6-yl)-3-methoxy-benzamide

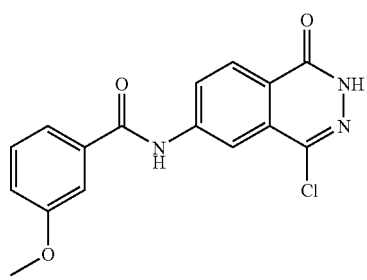

A mixture of 6-bromo-4-chloro-2H-phthalazin-1-one (100 mg, 0.39 mmol), 3-methoxy-benzamide (64 mg, 0.42 mmol), Pd₂(dba)₃ (36 mg, 0.039 mmol), xantphos (68 mg, 0.12 mmol) and Cs₂CO₃ (607 mg, 0.98 mmol) in dioxane (5 mL) was purged with nitrogen for 10 min. The mixture was place in a microwave reactor for 5 min. After this time the mixture was filtered and purified by preparative HPLC to yield the title compound hydroformate. m/z (M+H)=329.96, ¹H-NMR (DMSO-d6) δ: 12.75 (s, 1H), 10.85 (s, 1H), 8.63 (s, 1H), 8.25 (m, 2H), 7.60 (d, 1H), 7.56 (s, 1H), 7.45 (t, 1H), 7.20 (dd, 1H), 3.85 (s, 3H).

Example 172

4-Chloro-6-{4-[3-(2-pyrrolidin-1-yl-ethylamino)-phenyl]-piperazin-1-yl}-2H-phthalazin-1-one.HCO₂H

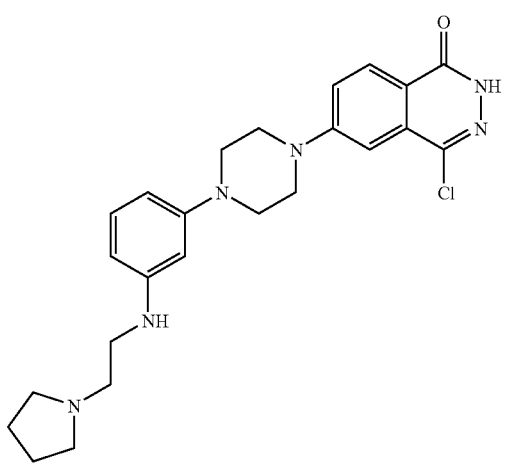

4-[3-(2-Pyrrolidin-1-yl-ethylamino)-phenyl]-piperazine-1-carboxylic acid tert-butyl ester A mixture of 4-(3-bromo-phenyl)-piperazine-1-carboxylic acid tert-butyl ester (300 mg, 0.88 mmol), 2-pyrrolidin-1-yl-ethylamine (0.165 mL, 1.32 mmol), Pd₂(dba)₃ (40 mg, 0.044 mmol), xantphos (50 mg, 0.088 mmol) and NaOt-Bu (124 mg, 1.32 mmol) in dioxane (15 mL) was bubbled with nitrogen in a sealed tube for 10 min. The mixture was heated at 120° C. for 2 h. After this time the mixture was cooled and filtered through celite and concentrated. Chromatography on silica (ethyl acetate/MeOH) provided the title compound (203 mg, 62%). m/z (M+1) 375.53

(3-piperazin-1-yl-phenyl)-(2-pyrrolidin-1-yl-ethyl)-amine.2HCl

To a solution of 4-[3-(2-pyrrolidin-1-yl-ethylamino)-phenyl]-piperazine-1-carboxylic acid tert-butyl ester (338 mg, 0.90 mmol) in MeOH (10 mL) was added a solution of HCl in EPA (5M, 1.8 mL). The mixture was stirred for 18 h then concentrated to provide the title compound (339 mg, 99%). m/z (M+1) 275.49 (free base).

4-Chloro-6-{4-[3-(2-pyrrolidin-1-yl-ethylamino)-phenyl]-piperazin-1-yl}-2H-phthalazin-1-one.HCO₂H A mixture of 6-bromo-4-chloro-2H-phthalazin-1-one and 7-bromo-4-chloro-2H-phthalazin-1-one (100 mg, 0.39 mmol), (3-piperazin-1-yl-phenyl)-(2-pyrrolidin-1-yl-ethyl)-amine.2HCl (162 mg, 0.42 mmol), Pd₂(dba)₃ (36 mg, 0.039 mmol), BINAP (73 mg, 0.12 mmol) and NaOt-Bu (183 mg, 1.95 mmol) in DMA (10 mL) was purged with nitrogen for 10 min. The mixture was heated at 110° C. for 2 h. The mixture was allowed to cool, filtered through celite and purified by preparative HPLC to provide the title compound hydroformate. m/z (M+H)=453.10; ¹H-NMR (DMSO-d6) δ: 12.05 (s, 1H), 8.15 (d, 2H), 7.60 (s, 1H), 7.35 (m, 1H), 7.12 (m, 1H), 6.95 (t, 2H), 6.24 (d, 1H), 6.19 (s, 1H), 6.12 (d, 1H), 3.58 (m, 4H), 3.30 (m, 8H), 2.90 (m, 2H), 2.80 (m, 4H), 1.80 (m, 4H).

Example 173

4-Chloro-6-{4-[5-ethoxymethyl-2-methyl-3-(2-pyrrolidin-1-yl-ethylamino)-phenyl]-piperazin-1-yl}-2H-phthalazin-1-one.HCO₂H

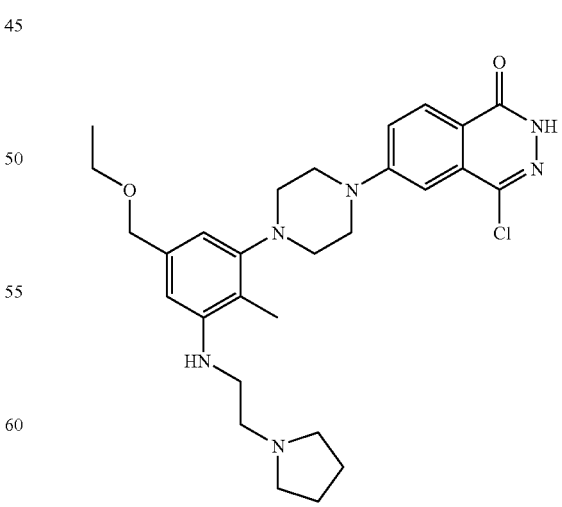

A mixture of 6-bromo-4-chloro-2H-phthalazin-1-one and 7-bromo-4-chloro-2H-phthalazin-1-one (200 mg, 0.77 mmol), (5-ethoxymethyl-2-methyl-3-piperazin-1-yl-phenyl)-(2-pyrrolidin-1-yl-ethyl)-amine.2HCl (351 mg, 0.77 mmol), Pd$_2$(dba)$_3$ (71 mg, 0.077 mmol), BINAP (144 mg, 0.23 mmol) and NaOt-Bu (398 mg, 4.24 mmol) in DMA (10 mL) was purged with nitrogen for 10 min. The mixture was heated at 110° C. for 2 h. The mixture was allowed to cool, filtered through celite and purified by preparative HPLC to provide the title compound as the formic acid salt. m/z (M+H)=525.11; $^1$H-NMR (DMSO-d6) δ: 9.45 (s, 1H), 8.17 (d, 1H), 7.30 (dd, 1H), 7.15 (d, 1H), 6.45 (s, 1H), 6.28 (s, 1H), 4.40 (s, 2H), 3.63 (t, 3H), 3.50 (m, 5H), 3.25 (t, 2H), 3.01 (m, 4H), 2.19 (s, 3H), 2.05 (m, 4H), 1.17 (m, 7H).

Example 174 and 175

2-(4-Chloro-1-oxo-1,2-dihydro-phthalazin-6-yl)-N-{2-[(2-dimethylamino-ethyl)-methyl-amino]-phenyl}-acetamide and 2-(1-Chloro-4-oxo-3,4-dihydro-phthalazin-6-yl)-N-{2-[(2-dimethylamino-ethyl)-methyl-amino]-phenyl}-acetamide

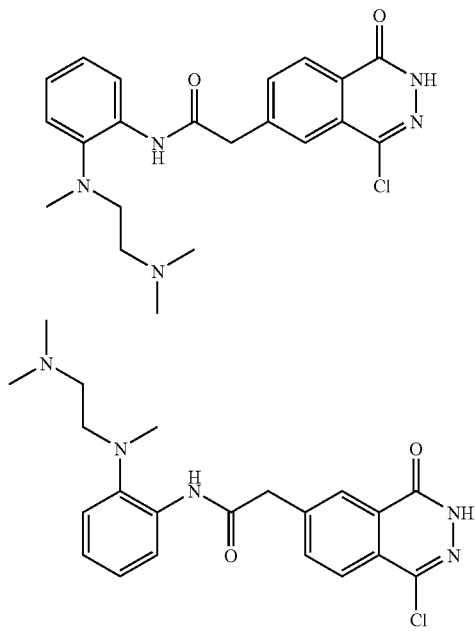

6-Methyl-2,3-dihydro-phthalazine-1,4-dione

A mixture of 5-methyl-isobenzofuran-1,3-dione (6.0 g, 34.1 mmol) and hydrazine hydrate (2.48 mL, 51.1 mmol) in isopropanol (120 mL) was heated at reflux for 4 h. The mixture was allowed to cool and the precipitate was filtered and washed with water (50 mL). The filter cake was dried to afford the title compound (4.32 g, 72%) as a white solid. m/z (M+1)=177.18

4-Chloro-6-methyl-2H-phthalazin-1-one and 4-Chloro-7-methyl-2H-phthalazin-1-one

A mixture 5-methyl-isobenzofuran-1,3-dione (10.8 g, 61.4 mmol) in SOCl$_2$ (50 mL) and POCl$_3$ (50 mL) was heated at reflux for 4 h. The mixture was allowed to cool and concentrated. The residue was taken up in EtOAc (100 mL) and neutralized with sodium bicarbonate. The layers were separated and the organic layer was dried over anhydrous sodium sulfate and concentrated. The residue was dissolved in dioxane (200 mL) and 2N NaOH (96 mL, 191 mmol). The mixture was heated at 50° C. for 4 h then allowed to cool and concentrated. The residue was triturated with EtOAc (300 mL) and water (200 mL) and the solids were filtered. The organic phase was dried over anhydrous sodium sulfate and concentrated to yield the title compounds (6.07 g, 51%); m/z (M+1)=195.59.

4-Chloro-6-methyl-2H-phthalazin-1-one

A mixture 5-methyl-isobenzofuran-1,3-dione (10.8 g, 61.4 mmol) in SOCl$_2$ (50 mL) and POCl$_3$ (50 mL) was heated at reflux for 4 h. The mixture was allowed to cool and concentrated. The residue was taken up in EtOAc (100 mL) and neutralize with sodium bicarbonate. The layers were separated and the organic layer was dried over anhydrous sodium sulfate and concentrated. The residue was dissolved in dioxane (200 mL) and 2N NaOH (96 mL, 191 mmol). The mixture was heated at 50° C. for 4 h then allowed to cool and stirred at ambient temperature for 15 h. The precipitate was filtered and dried to yield the title compound (2.98 g, 25%); m/z (M+1)=195.59.

(4-Chloro-1-oxo-1,2-dihydro-phthalazin-6-yl)-acetic acid and (1-Chloro-4-oxo-3,4-dihydro-phthalazin-6-yl)-acetic acid A mixture of 4-chloro-6-methyl-2H-phthalazin-1-one and 4-chloro-7-methyl-2H-phthalazin-1-one (900 mg, 4.64 mmol) in anhydrous THF (75 mL) under nitrogen was cooled in an ice bath. Sodium hydride (60% in mineral oil) (223 mg, 5.57 mmol) was added and the mixture was warmed to rt and stirred for 15 min. The mixture was then cooled to –78° C. and n-BuLi (1.6M in hexanes, 3.3 mL, 5.34 mmol) was added. The dark mixture was stirred for 30 min and freshly crushed dry ice was added and the mixture was allowed to warm to room temperature. The mixture was quenched with water and concentrated. Aqueous sodium bicarbonate was added and the mixture was extracted with EtOAc (25 mL). The aqueous phase was acidified with 2N HCl and extracted with EtOAc (2×50 mL). The combined organic layers were dried over anhydrous sodium sulfate and concentrated to yield the title compound (450 mg, 41%). m/z (M+1)=239.63.

2-(4-Chloro-1-oxo-1,2-dihydro-phthalazin-6-yl)-N-{2-[(2-dimethylamino-ethyl)-methyl-amino]-phenyl}-acetamide and 2-(1-Chloro-4-oxo-3,4-dihydro-phthalazin-6-yl)-N-{2-[(2-dimethylamino-ethyl)-methyl-amino]-phenyl}-acetamide (4-Chloro-1-oxo-1,2-dihydro-phthalazin-6-yl)-acetic acid and (1-chloro-4-oxo-3,4-dihydro-phthalazin-6-yl)-acetic acid (250 mg, 1.05 mmol), N-(2-dimethylamino-ethyl)-N-methyl-benzene-1,2-diamine (242 mg, 1.26 mmol), EDC (706 mg, 3.68 mmol), HOBt (170 mg, 1.26 mmol) and triethylamine (0.73 mL, 5.25 mmol) in DMF was stirred at ambient temperature for 15 h. The mixture was diluted with ethyl acetate (25 mL) and washed with aq. sat. sodium bicarbonate. The aqueous layer was extracted with EtOAc (2×20 mL) and the combined organic layers were dried over anhydrous sodium sulfate and concentrated. Chromatography on silica (EtOAc/MeOH) yielded the title compounds as a mixture of regioisomers (265 mg, 61%). m/z (M+H)=414.00; $^1$H-NMR (DMSO-d6) δ: 12.5 (s, 1H), 9.95 (m, 1H), 8.25 (s, 0.5H), 8.22 (d, 0.5H), 8.00 (m, 3H), 7.23 (m, 1H), 7.05 (m, 2H), 4.00 (m, 2H), 2.80 (t, 2H), 2.60 (s, 3H), 2.20 (t, 2H), 2.16 (s, 6H).

Example 176 and 177

4-Chloro-6-(2-{2-[(2-dimethylamino-ethyl)-methyl-amino]-phenylamino}-ethyl)-2H-phthalazin-1-one and 4-Chloro-7-(2-{2-[(2-dimethylamino-ethyl)-methyl-amino]-phenylamino}-ethyl)-2H-phthalazin-1-one

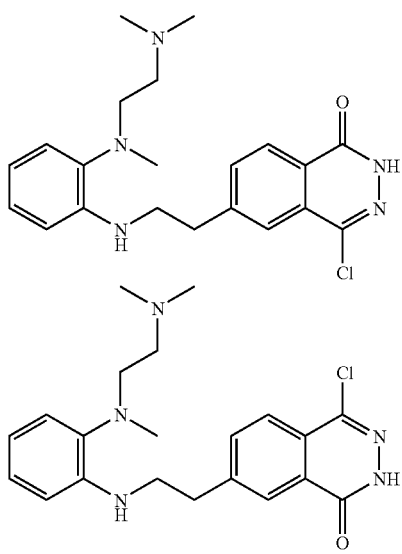

A mixture of 2-(4-chloro-1-oxo-1,2-dihydro-phthalazin-6-yl)-N-{2-[(2-dimethylamino-ethyl)-methyl-amino]-phenyl}-acetamide and 2-(1-chloro-4-oxo-3,4-dihydro-phthalazin-6-yl)-N-{2-[(2-dimethylamino-ethyl)-methyl-amino]-phenyl}-acetamide (194 mg, 0.47 mmol), and borane-THF complex (1M in THF, 0.23 mL, 2.34 mmol) in THF (10 mL) was heated at reflux for 4 h. After this time MeOH (5 mL) was added and the mixture was concentrated. The residue was re-dissolved in MeOH (10 mL) and 4N HCl/IPA was added (20 mL). The mixture was heated at reflux for 5 h and concentrated. The residue was diluted with EtOAc and washed with sat. aq. sodium bicarbonate. The aqueous layer was extracted with EtOAc (2×20 mL) and the combined organic layers were dried over anhydrous sodium sulfate and concentrated. Chromatography on silica (EtOAc/MeOH) yielded the title compounds as a mixture of regioisomers (62 mg, 33%). m/z (M+H)=400.02; ¹H-NMR (DMSO-d6) δ: 12.5 (s, 1H), 9.95 (m, 1H), 8.25 (s, 0.5H), 8.22 (d, 0.5H), 8.00 (m, 3H), 7.23 (m, 1H), 7.05 (m, 2H), 5.45 (m, 1H), 3.40 (m, 2H), 3.20 (s, 3H), 3.05 (m, 2H), 2.75 (m, 2H), 2.20 (m, 3H), 2.02 (s, 6H)

Example 178 and 179

4-Chloro-1-hydroxy-phthalazine-6-carboxylic acid [4-chloro-3'-(2-dimethylamino-ethoxy)-biphenyl-3-yl]-amide, and 1-Chloro-4-hydroxy-phthalazine-6-carboxylic acid [4-chloro-3'-(2-dimethylamino-ethoxy)-biphenyl-3-yl]-amide

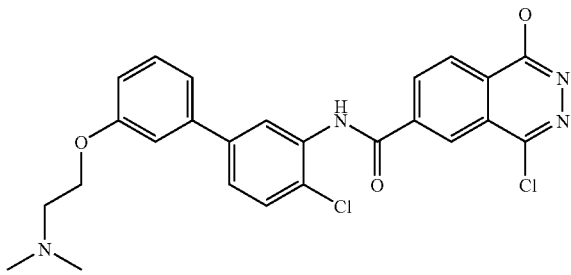

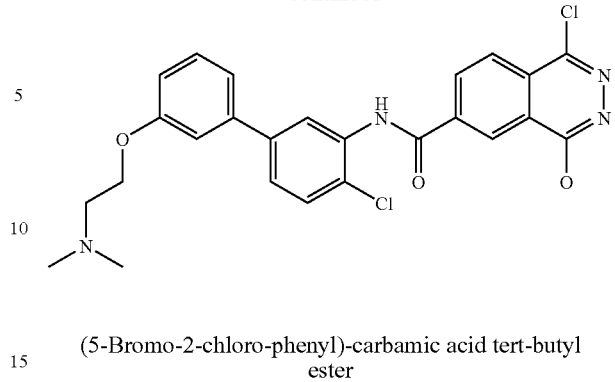

(5-Bromo-2-chloro-phenyl)-carbamic acid tert-butyl ester

A solution of 5-Bromo-2-Chloro benzoic acid (24 g, 0.1 mol), di-phenylphosphoryl azide (28 mL, 1.3 eq), and Et3N (140 mL, 10 eq) in tert-butanol (300 mL) was refluxed for 3 hrs. The resulting solution was concentrated under reduced pressure, diluted with ether (300 mL) and washed with HCl 1N (300 mL), saturated solution of NaHCO3 (200 mL), and brine (200 mL). The organic layers was dried over anhydrous sodium sulfate and concentrated. Chromatography on silica (EtOAc/n-hexane) yielded, (26 g, 85%).

(4-chloro-3'-hydroxy-biphenyl-3-yl)-carbamic acid tert-butyl ester

A mixture of the above intermediate (8.55 g, 0.028 mol), 3-hydroxy benzyl boronic acid (5 g, 1.3 eq), sodium carbonate (7.1 g, 2.4 eq), and palladium tetrakis (catalytic amount) in DME (70 mL) and water (35 mL) was heated at 100° C. in a sealed tube for 5 hrs. The reaction mixture was diluted with ether (100 mL), washed with water (100 mL0, brine (100 mL), dried over anhydrous sodium sulfate and concentrated Chromatography on silica (EtOAc/n-hexane) yielded (4-chloro-3'-hydroxy-biphenyl-3-yl)-carbamic acid tert-butyl ester (6 g, 67%).

[4-Chloro-3'-(2-dimethylamino-ethoxy)-biphenyl-3-yl]-carbamic acid tert-butyl ester A solution of the above intermediate (1 g, 3.13 mmol), 2-dimethyl ethyl amino ethanol (0.47 mL, 1.5 eq), triphenyl phosphine (1.23 g, 1.5 eq), and diisopropyl azodicarboxylate (0.92 mL, 1.5 eq) in THF (20 mL) was stirred at RT for 24 hrs. The solution was concentrated and purified by chromatography on silica (EtOAc/n-hexane) to yield [4-Chloro-3'-(2-dimethylamino-ethoxy)-biphenyl-3-yl]-carbamic acid tert-butyl ester (0.8 g, 65%).

4-chloro-3'-(2-dimethylamino-ethoxy)-biphenyl-3-ylamine hydrochloride

The above intermediate (0.8 g, 2.0 mmol) was dissolved in a solution of HCl in i-PrOH (5-6M, 20 mL). The resulting solution was stirred at RT for 6 hrs then concentrated to provide 4-chloro-3'-(2-dimethylamino-ethoxy)-biphenyl-3-ylamine hydrochloride (0.6 g, 90%) as a white solid.

4-Chloro-1-hydroxy-phthalazine-6-carboxylic acid [4-chloro-3'-(2-dimethylamino-ethoxy)-biphenyl-3-yl]-amid, and 1-chloro-4-hydroxy-phthalazine-6-carboxylic acid [4-chloro-3'-(2-dimethylamino-ethoxy)-biphenyl-3-yl]-amide A mixture of 4-chloro-3'-(2-dimethylamino-ethoxy)-biphenyl-3-ylamine hydrochloride (0.6 g, 1.8 mmol), 1-chloro- 4-oxo-3,4-dihydro-phthalazine-6-carboxylic acid and 4-chloro-1-oxo-1,2-dihydro-phthalazine-6-carboxylic acid (336 mg, 1.5 mmol), N-(3-dimethylaminopropyl)-N'-ethylcarbodiimide hydrochloride (0.373 g, 1.95 mmol), 4-NMM (0.82 mL, 7.5 mmol), 1-hydroxybenzotriazole hydrate (263 mg, 1.95 mmol) and anhydrous DMF (5 mL) was stirred at room temperature for 48 hrs. The reaction mixture was diluted with EtOAc (100 mL), washed with saturated solution of ammonium chloride (50 mL), saturated solution of NaHCO3 (50 mL), dried and concentrated under reduced pressure. Preparatory HPLC afforded the title compounds as solid: 4-Chloro-1-hydroxy-phthalazine-6-carboxylic acid [4-chloro-3'-(2-dimethylamino-ethoxy)-biphenyl-3-yl]-amid, $^1$H NMR (400 MHz, CDCl$_3$) δ: 2.52 (s, 6H), 2.97 (t, 2H), 4.24 (t, 2H), 6.92 (dd, 1H), 7.14 (m, 1H), 7.20 (d, 1H), 7.32-7.39 (m, 2H), 7.49 (d, 1H), 8.30 (dd, 1H), 8.52-8.58 (m, 3H), 8.74 (bd, 1H) ppm; m/z (M+1) 497; and 1-chloro-4-hydroxy-phthalazine-6-carboxylic acid [4-chloro-3'-(2-dimethylamino-ethoxy)-biphenyl-3-yl]-amide hydroformate as a solid. $^1$H NMR (400 MHz, CDCl$_3$) δ: 2.60 (s, 6H), 3.07 (t, 2H), 4.28 (t, 2H), 6.90 (dd, 1H), 7.12 (m, 1H), 7.19 (d, 1H), 7.31-7.37 (m, 2H), 7.47 (d, 1H), 8.14 (dd, 1H), 8.50 (dd, 1H), 8.60 (s, 1H), 8.68 (d, 1H), 8.84 (d, 1H) ppm; m/z (M+1) 497.

Example 180 and 181

4-Chloro-1-hydroxy-phthalazine-6-carboxylic acid (3'-hydroxy-biphenyl-3-yl)-amide and 1-Chloro-4-hydroxy-phthalazine-6-carboxylic acid (3'-hydroxy-biphenyl-3-yl)-amide

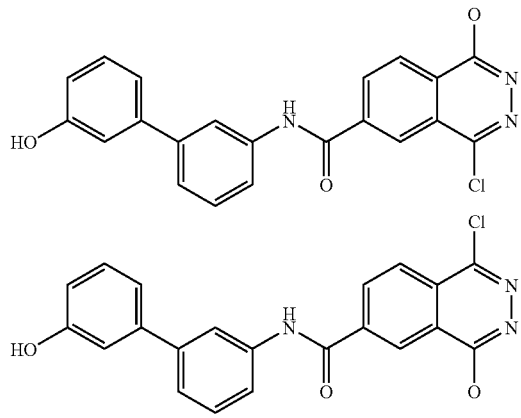

3'-Amino-biphenyl-3-ol

A solution of (4-chloro-3'-hydroxy-biphenyl-3-yl)-carbamic acid tert-butyl ester (1.8 g, 5.64 mmol) was dissolved in a solution of HCl in i-PrOH (5-6M, 20 mL). The resulting solution was stirred at RT for 6 hrs then concentrated to provided 3'-amino-4'-chloro-biphenyl-3-ol hydrochloride.

The above intermediate was dissolved in MeOH (50 mL), palladium on carbon (catalytic amount) was added and the resulting mixture was hydrogenated (1 atm) for 5 hrs. Filtration through celite and concentration gave the desired intermediate 3'-amino-biphenyl-3-ol hydrochloride (1.0 g, 81%)

4-Chloro-1-hydroxy-phthalazine-6-carboxylic acid (3'-hydroxy-biphenyl-3-yl)-amide and 1-Chloro-4-hydroxy-phthalazine-6-carboxylic acid (3'-hydroxy-biphenyl-3-yl)-amide A mixture of 3'-Amino-biphenyl-3-ol hydrochloride (1.0 g, 4.5 mmol), 1-chloro-4-oxo-3,4-dihydro-phthalazine-6-carboxylic acid and 4-chloro-1-oxo-1,2-dihydro-phthalazine-6-carboxylic acid (1.5 g, 6.7 mmol), N-(3-dimethylaminopropyl)-N'-ethylcarbodiimide hydrochloride (1.3 g, 6.7 mmol), 4-NMM (3.0 mL, 28 mmol), 1-hydroxybenzotriazole hydrate (0.91 g, 6.7 mmol) and anhydrous DMF (20 mL) was stirred at room temperature for 48 hrs. The reaction mixture was diluted with EtOAc (100 mL), washed with saturated solution of ammonium chloride (50 mL), saturated solution of NaHCO$_3$ (50 mL), dried and concentrated under reduced pressure. Preparatory HPLC afforded the title compounds as solid: 4-Chloro-1-hydroxy-phthalazine-6-carboxylic acid (3'-hydroxy-biphenyl-3-yl)-amide $^1$H NMR (400 MHz, d6-DMSO) δ: 6.78 (dd, 1H), 7.04 (t, 1H), 7.05-7.10 (m, 1H), 7.27 (t, 1H), 7.35-7.41 (m, 1H), 7.46 (t, 1H), 7.77-7.82 (m, 1H), 8.08 (m, 1H), 8.41 (d, 1H), 8.47 (dd, 1H), 8.51 (d, 1H), 9.56 (s, 1H), 10.80 (s, 1H), 13.02 (s, 1H) ppm; m/z (M+1) 392; and 1-Chloro-4-hydroxy-phthalazine-6-carboxylic acid (3'-hydroxy-biphenyl-3-yl)-amide as a solid. $^1$H NMR (400 MHz, d6-DMSO) δ: 6.78 (dd, 1H), 7.04 (t, 1H), 7.07 (dd, 1H), 7.28 (t, 1H), 7.36-7.40 (m, 1H), 7.46 (t, 1H), 7.82 (dd, 1H), 8.10 (t, 1H), 8.15 (d, 1H), 8.56 (dd, 1H), 8.92 (d, 1H), 9.56 (s, 1H), 10.81 (s, 1H), 13.05 (s, 1H) ppm; m/z (M+1) 392.

Example 182

Synthesis of 4-Chloro-6-(3-pyrrolidin-1-ylmethyl-benzylamino)-2H-phthalazin-1-one

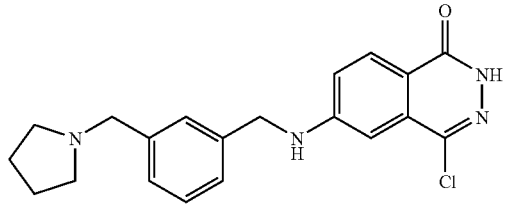

A mixture 6-bromo-4-chloro-2H-phthalazin-1-one (200 mg, 0.770 mmol), [3-(1-pyrrolidinylmethyl)phenyl]methanamine (161 mg, 0.848 mmol), Pd$_2$(dba)$_3$ (71 mg, 0.077 mmol), rac-BINAP (144 mg, 0.231 mmol) and NaO$^t$Bu (230 mg, 2.393 mmol) in DMA (6 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography (Hexanes/EtOAc) afforded 4-chloro-6-(3-pyrrolidin-1-ylmethyl-benzylamino)-2H-phthalazin-1-one (15 mg) as a yellow solid. $^1$H (400 MHz, d$_6$-DMSO) δ: 1.62 (m, 4H), 2.38 (m, 4H), 3.55 (m, 2H), 4.44 (d, 2H), 6.80 (s, 1H), 7.17 (m, 2H), 7.3 (m, 3H), 7.68 (m, 1H), 7.92 (d, 1H), 12.34 (s, 1H) ppm; m/z (M+1) 369.26.

Example 183

Synthesis of 4-Chloro-6-(3-pyrrolidin-1-yl-benzylamino)-2H-phthalazin-1-one

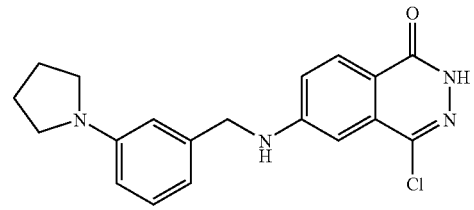

A mixture 6-bromo-4-chloro-2H-phthalazin-1-one (200 mg, 0.770 mmol), (3-pyrrolidin-1-ylphenyl)methylamine (149 mg, 0.848 mmol), Pd$_2$(dba)$_3$ (71 mg, 0.077 mmol), rac-BINAP (153 mg, 0.246 mmol) and NaO$^t$Bu (200 mg, 2.081 mmol) in DMA (6 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography (Hexanes/EtOAc) afforded 4-chloro-6-(3-pyrrolidin-1-yl-benzylamino)-2H-phthalazin-1-one (11 mg) as a white solid. 1H (400 MHz, d$_6$-DMSO) δ: 1.94 (m, 4H), 3.20 (m, 4H), 4.32 (d, 2H), 6.41 (d, 1H), 6.57 (s, 1H), 6.60 (d, 1H), 6.85 (s, 1H), 7.11 (t, 1H), 7.15 (dd, 1H), 7.62 (t, 1H), 7.01 (d, 1H), 12.33 (s, 1H) ppm; m/z (M+1) 355.31.

Example 184

Synthesis of 4-Chloro-6-[(6-pyrrolidin-1-yl-pyridin-2-ylmethyl)-amino]-2H-phthalazin-1-one

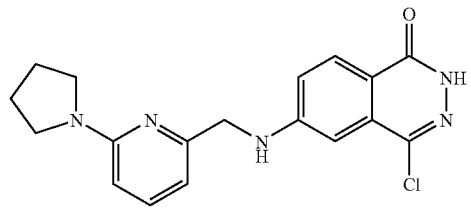

A mixture 6-bromo-4-chloro-2H-phthalazin-1-one (200 mg, 0.770 mmol), (6-pyrrolidin-ylpyrid-2-yl)methylamine (150 mg, 0.848 mmol), Pd$_2$(dba)$_3$ (71 mg, 0.077 mmol), rac-BINAP (153 mg, 0.246 mmol) and NaO$^t$Bu (190 mg, 1.977 mmol) in DMA (6 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography (Hexanes/EtOAc) afforded 4-chloro-6-[(6-pyrrolidin-1-yl-pyridin-2-ylmethyl)-amino]-2H-phthalazin-1-one (25 mg) as a white solid. $^1$H (400 MHz, d$_6$-DMSO) δ: 2.12 (m, 4H), 3.39 (m, 4H), 4.32 (d, 2H), 6.30 (d, 1H), 6.51 (d, 1H), 6.91 (s, 1H), 7.18 (dd, 1H), 7.42 (t, 1H), 7.61 (t, 1H), 7.93 (d, 1H), 12.33 (s, 1H) ppm; m/z (M+1) 356.21.

Example 185

Synthesis of 4-Chloro-6-(2-pyrrolidin-1-yl-benzylamino)-2H-phthalazin-1-one

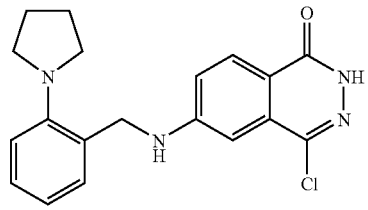

A mixture 6-bromo-4-chloro-2H-phthalazin-1-one (200 mg, 0.770 mmol), (2-pyrrolidin-4-ylphenyl)methylamine (156 mg, 0.885 mmol), Pd$_2$(dba)$_3$ (71 mg, 0.077 mmol), rac-BINAP (155 mg, 0.249 mmol) and NaO$^t$Bu (198 mg, 2.060 mmol) in DMA (6 mL) was heated at 85° C. for 1.5 h. The mixture was allowed to cool, diluted with EtOAc and washed with water. The organic layer was washed with sat.aq. NaHCO$_3$, brine and dried (Na$_2$SO$_4$). Chromatography (Hexanes/EtOAc) afforded 4-chloro-6-(2-pyrrolidin-1-yl-benzylamino)-2H-phthalazin-1-one (35 mg) as a white solid. $^1$H (400 MHz, d$_6$-DMSO) δ: 1.90 (m, 4H), 3.16 (m, 4H), 4.38 (d, 2H), 6.73 (bs, 1H), 6.87 (d, 1H), 7.00 (d, 1H), 7.14 (m, 2H), 7.26 (dd, 1H), 7.64 (t, 1H), 7.90 (d, 1H), 12.32 (s, 1H) ppm; m/z (M+1) 355.23.

Example 186

Synthesis of 4-Chloro-6-(2-morpholin-4-yl-benzylamino)-4a,8a-dihydro-2H-phthalazin-1-one

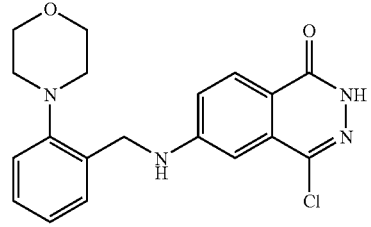

A mixture 6-bromo-4-chloro-2H-phthalazin-1-one (1.227 g, 4.728 mmol), (2-morpholino)benzylamine (1.00 g, 5.201 mmol), Pd$_2$(dba)$_3$ (450 mg, 0.491 mmol), rac-BINAP (883 mg, 1.418 mmol) and NaO$^t$Bu (1.17 g, 12.175 mmol) in DMA (20 mL) was heated at 80° C. for 1.5 h. The mixture was allowed to cool, diluted with EtOAc and washed with water. The organic layer was washed with sat.aq. NaHCO$_3$, brine and dried (Na$_2$SO$_4$). Chromatography (Hexanes/EtOAc) afforded 4-chloro-6-(2-morpholin-4-yl-benzylamino)-4a,8a-dihydro-2H-phthalazin-1-one (180 mg) as a white solid. $^1$H (400 MHz, d$_6$-DMSO) δ: 2.90 (m, 4H), 3.79 (m, 4H), 4.46 (d, 2H), 6.66 (bs, 1H), 7.04 (t, 1H), 7.15 (m, 2H), 7.24 (m, 1H), 7.35 (d, 1H), 7.77 (t, 1H), 7.90 (d, 1H), 12.32 (s, 1H) ppm; m/z (M+1) 371.23.

Example 187

Synthesis of 4-Chloro-6-{methyl-[3-(6-methyl-pyrazin-2-yloxy)-benzyl]-amino}-4a,8a-dihydro-2H-phthalazin-1-one

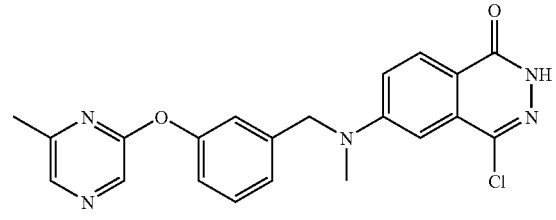

A mixture 6-bromo-4-chloro-2H-phthalazin-1-one (225 mg, 0.867 mmol), N-methyl-3-[(6-methylpyrazin-2-yl)oxy] benzylamine (250 mg, 1.09 mmol), Pd$_2$(dba)$_3$ (95 mg, 0.104 mmol), xantphos (180 mg, 0.312 mmol) and NaO$^t$Bu (300 g, 3.12 mmol) in dioxane (6 mL) was heated at 80° C. for 3.5 h. The mixture was allowed to cool, diluted with EtOAc and washed with water. The organic layer was washed with sat.aq. NaHCO$_3$, brine and dried (Na$_2$SO$_4$). Chromatography (Hexanes/EtOAc) afforded 4-chloro-6-{methyl-[3-(6-methyl-pyrazin-2-yloxy)-benzyl]-amino}-4a,8a-dihydro-2H-phthalazin-1-one (6 mg) as a yellow solid. $^1$H (400 MHz, d$_6$-DMSO) δ: 2.27 (s, 3H), 3.24 (s, 3H), 4.83 (s, 2H), 6.88 (d, 1H), 7.03 (s, 1H), 7.07 (d, 1H), 7.12 (d, 1H), 7.32 (dd, 1H), 7.40 (t, 1H), 8.00 (d, 1H), 8.24 (d, 2H), 12.41 (s, 1H) ppm; m/z (M+1) 408.27.

Example 188

Synthesis of 4-Chloro-6-[methyl-(4-methyl-3,4-dihydro-2H-pyrido[3,2-b][1,4]oxazin-7-ylmethyl)-amino]-4a,8a-dihydro-2H-phthalazin-1-one

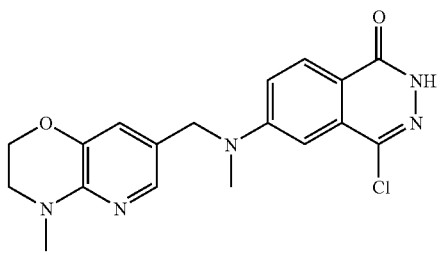

A mixture 6-bromo-4-chloro-2H-phthalazin-1-one (275 mg, 1.06 mmol), N-methyl-(4-methyl-3,4-dihydro-2H-pyrido[3,2-b][1,4]oxazin-7-yl)methylamine (250 mg, 1.29 mmol), Pd$_2$(dba)$_3$ (113 mg, 0.123 mmol), xantphos (214 mg, 0.370 mmol) and NaO$^t$Bu (380 g, 3.696 mmol) in dioxane (6 mL) was heated at 80° C. for 3.5 h. The mixture was allowed to cool, diluted with EtOAc and washed with water. The organic layer was washed with sat.aq. NaHCO$_3$, brine and dried (Na$_2$SO$_4$). Chromatography (Hexanes/EtOAc) afforded 4-chloro-6-[methyl-(4-methyl-3,4-dihydro-2H-pyrido[3,2-b][1,4]oxazin-7-ylmethyl)-amino]-4a,8a-dihydro-2H-phthalazin-1-one (5 mg) as a yellow solid. $^1$H (400 MHz, d$_6$-DMSO) δ: 2.98 (s, 3H), 3.18 (s, 3H), 3.38 (t, 2H), 4.18 (t, 2H), 4.6 (s, 2H), 6.81 (d, 1H), 6.90 (d, 1H), 7.37 (dd, 1H), 7.61 (d, 1H), 8.00 (d, 1H), 12.40 (s, 1H) ppm; m/z (M+1) 372.21.

Example 189

Synthesis of 4-Chloro-6-[2-((R)-3-methyl-piperazin-1-yl)-benzyl amino]-4a,8a-dihydro-2H-phthalazin-1-one

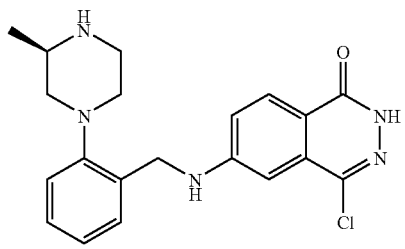

2-((R)-3-Methyl-piperazin-1-yl)-benzonitrile

A mixture 2-bromobenzonitrile (1.0 g, 5.494 mmol), (S)-(+)-2-methylpiperazine (0.60 g, 5.99 mmol), Pd$_2$(dba)$_3$ (0.503 g, 0.549 mmol), rac-BINAP (1.026 g, 1.648 mmol) and NaO$^t$Bu (2.11 g, 21.976 mmol) in DMA (27 mL) was heated at 80° C. for 2.5 h. The mixture was allowed to cool, diluted with EtOAc and washed with water. The organic layer was washed with sat.aq. NaHCO$_3$, brine and dried (Na$_2$SO$_4$). Chromatography (EtOAc/MeOH) afforded 2-((R)-3-methyl-piperazin-1-yl)-benzonitrile (540 mg) as a white solid. $^1$H (400 MHz, d$_6$-DMSO) δ: ppm; m/z (M+1) 202.21.

2-((R)-3-Methyl-piperazin-1-yl)-benzylamine

A mixture of 2-((R)-3-methyl-piperazin-1-yl)-benzonitrile (542 mg, 2.69 mmol), Raney Nickel (3 mL of a slurry in water), ammonia (15 mL, 2M solution in EtOH) was evacuated and flushed with H$_2$, then stirred at room temperature for 3 h. The reaction mixture was filtered through celite, rinsed with MeOH, concentrated and dried in vacuum to afford 2-((R)-3-methyl-piperazin-1-yl)-benzylamine (526 mg) as an orange viscous oil. m/z (M+1) 206.29.

4-Chloro-6-[2-((R)-3-methyl-piperazin-1-yl)-benzylamino]-4a,8a-dihydro-2H-phthalazin-1-one A mixture 6-bromo-4-chloro-2H-phthalazin-1-one (670 mg, 2.582 mmol), 2-((R)-3-methyl-piperazin-1-yl)-benzylamine (542 mg, 2.693 mmol), Pd$_2$(dba)$_3$ (246 mg, 0.269 mmol), rac-BINAP (505 mg, 0.811 mmol) and NaO$^t$Bu (774 mg, 8.054 mmol) in DMA (13 mL) was heated at 80° C. for 2 h. The mixture was allowed to cool, filtered through celite and rinsed with EtOAc (this layer was discarded), then MeOH. The MeOH filtrate was concentrated followed by column chromatography (EtOAc/MeOH+0.1% NH$_4$OH) afforded 4-chloro-6-[2-((R)-3-methyl-piperazin-1-yl)-benzylamino]-4a,8a-dihydro-2H-phthalazin-1-one (121 mg) as a brown solid. $^1$H (400 MHz, d$_6$-DMSO) δ: 1.22 (d, 3H), 2.73 (m, 1H), 2.95 (m, 1H), 3.1 (m, 5H), 4.47 (d, 2H), 6.67 (s, 1H), 7.06 (m, 1H), 7.14 (d, 2H), 7.25 (m, 1H), 7.35 (d, 1H), 7.78 (t, 1H), 7.90 (d, 1H), 12.33 (s, 1H) ppm; m/z (M+1) 384.28.

Example 190

4-Chloro-6-[2-(hexahydro-pyrrolo[3,4-c]pyrrol-2-yl)-benzylamino]-2H-phthalazin-1-one

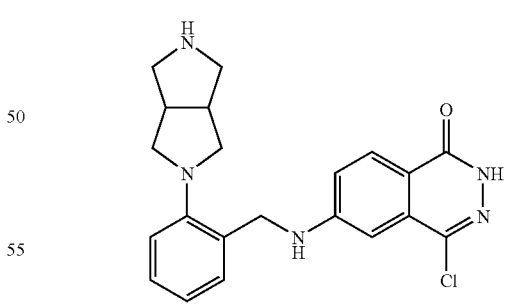

5-(2-Cyano-phenyl)-hexahydro-pyrrolo[3,4-c]pyrrole-2-carboxylic acid tert-butyl ester A mixture of hexahydro-pyrrolo[3,4-c]pyrrole-2-carboxylic acid tert-butyl ester (464 mg, (2.19 mmol), 2-bromobenzonitrile (400 mg, 2.19 mmol), Pd$_2$(dba)$_3$ (100 mg, 0.11 mmol), xantphos (190 mg, 0.33 mmol), sodium t-butoxide (618 mg, 6.57 mmol) in degassed anhydrous dioxane (10 mL)

was heated at 120° C. in a sealed tube for 1 h. The mixture was allowed to cool and filtered through celite. The filtrate was concentrated and purified by chromatography (EtOAc/hexanes) to yield the title compound (505 mg, 74%). m/z (M+1) 313.41.

5-(2-Aminomethyl-phenyl)-hexahydro-pyrrolo[3,4-c]pyrrole-2-carboxylic acid tert-butyl ester To a solution of 5-(2-cyano-phenyl)-hexahydro-pyrrolo[3,4-c]pyrrole-2-carboxylic acid tert-butyl ester (150 mg, 0.48 mmol) in NH$_3$/EtOH (2M, 10 mL) was added Raney Nickel (3 mL slurry in water). The atmosphere was exchanged with hydrogen via balloon and the mixture was allowed to stir for 2.5 h. After this time the mixture was filtered through celite and concentrated to yield the title compound (140 mg). m/z (M+1) 318.29.

5-{2-[(4-Chloro-1-oxo-1,2-dihydro-phthalazin-6-ylamino)-methyl]-phenyl}-hexahydro-pyrrolo[3,4-c]pyrrole-2-carboxylic acid tert-butyl ester A mixture of 6-bromo-4-chloro-2H-phthalazin-1-one (136 mg, 0.52 mmol), 5-(2-aminomethyl-phenyl)-hexahydro-pyrrolo[3,4-c]pyrrole-2-carboxylic acid tert-butyl ester (150 mg, 0.48 mmol), Pd$_2$(dba)$_3$ (22 mg, 0.024 mmol), BINAP (49 mg, 0.078 mmol) and NaOt-Bu (147 mg, 1.56 mmol) in DMA (10 mL) was purged with nitrogen for 10 min. The mixture was heated at 90° C. for 2 h. The mixture was allowed to cool and diluted with ethyl acetate (30 mL) and washed with ammonium chloride (25 mL). The organic layer was dried and concentrated. Chromatography on silica yielded the title compound (50 mg, 19%) m/z (M+H)=496.12.

To a solution of 5-{2-[(4-chloro-1-oxo-1,2-dihydro-phthalazin-6-ylamino)-methyl]-phenyl}-hexahydro-pyrrolo[3,4-c]pyrrole-2-carboxylic acid tert-butyl ester (50 mg, 0.10 mmol) in MeOH (5 mL) was added a solution of HCl in dioxane (5 mL, 4M). The mixture was stirred at ambient temperature for 4 h. The residue was crystallized from MeOH/Et$_2$O to yield the title compound as the HCl salt (15 mg) m/z (M+H)=396.28 $^1$H-NMR (DMSO-d6) δ: 12.27 (s, 1H), 8.85 (m, 2H), 7.85 (d, 1H), 7.24 (m, 1H), 7.18 (m, 1H), 7.08 (m, 2H), 6.90 (m, 1H), 6.60 (m, 1H), 4.37 (m, 2H), 3.45 (m, 2H), 3.0 (m, 8H).

Example 191

4-Chloro-6-(2-perhydro-1,4-diazepin-1-yl-benzylamino)-2H-phthalazin-1-one

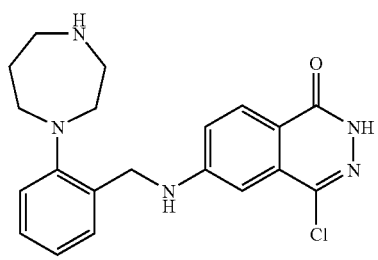

4-(2-Cyano-phenyl)-perhydro-1,4-diazepine-1-carboxylic acid tert-butyl ester

A mixture of Boc-homopiperazine (900 mg, (4.63 mmol), 2-bromobenzonitrile (766 mg, 4.211 mmol), Pd$_2$(dba)$_3$ (193 mg, 0.21 mmol), xantphos (366 mg, 0.63 mmol), sodium t-butoxide (1.19 g, 12.6 mmol) in degassed anhydrous dioxane (10 mL) was heated at 120° C. in a sealed tube for 2 h. The mixture was allowed to cool and filtered through celite. The filtrate was concentrated and purified by chromatography (EtOAc/hexanes) to yield the title compound (905 mg, 71%). m/z (M+1) 301.27.

4-(2-Aminomethyl-phenyl)-perhydro-1,4-diazepine-1-carboxylic acid tert-butyl ester To a solution of 4-(2-cyano-phenyl)-perhydro-1,4-diazepine-1-carboxylic acid tert-butyl ester (905 mg, 3.0 mmol) in NH$_3$/EtOH (2M, 15 mL) was added Raney Nickel (5 mL slurry in water). The atmosphere was exchanged with hydrogen via balloon and the mixture was allowed to stir for 2.5 h. After this time the mixture was filtered through celite and concentrated to yield the title compound (900 mg). m/z (M+1) 305.31.

4-{(2-[(4-Chloro-1-oxo-1,2-dihydro-phthalazin-6-ylamino)-methyl]-phenyl}-perhydro-1,4-diazepine-1-carboxylic acid tert-butyl ester A mixture of 6-bromo-4-chloro-2H-phthalazin-1-one (140 mg, 0.54 mmol), 4-(2-Aminomethyl-phenyl)-perhydro-1,4-diazepine-1-carboxylic acid tert-butyl ester (150 mg, 0.49 mmol), Pd$_2$(dba)$_3$ (45 mg, 0.049 mmol), BINAP (92 mg, 0.15 mmol) and NaOt-Bu (138 mg, 1.47 mmol) in DMA (10 mL) was purged with nitrogen for 10 min. The mixture was heated at 90° C. for 5 h. The mixture was allowed to cool and diluted with ethyl acetate (30 mL) and washed with ammonium chloride (25 mL). The organic layer was dried and concentrated. Chromatography on silica yielded the title compound (25 mg, 11%) m/z (M+H)=484.72.

To a solution of 4-{2-[(4-chloro-1-oxo-1,2-dihydro-phthalazin-6-ylamino)-methyl]-phenyl}-perhydro-1,4-diazepine-1-carboxylic acid tert-butyl ester (15 mg, 0.051 mmol) in MeOH (1 mL) was added a solution of HCl in dioxane (5 mL, 4M). The mixture was stirred at ambient temperature for 4 h. The residue was crystallized from MeOH/Et$_2$O to yield the title compound as the HCl salt (10 mg) m/z (M+H)=384.28 $^1$H-NMR (DMSO-d6) δ: 12.27 (s, 1H), 8.85 (m, 2H), 7.85 (d, 1H), 7.62 (m, 1H), 7.25 (d, 1H), 7.18 (m, 2H), 7.05 (m, 2H), 6.62 (m, 1H), 4.41 (d, 2H), 3.20 (m, 5H), 3.05 (m, 3H), 2.00 (m, 2H).

Example 192

4-Chloro-6-(2-piperazin-1-yl-5-trifluoromethyl-benzylamino)-2H-phthalazin-1-one

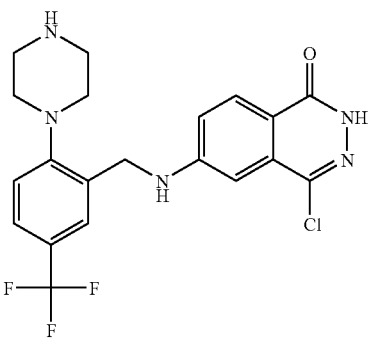

4-(2-Cyano-4-trifluoromethyl-phenyl)-piperazine-1-carboxylic acid tert-butyl ester A mixture of Boc-piperazine (573 mg, (3.08 mmol), 2-bromo-5-trifluoromethylbenzonitrile (700 mg, 2.80 mmol), $Pd_2(dba)_3$ (256 mg, 0.28 mmol), xantphos (486 mg, 0.84 mmol), sodium t-butoxide (660 mg, 7.0 mmol) in degassed anhydrous dioxane (10 mL) was heated at 85° C. for 1 h. The mixture was allowed to cool and filtered through celite. The filtrate was concentrated and purified by chromatography (EtOAc/hexanes) to yield the title compound (150 mg, 15%). m/z (M+1) 356.37.

4-(2-Aminomethyl-4-trifluoromethyl-phenyl)-piperazine-1-carboxylic acid tert-butyl ester To a solution 4-(2-cyano-4-trifluoromethyl-phenyl)-piperazine-1-carboxylic acid tert-butyl ester (150 mg, 0.42 mmol) in $NH_3$/EtOH (2M, 10 mL) was added Raney Nickel (3 mL slurry in water). The atmosphere was exchanged with hydrogen via balloon and the mixture was allowed to stir for 30 min. After this time the mixture was filtered through celite and concentrated to yield the title compound (148 mg). m/z (M+1) 360.23.

4-{(2-[(4-Chloro-1-oxo-1,2-dihydro-phthalazin-6-ylamino)-methyl]-4-trifluoromethyl-phenyl}-piperazine-1-carboxylic acid tert-butyl ester A mixture of 6-bromo-4-chloro-2H-phthalazin-1-one (183 mg, 0.70 mmol), 4-(2-aminomethyl-4-trifluoromethyl-phenyl)-piperazine-1-carboxylic acid tert-butyl ester (230 mg, 0.64 mmol), $Pd_2(dba)_3$ (59 mg, 0.064 mmol), BINAP (120 mg, 0.19 mmol) and NaOt-Bu (180 mg, 1.92 mmol) in DMA (10 mL) was purged with nitrogen for 10 min. The mixture was heated at 90° C. for 5 h. The mixture was allowed to cool and diluted with ethyl acetate (30 mL) and washed with ammonium chloride (25 mL). The organic layer was dried and concentrated. Chromatography on silica yielded the title compound (25 mg) m/z (M+H)=538.90.

To a solution 4-{2-[(4-chloro-1-oxo-1,2-dihydro-phthalazin-6-ylamino)-methyl]-4-trifluoromethyl-phenyl}-piperazine-1-carboxylic acid tert-butyl ester (25 mg, 0.046 mmol) in MeOH (1 mL) was added a solution of HCl in dioxane (5 mL, 4M). The mixture was stirred at ambient temperature for 4 h. The residue was crystallized from MeOH/$Et_2O$ to yield the title compound as the HCl salt (10 mg) m/z (M+H)=438.23 $^1$H-NMR (DMSO-d6) δ: 12.34 (s, 1H), 8.79 (m, 2H), 7.98 (d, 1H), 7.78 (t, 1H), 7.62 (s, 1H), 7.52 (m, 1H), 7.29 (d, 1H), 7.08 (m, 1H), 6.58 (m, 1H), 4.42 (d, 2H), 3.55 (m, 4H), 3.10 (m, 4H).

Example 193

4-Chloro-6-(5-methoxy-2-piperazin-1-yl-benzylamino)-2H-phthalazin-1-one

4-(2-Cyano-4-methoxy-phenyl)-piperazine-1-carboxylic acid tert-butyl ester

A mixture of Boc-homopiperazine (483 mg, 2.59 mmol), 2-bromo-5-methoxybenzonitrile (500 mg, 2.36 mmol), $Pd_2(dba)_3$ (108 mg, 0.12 mmol), xantphos (205 mg, 0.35 mmol), sodium t-butoxide (666 mg, 7.08 mmol) in degassed anhydrous dioxane (10 mL) was heated at 90° C. for 2 h. The mixture was allowed to cool and filtered through celite. The filtrate was concentrated and purified by chromatography (EtOAc/hexanes) to yield the title compound (691 mg, 92%). m/z (M+1) 318.39.

4-(2-Aminomethyl-4-methoxy-phenyl)-piperazine-1-carboxylic acid tert-butyl ester To a solution of 4-(2-cyano-4-methoxy-phenyl)-piperazine-1-carboxylic acid tert-butyl ester (680 mg, 2.14 mmol) in $NH_3$/EtOH (2M, 15 mL) was added Raney Nickel (5 mL slurry in water). The atmosphere was exchanged with hydrogen via balloon and the mixture was allowed to stir for 2.5 h. After this time the mixture was filtered through celite and concentrated to yield the title compound (650 mg). m/z (M+1) 321.57.

4-(2-[(4-Chloro-1-oxo-1,2-dihydro-phthalazin-6-ylamino)-methyl]-4-methoxy-phenyl)-piperazine-1-carboxylic acid tert-butyl ester A mixture of 6-bromo-4-chloro-2H-phthalazin-1-one and 7-bromo-4-chloro-2H-phthalazin-1-one (300 mg, 1.16 mmol), 4-(2-aminomethyl-4-methoxy-phenyl)-piperazine-1-carboxylic acid tert-butyl ester (338 mg, 1.05 mmol), $Pd_2(dba)_3$ (110 mg, 0.12 mmol), BINAP (217 mg, 0.35 mmol) and NaOt-Bu (327 mg, 3.48 mmol) in DMA (10 mL) was purged with nitrogen for 10 min. The mixture was heated at 90° C. for 1.5 h. The mixture was allowed to cool and diluted with ethyl acetate (30 mL) and washed with ammonium chloride (25 mL). The organic layer was dried and concentrated. Chromatography on silica yielded the title compound (102 mg, 18%) m/z (M+H)=500.32.

To a solution of 4-{2-[(4-chloro-1-oxo-1,2-dihydro-phthalazin-6-ylamino)-methyl]-4-methoxy-phenyl}-piperazine-1-carboxylic acid tert-butyl ester (100 mg, 0.20 mmol) in MeOH (1 mL) was added a solution of HCl in dioxane (5 mL, 4M). The mixture was stirred at ambient temperature for 4 h. The residue was crystallized from MeOH/$Et_2O$ to yield the title compound as the HCl salt (10 mg) m/z (M+H)=400.20 $^1$H-NMR (DMSO-d6) δ: 12.28 (s, 1H), 8.90 (bs, 2H), 7.86 (d, 1H), 7.68 (bs, 1H), 7.10 (m, 2H), 6.86 (d, 1H), 6.78 (dd, 1H), 6.57 (bs, 1H), 4.40 (m, 2H), 3.61 (s, 3H), 3.20 (m, 4H), 2.90 (m, 4H).

Example 194

6-[2-(4-Amino-piperidin-1-yl)-benzylamino]-4-chloro-2H-phthalazin-1-one

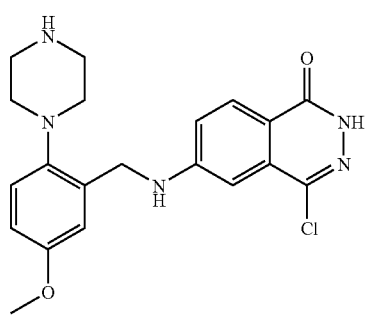

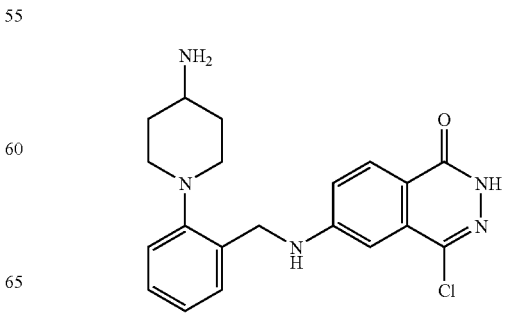

[1-(2-Cyano-phenyl)-piperidin-4-yl]-carbamic acid tert-butyl ester

A mixture of piperidin-4-yl-carbamic acid tert-butyl (695 mg, 3.47 mmol), 2-bromo-benzonitrile (631 mg, 3.47 mmol), Pd$_2$(dba)$_3$ (159 mg, 0.174 mmol), xanthphos (300 mg, 0.52 mmol), sodium tert-butoxide (1 g, 10.41 mmol) in anhydrous 1,4-dioxane (6 ml) was heated at 100-110° C. in a sealed tube for 1 h. After cooled to room temperature, the mixture was filtered through celite then concentrated before purified by chromatography (hexanes/EtOAc) to provide the titled compound (240 mg, 23%). m/z (M+1) 302.30.

[1-(2-Aminomethyl-phenyl)-piperidin-4-yl]-carbamic acid tert-butyl ester]

To a solution of [1-(2-cyano-phenyl)-piperidin-4-yl]-carbamic acid tert-butyl ester (0.224 g, 0.741 mmol) in NH$_3$/EtOH (2M, 15.5 ml) was added Raney Nickel (3.5 ml slurry in water). The mixture was stirred under hydrogen (balloon) for 5 h before filtered through celite and concentrated to give the primary amine (183 mg, 81%). m/z (M+1) 306.30.

(1-{2-[(4-Chloro-1-oxo-1,2-dihydro-phthlalzin-6-ylamino)-methyl]-phenyl}-piperidin-4-yl)-carbamic acid tert-butyl ester A mixture of [1-(2-aminomethyl-phenyl)-piperidin-4-yl]-carbamic acid tert-butyl ester] (97 mg, 0.318 mmol), 6-bromo-4-chloro-2H-phthalazin-1-one (82.4 mg, 0.318 mmol), Pd$_2$(dba)$_3$ (29 mg, 0.032 mmol), BINAP (59 mg, 0.095 mmol), sodium tert-butoxide (182 mg, 1.9 mmol) in DMA (2.5 ml) was purged with nitrogen before heated at 100° C. for 1 h. The mixture was cooled and diluted with EtOAc and washed with NH$_4$Cl. The organic layer was dried and concentrated before chromatography using hexanes/EtOAc to yield the titled compound (49 mg, 31%). m/z (M+1) 484.15.

Methanol (3 ml) was added to a solution (1-{2-[(4-chloro-1-oxo-1,2-dihydro-phthlalzin-6-ylamino)-methyl]-phenyl}-piperidin-4-yl)-carbamic acid tert-butyl ester (0.10 mmol) followed by the addition of 4M HCl solution in dioxane (3 ml). The mixture was stirred at room temperature for 2 h before evaporated to give the HCl salt. The salt was dissolved in water/EtOAc and neutralized by the addition of K$_2$CO$_3$ to give the final product, 6-[2-(4-Amino-piperidin-1-yl)-benzylamino]-4-chloro-2H-phthalazin-1-one (31 mg, 82%). m/z (M+1) 384.15. $^1$H NMR (CDCl$_3$): δ 8.16 (1H), 7.36 (1H), 7.28 (2H), 7.18 (1H), 7.08 (1H), 7.03 (1H), 6.88 (1H), 5.61 (1H), 4.58 (2H), 3.10 (2H), 2.91 (1H), 2.81 (2H), 1.92 (3H), 1.51 (3H) ppm.

Example 195

4-Chloro-6-(5-fluoro-2-piperazin-1-yl-benzylamino)-2H-phthalazin-1-one

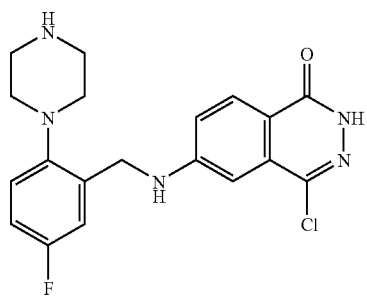

4-(2-Cyano-4-fluoro-phenyl)-piperazine-1-carboxylic acid tert-butyl ester

A mixture of piperazine-1-carboxylic acid tert-butyl ester (1.05 g, 5.65 mmol), 2-bromo-5-fluoro-benzonitrile (1.13 g, 5.65 mmol), Pd$_2$(dba)$_3$ (259 mg, 0.283 mmol), xanthphos (490 mg, 0.848 mmol), sodium tert-butoxide (1.63 g, 16.95 mmol) in anhydrous 1,4-dioxane (10 ml) was heated at 100-110° C. in a sealed tube for 1 h. After cooled to room temperature, the mixture was filtered through celite then concentrated before purified by chromatography (hexanes/EtOAc) to provide compound as indicated (1.31 g, 76%). m/z (M+1) 306.21.

4-(2-Aminomethyl-4-fluoro-phenyl)-piperazine-1-carboxylic acid tert-butyl ester To a solution of 4-(2-cyano-4-fluoro-phenyl)-piperazine-1-carboxylic acid tert-butyl ester (0.778 g, 2.55 mmol) in NH$_3$/EtOH (2M, 30 ml) was added Raney Nickel (4 ml slurry in water). The mixture was stirred under hydrogen (balloon) for 3 h before filtered through celite and concentrated to give the primary amine (690 mg, 88%). m/z (M+1) 310.19.

4-{2-[(4-Chloro-1-oxo-1,2-dihydro-phthalzin-6-ylamino)-methyl]-4-fluoro-phenyl}-piperazine-1-carboxylic acid tert-butyl ester A mixture of 4-(2-aminomethyl-4-fluoro-phenyl)-piperazine-1-carboxylic acid tert-butyl ester (78 mg, 0.252 mmol), 6-bromo-4-chloro-2H-phthalazin-1-one (66 mg, 0.252 mmol), Pd$_2$(dba)$_3$ (23 mg, 0.025 mmol), BINAP (47 mg, 0.076 mmol), sodium tert-butoxide (145 mg, 1.51 mmol) in DMA (2 ml) was purged with nitrogen before heated at 100° C. for 1 h. The mixture was cooled and diluted with EtOAc and washed with NH$_4$Cl. The organic layer was dried and concentrated before chromatography using hexanes/EtOAc to yield the couple product (26 mg, 22%). m/z (M+1) 488.18. Methanol (1.5 ml) was added to a solution 4-{2-[(4-chloro-1-oxo-1,2-dihydro-phthalzin-6-ylamino)-methyl]-4-fluoro-phenyl}-piperazine-1-carboxylic acid tert-butyl ester (0.053 mmol) followed by the addition of 4M HCl solution in dioxane (1.5 ml). The mixture was stirred at room temperature for 4 h before evaporated to give the HCl salt. The salt was dissolved in water/EtOAc and neutralized by the addition of K$_2$CO$_3$ to give the final product, 4-chloro-6-(5-fluoro-2-piperazin-1-yl-benzylamino)-2H-phthalazin-1-one (19 mg, 92%). m/z (M+1) 388.18. $^1$H NMR (DMSO-d$_6$): δ 12.35 (1H), 7.95 (1H), 7.75 (1H), 7.25 (2H), 7.15 (3H), 6.50 (1H), 4.48 (2H), 3.28 (4H), 3.05 (4H) ppm.

Enzyme Inhibition Assay (p70S6K(h))

In a final reaction volume of 25 uL, p70S6K(h) (5-10 mU) is incubated with 8 mM MOPS pH 7.0, 0.2 mM EDTA, 100 iM KKRNRTLTV, 10 mM MgAcetate and [gamma-33P-ATP] (specific activity approx. 500 cpm/pmol, concentration as required). The reaction is initiated by the addition of the MgATP mix. After incubation for 40 minutes at room temperature, the reaction is stopped by the addition of 5 uL of a 3% phosphoric acid solution. 10 uL of the reaction is then spotted onto a P30 filtermat and washed three times for 5 minutes in 75 mM phosphoric acid and once in methanol prior to drying and scintillation counting.

Evaluation of Anti-Proliferative Activity

The assays used to detect the effect of compounds on tumor cell proliferation were based on the ability of viable cells to cause alamarBlue to change from its oxidized (non-fluorescent, blue) to a reduced (fluorescent, red) form. With the results obtained from the alamarBlue reaction, cell proliferation can be quantified and metabolic activity of viable cells can be examined. All of the human tumor cell lines were obtained from American Type Culture Collection (ATCC).

Aliquots of 100 μl of cell suspension (3.0-5.0×10³ cells/well) in growth media were placed in 96-well cell culture plates in an atmosphere of 5% CO2 at 37° C. After 24-hour incubation, the growth media were replaced with 100 μl of growth media containing increasing concentrations of test compounds, rapamycin, mitomycin, or vehicle, respectively. The cells were grown for an additional 72-hour. The test compound was evaluated at increasing concentrations of 100, 10, 1, 0.1 and 0.01 μM. At the end of incubation, 20 μl of 90% alamarBlue reagent was added to each well for 6-hour incubation before detection of cell viability by fluorescent intensity. Fluorescent intensity was measured using a fluorescence microplate reader with excitation at 530 nm and emission at 590 nm.

Determination of IC50 and LC50: The measured results were calculated by the following formula:

$$PG(\%) = 100\% \times (\text{Mean } F\text{test} - \text{Mean } F\text{time0})/(\text{Mean } F\text{ctrl} - \text{Mean } F\text{time0})$$

If (Mean Ftest−Mean Ftime0)<0, then $$PG(\%) = 100\% \times (\text{Mean } F\text{test} - \text{Mean } F\text{time0})/(\text{Mean } F\text{time0} - \text{Mean } F\text{blank})$$

Where:
PG: percent growth
Mean Ftime0=The average of measured fluorescent intensities of reduced alamarBlue at the time just before exposure of cells to the test substance.
Mean Ftest=The average of measured fluorescent intensities of alamarBlue after 72-hour exposure of cells to the test substance.
Mean Fctrl=The average of measured fluorescent intensities of alamarBlue after 72-hour incubation without the test substance.
Mean Fblank=The average of measured fluorescent intensities of alamarBlue in medium without cells after 72-hour incubation.

The compounds of the present invention typically show more then 50% inhibition of P70S6K enzyme at 10 μM concentration. For example the compounds of Examples 24, 26, 42, 64, 107 and 126 show more than 50% inhibition at 0.3 μM concentration.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

All references cited herein are hereby incorporated by reference in their entirety.

What is claimed is:
1. A compound of formula III:

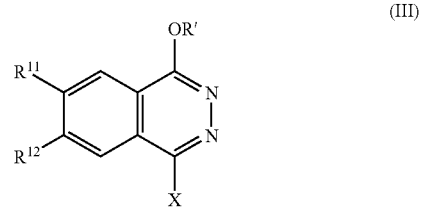

wherein
X is hydrogen, halogen, alkyl, aryl, heteroaryl, cyano or alkoxy;
R' is hydrogen, alkyl, —C(O)$R_x$, —SO$_2$$R_x$ or —P(O)(O$R_x$)$_2$, where $R_x$ is hydrogen or alkyl;
$R^{11}$ and $R^{12}$ are each independently hydrogen, halogen, hydroxy, cyano, amino, alkyl, alkenyl, alkynyl, heterocyclyl, alkoxy, alkythio, arylthio, -alkylene-NR$^a$R$^b$, C(O)R$^a$, —C(O)NR$^a$R$^b$, -alkylene-C(O)NR$^a$R$^b$, —C(O)OR$^a$, —C(S)NR$^a$R$^b$, —C(S)R$^a$, —C(O)SR$^a$, NO$_2$, NH$_2$, —NR$^a$C(O)R$^b$, —NR$^a$R$^b$, —NR$^a$OR$^b$, —NR$^a$C(S)R$^b$, —NR$^a$C(O)NR$^b$R$^c$, —NR$^a$C(S)NR$^b$R$^c$, —NR$^a$(COOR$^b$), —NR$^a$S(O)$_2$NR$^b$R$^c$, —NR$^a$S(O)R$^b$, —NR$^a$S(O)$_2$R$^b$, —OR$^a$, —OC(O)R$^a$, —ONR$^a$R$^b$, —OC(O)NR$^a$R$^b$, —SR$^a$, —S(O)$_2$R$^a$, or —S(O)$_2$NR$^a$R$^b$, wherein R$^a$, R$^b$ and R$^c$ are each independently hydrogen, hydroxy, cyano, nitro, alkyl, alkenyl, alkynyl, cycloalkyl, aryl, alkylaryl, haloaryl, heteroaryl, alkylheteroaryl, alkylheterocyclyl, alkoxy, alkythio, arylthio, or alkoxycarbonyl, wherein, if present, an aryl, alkylaryl, heteroaryl, alkylheteroaryl, heterocyclyl, or alkylheterocycyl may be substituted, in one or more positions with a substituent or a combination of substituents selected from halogen, hydroxy, cyano, nitro, amino, carboxyl, alkyl, alkenyl, alkynyl, alkoxy, alkylamino, alkylthio, —C(O)NR$^d$-alkylheterocyclyl (in which R$^d$ is H or alkyl), O-alkylheterocyclyl, alkylheterocyclyl, aryl, heteroaryl, heterocyclyl, aryloxy, alkylamino, dialkylamino, aminoalkyl, -alkylene-O-alkyl, —NR$^e$C(O)R$^f$, —NR$^e$(alkylene-NR$^e$R$^f$), —NR$^e$(alkylheterocyclyl), and —O-alkylene-NR$^e$R$^f$ (in which R$^e$ and R$^f$ are independently hydrogen or alkyl;
wherein at least one of $R^{11}$ or $R^{12}$ is -alkylene-C(O)NR$^a$R$^b$, -alkylene-NR$^a$R$^b$, —C(O)NR$^a$R$^b$, —NR$^a$C(O)R$^b$ or —NR$^a$R$^b$;
and pharmaceutically acceptable salts thereof,
provided that said compound is not:
N-(3,4-dihydro-4-oxo-6-phthalazinyl)-2-methyl-2-propenamide,
N-(1,2-dihydro-1-oxo-6-phthalazinyl)-2-methyl-2-propenamide,
7-(cyclohexylamino)-6-(phenylamino)-1(2H)-phthalazinone,
6,7-bis(phenylamino)-1(2H)-phthalazinone,
6-amino-7-chloro-1(2H)-phthalazinone,
or a pharmaceutically acceptable salt thereof.

2. A compound according to claim 1, wherein R' is hydrogen or alkyl.

3. A compound according to claim 1, wherein
X is hydrogen, halogen, alkyl, aryl, heteroaryl, cyano or alkoxy;
R' is hydrogen or alkyl;
$R^{11}$ and $R^{12}$ are each independently hydrogen, -alkylene-NR$^a$R$^b$, —C(O)NR$^a$R$^b$, -alkylene-C(O)NR$^a$R$^b$, —NR$^a$C(O)R$^b$ or —NR$^a$R$^b$;

wherein $R^a$, $R^b$ and $R^c$ are each independently hydrogen, alkyl, aryl, alkylaryl, alkylheteroaryl or alkylheterocyclyl, wherein, if present, an aryl, alkylaryl, alkylheteroaryl or alkylheterocyclyl may be substituted, in one or more positions with a substituent or a combination of substituents selected from halogen, hydroxy, cyano, nitro, amino, carboxyl, alkyl, alkenyl, alkynyl, alkoxy, alkylamino, alkylthio, —C(O)NR$^d$-alkylheterocyclyl (in which $R^d$ is H or alkyl), O-alkylheterocyclyl, alkylheterocyclyl, aryl, heteroaryl, heterocyclyl, aryloxy, alkylamino, dialkylamino, aminoalkyl, -alkylene-O-alkyl, —NR$^e$C(O)R$^f$, —NR$^e$(alkylene-NR$^e$R$^f$), —NR$^e$(alkylheterocyclyl), and —O-alkylene-NR$^e$R$^f$, (in which $R^e$ and $R^f$ are independently hydrogen or alkyl).

4. A compound according to claim 1, wherein one of $R^{11}$ and $R^{12}$ is hydrogen and the other of $R^{11}$ and $R^{12}$ is -alkylene-NR$^a$R$^b$, —C(O)NR$^a$R$^b$, -alkylene-C(O)NR$^a$R$^b$, —NR$^a$C(O)R$^b$ or —NR$^a$R$^b$.

5. A compound according to claim 1, wherein the compound of formula III is represented by formulas IIIa-IIIj and R is -alkylene-:

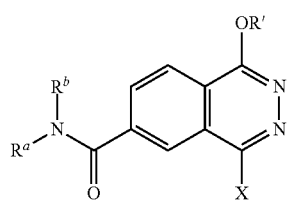
(IIIa)

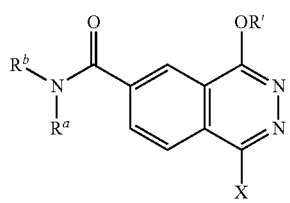
(IIIb)

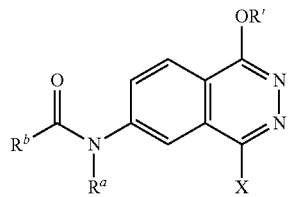
(IIIc)

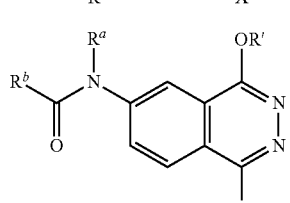
(IIId)

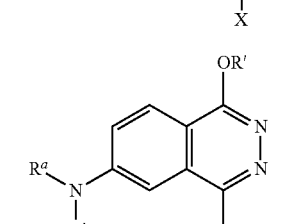
(IIIe)

-continued

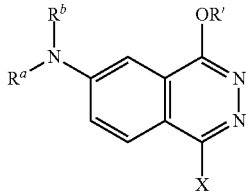
(IIIf)

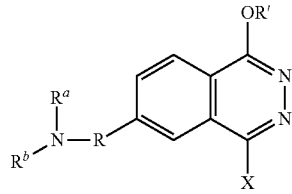
(IIIg)

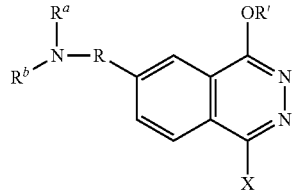
(IIIh)

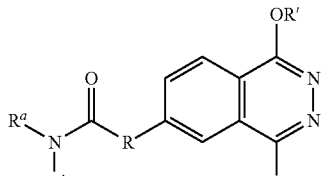
(IIIi)

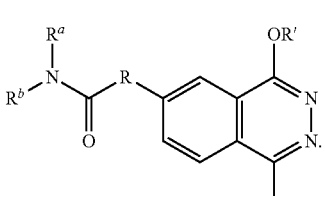
(IIIj)

6. A compound according to claim 5, wherein X is hydrogen, halogen, alkyl, aryl, alkoxy, cyano or heteroaryl; R' is hydrogen or alkyl, R is alkylene and $R^a$ and $R^b$ are each independently hydrogen, alkyl, aryl, heteroaryl, alkylaryl, alkylheterocyclyl or alkylheteroaryl, wherein if present, any aryl, heteroaryl or alkylheterocyclyl group may be optionally substituted.

7. A compound according to claim 5, wherein X is hydrogen, halogen, alkyl, aryl, alkoxy, cyano or heteroaryl; R' is hydrogen or alkyl, R is alkylene and $R^a$ and $R^b$ are each independently hydrogen, methyl, or optionally substituted phenyl, pyridinyl, benzyl, phenethyl, morpholinylethyl, piperidinylethyl or furanylmethyl.

8. A compound according to claim 5 represented by formula IIIa or IIIb wherein X is halogen, alkyl, aryl or heteroaryl and $R^a$ and $R^b$ are each independently hydrogen, aryl, heteroaryl or alkylaryl, wherein if present, any aryl, arylalkyl or heteroaryl group may be optionally substituted.

9. A compound according to claim 5, wherein one of $R^a$ and $R^b$ is hydrogen or alkyl and the other is phenyl, hydroxybiphenyl, trifluoromethylphenyl, bis(trifluoromethyl)phenyl, difluorophenyl, fluoro(trifluoromethyl)phenyl, fluoro(methyl)phenyl, trifluoromethylpyridyl, methyl(trifluoromethyl)phenyl, methoxybenzyl, trifluoromethylbenzyl, (trifluoromethyl)(morpholinyl)phenyl, (piperidinylmethyl)phenyl, furanylphenyl, methylphenyl, difluoromethoxyphenyl, trifluoromethoxyphenyl, chloro(dimethylethoxyphenyl)phenyl or (ethoxymethyl)(methyl)-(pyrrolidinylethylamino)phenyl.

10. A compound according to claim 5 represented by formula IIIc or IIId wherein X is halogen and $R^a$ and $R^b$ are each independently hydrogen or aryl, wherein if present, any aryl group may be optionally substituted.

11. A compound according to claim 5 represented by formula IIIe or IIIf wherein X is halogen or alkyl and $R^a$ and $R^b$ are each independently hydrogen, alkyl, aryl, alkylheteroaryl, heteroaryl or alkylaryl, wherein if present, any aryl, alkylheteroaryl, alkylaryl or heteroaryl group may be optionally substituted.

12. A compound according to claim 5 represented by formula IIIe or IIIf wherein X is halogen or alkyl and $R^a$ and $R^b$ are each independently hydrogen, alkyl, or optionally substituted phenyl, pyridinylmethyl, furanyl, benzyl or phenethyl).

13. A compound according to claim 5 represented by formula IIIe or IIIf wherein one of $R^a$ and $R^b$ is hydrogen or alkyl and the other is benzyl, trifluoromethylbenzyl, dichlorobenzyl, chlorobenzyl, methoxybenzyl, fluorobenzyl, difluorobenzyl, methylbenzyl, trifluoromethylphenyl, phenethyl, (morpholinylethoxy)benzyl, (pyrrolidinylethylamido)benzyl, (piperidinylmethyl)benzyl, piperidinylbenzyl, chlorofluorobenzyl, (pyrazolyl)benzyl, (pyridinyl)benzyl, (thiophenyl)benzyl, (furanyl)benzyl, (piperazinyl)benzyl, (methylpiperazinyl)benzyl, (morpholinylmethyl)benzyl, (phenoxy)benzyl, dihydrobenzodioxinylmethyl, dihydrobenzofuranylmethyl, (fluoro)(trifluoromethyl)benzyl, (methyl)(chloro)benzyl, (chloro)(trifluoromethyl)benzyl, (fluoro)(trifluoromethyl)benzyl, (chloro)(phenoxy)benzyl, dimethylbenzyl, (morpholinyl)benzyl, dihydrobenzodioxepinylmethyl, fluoro(benzodioxinylmethyl, (methyl)(phenyl)furanylmethyl, trifluoromethoxybenzyl, difluoromethoxybenzyl, dimethoxybenzyl, hydroxybenzyl, ($CH_3C(O)NH$)benzyl, biphenylmethyl, dimethylminobenzyl, isopropoxybenzyl, (pyrrolyl)benzyl, pyridinylmethyl, (imidazolyl)benzyl, (triazolyl)benzyl, (methylpiperidinylmethyl)benzyl, (dimethylaminopropylamino)benzyl, (morpholinylethylamino)benzyl, (methyldiazepanyl)benzyl, (dimethylaminomethyl)benzyl, (dimethylaminoethylamino)benzyl, (pyrrolidinylmethyl)benzyl, (pyrrolidinyl)benzyl, (pyrrolidinyl)pyridinylmethyl, (morpholinyl)benzyl, pyrazinyloxybenzyl, dihydropyridooxazinylmethyl, hexahydropyrrolo[3,4-c]pyrrolyl-benzyl, (perhydrodiazepinyl)benzyl, (piperazinyl)(trifluoromethyl)benzyl, (piperazinyl(methoxy)benzyl, aminopiperidinylbenzyl or (fluoro)piperazinylbenzyl.

14. A compound according to claim 5 represented by formula IIIe or IIIf wherein one of $R^a$ and $R^b$ is hydrogen or alkyl and the other is benzyl, 2-trifluromethylbenzyl, 3-trifluoromethylbenzyl, 2,4-dichlorophenyl, 2,5-dichlorobenzyl, 3,5-dichlorobenzyl, 2-chlorobenzyl, 3-chlorobenzyl, 4-chlorobenzyl, 2-methoxybenzyl, 3-methoxybenzyl, 4-methoxybenzyl, 3-fluorobenzyl, 2,3-difluorobenzyl, 2,5-difluorobenzyl, 3,4-difluorophenyl, 3,5-difluorobenzyl, 3-methylbenzyl, 3-trifluoromethylphenyl, phenethyl, 3-(2-morpholin-4-yl-ethoxy)benzyl, 2-(2-morpholin-4-yl-ethoxy)benzyl, $CH_2$—$C_6H_4$—$C(O)NH$—$CH_2CH_2$-pyrrolidinyl, 2-piperidin-1-ylmethyl-benzyl, 3-piperidin-1-ylmethylbenzyl, 2-piperidinyl-1ylbenzyl, 2-chloro-6-fluorobenzyl, 2-pyrazol-1-ylbenzyl, 3-pyrazol-1-ylbenzyl, 2-pyridin-3-ylbenzyl, 2-thiophen-2-ylbenzyl, 3-thiophen-2-ylbenzyl, 3-thiophen-3-ylbenzyl), 2-furan-2-ylbenzyl, 3-furan-2-ylbenzyl, 2-piperazinylbenzyl, 2-(4-methylpiperazin-1-yl)benzyl, 3-(4-methylpiperazin-1-yl)benzyl), 2-(3-methylpiperazin-1-yl)benzyl), 2-morpholin-4-ylmethylbenzyl, 3-morpholin-4-ylmethylbenzyl, 2-phenoxybenzyl, 2,3-dihydro-benzo[1,4]dioxin-5-ylmethyl, 2,3-dihydro-benzofuran-5-ylmethyl, 2-fluoro-5-trifluoromethylbenzyl, 5-chloro-2-methylbenzyl, 2-chloro-5-trifluoromethylbenzyl, 2-fluoro-3-trifluoromethylbenzyl), 2-chloro-6-phenoxybenzyl, 2,3-dimethylbenzyl, 3,4-dimethylbenzyl, 2,5-dimethylbenzyl, 3-morpholin-4-ylbenzyl, 3,4-dihydro-2H-benzo[b][1,4]dioxepin-6-ylmethyl, 6-fluoro-4H-benzo[1,3]dioxin-8-ylmethyl, 5-methyl-2-phenyl-furan-3-ylmethyl, 2-trifluoromethoxybenzyl, 3-trifluoromethoxybenzyl, 4-trifluoromethoxybenzyl, 2-difluoromethoxybenzyl, 3-difluoromethoxybenzyl, 3,5-dimethoxybenzyl, 2,3-dimethoxybenzyl, 2,5-dimethoxybenzyl, 3-hydroxybenzyl, ($CH_3C(O)NH$)benzyl, biphenyl-3-ylmethyl, 3-dimethylaminobenzyl, 3-isopropoxybenzyl, 2-pyrrol-1-yl-benzyl, 3-pyrrol-1-yl-benzyl, pyridin-3-ylmethyl, pyridin-2-ylmethyl, 2-imidazol-1-yl-benzyl, 2-[1,2,4]triazol-1-yl-benzyl, 3-(4-methyl-piperidin-1-ylmethyl)benzyl, 3-(3-dimethylaminopropylamino)benzyl, 3-(2-morpholin-4-yl-ethylamino)benzyl, (3-(4-methyl-[1,4]diazepam-1-yl)benzyl), 3-dimethylaminomethyl-benzyl, 3-(2-dimethylamino-ethylamino)benzyl, 3-pyrrolidin-1-ylmethylbenzyl, 2-pyrrolidin-1-ylbenzyl, 3-pyrrolidin-1-ylbenzyl, 6-pyrrolidin-1-yl-pyridin-2-ylmethyl, 2-morpholin-4-ylbenzyl, 3-(6-methyl-pyrazin-2-yloxy)benzyl, 3-methyl-3,4-dihydro-2H-pyrido[3,2-b][1,4]oxazin-7-ylmethyl, 2-(hexahydro-pyrrolo[3,4-c]pyrrol-2-ylbenzyl, 2-perhydro-1,4-diazepin-1-ylbenzyl, 2-piperazin-1-yl-5-trifluoromethylbenzyl, 5-methoxy-2-piperazin-1-ylbenzyl, 4-amino-piperidin-1-ylbenzyl or 5-fluoro-2-piperazin-1-ylbenzyl.

15. A compound according to claim 5 represented by formula IIIg or IIIh wherein X is halogen, R is —$CH_2$— and $R^a$ and $R^b$ are each independently hydrogen or aryl, wherein the aryl may be substituted.

16. A compound according to claim 15, wherein one of $R^a$ and $R^b$ is hydrogen and the other is (dimethylaminoethyl)methylamino)phenyl.

17. A compound according to claim 5 represented by formula IIIi or IIIj wherein X is halogen, R is —$CH_2CH_2$— and $R^a$ and $R^b$ are each independently hydrogen or aryl, wherein the aryl may be substituted.

18. A compound according to claim 17, wherein one of $R^a$ and $R^b$ is hydrogen and the other is (dimethylaminoethyl)methylamino)phenyl.

19. A compound according to claim 5, selected from
1-Methoxy-4-chloro-phthalazine-6-carboxylic acid (3-trifluoromethyl-phenyl)-amide,
4-Methoxy-1-chloro-phthalazine-6-carboxylic acid (3-trifluoromethyl-phenyl)-amide,
4-Chloro-7-(3-trifluoromethyl-benzylamino)-phthalazin-1-ol
4-chloro-6-(3-trifluoromethyl-benzylamino)-phthalazin-1-ol,
4-Chloro-1-hydroxy-phthalazine-6-carboxylic acid (3-trifluoromethyl-phenyl)-amide,
1-Chloro-4-hydroxy-phthalazine-6-carboxylic acid (3-trifluoromethyl-phenyl)-amide,
1-chloro-4-hydroxy-phthalazine-6-carboxylic acid (4-trifluoromethyl-phenyl)amide,
4-chloro-1-hydroxy-phthalazine-6-carboxylic acid (4-trifluoromethyl-phenyl)amide,
1-Chloro-4-hydroxy-phthalazine-6-carboxylic acid phenylamide,
4-Chloro-1-hydroxy-phthalazine-6-carboxylic acid phenylamide, 1-Chloro-4-hydroxy-phthalazine-6-carboxylic acid (2-methyl-3-trifluoromethyl-phenyl) amide,
4-chloro-1-hydroxy-phthalazine-6-carboxylic acid (2-methyl-3-trifluoromethyl-phenyl) amide,
1-chloro-4-hydroxy-phthalazine-6-carboxylic acid (2,5-difluoro-phenyl) amide,
4-chloro-1-hydroxy-phthalazine-6-carboxylic acid (2,5-difluoro-phenyl) amide,
1-chloro-4-hydroxy-phthalazine-6-carboxylic acid (2-fluoro-5-trifluoromethyl-phenyl) amide,
4-chloro-1-hydroxy-phthalazine-6-carboxylic acid (2-fluoro-5-trifluoromethyl-phenyl) amide,
1-chloro-4-hydroxy-phthalazine-6-carboxylic acid (2-fluoro-5-methyl-phenyl) amide,
4-chloro-1-hydroxy-phthalazine-6-carboxylic acid (2-fluoro-5-methyl -phenyl) amide,
1-Iodo-4-hydroxy-phthalazine-6-carboxylic acid (3-trifluoromethyl-phenyl)-amide,
4-Iodo-1-hydroxy-phthalazine-6-carboxylic acid (3-trifluoromethyl-phenyl)-amide,
1-Hydroxy-phthalazine-6-carboxylic acid (3-trifluoromethyl-phenyl)-amide,
1-hydroxy-4-phenyl-phthalazine-6-carboxylic acid (3-trifluoromethyl-phenyl)-amide,
1-hydroxy-4-pyridin-2-yl-phthalazine-6-carboxylic acid (3-trifluoromethyl-phenyl)-amide,
4-hydroxy-1-methoxy-phthalazine-6-carboxylic acid (4-trifluoromethyl-pyridin-2-yl) -amide,
1-hydroxy-4-methoxy-phthalazine-6-carboxylic acid (4-trifluoromethyl-pyridin-2-yl)-amide,
6-{[(2,4-Dichlorophenyl)methyl]amino}-4-chloro-2H-phthalazin-1-one,
7-{[(2,4-dichlorophenyl)methyl]amino}-4-chloro-2H-phthalazin-1-one,
6-{[(4-Chlorophenyl)methyl]amino}-4-chloro-2H-phthalazin-1-one,
7-{[(4-Chlorophenyl)methyl]amino}-4-chloro-2H-phthalazin-1-one,
6-{[(3-Methoxyphenyl)methyl]amino}-4-chloro-2H-phthalazin-1-one,
7-{[(3-Methoxyphenyl)methyl]amino}-4-chloro-2H-phthalazin-1-one,
6-{[(3,4-Difluorophenyl)methyl]amino}-4-chloro-2H-phthalazin-1-one,
7-{[(3,4-Difluorophenyl)methyl]amino}-4-chloro-2H-phthalazin-1-one,
6-{[(3-Methylphenyl)methyl]amino}-4-chloro-2H-phthalazin-1-one,
7-{[(3-Methylphenyl)methyl]amino}-4-chloro-2H-phthalazin-1-one,
6-{[(2-Methoxyphenyl)methyl]amino}-4-chloro-2H-phthalazin-1-one,
7-{[(2-Methoxyphenyl)methyl]amino}-4-chloro-2H-phthalazin-1-one,
6-(4-Methoxy-benzylamino)-2H-phthalazin-1-one,
6-Benzylamino-4-chloro-2H-phthalazin-1-one
7-Benzylamino-4-chloro-2H-phthalazin-1-one,
4-Chloro-6-(3-trifluoromethyl-phenylamino)-2H-phthalazin-1-one,
4-Chloro-7-(3-trifluoromethyl-phenylamino)-2H-phthalazin-1-one,
4-Chloro-6-phenethylamino-2H-phthalazin-1-one,
4-Chloro-7-phenethylamino-2H-phthalazin-1-one,
4-[(4-Chloro-1-oxo-1,2-dihydro-phthalazin-6-ylamino)-methyl]-N-(2-pyrrolidin-1-yl-ethyl)-benzamide,
4-[(1-Chloro-4-oxo-3,4-dihydro-phthalazin-6-ylamino)-methyl]-N-(2-pyrrolidin-1-yl-ethyl)-benzamide,
3-[(4-Chloro-1-oxo-1,2-dihydro-phthalazin-6-ylamino)-methyl]-N-(2-pyrrolidin-1-yl-ethyl) -benzamide,
3-[(1-Chloro-4-oxo-3,4-dihydro-phthalazin-6-ylamino)-methyl]-N-(2-pyrrolidin-1-yl-ethyl) -benzamide,
N-(4-Chloro-1-oxo-1,2-dihydro-phthalazin-6-yl)-3-trifluoromethyl-benzamide,
N-(1-Chloro-4-oxo-3,4-dihydro-phthalazin-6-yl)-3-trifluoromethyl-benzamide,
4-Chloro-6-[3-(2-morpholin-4-yl-ethoxy)-benzylamino]-phthalazin-1-ol,
4-Chloro-7-[3-(2-morpholin-4-yl-ethoxy)-benzylamino]-phthalazin-1-ol,
4-Methyl-1-oxo-1,2-dihydro-phthalazine-6-carboxylic acid (3-trifluoromethyl-phenyl) -amide,
4-Methyl-1-oxo-1,2-dihydro-phthalazine-6-carboxylic acid 3-trifluoromethyl-benzylamide,
4-Methyl-1-oxo-1,2-dihydro-phthalazine-6-carboxylic acid 3-methoxy-benzylamide,
4-Chloro-6-(3-piperidin-1-ylmethyl-benzylamino)-2H-phthalazin-1-one,
4-Chloro-6-[2-(2-morpholin-4-yl-ethoxy)-benzylamino]-2H-phthalazin-1-one,
6-(Benzyl-methyl-amino)-4-chloro-2H-phthalazin-1-one,
4-Chloro-6-(2,5-dichloro-benzylamino)-2H-phthalazin-1-one,
4-Chloro-6-(2-methyl-benzylamino)-2H-phthalazin-1-one,
4-Chloro-6-(2-chloro-6-fluoro-benzylamino)-2H-phthalazin-1-one,
4-Chloro-6-(2-pyrazol-1-yl-benzylamino)-2H-phthalazin-1-one,
4-Chloro-6-(3-pyrazol-1-yl-benzylamino)-2H-phthalazin-1-one,
4-Chloro-6-(2-pyridin-3-yl-benzylamino)-2H-phthalazin-1-one,
4-Chloro-6-(2-piperidin-1-yl-benzylamino)-2H-phthalazin-1-one,
4-Chloro-6-(2-thiophen-2-yl-benzylamino)-2H-phthalazin-1-one,
4-Chloro-6-(3-thiophen-2-yl-benzylamino)-2H-phthalazin-1-one,
4-Chloro-6-(2-furan-2-yl-benzylamino)-2H-phthalazin-1-one,
4-Chloro-6-[3-(4-methyl-piperazin-1-yl)-benzylamino]-2H-phthalazin-1-one,
4-Chloro-6-(2-morpholin-4-ylmethyl-benzylamino)-2H-phthalazin-1-one,
4-Chloro-6-(3-thiophen-3-yl-benzylamino)-2H-phthalazin-1-one,
4-Chloro-6-[2-(4-methyl-piperazin-1-yl)-benzylamino]-2H-phthalazin-1-one,
4-Chloro-6-(2-phenoxy-benzylamino)-2H-phthalazin-1-one,
4-Chloro-6-[(2,3-dihydro-benzo[1,4]dioxin-5-ylmethyl)-amino]-2H-phthalazin-1-one,
4-Chloro-6-[(2,3-dihydro-benzofuran-5-ylmethyl)-amino]-2H-phthalazin-1-one,
4-Chloro-6-(2-piperazin-1-yl-benzylamino)-2H-phthalazin-1-one,
4-Chloro-6-(2-fluoro-5-trifluoromethyl-benzylamino)-2H-phthalazin-1-one,
4-Chloro-6-(5-chloro-2-methyl-benzylamino)-2H-phthalazin-1-one,
4-Chloro-6-(2-chloro-5-trifluoromethyl-benzylamino)-2H-phthalazin-1-one,
4-Chloro-6-(2-chloro-3-trifluoromethyl-benzylamino)-2H-phthalazin-1-one, 4-Chloro-6-(2-chloro-6-phenoxy-benzylamino)-2H-phthalazin-1-one,
4-Chloro-6-(2,5-dimethyl-benzylamino)-2H-phthalazin-1-one,
4-Chloro-6-(3-morpholin-4-yl-benzylamino)-2H-phthalazin-1-one,
4-Chloro-6-(2,3-dimethyl-benzylamino)-2H-phthalazin-1-one,
4-Chloro-6-[(3,4-dihydro-2H-benzo[b][1,4]dioxepin-6-ylmethyl)-amino]-2H-phthalazin-1-one,
4-Chloro-6-(3-furan-2-yl-benzylamino)-2H-phthalazin-1-one,
4-Chloro-6-[(6-fluoro-4H-benzo[1,3]dioxin-8-ylmethyl)-amino]-2H-phthalazin-1-one,
4-Chloro-6-[(5-methyl-2-phenyl-furan-3-ylmethyl)-amino]-2H-phthalazin-1-one,
1-Chloro-4-oxo-3,4-dihydro-phthalazine-6-carboxylic acid (3-difluoromethoxy-phenyl)-amide,
4-Chloro-1-oxo-1,2-dihydro-phthalazine-6-carboxylic acid (3-difluoromethoxy-phenyl)-amide,
4-Chloro-7-(3-fluoro-benzylamino)-2H-phthalazin-1-one
4-Chloro-6-(3-fluoro-benzylamino)-2H-phthalazin-1-one,
4-Chloro-7-(3-trifluoromethoxy-benzylamino)-2H-phthalazin-1-one
4-Chloro-6-(3-trifluoromethoxy-benzylamino)-2H-phthalazin-1-one,
4-Chloro-6-(3-chloro-benzylamino)-2H-phthalazin-1-one,
4-Chloro-6-(2-trifluoromethyl-benzylamino)-2H-phthalazin-1-one,
4-Chloro-6-(3,5-dimethoxy-benzylamino)-2H-phthalazin-1-one,
4-Chloro-6-(3-hydroxy-benzylamino)-2H-phthalazin-1-one,
4-Chloro-6-(3,5-difluoro-benzylamino)-2H-phthalazin-1-one,
4-Chloro-6-(2,5-difluoro-benzylamino)-2H-phthalazin-1-one,
N-{3-[(4-Chloro-1-oxo-1,2-dihydro-phthalazin-6-ylamino)-methyl]-phenyl}-acetamide,
4-Chloro-6-(3,5-dichloro-benzylamino)-2H-phthalazin-1-one,
6-[(Biphenyl-3-ylmethyl)-amino]-4-chloro-2H-phthalazin-1-one,
4-Chloro-6-(3-difluoromethoxy-benzylamino)-2H-phthalazin-1-one,
4-Chloro-6-(2,3-difluoro-benzylamino)-2H-phthalazin-1-one,
4-Chloro-6-(2-chloro-benzylamino)-2H-phthalazin-1-one,
4-Chloro-6-(3,4-dimethyl-benzylamino)-2H-phthalazin-1-one,
4-Chloro-6-(3-dimethylamino-benzylamino)-2H-phthalazin-1-one,
4-Chloro-6-(3-isopropoxy-benzylamino)-2H-phthalazin-1-one,
4-Chloro-6-(2-pyrrol-1-yl-benzylamino)-2H-phthalazin-1-one,
6-(4-tert-Butoxy-benzylamino)-4-chloro-2H-phthalazin-1-one,
4-Chloro-6-[(pyridin-3-ylmethyl)-amino]-2H-phthalazin-1-one,
4-Chloro-6-(2,3-dimethoxy-benzylamino)-2H-phthalazin-1-one,
4-Chloro-6-(2,5-dimethoxy-benzylamino)-2H-phthalazin-1-one,
4-Chloro-6-[(pyridin-2-ylmethyl)-amino]-2H-phthalazin-1-one,
4-Chloro-6-(2-trifluoromethoxy-benzylamino)-2H-phthalazin-1-one,
4-Chloro-6-(2-difluoromethoxy-benzylamino)-2H-phthalazin-1-one,
4-Chloro-6-(2-imidazol-1-yl-benzylamino)-2H-phthalazin-1-one,
4-Chloro-6-(2-[1,2,4]triazol-1-yl-benzylamino)-2H-phthalazin-1-one,
4-Chloro-6-(3-morpholin-4-ylmethyl-benzylamino)-2H-phthalazin-1-one,
4-Chloro-6-(3-pyrrol-1-yl-benzylamino)-2H-phthalazin-1-one,
4-Chloro-6-[3-(4-methyl-piperidin-1-ylmethyl)-benzylamino]-2H-phthalazin-1-one,
4-Chloro-6-[3-(3-dimethylamino-propylamino)-benzylamino]-2H-phthalazin-1-one,
4-Chloro-6-[3-(2-morpholin-4-yl-ethylamino)-benzylamino]-2H-phthalazin-1-one,
4-Chloro-1-oxo-1,2-dihydro-phthalazine-6-carboxylic acid (3-piperidin-1-ylmethyl-phenyl)-amide,
4-Chloro-6-[3-(4-methyl-[1,4]diazepan-1-yl)-benzylamino]-2H-phthalazin-1-one,
1-Chloro-4-oxo-3,4-dihydro-phthalazine-6-carboxylic acid (2-morpholin-4-yl-5-trifluoromethyl-phenyl)-amide,
4-Chloro-1-oxo-1,2-dihydro-phthalazine-6-carboxylic acid (2-morpholin-4-yl-5-trifluoromethyl-phenyl)-amide,
1-chloro-4-oxo-3,4-dihydro-phthalazine-6-carboxylic acid (3-furan-2-yl-phenyl)-amide,
4-chloro-1-oxo-1,2-dihydro-phthalazine-6-carboxylic acid (3-furan-2-yl-phenyl)-amide,
4-Chloro-6-(3-dimethylaminomethyl-benzylamino)-2H-phthalazin-1-one,
4-Chloro-6-[3-(2-dimethylamino-ethylamino)-benzylamino]-2H-phthalazin-1-one,
1-Chloro-4-oxo-3,4-dihydro-phthalazine-6-carboxylic acid m-tolylamide,
4-Chloro-1-oxo-1,2-dihydro-phthalazine-6-carboxylic acid m-tolylamide,
1-Chloro-4-oxo-3,4-dihydro-phthalazine-6-carboxylic acid (3-trifluoromethoxy-phenyl)-amide,
4-Chloro-1-oxo-1,2-dihydro-phthalazine-6-carboxylic acid (3-trifluoromethoxy-phenyl)-amide,
1-Chloro-3-methyl-4-oxo-3,4-dihydro-phthalazine-6-carboxylic acid (3-trifluoromethyl-phenyl)-amide,
4-Chloro-2-methyl-1-oxo-1,2-dihydro-phthalazine-6-carboxylic acid (3-trifluoromethyl-phenyl)-amide,
1-chloro-4-oxo-3,4-dihydro-phthalazine-6-carboxylic acid [5-ethoxymethyl-2-methyl-3-(2-pyrrolidin-1-yl-ethylamino)-phenyl]-amide,
4-chloro-1-oxo-1,2-dihydro-phthalazine-6-carboxylic acid [5-ethoxy methyl-2-methyl-3-(2-pyrrolidin-1-yl-ethylamino)-phenyl]-amide,
1-Oxo-1,2-dihydro-phthalazine-6-carboxylic acid [5-ethoxymethyl-2-methyl-3-(2-pyrrolidin-1-yl-ethylamino)-phenyl]-amide,
1-Chloro-4-oxo-3,4-dihydro-phthalazine-6-carboxylic acid 3-trifluoromethyl-benzylamide,
4-Chloro-1-oxo-1,2-dihydro-phthalazine-6-carboxylic acid 3-trifluoromethyl-benzylamide,
N-(4-Chloro-1-oxo-1,2-dihydro-phthalazin-6-yl)-3-methoxy-benzamide, 2-(4-Chloro-1-oxo-1,2-dihydro-phthalazin-6-yl)-N-{2-[(2-dimethylamino-ethyl)-methyl -amino]-phenyl}-acetamide, 2-(1-Chloro-4-oxo-3,4-dihydro-phthalazin-6-yl)-N-{2-[(2-dimethylamino-ethyl)-methyl -amino]-phenyl}-acetamide, 4-Chloro-6-(2-{2-[(2-dimethylamino-ethyl)-methyl-amino]-phenylamino}-ethyl)-2H-phthalazin-1-one, 4-Chloro-7-(2-{2-[(2-dimethylamino-ethyl)-methyl-amino]-phenylamino}-ethyl)-2H-phthalazin-1-one, 4-Chloro-1-hydroxy-phthalazine-6-carboxylic acid [4-chloro-3'-(2-dimethylamino-ethoxy) -biphenyl-3-yl]-amide, 1-Chloro-4-hydroxy-phthalazine-6-carboxylic acid [4-chloro-3'-(2-dimethylamino-ethoxy) -biphenyl-3-yl]-amide, 4-Chloro-1-hydroxy-phthalazine-6-carboxylic acid (3'-hydroxy-biphenyl-3-yl)-amide, 1-Chloro-4-hydroxy-phthalazine-6-carboxylic acid (3'-hydroxy-biphenyl-3-yl)-amide, 4-Chloro-6-(3-pyrrolidin-1-ylmethyl-benzylamino)-2H-phthalazin-1-one, 4-Chloro-6-(3-pyrrolidin-1-yl-benzylamino)-2H-phthalazin-1-one, 4-Chloro-6-[(6-pyrrolidin-1-yl-pyridin-2-ylmethyl)-amino]-2H-phthalazin-1-one, 4-Chloro-6-(2-pyrrolidin-1-yl-benzylamino)-2H-phthalazin-1-one, 4-Chloro-6-(2-morpholin-4-yl-benzylamino)-4a,8a-dihydro-2H-phthalazin-1-one, 4-Chloro-6-{methyl-[3-(6-methyl-pyrazin-2-yloxy)-benzyl]-amino}-4a,8a-dihydro-2H-phthalazin-1-one, 4-Chloro-6-[methyl-(4-methyl-3,4-dihydro-2H-pyrido[3,2-b][1,4]oxazin-7-ylmethyl) -amino]-4a,8a-dihydro-2H-phthalazin-1-one, 4-Chloro-6-[2-((R)-3-methyl-piperazin-1-yl)-benzyl amino]-4a,8a-dihydro-2H-phthalazin-1-one, 4-Chloro-6-[2-(hexahydro-pyrrolo[3,4-c]pyrrol-2-yl)-benzylamino]-2H-phthalazin-1-one, 4-Chloro-6-(2-perhydro-1,4-diazepin-1-yl-benzylamino)-2H-phthalazin-1-one, 4-Chloro-6-(2-piperazin-1-yl-5-trifluoromethyl-benzylamino)-2H-phthalazin-1-one, 4-Chloro-6-(5-methoxy-2-piperazin-1-yl-benzylamino)-2H-phthalazin-1-one, 6-[2-(4-Amino-piperidin-1-yl)-benzylamino]-4-chloro-2H-phthalazin-1-one, 4-Chloro-6-(5-fluoro-2-piperazin-1-yl-benzylamino)-2H-phthalazin-1-one, and pharmaceutically acceptable salts thereof, wherein if the compound exhibits chirality it can be in the form of a mixture of enantiomers such as a racemate or a mixture of diastereomers, or can be in the form of a single enantiomer or a single diastereomer.

20. A compound according to claim 19, selected from

4-Chloro-1-hydroxy-phthalazine-6-carboxylic acid (3-trifluoromethyl-phenyl)-amide sodium salt, 4-Chloro-6-[(pyridin-3-ylmethyl)-amino]-2H-phthalazin-1-one hydroformate, 4-Chloro-6-[3-(3-dimethylamino-propylamino)-benzylamino]-2H-phthalazin-1-one hydroformate, 4-Chloro-6-[3-(2-morpholin-4-yl-ethylamino)-benzylamino]-2H-phthalazin-1-one hydroformate, 4-Chloro-1-oxo-1,2-dihydro-phthalazine-6-carboxylic acid (3-piperidin-1-ylmethyl-phenyl)-amide hydroformate, 4-Chloro-6-[3-(4-methyl-[1,4]diazepan-1-yl)-benzylamino]-2H-phthalazin-1-one hydroformate, 4-Chloro-6-(3-dimethylaminomethyl-benzylamino)-2H-phthalazin-1-one hydroformate, 4-Chloro-6-[3-(2-dimethylamino-ethylamino)-benzylamino]-2H-phthalazin-1-one hydroformate, 1-chloro-4-oxo-3,4-dihydro-phthalazine-6-carboxylic acid [5-ethoxymethyl-2-methyl-3-(2-pyrrolidin-1-yl-ethylamino)-phenyl]-amide hydroformate, 4-chloro-1-oxo-1,2-dihydro-phthalazine-6-carboxylic acid [5-ethoxy methyl-2-methyl-3-(2-pyrrolidin-1-yl-ethylamino)-phenyl]-amide hydroformate, wherein if the compound exhibits chirality it can be in the form of a mixture of enantiomers such as a racemate, or a mixture of diastereomers, or can be in the form of a single enantiomer or a single diastereomer.

21. A compound according to claim 19, selected from

4-Chloro-1-hydroxy-phthalazine-6-carboxylic acid [4-chloro-3'-(2-dimethylamino-ethoxy) -biphenyl-3-yl]-amide, 4-Chloro-1-hydroxy-phthalazine-6-carboxylic acid (3'-hydroxy-biphenyl-3-yl)-amide, 4-Chloro-6-(2-piperazin-1-yl-benzylamino)-2H-phthalazin-1-one, 4-Chloro-6-(2-phenoxy-benzylamino)-2H-phthalazin-1-one, 4-Chloro-6-(3-thiophen-2-yl-benzylamino)-2H-phthalazin-1-one, 4-Chloro-6-(2-morpholin-4-ylmethyl-benzylamino)-2H-phthalazin-1-one, 4-Chloro-6-(3-thiophen-3-yl-benzylamino)-2H-phthalazin-1-one, 4-Chloro-6-(2-thiophen-2-yl-benzylamino)-2H-phthalazin-1-one, 4-Chloro-6-(2-piperidin-1-yl-benzylamino)-2H-phthalazin-1-one, 4-Chloro-6-(2-pyridin-3-yl-benzylamino)-2H-phthalazin-1-one, 4-Chloro-6-(2-pyrazol-1-yl-benzylamino)-2H-phthalazin-1-one, 4-Chloro-6-(3-pyrrol-1-yl-benzylamino)-2H-phthalazin-1-one, 4-Chloro-1-oxo-1,2-dihydro-phthalazine-6-carboxylic acid (3-difluoromethoxy-phenyl) -amide, 4-Chloro-7-(3-trifluoromethyl-benzylamino)-phthalazin-1-ol, and 4-Chloro-1-hydroxy-phthalazine-6-carboxylic acid (3-trifluoromethyl-phenyl)-amide, and pharmaceutically acceptable salts thereof, wherein if the compound exhibits chirality it can be in the form of a mixture of enantiomers such as a racemate or a mixture of diastereomers, or can be in the form of a single enantiomer or a single diastereomer.

22. A pharmaceutical composition comprising a compound according to claim 1 and a pharmaceutically acceptable carrier.

23. A compound of formula IV:

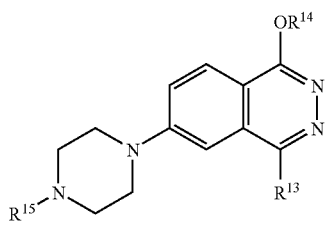

wherein
R¹³ is hydrogen, halogen, alkyl, aryl, heteroaryl, cyano or alkoxy;
R¹⁴ is hydrogen, alkyl, —C(O)R$_y$, —SO$_2$R$_y$, or —P(O)(OR$_y$)$_2$, where R$_y$ is hydrogen or alkyl; and
R¹⁵ is hydrogen, alkyl, aryl, heteroaryl, heterocyclyl, alkylaryl, alkylheteraryl, alkylheterocyclyl or aminoalkyl; wherein an aryl, heteroaryl, heterocyclyl, alkylaryl, alkylheteraryl, alkylheterocyclyl may be optionally substituted by halogen, alkyl, alkenyl, alkynyl, cyano, nitro, amino, alkylamino, dialkylamino, hydroxyl, carboxyl, aryl, heteroaryl, heterocyclyl, alkylaryl, alkylheteroaryl, alkylheterocyclyl, alkylalkoxy, or NR$^x$(alkylheterocyclyl) where R$^x$ is hydrogen or alkyl.

24. A compound according to claim 23, wherein R¹⁴ is hydrogen or alkyl.

25. A compound according to claim 23, wherein R¹⁵ is hydrogen, alkyl, aryl, heteroaryl, heterocyclyl, alkylaryl, alkylheteraryl, alkylheterocyclyl or aminoalkyl; wherein an aryl, heteroaryl, heterocyclyl, alkylaryl, alkylheteraryl, alkylheterocyclyl may be optionally substituted by alkyl, alkylalkoxy or NR$^x$(alkylheterocyclyl).

26. A compound according to claim 23, wherein R¹³ is halogen, R¹⁴ is hydrogen and R¹⁵ is aryl, heteroaryl, alkylheterocyclyl, or alkylamino.

27. A compound according to claim 23, wherein R¹⁵ is optionally substituted phenyl, pyrazinyl, morpholinylethyl or dimethylaminopropyl.

28. A compound according to claim 27, wherein R¹⁵ is phenyl, trifluoromethylphenyl, (pyrrolidinylethylamino)phenyl, (ethoxymethyl)(methyl)(pyrrolidinylethylamino)phenyl, pyrazinyl, morpholinylethyl or dimethylaminopropyl.

29. A compound according to claim 28, wherein R¹⁵ is phenyl, 3-trifluoromethylphenyl, 3-(2-pyrrolidin-1-yl-ethylamino)phenyl, 5-ethoxymethyl-2-methyl-3-(2-pyrrolidin-1-yl-ethylamino)phenyl, pyrazinyl, 2-morpholin-4-yl-ethyl or 3-dimethylaminopropyl).

30. A compound according to claim 23, selected from:
4-Chloro-6-(4-phenyl-piperazin-1-yl)-2H-phthalazin-1-one,
4-Chloro-6-[4-(3-trifluoromethyl-phenyl)-piperazin-1-yl]-2H-phthalazin-1-one,
4-Chloro-6-(2,3,5,6-tetrahydro-[1,2']bipyrazinyl-4-yl)-2H-phthalazin-1-one,
4-Chloro-6-[4-(2-morpholin-4-yl-ethyl)-piperazin-1-yl]-2H-phthalazin-1-one,
4-Chloro-6-[4-(3-dimethylamino-propyl)-piperazin-1-yl]-2H-phthalazin-1-one, and
4-Chloro-6-{4-[3-(2-pyrrolidin-1-yl-ethylamino)-phenyl]-piperazin-1-yl}-2H-phthalazin-1-one, and
4-Chloro-6-{4-[5-ethoxymethyl-2-methyl-3-(2-pyrrolidin-1-yl-ethylamino)-phenyl]-piperazin-1-yl}-2H-phthalazin-1-one,
and pharmaceutically acceptable salts thereof,
wherein if the compound exhibits chirality it can be in the form of a mixture of enantiomers such as a racemate or a mixture of diastereomers, or can be in the form of a single enantiomer or a single diastereomer.

31. A compound according to claim 30, selected from:
4-Chloro-6-[4-(2-morpholin-4-yl-ethyl)-piperazin-1-yl]-2H-phthalazin-1-one hydroformate,
4-Chloro-6-[4-(3-dimethylamino-propyl)-piperazin-1-yl]-2H-phthalazin-1-one hydroformate,
4-Chloro-6-{4-[3-(2-pyrrolidin-1-yl-ethylamino)-phenyl]-piperazin-1-yl}-2H-phthalazin-1-one hydroformate, and
4-Chloro-6-{4-[5-ethoxymethyl-2-methyl-3-(2-pyrrolidin-1-yl-ethylamino)-phenyl]-piperazin-1-yl}-2H-phthalazin-1-one hydroformate,
wherein if the compound exhibits chirality it can be in the form of a mixture of enantiomers such as a racemate or a mixture of diastereomers, or can be in the form of a single enantiomer or a single diastereomer.

32. A pharmaceutical composition comprising a compound according to claim 23 and a pharmaceutically acceptable carrier.

* * * * *